(12) United States Patent
An et al.

(10) Patent No.: US 10,428,390 B2
(45) Date of Patent: *Oct. 1, 2019

(54) METHOD FOR DETECTING METHYLATION OF COLORECTAL CANCER SPECIFIC METHYLATION MARKER GENE FOR COLORECTAL CANCER DIAGNOSIS

(71) Applicant: GENOMICTREE, INC., Daejeon (KR)

(72) Inventors: Sung Whan An, Daejeon (KR); Tae Jeong Oh, Daejeon (KR)

(73) Assignee: GENOMICTREE, INC., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/710,028

(22) Filed: Sep. 20, 2017

(65) Prior Publication Data

US 2018/0016644 A1 Jan. 18, 2018

Related U.S. Application Data

(63) Continuation-in-part of application No. 15/661,054, filed on Jul. 27, 2017, which is a continuation-in-part of application No. 15/010,379, filed on Jan. 29, 2016, now Pat. No. 9,752,197, which is a continuation-in-part of application No. 13/994,732, filed as application No. PCT/KR2011/009710 on Dec. 16, 2011, now Pat. No. 9,315,870.

(30) Foreign Application Priority Data

Dec. 16, 2010 (KR) .................. 10-2010-0129208

(51) Int. Cl.
  *C07H 21/04* (2006.01)
  *C12Q 1/68* (2018.01)
  *C12Q 1/6886* (2018.01)

(52) U.S. Cl.
  CPC ...... *C12Q 1/6886* (2013.01); *C12Q 2600/112* (2013.01); *C12Q 2600/154* (2013.01)

(58) Field of Classification Search
  None
  See application file for complete search history.

(56) References Cited

U.S. PATENT DOCUMENTS

| | | | |
|---|---|---|---|
| 5,474,796 A | 12/1995 | Brennan | |
| 5,786,146 A | 7/1998 | Herman et al. | |
| 7,112,404 B2* | 9/2006 | Laird ................ | C12Q 1/6858 435/6.14 |
| 9,315,870 B2* | 4/2016 | An ..................... | C07K 14/705 |
| 9,359,646 B2 | 6/2016 | An et al. | |
| 9,365,900 B2 | 6/2016 | An et al. | |
| 9,752,197 B2* | 9/2017 | An ..................... | C12Q 1/6886 |
| 2010/0303795 A1 | 12/2010 | Sorensen et al. | |
| 2012/0101023 A1* | 4/2012 | Zwarthoff ......... | C12Q 1/6886 514/1.1 |
| 2012/0264640 A1* | 10/2012 | An ..................... | C12Q 1/686 506/9 |
| 2014/0045180 A1 | 2/2014 | An et al. | |
| 2016/0145694 A1 | 5/2016 | An et al. | |

FOREIGN PATENT DOCUMENTS

| | | | | |
|---|---|---|---|---|
| DE | 20121960 U1 | | 1/2004 | |
| EP | 1862555 | * | 12/2007 | ........... C12Q 1/68 |
| EP | 1862555 A1 | | 12/2007 | |
| KR | 1020120055917 A | | 6/2012 | |
| WO | 2007149269 A2 | | 12/2007 | |
| WO | 2010123354 A2 | | 10/2010 | |
| WO | WO 2010/123354 | * | 10/2010 | ........... C12Q 1/68 |

OTHER PUBLICATIONS

"Homo sapiens BAC clone RP11-598O12 from 4, complete sequence", "GenBank", May 29, 2002, p. AC110794.3, Publisher: https://www.ncbi.nlm.nih.gov/nuccore/AC110794.3.

Sulewska, A., et al., "Detection of DNA methylation in eucaryotic cells", "Folio Histochemica Et Cytobiologica", 2007, pp. 315-324, vol. 45, No. 4.

Ahlquist, D., et al., "Colorectal Cancer Screening by Detection of Altered Human DNA in Stool: Feasibility of a Multitarget Assay Panel", "Gastroenterology", Nov. 2000, pp. 1219-1227, vol. 119, No. 5.

Alfonso, J., et al., "The stress-regulated protein M6a is a key modulator for neurite outgrowth and filopodium/spine formation", "Proceedings of National Academy of Sciences", Nov. 22, 2005, pp. 17196-17201, vol. 102, No. 47.

Bai, F., et al., "Establishment and characterization of a high metastatic potential in the peritoneum for human gastric cancer by orthotopic tumor cell implantation", "Dig Dis Sci.", Apr. 3, 2007, pp. 1571-1578, vol. 52, No. 6.

Chen, X., et al., "Detecting tumor-related alterations in plasma or serum DNA of patients diagnosed with breast cancer", "Clin Cancer Res.", Sep. 1999, pp. 2297-2303, vol. 5, No. 9.

Esteller, M., et al., "Detection of Aberrant Promoter Hypermethylation of Tumor Suppressor Genes in Serum DNA from Non-Small Cell Lung Cancer Patients", "Cancer Research", Jan. 1, 1999, pp. 67-70, vol. 59.

(Continued)

*Primary Examiner* — Jeanine A Goldberg
(74) *Attorney, Agent, or Firm* — Hultquist, PLLC; Steven J. Hultquist

(57) ABSTRACT

The present disclosure relates to a method for detecting methylation of the bowel-cancer-specific methylation marker GPM6A (NM_201591, glycoprotein M6A) gene in order to diagnose bowel cancer, and more specifically relates to a method for providing information for diagnosing bowel cancer by detecting the methylation of a bowel-cancer-specific marker gene that is specifically methylated in bowel cancer cells. The method for detecting methylation and a diagnostic composition, kit and nucleic-acid chip according to the present disclosure can be used to advantage in diagnosing bowel cancer more accurately and quickly than by normal methods as they permit bowel cancer to be diagnosed at the initial genetic transformation step and so allow early diagnosis.

5 Claims, 4 Drawing Sheets

Specification includes a Sequence Listing.

(56) References Cited

OTHER PUBLICATIONS

Fraga, M., et al., "The affinity of different MBD proteins for a specific methylated locus depends on their intrinsic binding properties", "Nucleic Acids Research", Mar. 15, 2003, pp. 1765-1774, vol. 31, No. 6.

Gitan, R., et al., "Methylation-Specific Oligonucleotide Microarray: A New Potential for High-Throughput Methylation Analysis", "Genome Research", Dec. 2001, pp. 158-164, vol. 12.

Goessl, C., et al., "Fluorescent Methylation-specific Polymerase Chain Reaction for DNA-based Detection of Prostate Cancer in Bodily Fluids", "Cancer Research", Nov. 1, 2000, pp. 5941-5945, vol. 60.

Hoehn, B., et al., "Abstract 4517: Syndecan-2 methylation is an early detection biomarker for colorectal cancer with high sensitivity and specificity in small serum sample volumes", "Cancer Research", Apr. 15, 2012, p. 4517 vol. 72 (8 Supplement).

"Illumina DNA Methylation Analysis Data Sheet", "Data Sheet: Epigenetics", Apr. 6, 2012, pp. 1-7; (http://www.Illumina.com/Documents/products/datasheets/datasheet_dna_methylation_analysis.pdf).

Jan, K., et al, "Abnormal DNA methylation according to the histologic types of early gastric adenocarcinoma", "Histopathology", Sep. 5, 2012, pp. 76-77, vol. 61 (Supplement 1).

Kimura, N., et al., "Methylation profiles of genes utilizing newly developed CpG island methylation microarray on colorectal cancer patients", "Nucleic acids research", Mar. 10, 2005, p. e46, vol. 33, No. 5.

Kopreski, M., et al., "Detection of Tumor Messenger RNA in the Serum of Patients with Malignant Melanoma", "Clinical Cancer Research", Aug. 1999, pp. 1961-1965, vol. 5.

Malik, K., et al., "Epigenetic gene deregulation in cancer", "British Journal of Cancer", Dec. 2000, pp. 1583-1588, vol. 83, No. 12.

Matsusaka, K., et al., "Classification of Epstein-Barr Virus-Positive Gastric Cancers by Definition of DNA Methylation Epigenotypes", "Cancer Research", Dec. 1, 2011, pp. 7187-7197, vol. 71, No. 23.

Miyashiro, I., et al., "Molecular Strategy for Detecting Metastatic Cancers with Use of Multiple Tumor-specific MAGE-A Genes", "Clinical Chemistry", Mar. 2001, pp. 505-512, vol. 47, No. 3.

Moon, Y.H., et al., "Methylated DNA Isolation Assay-Medicated DNA Methylation Detection and Whole-Genome Methylation Profiling", "American Biotechnology Laboratory", Oct. 2009, pp. 23-25, vol. 27, No. 10.

Mukobata, S., et al., "M6a acts as a nerve growth factor-gated Ca2+ channel in neuronal differentiation", "Biochemical and Biophysical Research Communications", Oct. 2002, pp. 722-728, vol. 297.

Palmisano, W., et al., "Predicting Lung Cancer by Detecting Aberrant Promoter Methylation in Sputum", "Cancer Research", Nov. 1, 2000, pp. 5954-5958, vol. 60.

Robertson, K., et al., "DNA Methylation: past, present and future directions", "Carcinogenesis", Mar. 2000, pp. 461-467, vol. 21, No. 3.

Sanchez-Cespedes, M., et al., "Gene Promoter Hypermethylation in Tumors and Serum of Head and Neck Cancer Patients", "Cancer Research", Feb. 15, 2000, pp. 892-895, vol. 60.

Sato, F., et al., "CpG Island Hypermethylation in Progression of Esophageal and Gastric Cancer", "Cancer", Dec. 16, 2005, pp. 483-493, vol. 106, No. 3.

Shimizu, F., et al., "Isolation and mapping of the human glycoprotein M6 gene (GPM6A) to 4q33→q34", "Cytogenetics and Cell Genetics", 1996, pp. 138-139, vol. 74, No. 1-2.

Singal, R., et al., "DNA Methylation", "Blood", Jun. 15, 1999, pp. 4059-4070, vol. 93, No. 12.

Sozzi, G., et al., "Detection of Microsatellite Alterations in Plasma DNA of Non-Small Cell Lung Cancer Patients: A Prospect for Early Diagnosis", "Clinical Cancer Research", Oct. 1999, pp. 2689-2692, vol. 5.

Sueoka, E., et al., "Heterogeneous Nuclear Ribonucleoprotein B1 as a New Marker of Early Detection for Human Lung Cancers", "Cancer Research", Apr. 1, 1999, pp. 1404-1407, vol. 59.

Toyota, M., et al., "Identification of differentially methylated sequences in colorectal cancer by methylated CpG island amplification", "Cancer Research", May 15, 1999, pp. 2307-2312, vol. 59.

Tran, A., et al., "In silico enhanced restriction enzyme based methylation analysis of the human glioblastoma genome using Agilent 244K CpG Island microarrays", "Frontiers in Neroscience", Jan. 4, 2010, pp. 1-13, vol. 3.

Unpublished U.S. Appl. No. 15/661,054, filed Jul. 27, 2017.

Wiksten, J., et al., "Epithelial and stromal syndecan-1 expression as predictor of outcome in patients with gastric cancer", "Int. J. Cancer (Pred. Oncol.)", Jan. 20, 2001, pp. 1-6, vol. 95.

Zouridis, H., et al., "Methylation Subtypes and Large-Scale Epigenetic Alterations in Gastric Cancer", "Science Translational Medicine", Oct. 17, 2012, pp. 1-12, vol. 4, No. 156.

\* cited by examiner

A. Colorectal cancer cell line

B. DNA isolated from feces

Normal person (n=4)

Colorectal cancer patients (n=8)

M: methylated, UM: unmethylated

METHOD FOR DETECTING METHYLATION OF COLORECTAL CANCER SPECIFIC METHYLATION MARKER GENE FOR COLORECTAL CANCER DIAGNOSIS

CROSS-REFERENCE TO RELATED APPLICATIONS

This is a continuation-in-part application under 35 U.S.C. § 120 of U.S. patent application Ser. No. 15/661,054 filed Jul. 27, 2017, which in turn is a continuation-in-part application of U.S. patent application Ser. No. 15/010,379 filed Jan. 29, 2016, now U.S. Pat. No. 9,752,197, which in turn is a continuation-in-part application of U.S. patent application Ser. No. 13/994,732 filed Jun. 15, 2013, now U.S. Pat. No. 9,315,870, which in turn is a U.S. national stage under the provisions of 35 U.S.C. § 371 of International Patent Application No. PCT/KR2011/009710 filed Dec. 16, 2011, which in turn claims priority of Korean Patent Application No. 10-2010-129208 filed Dec. 16, 2010. The disclosures of such U.S. patent applications, international patent application, and Korean priority patent application are hereby incorporated herein by reference in their respective entireties, for all purposes.

TECHNICAL FIELD

The present disclosure relates to a method for detecting the methylation of colorectal cancer-specific marker genes for colorectal cancer diagnosis, and more particularly to a method of detecting the methylation of a colorectal cancer-specific marker gene, which are methylated specifically in colorectal cancer cells, to provide information for diagnosing colorectal cancer.

BACKGROUND ART

In current clinical practice, the diagnosis of cancer is confirmed by performing tissue biopsy after history taking, physical examination and clinical assessment, followed by radiographic testing and endoscopy if cancer is suspected. However, the diagnosis of cancer by the existing clinical practices is possible only when the number of cancer cells is more than a billion and the diameter of cancer is more than 1 cm. In this case, the cancer cells already have metastatic ability, and at least half thereof have already metastasized. Meanwhile, tumor markers for monitoring substances that are directly or indirectly produced from can92cers are used in cancer screening, but they cause confusion due to limitations in accuracy, since up to about half thereof appear normal even in the presence of cancer, and they often appear positive even in the absence of cancer. Furthermore, the anticancer agents that are mainly used in cancer therapy have the problem that they show an effect only when the volume of cancer is small.

Recently, genetic analysis has been actively attempted to diagnose cancer. The simplest typical method is to detect the presence of ABL:BCR fusion genes (the genetic characteristic of leukemia) in blood by PCR. The method has an accuracy rate of more than 95%, and after the diagnosis and therapy of chronic myelocytic leukemia using this simple and easy genetic analysis, this method is being used for the assessment of the result and follow-up study. However, this method has a shortcoming in that it can be applied only to some blood cancers.

Furthermore, another method has been attempted, in which the presence of genes expressed by cancer cells is detected by RT-PCR and blotting, thereby diagnosing cancer cells present in blood cells. However, this method has shortcomings in that it can be applied only to some cancers, including prostate cancer and melanoma, has a high false positive rate. In addition, it is difficult to standardize detection and reading in this method, and its utility is also limited (Kopreski, M. S. et al., *Clin. Cancer Res.*, 5:1961, 1999; Miyashiro, I. et al., *Clin. Chem.*, 47:505, 2001).

Recently, genetic testing that uses a DNA in serum or blood plasma has been actively attempted. This is a method of detecting a cancer-related gene that is isolated from cancer cells and released into blood and present in the form of a free DNA in serum. It is found that the concentration of DNA in serum is increased by a factor of 5-10 times in actual cancer patients as compared to that of normal persons, and such increased DNA is released mostly from cancer cells. The analysis of cancer-specific gene abnormalities, such as the mutation, deletion and functional loss of oncogenes and tumor-suppressor genes, using such DNAs isolated from cancer cells, allows the diagnosis of cancer. In this effort, there has been an active attempt to diagnose lung cancer, head and neck cancer, breast cancer, colorectal cancer, and liver cancer by examining the promoter methylation of mutated K-Ras oncogenes, p53 tumor-suppressor genes and p16 genes in serum, and the labeling and instability of microsatellite (Chen, X. Q. et al., *Clin. Cancer Res.*, 5:2297, 1999; Esteller, M. et al., *Cancer Res.*, 59:67, 1999; Sanchez-Cespedes, M. et al., *Cancer Res.*, 60:892, 2000; Sozzi, G. et al., *Clin. Cancer Res.*, 5:2689, 1999).

Meanwhile, in samples other than blood, the DNA of cancer cells can also be detected. A method has been attempted in which the presence of cancer cells or oncogenes in sputum or bronchoalveolar lavage of lung cancer patients is detected by a gene or antibody test (Palmisano, W. A. et al., *Cancer Res.*, 60:5954, 2000; Sueoka, E. et al., *Cancer Res.*, 59:1404, 1999). Additionally, other methods of detecting the presence of oncogenes in feces of colorectal cancer patients (Ahlquist, D. A. et al., *Gastroenterol.*, 119: 1219-27, 2000) and detecting promoter methylation abnormalities in urine and prostate fluid (Goessl, C. et al., *Cancer Res.*, 60:5941, 2000) have been attempted. However, in order to accurately diagnose cancers that cause a large number of gene abnormalities and show various mutations characteristic of each cancer, a method in which a large number of genes are simultaneously analyzed in an accurate and automatic manner is required. However, such a method has not yet been established.

Accordingly, methods of diagnosing cancer by measuring DNA methylation have recently been proposed. When the promoter CpG island of a certain gene is hyper-methylated, the expression of such a gene is silenced. This is interpreted to be a main mechanism by which the function of this gene is lost even when there is no mutation in the protein-coding sequence of the gene in a living body. In addition, this is analyzed as a factor by which the function of a number of tumor-suppressor genes in human cancer is lost. Thus, analysis of the methylation of the promoter CpG island of tumor-suppressor genes is very helpful in cancer research. An active attempt has been made to analyze the methylation of the promoter CpG island by methods such as methylation-specific PCR (hereinafter, referred to as "MSP") or automatic base sequencing and to use the analysis results for the diagnosis and screening of cancer.

A significant number of diseases are caused by genetic abnormalities, and the most frequent form of genetic abnormality is a change in the coding sequence of a gene. This genetic change is referred to as mutation. When any gene has a mutation, the structure and function of a protein encoded by the gene change, resulting in abnormalities and deletions, and this mutant protein causes disease. However, an abnormality in the expression of a specific gene can cause disease even in the absence of a mutation in the gene. A typical example thereof is methylation in which a methyl group is attached to the transcription regulatory region of a gene, that is, the cytosine base of the promoter CpG islands, and in this case, the expression of the gene is silenced. This is known as epigenetic change. This is transmitted to offspring and results in the loss of the expression of the relevant protein in the same manner as mutation. Most typically, the expression of tumor suppressor genes is silenced by the methylation of promoter CpG islands in cancer cells, resulting in carcinogenesis (Robertson, K. D. et al., *Carcinogensis*, 21:461, 2000).

During a cancer-causing process, methylation is found in promoter CpG islands, and the restriction on the corresponding gene expression occurs. Particularly, if methylation occurs in the promoter CpG islands of tumor-suppressor genes that regulate cell cycle or apoptosis, restore DNA, are involved in the adhesion of cells and the interaction between cells, and/or suppress cell invasion and metastasis, such methylation blocks the expression and function of such genes in the same manner as the mutations of a coding sequence, thereby promoting the development and progression of cancer. In addition, partial methylation also occurs in the CpG islands according to aging.

An interesting fact is that, in the case of genes whose mutations are attributed to the development of cancer in congenital cancer but do not occur in acquired cancer, the methylation of promoter CpG islands occurs instead of mutation. Typical examples include the promoter methylation of genes, such as acquired renal cancer VHL (von Hippel Lindau), breast cancer BRCA1, colorectal cancer MLH1, and stomach cancer E-CAD. In addition, in about half of all cancers, the promoter methylation of p16 or the mutation of Rb occurs, and the remaining cancers show the mutation of p53 or the promoter methylation of p73, p 14 and the like.

An important fact is that an epigenetic change caused by promoter methylation causes a genetic change (i.e., the mutation of a coding sequence), and the development of cancer is progressed by the combination of such genetic and epigenetic changes. In a MLH1 gene as an example, there is the circumstance in which the function of one allele of the MLH1 gene in colorectal cancer cells is lost due to its mutation or deletion, and the remaining one allele does not function due to promoter methylation. In addition, if the function of MLH1, which is a DNA restoring gene, is lost due to promoter methylation, the occurrence of mutation in other important genes is facilitated to promote the development of cancer.

Most cancers show three common characteristics with respect to CpG, namely, hypermethylation of the promoter CpG islands of tumor-suppressor genes, hypomethylation of the remaining CpG base sites, and an increase in the activity of methylation enzyme, namely, DNA cytosine methyltransferase (DNMT) (Singal, R. & Ginder, G. D., *Blood,* 93:4059, 1999; Robertson, K. et al., *Carcinogensis,* 21:461, 2000; Malik, K. & Brown, K. W., *Brit. J. Cancer,* 83:1583, 2000).

When promoter CpG islands are methylated, the reason why the expression of the corresponding genes is blocked is not clearly established, but is presumed to be because a methyl CpG-binding protein (MECP) or a methyl CpG-binding domain protein (MBD), and histone deacetylase, bind to methylated cytosine, thereby causing a change in the chromatin structure of chromosomes and a change in histone protein.

It is unsettled whether the methylation of promoter CpG islands directly causes the development of cancer or is a secondary change after the development of cancer. However, it is clear that the promoter methylation of tumor-related genes is an important index to cancer, and thus can be used in many applications, including the diagnosis and early detection of cancer, the prediction of the risk of the development of cancer, the prognosis of cancer, follow-up examination after treatment, and the prediction of a response to anticancer therapy. Recently, an attempt to examine the promoter methylation of tumor-related genes in blood, sputum, saliva, feces or urine and to use the examined results for the diagnosis and treatment of various cancers, has been actively conducted (Esteller, M. et al., *Cancer Res.,* 59:67, 1999; Sanchez-Cespedez, M. et al., *Cancer Res.,* 60:892, 2000; Ahlquist, D. A. et al., *Gastroenterol.,* 119:1219, 2000).

In order to maximize the accuracy of cancer diagnosis using promoter methylation, analyze the development of cancer according to each stage and discriminate a change according to cancer and aging, an examination that can accurately analyze the methylation of all the cytosine bases of promoter CpG islands is required. Currently, a standard method for this examination is a bisulfite genome-sequencing method, in which a sample DNA is treated with sodium bisulfite, and all regions of the CpG islands of a target gene to be examined is amplified by PCR, and then, the base sequence of the amplified regions is analyzed. However, this examination has the problem that there are limitations to the number of genes or samples that can be examined at a given time. Other problems are that automation is difficult, and much time and expense are required.

In the Johns Hopkins School of Medicine, the MD Anderson Cancer Center, Charité-Universitatsmedizin Berlin, etc., studies on promoter methylation of cancer-related genes have been actively conducted. The fundamental data thus obtained are interchanged through the DNA Methylation Society (DMS) and stored in MethDB (http://www.methdb.de). Meanwhile, EpiGenX Pharmaceuticals, Inc. is now developing therapeutic agents associated with the methylation of CpG islands, and Epigenomics, Inc. is now conducting studies to apply promoter methylation to cancer diagnosis by examining the promoter methylation using various techniques, such as DNA chips and MALDI-TOF.

Accordingly, the present inventors have made extensive efforts to develop an effective colon-cancer-specific methylation marker which makes it possible to diagnose cancer and the risk of carcinogenesis at an early stage and predict cancer prognosis. As a result, the present inventors have found that GPM6A (NM_005277, Glycoprotein M6A) gene is methylated specifically in colorectal cancer cells and that colorectal cancer can be diagnosed by measuring the degree of methylation using this gene as a biomarker, thereby completing the present disclosure.

DISCLOSURE OF INVENTION

It is a main object of the present disclosure to provide a colorectal cancer-specific methylation biomarker, which is methylated specifically in colorectal cancer cells and can be effectively used for diagnosis of colorectal cancer.

Another object of the present disclosure is to provide a method for detecting colorectal cancer, the method comprising identifying the degree of methylation of the biomarker.

Still another object of the present disclosure is to provide a nucleic acid chip for diagnosing colorectal cancer, which comprises a probe capable of hybridizing with a fragment comprising the CpG island of the colorectal cancer-specific methylation biomarker.

To achieve the above objects, the present disclosure provides a biomarker for diagnosing colorectal cancer, which comprises either the methylated CpG island of the promoter of GPM6A (NM_201591, glycoprotein M6A) gene or the methylated CpG island of a first intron of GPM6A (NM_201591, glycoprotein M6A) gene.

The present disclosure also provides a method for detecting the methylation of a biomarker for colorectal cancer diagnosis, the method comprising the steps of:
(a) isolating DNAs from a clinical sample;
(b) detecting the methylation of the CpG island of the promoter of GPM6A (NM_201591, glycoprotein M6A) gene or the CpG island of a first intron of GPM6A (NM_201591, glycoprotein M6A) gene from the isolated DNAs.

The present disclosure also provides a method for detecting CpG methylation of GPM6A (glycoprotein M6A) gene, the method comprising the steps of:
(a) isolating genomic DNA from a clinical sample;
(b) treating the genomic DNA or a fragment thereof with bisulfite;
(c) amplifying a methylated CpG of GPM6A gene in the bisulfite-treated genomic DNA or fragment thereof from step (b) by using primer(s) to amplify a methylated CpG of the bisulfite-treated GPM6A gene; and
(d) determining whether the CpG of GPM6A was methylated based on whether the DNA was amplified in step (c).

The present disclosure also provides a nucleic acid chip for diagnosing colorectal cancer, which comprises a probe capable of hybridizing with a fragment comprising either the CpG island of the promoter of GPM6A (NM_201591, glycoprotein M6A) gene or the CpG island of a first intron of GPM6A (NM_201591, glycoprotein M6A) gene.

The present disclosure also provides a kit for diagnosing colorectal cancer, which contains: a PCR primer pair for amplifying a fragment comprising the methylated CpG island of a first intron of GPM6A (NM_201591, glycoprotein M6A) gene; and a sequencing primer for pyrosequencing a PCR product amplified by the primer pair.

The present disclosure also provides a kit for detecting CpG methylation of GPM6A (glycoprotein M6A) gene, comprising primer(s) to amplify a methylated CpG of the GPM6A gene.

Other features and embodiments of the present disclosure will be more apparent from the following detailed descriptions and the appended claims

BEST MODE FOR CARRYING OUT THE INVENTION

Figure 1:
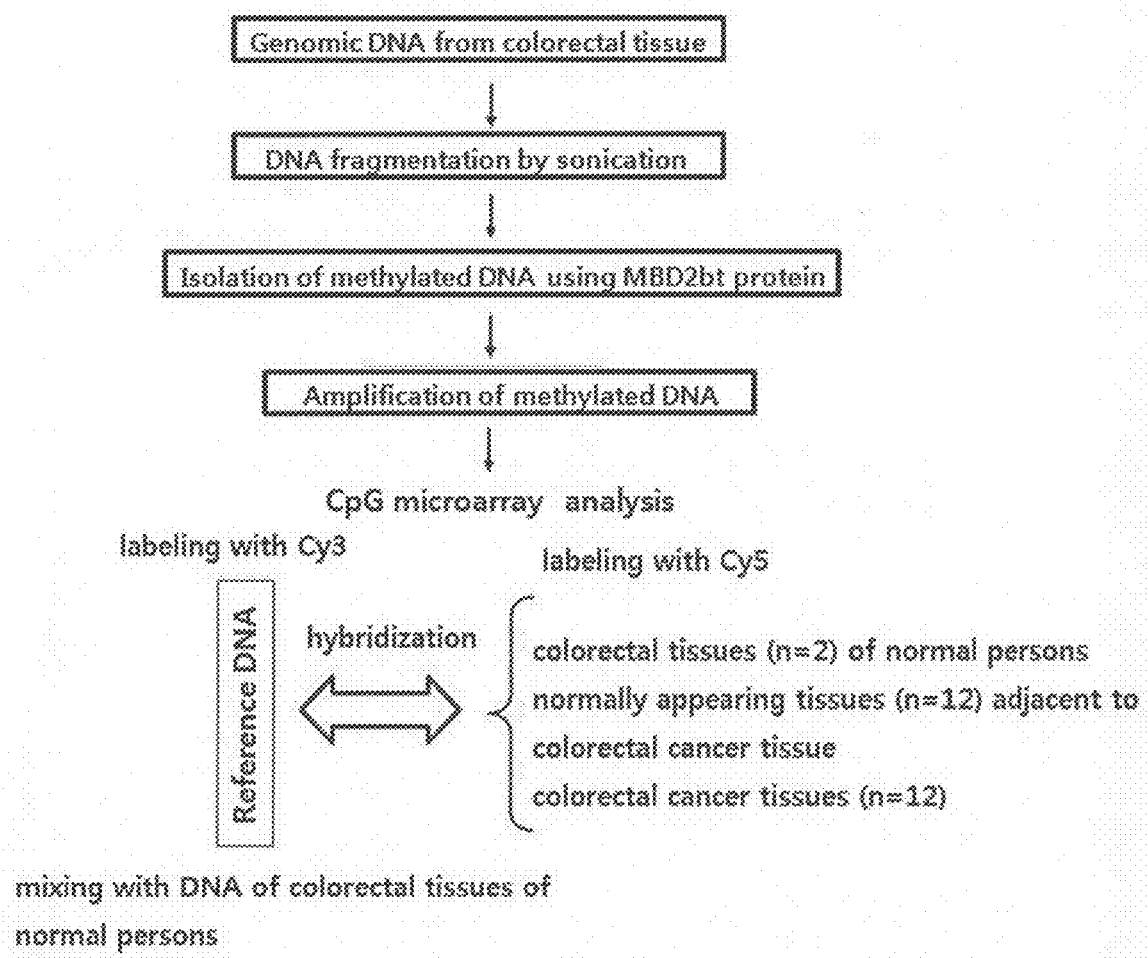
FIG. 1 is a schematic diagram showing a process of discovering a methylation biomarker for colorectal cancer diagnosis from the tissue cells of a normal person and a colorectal cancer patient by a CpG microassay.

Unless defined otherwise, all technical and scientific terms used herein have the same meaning as commonly understood by one of ordinary skill in the art to which the invention pertains. Generally, the nomenclature used herein is well known and are commonly employed in the art.

In one aspect, the present disclosure is directed to a biomarker for diagnosing colorectal cancer, which comprises either the methylated CpG island of the promoter of GPM6A (NM_201591, glycoprotein M6A) gene or the methylated CpG island of a first intron of GPM6A (NM_201591, glycoprotein M6A) gene.

In the present disclosure, the CpG island may be located in the intron region of the gene. Herein, the intron region of the GPM6A gene may be located between +501 and +1200 nucleotides (nt) from the transcription start site and may comprise a nucleotide sequence of SEQ ID NO: 1.

In another aspect, the present disclosure is directed to a method for detecting the methylation of a biomarker for colorectal cancer diagnosis, the method comprising the steps of:
(a) isolating DNA from a clinical sample;
(b) detecting the methylation of the CpG island of the promoter of GPM6A (NM_201591, glycoprotein M6A) gene or the CpG island of a first intron of GPM6A (NM_201591, glycoprotein M6A) gene from the isolated DNA.

In the present disclosure, step (b) of detecting the methylation of the CpG island of a first intron of GPM6A (NM_201591, glycoprotein M6A) gene may be performed by detecting the methylation of the region shown by SEQ ID NO: 1.

In the present disclosure, step (b) may be performed by detecting the methylation based on the presence/absence or a change in the base sequence of product amplified by using primers capable of amplifying a fragment comprising the CpG island of the first intron of GPM6A (NM_201591, glycoprotein M6A) gene.

In the present disclosure, step (b) may be performed by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfate sequencing.

In the present disclosure, the clinical sample may be selected from the group consisting of a tissue, cell, blood, blood plasma, feces, and urine from a patient suspected of cancer or a subject to be diagnosed.

In the present disclosure, 4 biomarker candidate genes showing the greatest difference in the degree of methylation between normal persons and colorectal cancer patients were screened, and among these genes, SDC2, SIM1 and SORCS3 genes were confirmed for diagnosis of colorectal cancer. A method for screening methylation marker genes according to the present disclosure comprises the steps of:
(a) isolating genomic DNAs from transformed cells and non-transformed cells; (b) reacting the isolated genomic DNAs with a methylated DNA-binding protein, thereby isolating methylated DNAs; and (c) amplifying the methylated DNAs, hybridizing the amplified DNAs to a CpG microarray, and then selecting genes showing the greatest difference in the degree of methylation between the normal cells and the cancer cells, thereby ensuring methylation marker genes.

The above method for screening biomarker genes can find genes which are differentially methylated in colorectal cancer as well as at various dysplasic stages of the tissue that progresses to colorectal cancer. The screened genes can be used for colorectal cancer screening, risk-assessment, prognosis, disease identification, the diagnosis of disease stages, and the selection of therapeutic targets.

The identification of genes that are methylated in colorectal cancer and abnormalities at various stages of colorectal cancer makes it possible to diagnose colorectal cancer at an early stage in an accurate and effective manner and allows methylation profiling of multiple genes and the identification of new targets for therapeutic intervention. Furthermore, the methylation data according to the present disclosure may be combined with other non-methylation related biomarker detection methods to obtain a more accurate system for colorectal cancer diagnosis.

According to the method of the present disclosure, the progression of colorectal cancer at various stages or phases can be diagnosed by determining the methylation stage of one or more nucleic acid biomarkers obtained from a sample. By comparing the methylation stage of a nucleic acid isolated from a sample at each stage of colorectal cancer with the methylation stage of one or more nucleic acids isolated from a sample in which there is no cell proliferative disorder of colon tissue, a specific stage of colorectal cancer in the sample can be detected. Herein, the methylation stage may be hypermethylation.

In one embodiment of the present disclosure, nucleic acid may be methylated in the regulatory region of a gene. In another embodiment, a gene which is involved in cell transformation can be diagnosed by detecting methylation outside of the regulatory region of the gene, because methylation proceeds inwards from the outside of the gene.

In yet another embodiment of the present disclosure, cells that are likely to form colorectal cancer can be diagnosed at an early stage using the methylation marker genes. When genes confirmed to be methylated in cancer cells are methylated in cells that appear normal clinically or morphologically, this indicates that the normally appearing cells progress to cancer. Thus, colorectal cancer can be diagnosed at an early stage by detecting the methylation of colorectal cancer-specific genes in cells that appear normal.

The use of the methylation marker gene of the present disclosure allows for detection of a cellular proliferative disorder (dysplasia) of colon tissue in a sample. The detection method comprises bringing a sample comprising at least one nucleic acid isolated from a subject into contact with at least one agent capable of determining the methylation state of the nucleic acid. The method comprises detecting the methylation of at least one region in at least one nucleic acid, wherein the methylation of the nucleic acid differs from the methylation state of the same region of a nucleic acid present in a sample in which there is no abnormal growth (dysplastic progression) of colon cells.

In yet another embodiment of the present disclosure, the likelihood of progression of tissue to colorectal cancer can be evaluated by examining the frequency of the methylation of a gene which is specifically methylated in colorectal cancer, and determining the methylation frequency of tissue that is likely to progress to colorectal cancer.

Thus, in still another aspect, the present disclosure is directed to a method for detecting the methylation of colorectal cancer-specific methylation marker gene for colorectal cancer diagnosis, the method comprising the steps of:

(a) preparing a clinical sample containing DNA; and (b) detecting the methylation of the CpG island of a first intron of GPM6A (NM_005277, glycoprotein M6A) gene in the DNA of the clinical sample.

In the present disclosure, step (b) may be performed by detecting the methylation of the CpG island in the intron region of the gene. Herein, the intron region of the GPM6A gene may be located between +501 and +1200 nucleotides (nt) from the transcription start site and may comprise a nucleotide sequence of SEQ ID NO: 1.

In the present disclosure, step (b) may be performed by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfate sequencing. In addition, the clinical sample may be selected from the group consisting of a tissue, cell, blood, blood plasma, feces, and urine from a patient suspected of cancer or a subject to be diagnosed, but is not limited thereto.

In one embodiment of the present disclosure, the method for detecting the methylation of a gene may comprise: (a) preparing a clinical sample containing DNA; (b) isolating DNA from the clinical sample; (c) amplifying the isolated DNA using primers capable of amplifying a fragment comprising the CpG island of a first intron of GPM6A (NM_005277, glycoprotein M6A) gene; and (d) determining whether the intron was methylated based on whether the DNA was amplified in step (c).

In yet another aspect, the present disclosure is directed to a nucleic acid chip for diagnosing colorectal cancer, which comprises a probe capable of hybridizing with a fragment comprising the CpG island of a first intron of GPM6A (NM_201591, glycoprotein M6A) gene.

In the present disclosure, the CpG island may be located in the intron region of the gene. Herein, the intron region of the GPM6A gene may be located between +501 and +1200 nucleotides (nt) from the transcription start site and may comprise a nucleotide sequence of SEQ ID NO: 1.

In a further another aspect, the present disclosure is directed to a kit for diagnosing colorectal cancer, which contains: a PCR primer pair for amplifying a fragment comprising the methylated CpG island of a first intron of GPM6A (NM_201591, glycoprotein M6A) gene; and a sequencing primer for pyrosequencing a PCR product amplified by the primer pair.

In the present disclosure, the PCR primer pair may be a primer pair comprising base sequences shown by SEQ ID NOS: 16 and 17 or SEQ ID NO: 18 and 19, and the sequencing primer may comprise a base sequence shown by SEQ ID NO: 15.

In yet another embodiment of the present disclosure, the abnormal growth (dysplasia) of colorectal tissue cells in a sample can be diagnosed by detecting the methylation state of CpG island of a first intron of GPM6A (NM_201591, glycoprotein M6A) gene using a kit.

In the present disclosure, the probe may be selected from the group consisting of the base sequences shown by SEQ ID NOS: 2 to 6, and specific examples thereof are as follows.

The probe capable of hybridizing with the CpG island of a first intron of GPM6A:

1)
(SEQ ID NO: 2)
gtatttggga aataaagaaa 2)
(SEQ ID NO: 3)
gactaagaga cccaggatcc gaatagcgag 3)
(SEQ ID NO: 4)
gttcccacgt tttcatgttc tctttgggga gcaagttgaa 4)
(SEQ ID NO: 5)
ggcgtccaca ctggctcggg tcactggacg gtggagttcg
gcgcagttca 5)
(SEQ ID NO: 6)
agtttccagg cagggtccgc ttattcggtg cttagcggag
gcagcttgga atagctccag The use of the diagnostic kit or nucleic acid chip of the present disclosure makes it possible to determine the abnormal growth (dysplastic progression) of colon tissue cells in a sample. The method comprises determining the methylation state of at least one nucleic acid isolated from a sample, wherein the methylation state of the at least one nucleic acid is compared with the methylation stage of a nucleic acid isolated from a sample in which there is no abnormal growth (dysplastic progression) of colorectal cells.

In another embodiment of the present disclosure, transformed colorectal cancer cells can be detected by examining the methylation of the marker gene using said nucleic acid chip.

In still another embodiment of the present disclosure, colorectal cancer can be diagnosed by examining the methylation of the marker gene using said nucleic acid chip.

In yet another embodiment of the present disclosure, the likelihood of progression to colorectal cancer can be diagnosed by examining the methylation of the marker gene in a sample showing a normal phenotype using said kit or nucleic acid chip. The sample that is used in the present disclosure may be solid or liquid tissue, cells, feces, urine, serum, or blood plasma.

Major terms which are used herein are defined as follows.

As used herein, the term "cell transformation" refers to the change in characteristics of a cell from one form to another form such as from normal to abnormal, non-tumorous to tumorous, undifferentiated to differentiated, stem cell to non-stem cell. In addition, the transformation can be recognized by the morphology, phenotype, biochemical characteristics and the like of a cell.

As used herein, the term "early detection" of cancer refers to discovering the likelihood of cancer prior to metastasis, and preferably before observation of a morphological change in a tissue or cell. Furthermore, the term "early detection" of cell transformation refers to the high probability of a cell to undergo transformation in its early stages before the cell is morphologically designated as being transformed.

As used herein, the term "hypermethylation" refers to the methylation of a CpG island.

As used herein, the term "sample" or "clinical sample" is referred to in its broadest sense, and includes any biological sample obtained from an individual, body fluid, a cell line, a tissue culture, depending on the type of assay that is to be performed. Methods for obtaining tissue biopsies and body fluids from mammals are well known in the art. A tissue biopsy of the colon is a preferred source.

Biomarker for Colorectal Cancer—Use of Cancer Cells for Comparison with Normal Cells In the present disclosure, "normal" cells refer to those that do not show any abnormal morphological or cytological changes. "Tumor" cells are cancer cells. "Non-tumor" cells are those cells that are part of the diseased tissue but are not considered to be the tumor portion.

In one aspect, the present disclosure is based on the discovery of the relationship between colorectal cancer and the hypermethylation of GPM6A (NM_005277, glycoprotein M6A) gene.

In another embodiment of the present disclosure, a cellular proliferative disorder of colorectal tissue cell can be diagnosed at an early stage by determining the methylation stage of at least one nucleic acid from a subject using the kit or nucleic acid chip of the present disclosure. Herein, the methylation stage of the at least one nucleic acid may be compared with the methylation state of at least one nucleic acid isolated from a subject not having a cellular proliferative disorder of colon tissue. The nucleic acid is preferably a CpG-containing nucleic acid such as a CpG island.

In another embodiment of the present disclosure, a cellular proliferative disorder of colon tissue can be diagnosed by determining the methylation of at least one nucleic acid from a subject using the kit or nucleic acid chip of the present disclosure. Herein, the nucleic acid may be a CpG island gene of GPM6A (NM_005277, glycoprotein M6A) gene. In this embodiment, the methylation of the at least one nucleic acid may be compared with the methylation state of at least one nucleic acid isolated from a subject having no predisposition to a cellular proliferative disorder of colon tissue.

As used herein, "predisposition" refers to the property of being susceptible to a cellular proliferative disorder. A subject having a predisposition to a cellular proliferative disorder has no cellular proliferative disorder, but is a subject having an increased likelihood of having a cellular proliferative disorder.

In another aspect, the present disclosure provides a method for diagnosing a cellular proliferative disorder of colon tissue, the method comprising brining a sample comprising a nucleic acid into contact with an agent capable of determining the methylation state of the sample, and determining the methylation of at least one region of the at least one nucleic acid. Herein, the methylation of the at least one region in the at least one nucleic acid differs from the methylation stage of the same region in a nucleic acid present in a subject in which there is no abnormal growth of cells.

The method of the present disclosure comprises a step of determining the methylation of at least one region of at least one nucleic acid isolated from a subject.

The term "nucleic acid" or "nucleic acid sequence" as used herein refers to an oligonucleotide, nucleotide or polynucleotide, or fragments thereof, or single-stranded or double-stranded DNA or RNA of genomic or synthetic origin, sense- or antisense-strand DNA or RNA of genomic or synthetic origin, peptide nucleic acid (PNA), or any DNA-like or RNA-like material of natural or synthetic origin. It will apparent to those of skill in the art that, when the nucleic acid is RNA, the deoxynucleotides A, G, C, and T are replaced by the ribonucleotides A, G, C, and U, respectively.

Any nucleic acid may be used in the present disclosure, given the presence of differently methylated CpG islands can be detected therein. The CpG island is a CpG-rich region in a nucleic acid sequence.

Methylation

In the present disclosure, any nucleic acid sample, in purified or nonpurified form, can be used, provided it contains or is suspected of containing a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten-fold relative to the rest of the genome. CpG islands have an average G*C content of about 60%, compared with the 40% average in bulk DNA. The islands take the form of stretches of DNA typically about one to two kilobases long. There are about 45,000 islands in the human genome.

In many genes, the CpG islands begin just upstream of a promoter and extend downstream into the transcribed region. Methylation of a CpG island at a promoter usually suppresses expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns.

Typically, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. Nucleic acids contained in a sample used for detection of methylated CpG islands may be extracted by a variety of techniques such as that described by Sambrook, et al. (Molecular Cloning: A Laboratory Manual, Cold Spring Harbor, N.Y., 1989).

Nucleic acids isolated from a subject are obtained in a biological sample from the subject. If it is desired to detect colorectal cancer or stages of colorectal cancer progression, the nucleic acid may be isolated from colon tissue by scraping or biopsy. Such samples may be obtained by various medical procedures known to those of skill in the art.

In one aspect of the invention, the state of methylation in nucleic acids of the sample obtained from a subject is hypermethylation compared with the same regions of the nucleic acid in a subject not having a cellular proliferative disorder of colon tissue. Hypermethylation as used herein refers to the presence of methylated alleles in one or more nucleic acids. Nucleic acids from a subject not having a cellular proliferative disorder of colon tissue contain no detectable methylated alleles when the same nucleic acids are examined.

Method for Detection of Methylation

Methylation-Specific PCR

When genomic DNA is treated with bisulfite, cytosine in the 5'-CpG'-3 region remains intact, if it was methylated, but the cytosine changes to uracil, if it was unmethylated. Accordingly, based on the base sequence converted after bisulfite treatment, PCR primer sets corresponding to a region having the 5'-CpG-3' base sequence are constructed. Herein, the constructed primer sets are two kinds of primer sets: a primer set corresponding to the methylated base sequence, and a primer set corresponding to the unmethylated base sequence. When genomic DNA is converted with bisulfite and then amplified by PCR using the above two kinds of primer sets, the PCR product is detected in the PCR mixture employing the primers corresponding to the methylated base sequence, if the genomic DNA was methylated, but the genomic DNA is detected in the PCR mixture employing the primers corresponding to the unmethylated, if the genomic DNA was unmethylated. This methylation can be quantitatively analyzed by agarose gel electrophoresis.

Real-Time Methylation Specific PCR

Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using a TanMan probe complementary to the amplified base sequence; and a method of detection using Sybergreen. Thus, the real-time methylation-specific PCR allows selective quantitative analysis of methylated DNA. Herein, a standard curve is plotted using an in vitro methylated DNA sample, and a gene containing no 5'-CpG-3' sequence in the base sequence is also amplified as a negative control group for standardization to quantitatively analyze the degree of methylation.

Primer(s) that could amplify a methylated CpG of GPM6A might be used, and primer(s) comprises at least one or more CpG dinucleotide in a region which hybridizes to the methylated CpG of GPM6A. Specifically, the primer(s) for amplifying a methylated CpG of GPM6A comprise sequence(s) having a homology of 50% or more, specifically at least 81%, 82%, 83%, 84%, 85%, 86%, 87%, 88%, 89%, 90%, 91%, 92%, 93%, 94%, 95%, 96%, 97%, 98% or 99%, with one or more sequence(s) selected from the group consisting of SEQ ID NOs: 24-25, 27-106, 108-189, 191-392, 394-535, 537-658, 660-761, 763-844, 846-967, 969-1070, 1072-1193, 1195-1276, 1278-1359, and 1361-1408.

If required, probe(s) capable of hybridizing with a methylated CpG of GPM6A might be used. The probe(s) capable of hybridizing with a methylated CpG of GPM6A comprise at least one or more CpG dinucleotide in a region which hybridizes to the methylated CpG of GPM6A. Specifically, probe(s) might comprise sequence(s) having a homology of 50% or more, specifically at least 81%, 82%, 83%, 84%, 85%, 86%, 87%, 88%, 89%, 90%, 91%, 92%, 93%, 94%, 95%, 96%, 97%, 98% or 99%, with one or more sequence(s) selected from the group consisting of SEQ ID NOs: 26, 107, 190, 393, 536, 659, 762, 845, 968, 1071, 1194, 1277 and 1360.

Pyrosequencing

The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

PCR Using Methylated DNA-Specific Binding Protein, Quantitative PCR, and DNA Chip Assay When a protein binding specifically only to methylated DNA is mixed with DNA, the protein binds specifically only to the methylated DNA. Thus, either PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA. Herein, the methylated DNA-specific binding protein may be, but not limited to, McrBt.

Detection of Differential Methylation-Methylation-Sensitive Restriction Endonuclease Detection of differential methylation can be accomplished by bringing a nucleic acid sample into contact with a methylation-sensitive restriction endonuclease that cleaves only unmethylated CpG sites.

In a separate reaction, the sample is further brought into contact with an isoschizomer of the methylation-sensitive restriction enzyme that cleaves both methylated and unmethylated CpG-sites, thereby cleaving the methylated nucleic acid.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

As used herein, the term "methylation-sensitive restriction enzyme" refers to a restriction enzyme (e.g., SmaI) that includes CG as part of its recognition site and has activity when the C is methylated as compared to when the C is not methylated. Non-limiting examples of methylation-sensitive restriction enzymes include MspI, HpaII, BssHII, BstUI and NotI. Such enzymes can be used alone or in combination. Examples of other methylation-sensitive restriction enzymes include, but are not limited to SacII and EagI.

The isoschizomer of the methylation-sensitive restriction enzyme is a restriction enzyme that recognizes the same recognition site as the methylation-sensitive restriction enzyme but cleaves both methylated and unmethylated CGs. An example thereof includes MspI.

Primers of the present disclosure are designed to be "substantially" complementary to each strand of the locus to be amplified and include the appropriate G or C nucleotides as discussed above. This means that the primers must be sufficiently complementary to hybridize with their respective strands under polymerization reaction conditions. Primers of the present disclosure are used in the amplification process, which is an enzymatic chain reaction (e.g., PCR) in which that a target locus exponentially increases through a number of reaction steps. Typically, one primer is homologous with the negative (−) strand of the locus (antisense primer), and the other primer is homologous with the positive (+) strand (sense primer). After the primers have been annealed to denatured nucleic acid, the nucleic acid chain is extended by an enzyme such as DNA Polymerase I (Klenow), and reactants such as nucleotides, and, as a result, + and − strands containing the target locus sequence are newly synthesized. When the newly synthesized target locus is used as a template and subjected to repeated cycles of denaturing, primer annealing, and extension, exponential synthesis of the target locus sequence occurs. The resulting reaction product is a discrete nucleic acid duplex with termini corresponding to the ends of specific primers employed.

The amplification reaction is PCR which is commonly used in the art. However, alternative methods such as real-time PCR or linear amplification using isothermal enzyme may also be used. In addition, multiplex amplification reactions may also be used.

Detection of Differential Methylation—Bisulfite Sequencing Method

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfite sequencing for detection of methylated nucleic acid.

Kit

The present disclosure provides a kit useful for the detection of a cellular proliferative disorder in a subject.

The present disclosure provides a kit useful for detecting CpG methylation of GPM6A (glycoprotein M6A) gene, comprising primer(s) to amplify a methylated CpG of the GPM6A gene.

Primer(s) that could amplify a methylated CpG of GPM6A might be used, and primer(s) comprises at least one or more CpG dinucleotide in a region which hybridizes to the methylated CpG of GPM6A. Specifically, the primer(s) for amplifying a methylated CpG of GPM6A comprise sequence(s) having a homology of 50% or more, specifically at least 81%, 82%, 83%, 84%, 85%, 86%, 87%, 88%, 89%, 90%, 91%, 92%, 93%, 94%, 95%, 96%, 97%, 98% or 99%, with one or more sequence(s) selected from the group consisting of SEQ ID NOs: 24-25, 27-106, 108-189, 191-392, 394-535, 537-658, 660-761, 763-844, 846-967, 969-1070, 1072-1193, 1195-1276, 1278-1359, and 1361-1408.

If required, probe(s) capable of hybridizing with a methylated CpG of GPM6A might be used. The probe(s) capable of hybridizing with a methylated CpG of GPM6A comprise at least one or more CpG dinucleotide in a region which hybridizes to the methylated CpG of GPM6A. Specifically, probe(s) might comprise sequence(s) having a homology of 50% or more, specifically at least 81%, 82%, 83%, 84%, 85%, 86%, 87%, 88%, 89%, 90%, 91%, 92%, 93%, 94%, 95%, 96%, 97%, 98% or 99%, with one or more sequence(s)

selected from the group consisting of SEQ ID NOs: 26, 107, 190, 393, 536, 659, 762, 845, 968, 1071, 1194, 1277 and 1360.

The kit of the present disclosure comprises a carrier means compartmentalized to receive a sample therein, one or more containers comprising a second container containing PCR primers for amplification of a 5'-CpG-3' base sequence, and a third container containing a sequencing primer for pyrosequencing an amplified PCR product.

Carrier means are suited for containing one or more containers such as vials, tubes, and the like, each of the containers comprising one of the separate elements to be used in the method. In view of the description provided herein of the inventive method, those of skill in the art can readily determine the apportionment of the necessary reagents among the containers.

Substrates

After the target nucleic acid region has been amplified, the nucleic acid amplification product can be hybridized to a known gene probe attached to a solid support (substrate) to detect the presence of the nucleic acid sequence.

As used herein, the term "substrate", when used in reference to a substance, structure, surface or material, means a composition comprising a nonbiological, synthetic, nonliving, planar or round surface that is not heretofore known to comprise a specific binding, hybridization or catalytic recognition site or a plurality of different recognition sites or a number of different recognition sites which exceeds the number of different molecular species comprising the surface, structure or material. Examples of the substrate include, but are not limited to, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes silicon, silicates, glass, metals and ceramics; and wood, paper, cardboard, cotton, wool, cloth, woven and nonwoven fibers, materials and fabrics; and amphibious surfaces.

It is known in the art that several types of membranes have adhesion to nucleic acid sequences. Specific non-limiting examples of these membranes include nitrocellulose or other membranes used for detection of gene expression such as polyvinylchloride, diazotized paper and other commercially available membranes such as GENE-SCREEN™, ZETAPROBE™ (Biorad) and NYTRAN™. Beads, glass, wafer and metal substrates are also included. Methods for attaching nucleic acids to these objects are well known in the art. Alternatively, screening can be done in a liquid phase.

Hybridization Conditions

In nucleic acid hybridization reactions, the conditions used to achieve a particular level of stringency will vary depending on the nature of the nucleic acids being hybridized. For example, the length, degree of complementarity, nucleotide sequence composition (e.g., GC/AT content), and nucleic acid type (e.g., RNA/DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at room temperature (hybridization conditions); 0.2×SSC/0.1% SDS at room temperature (low stringency conditions); 0.2×SSC/0.1% SDS at 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary depending on the particular hybridization reaction involved, and can be determined empirically. In general, conditions of high stringency are used for the hybridization of the probe of interest.

Label

The probe of interest can be detectably labeled, for example, with a radioisotope, a fluorescent compound, a bioluminescent compound, a chemiluminescent compound, a metal chelator, or an enzyme. Appropriate labeling with such probes is widely known in the art and can be performed by any conventional method.

EXAMPLES

Hereinafter, the present disclosure will be described in further detail with reference to examples. It will be obvious to a person having ordinary skill in the art that these examples are illustrative purposes only and are not to be construed to limit the scope of the present disclosure.

Example 1: Discovery of Colorectal Cancer-Specific Methylated Genes

In order to screen biomarkers which are methylated specifically in colorectal cancer, 500 ng of each of genomic DNAs from 2 normal persons and genomic DNAs from the cancer tissue and adjacent normal tissue from 12 colorectal cancer patients was sonicated (Vibra Cell, SONICS), thus constructing about 200-300-bp-genomic DNA fragments.

To obtain only methylated DNA from the genomic DNA, a methyl binding domain (Methyl binding domain; MBD) (Fraga et al., *Nucleic Acid Res.*, 31: 1765, 2003) known to bind to methylated DNA was used. Specifically, 2 μg of 6×His-tagged MBD2bt was pre-incubated with 500 ng of the genomic DNA of *E. coli* JM110 (No. 2638, Biological Resource Center, Korea Research Institute of Bioscience & Biotechnology), and then bound to Ni-NTA magnetic beads (Qiagen, USA). 500 ng of each of the sonicated genomic DNAs isolated from the normal persons and the colorectal cancer patient patients was allowed to react with the beads in the presence of binding buffer solution (10 mM Tris-HCl (pH 7.5), 50 mM NaCl, 1 mM EDTA, 1 mM DTT, 3 mM MgCl$_2$, 0.1% Triton-X100, 5% glycerol, 25 mg/ml BSA) at 4° C. for 20 minutes. Then, the beads were washed three times with 500 μL of a binding buffer solution containing 700 mM NaCl, and then methylated DNA bound to the MBD2bt was isolated using the QiaQuick PCR purification kit (Qiagen, USA).

Then, the methylated DNAs bound to the MBD2bt were amplified using a genomic DNA amplification kit (Sigma, USA, Cat. No. WGA2), and 4 μg of the amplified DNAs were labeled with Cy5 using a BioPrime Total Genomic Labeling system I (Invitrogen Corp., USA). To indirectly compare the degree of methylation between the normal person and the colorectal cancer patient, a reference DNA was constructed. Herein, the reference DNA was constructed by mixing the genomic DNAs from the 12 colorectal cancer patients with each other in the same amount, amplifying the genomic DNA mixture using a genomic DNA amplification kit (Sigma, USA, Cat. No. WGA2), and labeling 4 μg of the amplified genomic DNA with Cy3 using a BioPrime Total Genomic Labeling system I (Invitrogen Corp., USA). The reference DNA was mixed with each of the DNAs of the normal persons and the colorectal cancer patients, and then hybridized to 244K human CpG microarrays (Agilent, USA) (see FIG. 1). After the hybridization, the DNA mixture was subjected to a series of washing processes, and then scanned using an Agilent scanner. The calculation of signal values from the microarray images was performed by calculating the relative difference in signal strength between the normal person sample and the colorectal cancer patient sample using Feature Extraction program v. 9.5.3.1 (Agilent).

Figure 2:
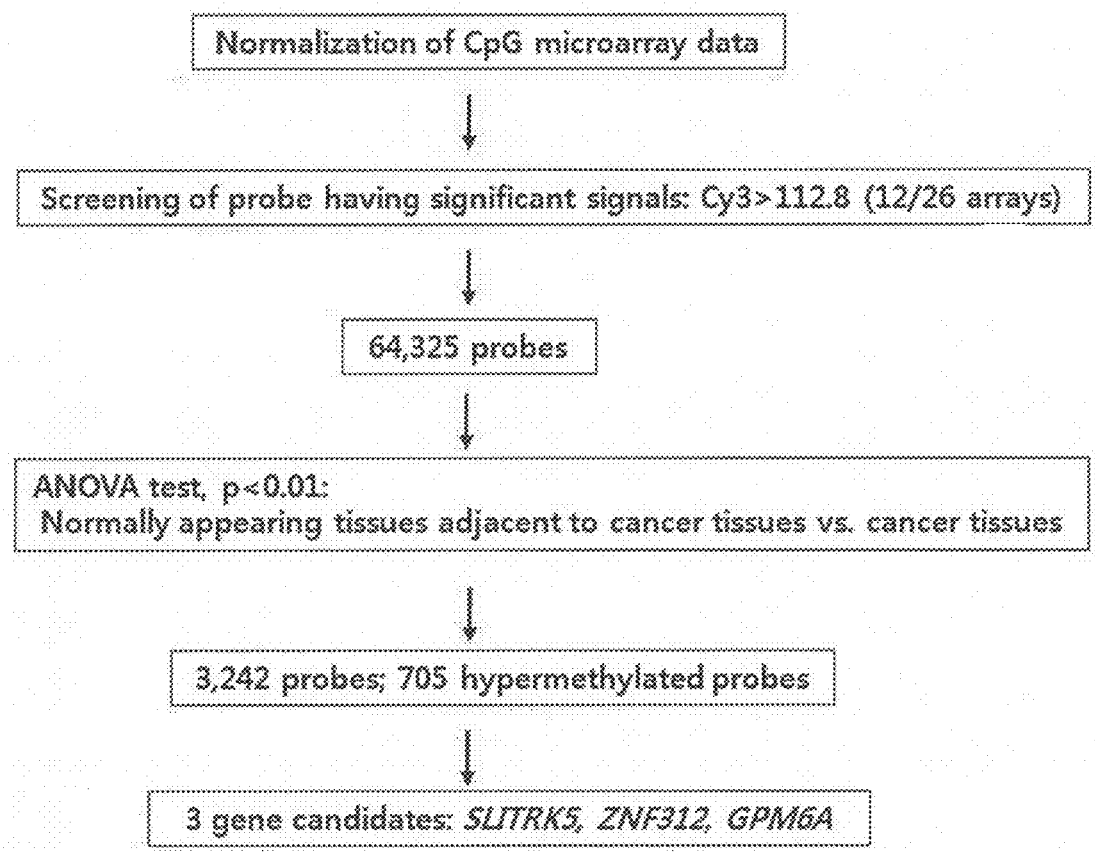
FIG. 2 is a schematic diagram showing a process of screening colorectal cancer-specific hypermethylated genes from the CpG microarray data of colorectal cancer.

In order to screen probes having reliable hybridization signals, 64,325 probes having a Cy3 signal value of more than 112.8 in at least 21 arrays among a total of 26 arrays were screened by the cross gene error model using Gene-Spring 7.3 program (Agilent, USA). In order to screen probes hypermethylated specifically in colorectal cancer from the above probes, the normally appearing tissue adjacent to the colorectal cancer tissue and the colorectal cancer tissue are compared with each other, and in order to screen probes showing differential methylation, the ANOVA test was performed, thereby screening 3,242 probes (p<0.01). From these probes, 705 probes hypermethylated in the colorectal cancer tissue were further screened, and from these probes, 3 biomarker gene candidates (SLITRK5, ZNF312, GPM6A) showing hypermethylation in two or more adjacent probes present within a distance of about 400 bp were selected (see FIG. 2).

The 4 biomarker candidate genes analyzed using the above analysis method were listed in Table 1 below. In addition, the nucleotide sequence corresponding to the probe of each of the 4 genes showing hypermethylation in the CpG microarray was analyzed using MethPrimer (http://it-sa.ucsf.edu/~urolab/methprimer/index1.html), thereby confirming CpG islands in the probes.

TABLE 1

List of methylation biomarker candidate genes for colorectal cancer diagnosis

| Candidate genes | Probe locations [a] | GenBank No. | Description |
|---|---|---|---|
| SLITRK5 | +1,811, +2,046 | NM_015567 | SLIT and NTRK-like family, member 5 |
| ZNF312 | +2,558, +2,646 | NM_018008 | zinc finger protein 312 |
| GPM6A | +554, +786 | NM_005277 | Glycoprotein M6A |

[a] base pairs (bp) from the transcription start site (+1)

Example 2: Measurement of Methylation of Biomarker Genes in Cancer Cell Lines

In order to additionally confirm the methylation state of the biomarker candidate genes selected in Example 1, pyrosequencing for the promoter and intron region of each gene was performed.

In order to modify unmethylated cytosine to uracil using bisulfite, total genomic DNA was isolated from each of the colorectal cancer cell lines Caco-2 (KCLB No. 30037.1) and HCT116 (KCLB No. 10247), and 200 ng of the genomic DNA was treated with bisulfite using the EZ DNA methylation-gold kit (Zymo Research, USA). When the DNA was treated with bisulfite, unmethylated cytosine was modified to uracil, and the methylated cytosine remained without changes. The DNA treated with bisulfite was eluted in 20 µl of sterile distilled water and subjected to pyrosequencing.

PCR and sequencing primers for performing pyrosequencing for the 3 genes were designed using PSQ assay design program (Biotage, USA). The PCR and sequencing primers for measuring the methylation of each gene are shown in Tables 2 and 3 below.

TABLE 2

PCR primers

| Genes | Primers | Sequences (5'3')[a] | SEQ ID NOS | CpG location[b] | Size of amplicon (bp) |
|---|---|---|---|---|---|
| SLITRK5 | forward | TGTTGATTTTTGGTGTATTGA | 7 | +1949, +1960 +1963, +1989 | 253 |
| SLITRK5 | reverse | AACACATCAACRTCCTAATTACATA | 8 | +1949, +1960 +1963, +1989 | 253 |
| ZNF312 | forward | TGTTTGGTGTAGGGGGAAGT | 9 | +2521, +2527 +2535, +2546 | 224 |
| ZNF312 | reverse | CCCRAAAAAATTATTTTACCTCCA | 10 | +2521, +2527 +2535, +2546 | 224 |
| GPM6A | forward | GGGAAATAAAGAAAGATTAAGAGA | 11 | +560, +567, +572, +598 | 121 |
| GPM6A | reverse | ACCCCRTTTCAACTTACTC | 12 | +560, +567, +572, +598 | 121 |

[a] Y = C or T; R = A or G

[b] distances (nucleotides) from the transcription start site (+1): the positions of CpG regions on the genomic DNA used in the measurement of methylation

TABLE 3

Sequences of sequencing primers for methylation marker genes

| Genes | Sequences (5'→3')[a] | SEQ ID NOS |
|---|---|---|
| SLITRK5 | ATTTTAGTGGTTTAAAGATG | 13 |
| ZNF312 | TGGGTGTATTGAGAGATTT | 14 |
| GPM6A | AAGATTAAGAGATTTAGGAT | 15 |

[a]Y = C or T; R = A or G 20 ng of the genomic DNA treated with bisulfite was amplified by PCR. In the PCR amplification, a PCR reaction solution (20 ng of the genomic DNA treated with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index. The methylation index was calculated by determining the average rate of cytosine binding to each CpG island.

Figure 3:
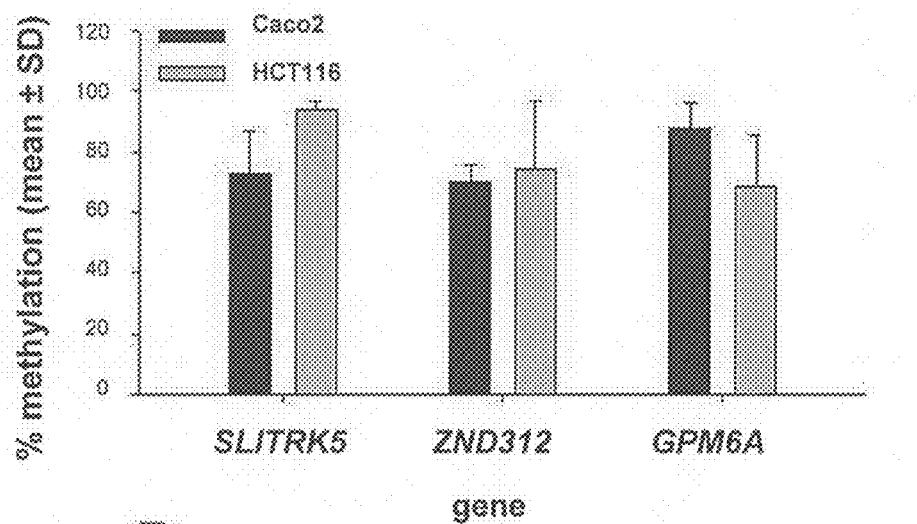
FIG. 3 is a graphic diagram showing the results of measuring the degree of methylation of 3 biomarker candidate genes in a colorectal cancer cell line and the colon tissues of normal persons by pyrosequencing.
Figure 3:
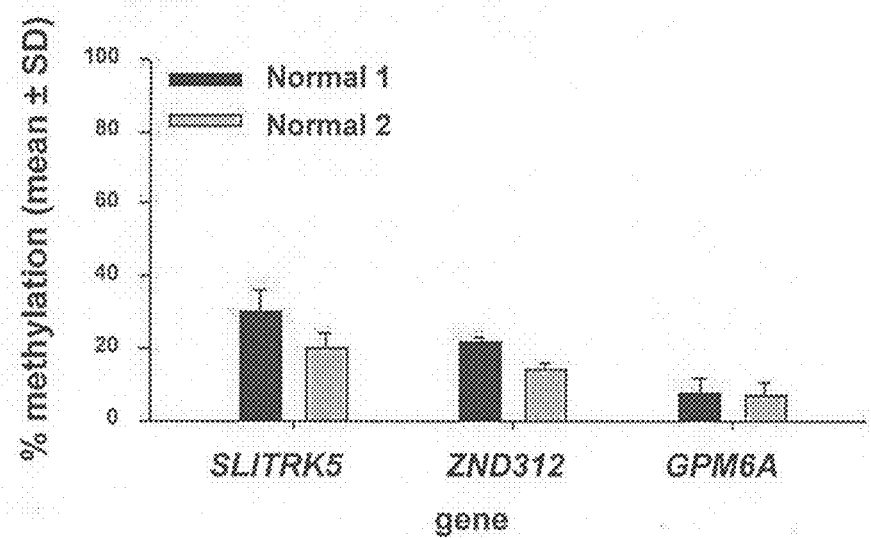

As described above, the degrees of methylation of the biomarker candidate genes in the colorectal cancer cell lines were measured using the pyrosequencing method. As a result, as can be seen in FIG. 3A, the 3 marker genes were all methylated at high levels of 50% in at least one of the cell lines. The 3 genes showed high levels of methylation in the colorectal cancer cell lines, suggesting that these genes are useful as biomarkers for colorectal cancer diagnosis. In order to verify whether these genes are used as biomarkers, the following test was additionally performed using a tissue sample.

Example 3: Measurement of Methylation of Biomarker Candidate Genes in Colon Tissue of Normal Persons In order for the 3 biomarker candidate gene to have utility as biomarkers for colorectal cancer diagnosis, these genes should show low levels of methylation in the colon tissue of normal persons other than patients, but should show high levels of methylation in colorectal cancer tissue.

To verify whether these genes satisfy these requirements, genomic DNA was isolated from two normal person's colorectal tissues (Biochain) using the QIAamp DNA minikit (QIAGEN, USA), and 200 ng of the isolated genomic DNA was treated with bisulfite using the EZ DNA methylation-gold kit (Zymo Research, USA). The treated DNA was eluted in 20 µl of sterile distilled water and subjected to pyrosequencing.

20 ng of the genomic DNA treated with bisulfite was amplified by PCR. In the PCR amplification, a PCR reaction solution (20 ng of the genomic DNA treated with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system (Biotage, USA). After the pyrosequencing, the methylation degree of the DNA was measured by calculating the methylation index thereof. The methylation index was calculated by determining the average rate of cytosine binding to each CpG region.

As a result, as can be seen in FIG. 3B, the GPM6A gene among the 3 genes showed the lowest methylation level in the normal tissue. Thus, in order to verify whether the GPM6A gene is useful as a biomarker, the following test was performed using the tissue of colorectal cancer patients.

Example 4: Measurement of Methylation of Biomarker Genes in Tissue of Colorectal Cancer Patients In order to verify whether the GPM6A gene showing low level of methylation in the colon tissue of normal persons is useful as a biomarker for colorectal cancer diagnosis, genomic DNAs were isolated from colorectal cancer tissues isolated from 96 colorectal cancer patients (the Biochip Research Center in Yonsei University, appointed by the Korean Ministry of Health and Welfare) and the normally appearing tissues adjacent thereto.

200 ng of each of the isolated genomic DNAs was treated with bisulfite using the EZ DNA methylation-gold kit (Zymo Research, USA). Each of the treated DNAs was eluted in 20 µl of sterile distilled water and subjected to pyrosequening.

20 ng of the genomic DNA treated with bisulfite was amplified by PCR. In the PCR amplification, a PCR reaction solution (20 ng of the genomic DNA treated with bisulfite, 5 µl of 10×PCR buffer (Enzynomics, Korea), 5 units of Taq polymerase (Enzynomics, Korea), 4 µl of 2.5 mM dNTP (Solgent, Korea), and 2 µl (10 pmole/µl) of PCR primers) was used, and the PCR reaction solution was performed under the following conditions: predenaturation at 95° C. for 5 min, and then 45 cycles of denaturation at 95° C. for 40 sec, annealing at 60° C. for 45 sec and extension at 72° C. for 40 sec, followed by final extension at 72° C. for 5 min. The amplification of the PCR product was confirmed by electrophoresis on 2.0% agarose gel.

The amplified PCR product was treated with PyroGold reagents (Biotage, USA), and then subjected to pyrosequencing using the PSQ96MA system. After the pyrosequencing, the methylation degree of the DNA was measured by calculating the methylation index thereof. The methylation index was calculated by determining the average rate of cytosine binding to each CpG region.

Figure 4:
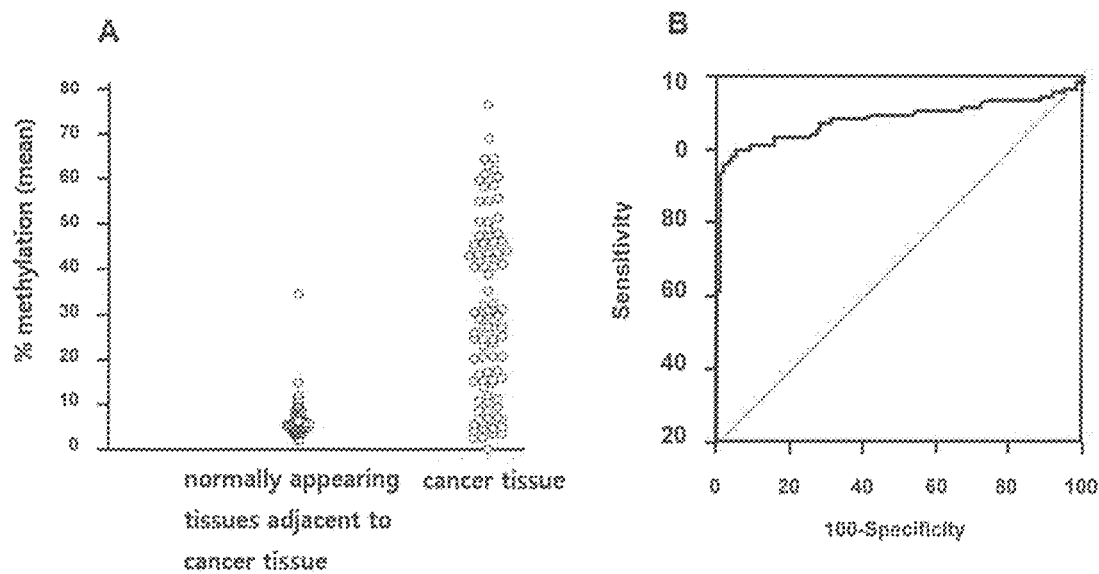
FIG. 4 is a graphic diagram showing the results of measuring the degrees of methylation of GPM6A methylation biomarker in colorectal cancer tissue and adjacent normal tissue by pyrosequencing, and the results of measuring the sensitivity and specificity of GPM6A methylation biomarker for colorectal cancer by ROC curve analysis.

The degree of methylation of the GPM6A gene was measured. As a result, as can be seen in FIG. 4A, the GPM6A gene showed higher levels of methylation in the colorectal cancer tissues of 72 patents (80.2%) of the 96 patients compared to those in the normally appearing tissues. Table 4 below shows the average values of the methylation levels of the GPM6A biomarker gene in the colorectal cancer tissues and the normally appearing tissues adjacent thereto. In order to confirm whether the level of methylation of the genes statistically significantly differs between the colorectal cancer tissue and the normally appearing tissue, the Chi-Square test was performed. As a result, it could be seen that all the three genes showed statistically significant levels (p<0.01) (see Table 4).

TABLE 4

Results of quantitative analysis of methylation of GPM6A biomarker

| Average methylation level (%, average ± standard deviation) | | |
|---|---|---|
| Normally appearing tissues | Colorectal cancer tissues | P values [a] |
| 6.8 ± 5.7 | 30.3 ± 19.6 | <0.0001 |

[a] p values obtained through the Chi-Square test colorectal cancer. Table 5 shows the results of ROC curve analysis of the GPM6A gene for colorectal cancer diagnosis.

TABLE 5

Results of ROC curve analysis for colorectal cancer diagnosis of the GPM6A methylation biomarker gene

| | |
|---|---|
| AUC (95% C.I) | 0.884 (0.830-0.926) |
| Cut-off[a] | >10.31 |
| p | 0.0001 |
| Sensitivity (%)(95% C.I) | 80.2 (70.8-87.6) |
| Specificity (%)(95% C.I) | 94.8 (88.3-98.3) |

[a] methylation index critera for distinction between normal and cancer samples

Additionally, the GPM6A gene was evaluated for its ability to diagnose colorectal cancer in a fecal sample.

Figure 5:
FIG. 5 shows the results of verifying the methylation of a GPM6A biomarker gene in the fecal tissues of normal persons and colorectal cancer patients by methylation-specific PCR.
Figure 5:
Figure 5:

Specifically, measurement of the methylation was performed on two kinds of colorectal cancer cell lines using a nested methylation-specific PCR (MSP) technique, and it was confirmed that all the two kinds of colorectal cancer cell lines were methylated as shown in FIG. 5A. This result is identical to the result of pyrosequencing performed in the above Example 2. Genomic DNAs were isolated from the fecal samples of 4 normal persons and 8 colorectal cancer patients (the Biochip Research Center in Yonsei University, appointed by the Korean Ministry of Health and Welfare). 4 μg of each of the isolated genomic DNAs was treated with bisulfite using the EZ DNA methylation-gold kit (Zymo Research, USA). Each of the treated DNAs was eluted in 20 μl of sterile distilled water and subjected to a nested MSP test. The primer sequences used in the nested MSP test are shown in Table 6 below.

TABLE 6

Primer sequences used in MSP test of GPM6A gene

| Methylation | Primers | Primer sequences (5'→3') | Size of amplified product (bp) | SEQ ID NOS |
|---|---|---|---|---|
| Methylation | Outer-F | TTAAAAGGGCGTTTATATTGGTTCG | 233 | 16 |
| | Outer-R | CCTCGCTCTTCGAAATAACTCGTA | | 17 |
| | Inner-F | TAGGGTTCGTTTATTCGGTGTTTAGC | 156 | 18 |
| | Inner-R | CCTCGCTCTTCGAAATAACTCGTA | | 19 |
| Non-methylation | Outer-F | TAAAAGGGTGTTTATATTGGTTTGG | 233 | 20 |
| | Outer-R | CCCTCACTCTTCAAAATAACTCATA | | 21 |
| | Inner-F | GGTAGGGTTTGTTTATTTGGTGTTTAGTG | 160 | 22 |
| | Inner-R | TCCCTCACTCTTCAAAATAACTCATA | | 23 |

Example 5: Evaluation of the Ability of GPM6A Biomarker to Diagnose Colorectal Cancer For the GPM6A gene confirmed to be useful as colorectal cancer markers in Example 4, receiver operating characteristic (ROC) analysis was performed using MedCalc program (MEDCALC, Belgium) in order to evaluate the ability of the genes to diagnose colorectal cancer.

As a result, as shown in FIG. 4B, the sensitivity and specificity of the GPM6A gene for colorectal cancer were, respectively, 80.2% and 94.8%. This suggests that the GPM6A gene has a very excellent ability to diagnose 1 μg of the genomic DNA treated with bisulfite was amplified by PCR. In the PCR amplification, a PCR reaction solution (20 μg of the genomic DNA treated with bisulfite, 5 μl of 10×PCR buffer (Enzynomics, Korea), 5 units of Taq polymerase (Enzynomics, Korea), 4 μl of 2.5 mM Dntp (Solgent, Korea), and 2 μl (10 pmole/μl) of PCR primers) was used, and the PCR reaction was performed under the following conditions: predenaturation at 95° C. for 5 min, and then 30 cycles of denaturation at 95° C. for 40 sec, annealing at 60° C. for 45 sec and extension at 72° C. for 40 sec, followed by final extension at 72° C. for 5 min. ½ of the PCR product was taken and amplified by PCR for 45 cycles in the same manner as above. The amplification of the PCR products was confirmed by electrophoresis on 2.0% agarose gel.

As a result, as shown in FIG. 5B, it was observed that the GPM6A gene was not methylated in the tissues of the 4 normal persons, but was methylated in 5 (62.5%) of the 8 colorectal cancer patients. This suggests that the GPM6A gene is useful for the diagnosis of colorectal cancer in feces.

Example 6: Evaluation of the Ability of GPM6A Gene to Diagnose Colorectal Cancer by Using qMSP In order to analyze the ability of GPM6A gene to diagnose colorectal cancer, 686 sets of primers and probes, which could amplify whole CpG island of GPM6A gene and detect methylation specific sites, were designed (Table 7) and methylation specific real time PCR (qMSP) was performed. To achieve the purpose, genome DNA was isolated by using cancer tissues and normal tissues adjacent to cancer tissues from 20 colorectal cancer patients. Treating bisulfite to the above isolated genome DNA (2.0 ug) by using EZ DNA methylation-Gold kit (Zymo Research, USA), and the DNA was subjected to methylation specific real time PCR (qMSP) by eluting with 10 µl distilled water. The qMSP was performed with bisulfite treated genome DNA as a template by using methylation specific primers and probes designed according to Table 7. qMSP used Rotor-Gene Q PCR equipment (Qiagen). Total 20 µl PCR reaction solution (template DNA, 2 µl; 5× AptaTaq DNA Master (Roche Diagnostics), 4 µl; PCR primers, 2 µl (2 pmole/µl), TaqMan probe, 2 µl (2 pmole/µl); D.W. 10 µl) was prepared. Total 40 times of PCR in which the condition is treated at 95° C. for 5 minutes, at 95° C. for 15 seconds and at annealing temperature (58° C.~61° C.) for 1 minute were performed. The amplification of the PCR product was confirmed by measuring the Ct (cycling threshold) value. Methylated and non-methylated control DNAs were tested with sample DNA by using EpiTect PCR control DNA set (Qiagen, cat. no. 59695). COL2A1 gene (Kristensen et al., 2008) was used as an internal control. The methylation level of each sample was measured by PMR value and the PMR value was calculated as follows:

$$PMR = 2^{-\Delta\Delta Ct} \times 100,\ \Delta\Delta Ct = [(Ct_{(GPM6A)} - Ct_{(COL2A1)sample})] - [(Ct_{(GPM6A)} - Ct_{(COL2A1)Methyl\ DNA})]$$

Sensitivity and specificity for set of respective primers and probes were calculated with ROC curve analysis (MedCalc program, Belgium) by using PMR value of cancer tissues and normal tissues adjacent to cancer tissues (Table 8).

TABLE 7

Sequences of primer and probes for GPM6A gene qMSP

| Set | Primer | Sequence (5'→3') | Size of amplified product (bp) | Sequence No. |
|---|---|---|---|---|
| 1 | F696 | GTTTATCGTGTTGG | 119 | 24 |
|   | R15 | AAACATAAAAACGT |  | 25 |
|   | P15 | GGGAGATTTTTGTTTTTCGAGTTTTT |  | 26 |
| 2 | F697 | TTTATCGTGTTGGG | 118 | 27 |
|   | R15 | AAACATAAAAACGT |  | 28 |
|   | P15 | GGGAGATTTTTGTTTTTCGAGTTTTT |  | 26 |
| 3 | F698 | TTATCGTGTTGGGG | 117 | 29 |
|   | R15 | AAACATAAAAACGT |  | 30 |
|   | P15 | GGGAGATTTTTGTTTTTCGAGTTTTT |  | 26 |
| 4 | F699 | TATCGTGTTGGGGG | 116 | 31 |
|   | R15 | AAACATAAAAACGT |  | 32 |
|   | P15 | GGGAGATTTTTGTTTTTCGAGTTTTT |  | 26 |
| 5 | F700 | ATCGTGTTGGGGGC | 115 | 33 |
|   | R15 | AAACATAAAAACGT |  | 34 |
|   | P15 | GGGAGATTTTTGTTTTTCGAGTTTTT |  | 26 |
| 6 | F701 | TCGTGTTGGGGGCG | 114 | 35 |
|   | R15 | AAACATAAAAACGT |  | 36 |
|   | P15 | GGGAGATTTTTGTTTTTCGAGTTTTT |  | 26 |
| 7 | F702 | CGTGTTGGGGGCGG | 113 | 37 |
|   | R15 | AAACATAAAAACGT |  | 38 |
|   | P15 | GGGAGATTTTTGTTTTTCGAGTTTTT |  | 26 |
| 8 | F703 | GTGTTGGGGGCGGT | 112 | 39 |
|   | R15 | AAACATAAAAACGT |  | 40 |
|   | P15 | GGGAGATTTTTGTTTTTCGAGTTTTT |  | 26 |
| 9 | F704 | TGTTGGGGGCGGTA | 111 | 41 |
|   | R15 | AAACATAAAAACGT |  | 42 |
|   | P15 | GGGAGATTTTTGTTTTTCGAGTTTTT |  | 26 |
| 10 | F705 | GTTGGGGGCGGTAT | 110 | 43 |
|   | R15 | AAACATAAAAACGT |  | 44 |
|   | P15 | GGGAGATTTTTGTTTTTCGAGTTTTT |  | 26 |

TABLE 7-continued

Sequences of primer and probes for GPM6A gene qMSP

| Set | Primer | Sequence (5'→3') | Size of amplified product (bp) | Sequence No. |
|---|---|---|---|---|
| 11 | F706 | TTGGGGGCGGTATTT | 109 | 45 |
|  | R15 | AAACATAAAAACGT |  | 46 |
|  | P15 | GGGAGATTTTGTTTTTTCGAGTTTTT |  | 26 |
| 12 | F707 | TGGGGGCGGTATTT | 108 | 47 |
|  | R15 | AAACATAAAAACGT |  | 48 |
|  | P15 | GGGAGATTTTGTTTTTTCGAGTTTTT |  | 26 |
| 13 | F708 | GGGGGCGGTATTTG | 107 | 49 |
|  | R15 | AAACATAAAAACGT |  | 50 |
|  | P15 | GGGAGATTTTGTTTTTTCGAGTTTTT |  | 26 |
| 14 | F709 | GGGGCGGTATTTGG | 106 | 51 |
|  | R15 | AAACATAAAAACGT |  | 52 |
|  | P15 | GGGAGATTTTGTTTTTTCGAGTTTTT |  | 26 |
| 15 | F710 | GGGCGGTATTTGGG | 105 | 53 |
|  | R15 | AAACATAAAAACGT |  | 54 |
|  | P15 | GGGAGATTTTGTTTTTTCGAGTTTTT |  | 26 |
| 16 | F711 | GGCGGTATTTGGGA | 104 | 55 |
|  | R15 | AAACATAAAAACGT |  | 56 |
|  | P15 | GGGAGATTTTGTTTTTTCGAGTTTTT |  | 26 |
| 17 | F712 | GCGGTATTTGGGAA | 103 | 57 |
|  | R15 | AAACATAAAAACGT |  | 58 |
|  | P15 | GGGAGATTTTGTTTTTTCGAGTTTTT |  | 26 |
| 18 | F713 | CGGTATTTGGGAAA | 102 | 59 |
|  | R15 | AAACATAAAAACGT |  | 60 |
|  | P15 | GGGAGATTTTGTTTTTTCGAGTTTTT |  | 26 |
| 19 | F714 | GGTATTTGGGAAAT | 101 | 61 |
|  | R15 | AAACATAAAAACGT |  | 62 |
|  | P15 | GGGAGATTTTGTTTTTTCGAGTTTTT |  | 26 |
| 20 | F715 | GTATTTGGGAAATA | 100 | 63 |
|  | R15 | AAACATAAAAACGT |  | 64 |
|  | P15 | GGGAGATTTTGTTTTTTCGAGTTTTT |  | 26 |
| 21 | F716 | TATTTGGGAAATAA | 99 | 65 |
|  | R15 | AAACATAAAAACGT |  | 66 |
|  | P15 | GGGAGATTTTGTTTTTTCGAGTTTTT |  | 26 |
| 22 | F717 | ATTTGGGAAATAAA | 98 | 67 |
|  | R15 | AAACATAAAAACGT |  | 68 |
|  | P15 | GGGAGATTTTGTTTTTTCGAGTTTTT |  | 26 |
| 23 | F718 | TTTGGGAAATAAAG | 97 | 69 |
|  | R15 | AAACATAAAAACGT |  | 70 |
|  | P15 | GGGAGATTTTGTTTTTTCGAGTTTTT |  | 26 |
| 24 | F719 | TTGGGAAATAAAGA | 96 | 71 |
|  | R15 | AAACATAAAAACGT |  | 72 |
|  | P15 | GGGAGATTTTGTTTTTTCGAGTTTTT |  | 26 |
| 25 | F720 | TGGGAAATAAAGAA | 95 | 73 |
|  | R15 | AAACATAAAAACGT |  | 74 |
|  | P15 | GGGAGATTTTGTTTTTTCGAGTTTTT |  | 26 |
| 26 | F721 | GGGAAATAAAGAAA | 94 | 75 |
|  | R15 | AAACATAAAAACGT |  | 76 |
|  | P15 | GGGAGATTTTGTTTTTTCGAGTTTTT |  | 26 |
| 27 | F722 | GGAAATAAAGAAAG | 93 | 77 |
|  | R15 | AAACATAAAAACGT |  | 78 |
|  | P15 | GGGAGATTTTGTTTTTTCGAGTTTTT |  | 26 |
| 28 | F723 | GAAATAAAGAAAGA | 92 | 79 |
|  | R15 | AAACATAAAAACGT |  | 80 |
|  | P15 | GGGAGATTTTGTTTTTTCGAGTTTTT |  | 26 |

TABLE 7-continued

Sequences of primer and probes for GPM6A gene qMSP

| Set | Primer | Sequence (5'→3') | Size of amplified product (bp) | Sequence No. |
|---|---|---|---|---|
| 29 | F724 | AAATAAAGAAAGAT | 91 | 81 |
|  | R15 | AAACATAAAAACGT |  | 82 |
|  | P15 | GGGAGATTTTGTTTTTCGAGTTTTT |  | 26 |
| 30 | F725 | AATAAAGAAAGATT | 90 | 83 |
|  | R15 | AAACATAAAAACGT |  | 84 |
|  | P15 | GGGAGATTTTGTTTTTCGAGTTTTT |  | 26 |
| 31 | F726 | ATAAAGAAAGATTA | 89 | 85 |
|  | R15 | AAACATAAAAACGT |  | 86 |
|  | P15 | GGGAGATTTTGTTTTTCGAGTTTTT |  | 26 |
| 32 | F727 | TAAAGAAAGATTAA | 88 | 87 |
|  | R15 | AAACATAAAAACGT |  | 88 |
|  | P15 | GGGAGATTTTGTTTTTCGAGTTTTT |  | 26 |
| 33 | F728 | AAAGAAAGATTAAG | 87 | 89 |
|  | R15 | AAACATAAAAACGT |  | 90 |
|  | P15 | GGGAGATTTTGTTTTTCGAGTTTTT |  | 26 |
| 34 | F729 | AAGAAAGATTAAGA | 86 | 91 |
|  | R15 | AAACATAAAAACGT |  | 92 |
|  | P15 | GGGAGATTTTGTTTTTCGAGTTTTT |  | 26 |
| 35 | F730 | AGAAAGATTAAGAG | 85 | 93 |
|  | R15 | AAACATAAAAACGT |  | 94 |
|  | P15 | GGGAGATTTTGTTTTTCGAGTTTTT |  | 26 |
| 36 | F731 | GAAAGATTAAGAGA | 84 | 95 |
|  | R15 | AAACATAAAAACGT |  | 96 |
|  | P15 | GGGAGATTTTGTTTTTCGAGTTTTT |  | 26 |
| 37 | F732 | AAAGATTAAGAGAT | 83 | 97 |
|  | R15 | AAACATAAAAACGT |  | 98 |
|  | P15 | GGGAGATTTTGTTTTTCGAGTTTTT |  | 26 |
| 38 | F733 | AAGATTAAGAGATT | 82 | 99 |
|  | R15 | AAACATAAAAACGT |  | 100 |
|  | P15 | GGGAGATTTTGTTTTTCGAGTTTTT |  | 26 |
| 39 | F734 | AGATTAAGAGATTT | 81 | 101 |
|  | R15 | AAACATAAAAACGT |  | 102 |
|  | P15 | GGGAGATTTTGTTTTTCGAGTTTTT |  | 26 |
| 40 | F735 | GATTAAGAGATTTA | 80 | 103 |
|  | R15 | AAACATAAAAACGT |  | 104 |
|  | P15 | GGGAGATTTTGTTTTTCGAGTTTTT |  | 26 |
| 41 | F736 | ATTAAGAGATTTAG | 120 | 105 |
|  | R16 | TTTCCATTTCTCGT |  | 106 |
|  | P16 | GGGAGTAAGTTGAAACGGGGT |  | 107 |
| 42 | F737 | TTAAGAGATTTAGG | 119 | 108 |
|  | R16 | TTTCCATTTCTCGT |  | 109 |
|  | P16 | GGGAGTAAGTTGAAACGGGGT |  | 107 |
| 43 | F738 | TAAGAGATTTAGGA | 118 | 110 |
|  | R16 | TTTCCATTTCTCGT |  | 111 |
|  | P16 | GGGAGTAAGTTGAAACGGGGT |  | 107 |
| 44 | F739 | AAGAGATTTAGGAT | 117 | 112 |
|  | R16 | TTTCCATTTCTCGT |  | 113 |
|  | P16 | GGGAGTAAGTTGAAACGGGGT |  | 107 |
| 45 | F740 | AGAGATTTAGGATT | 116 | 114 |
|  | R16 | TTTCCATTTCTCGT |  | 115 |
|  | P16 | GGGAGTAAGTTGAAACGGGGT |  | 107 |
| 46 | F741 | GAGATTTAGGATTC | 115 | 116 |
|  | R16 | TTTCCATTTCTCGT |  | 117 |
|  | P16 | GGGAGTAAGTTGAAACGGGGT |  | 107 |

TABLE 7-continued

Sequences of primer and probes for GPM6A gene qMSP

| Set | Primer | Sequence (5'→3') | Size of amplified product (bp) | Sequence No. |
|---|---|---|---|---|
| 47 | F742 | AGATTTAGGATTCG | 114 | 118 |
|  | R16 | TTTCCATTTCTCGT |  | 119 |
|  | P16 | GGGAGTAAGTTGAAACGGGGT |  | 107 |
| 48 | F743 | GATTTAGGATTCGA | 113 | 120 |
|  | R16 | TTTCCATTTCTCGT |  | 121 |
|  | P16 | GGGAGTAAGTTGAAACGGGGT |  | 107 |
| 49 | F744 | ATTTAGGATTCGAA | 112 | 122 |
|  | R16 | TTTCCATTTCTCGT |  | 123 |
|  | P16 | GGGAGTAAGTTGAAACGGGGT |  | 107 |
| 50 | F745 | TTTAGGATTCGAAT | 111 | 124 |
|  | R16 | TTTCCATTTCTCGT |  | 125 |
|  | P16 | GGGAGTAAGTTGAAACGGGGT |  | 107 |
| 51 | F746 | TTAGGATTCGAATA | 110 | 126 |
|  | R16 | TTTCCATTTCTCGT |  | 127 |
|  | P16 | GGGAGTAAGTTGAAACGGGGT |  | 107 |
| 52 | F747 | TAGGATTCGAATAG | 109 | 128 |
|  | R16 | TTTCCATTTCTCGT |  | 129 |
|  | P16 | GGGAGTAAGTTGAAACGGGGT |  | 107 |
| 53 | F748 | AGGATTCGAATAGC | 108 | 130 |
|  | R16 | TTTCCATTTCTCGT |  | 131 |
|  | P16 | GGGAGTAAGTTGAAACGGGGT |  | 107 |
| 54 | F749 | GGATTCGAATAGCG | 107 | 132 |
|  | R16 | TTTCCATTTCTCGT |  | 133 |
|  | P16 | GGGAGTAAGTTGAAACGGGGT |  | 107 |
| 55 | F750 | GATTCGAATAGCGA | 106 | 134 |
|  | R16 | TTTCCATTTCTCGT |  | 135 |
|  | P16 | GGGAGTAAGTTGAAACGGGGT |  | 107 |
| 56 | F751 | ATTCGAATAGCGAG | 105 | 136 |
|  | R16 | TTTCCATTTCTCGT |  | 137 |
|  | P16 | GGGAGTAAGTTGAAACGGGGT |  | 107 |
| 57 | F752 | TTCGAATAGCGAGG | 104 | 138 |
|  | R16 | TTTCCATTTCTCGT |  | 139 |
|  | P16 | GGGAGTAAGTTGAAACGGGGT |  | 107 |
| 58 | F753 | TCGAATAGCGAGGC | 103 | 140 |
|  | R16 | TTTCCATTTCTCGT |  | 141 |
|  | P16 | GGGAGTAAGTTGAAACGGGGT |  | 107 |
| 59 | F754 | CGAATAGCGAGGCG | 102 | 142 |
|  | R16 | TTTCCATTTCTCGT |  | 143 |
|  | P16 | GGGAGTAAGTTGAAACGGGGT |  | 107 |
| 60 | F755 | GAATAGCGAGGCGA | 101 | 144 |
|  | R16 | TTTCCATTTCTCGT |  | 145 |
|  | P16 | GGGAGTAAGTTGAAACGGGGT |  | 107 |
| 61 | F756 | AATAGCGAGGCGAT | 100 | 146 |
|  | R16 | TTTCCATTTCTCGT |  | 147 |
|  | P16 | GGGAGTAAGTTGAAACGGGGT |  | 107 |
| 62 | F757 | ATAGCGAGGCGATT | 99 | 148 |
|  | R16 | TTTCCATTTCTCGT |  | 149 |
|  | P16 | GGGAGTAAGTTGAAACGGGGT |  | 107 |
| 63 | F758 | TAGCGAGGCGATTA | 98 | 150 |
|  | R16 | TTTCCATTTCTCGT |  | 151 |
|  | P16 | GGGAGTAAGTTGAAACGGGGT |  | 107 |
| 64 | F759 | AGCGAGGCGATTAT | 97 | 152 |
|  | R16 | TTTCCATTTCTCGT |  | 153 |
|  | P16 | GGGAGTAAGTTGAAACGGGGT |  | 107 |

TABLE 7-continued

Sequences of primer and probes for GPM6A gene qMSP

| Set | Primer | Sequence (5'→3') | Size of amplified product (bp) | Sequence No. |
|---|---|---|---|---|
| 65 | F760 | GCGAGGCGATTATA | 96 | 154 |
|  | R16 | TTTCCATTTCTCGT |  | 155 |
|  | P16 | GGGAGTAAGTTGAAACGGGGT |  | 107 |
| 66 | F761 | CGAGGCGATTATAG | 95 | 156 |
|  | R16 | TTTCCATTTCTCGT |  | 157 |
|  | P16 | GGGAGTAAGTTGAAACGGGGT |  | 107 |
| 67 | F762 | GAGGCGATTATAGG | 94 | 158 |
|  | R16 | TTTCCATTTCTCGT |  | 159 |
|  | P16 | GGGAGTAAGTTGAAACGGGGT |  | 107 |
| 68 | F763 | AGGCGATTATAGGG | 93 | 160 |
|  | R16 | TTTCCATTTCTCGT |  | 161 |
|  | P16 | GGGAGTAAGTTGAAACGGGGT |  | 107 |
| 69 | F764 | GGCGATTATAGGGA | 92 | 162 |
|  | R16 | TTTCCATTTCTCGT |  | 163 |
|  | P16 | GGGAGTAAGTTGAAACGGGGT |  | 107 |
| 70 | F765 | GCGATTATAGGGAG | 91 | 164 |
|  | R16 | TTTCCATTTCTCGT |  | 165 |
|  | P16 | GGGAGTAAGTTGAAACGGGGT |  | 107 |
| 71 | F766 | CGATTATAGGGAGA | 90 | 166 |
|  | R16 | TTTCCATTTCTCGT |  | 167 |
|  | P16 | GGGAGTAAGTTGAAACGGGGT |  | 107 |
| 72 | F767 | GATTATAGGGAGAT | 89 | 168 |
|  | R16 | TTTCCATTTCTCGT |  | 169 |
|  | P16 | GGGAGTAAGTTGAAACGGGGT |  | 107 |
| 73 | F768 | ATTATAGGGAGATT | 88 | 170 |
|  | R16 | TTTCCATTTCTCGT |  | 171 |
|  | P16 | GGGAGTAAGTTGAAACGGGGT |  | 107 |
| 74 | F769 | TTATAGGGAGATTT | 87 | 172 |
|  | R16 | TTTCCATTTCTCGT |  | 173 |
|  | P16 | GGGAGTAAGTTGAAACGGGGT |  | 107 |
| 75 | F770 | TATAGGGAGATTTT | 86 | 174 |
|  | R16 | TTTCCATTTCTCGT |  | 175 |
|  | P16 | GGGAGTAAGTTGAAACGGGGT |  | 107 |
| 76 | F771 | ATAGGGAGATTTTT | 85 | 176 |
|  | R16 | TTTCCATTTCTCGT |  | 177 |
|  | P16 | GGGAGTAAGTTGAAACGGGGT |  | 107 |
| 77 | F772 | TAGGGAGATTTTTG | 84 | 178 |
|  | R16 | TTTCCATTTCTCGT |  | 179 |
|  | P16 | GGGAGTAAGTTGAAACGGGGT |  | 107 |
| 78 | F773 | AGGGAGATTTTTGT | 83 | 180 |
|  | R16 | TTTCCATTTCTCGT |  | 181 |
|  | P16 | GGGAGTAAGTTGAAACGGGGT |  | 107 |
| 79 | F774 | GGGAGATTTTTGTT | 82 | 182 |
|  | R16 | TTTCCATTTCTCGT |  | 183 |
|  | P16 | GGGAGTAAGTTGAAACGGGGT |  | 107 |
| 80 | F775 | GGAGATTTTTGTTT | 81 | 184 |
|  | R16 | TTTCCATTTCTCGT |  | 185 |
|  | P16 | GGGAGTAAGTTGAAACGGGGT |  | 107 |
| 81 | F776 | GAGATTTTTGTTTT | 80 | 186 |
|  | R16 | TTTCCATTTCTCGT |  | 187 |
|  | P16 | GGGAGTAAGTTGAAACGGGGT |  | 107 |
| 82 | F777 | AGATTTTTGTTTTT | 180 | 188 |
|  | R17 | TAAACACTTCGTTT |  | 189 |
|  | P17 | TTGGGGATAATTTTTAGTTTTTTTTT |  | 190 |

TABLE 7-continued

Sequences of primer and probes for GPM6A gene qMSP

| Set | Primer | Sequence (5'→3') | Size of amplified product (bp) | Sequence No. |
|---|---|---|---|---|
| 83 | F778 | GATTTTGTTTTTT | 179 | 191 |
|  | R17 | TAAACACTTCGTTT |  | 192 |
|  | P17 | TTGGGGATAATTTTTAGTTTTTTTTT |  | 190 |
| 84 | F779 | ATTTTGTTTTTTC | 178 | 193 |
|  | R17 | TAAACACTTCGTTT |  | 194 |
|  | P17 | TTGGGGATAATTTTTAGTTTTTTTTT |  | 190 |
| 85 | F780 | TTTTTGTTTTTCG | 177 | 195 |
|  | R17 | TAAACACTTCGTTT |  | 196 |
|  | P17 | TTGGGGATAATTTTTAGTTTTTTTTT |  | 190 |
| 86 | F781 | TTTTGTTTTTCGA | 176 | 197 |
|  | R17 | TAAACACTTCGTTT |  | 198 |
|  | P17 | TTGGGGATAATTTTTAGTTTTTTTTT |  | 190 |
| 87 | F782 | TTTGTTTTTCGAG | 175 | 199 |
|  | R17 | TAAACACTTCGTTT |  | 200 |
|  | P17 | TTGGGGATAATTTTTAGTTTTTTTTT |  | 190 |
| 88 | F783 | TTGTTTTTCGAGT | 174 | 201 |
|  | R17 | TAAACACTTCGTTT |  | 202 |
|  | P17 | TTGGGGATAATTTTTAGTTTTTTTTT |  | 190 |
| 89 | F784 | TGTTTTTCGAGTT | 173 | 203 |
|  | R17 | TAAACACTTCGTTT |  | 204 |
|  | P17 | TTGGGGATAATTTTTAGTTTTTTTTT |  | 190 |
| 90 | F785 | GTTTTTCGAGTTT | 172 | 205 |
|  | R17 | TAAACACTTCGTTT |  | 206 |
|  | P17 | TTGGGGATAATTTTTAGTTTTTTTTT |  | 190 |
| 91 | F786 | TTTTTCGAGTTTT | 171 | 207 |
|  | R17 | TAAACACTTCGTTT |  | 208 |
|  | P17 | TTGGGGATAATTTTTAGTTTTTTTTT |  | 190 |
| 92 | F787 | TTTTCGAGTTTTT | 170 | 209 |
|  | R17 | TAAACACTTCGTTT |  | 210 |
|  | P17 | TTGGGGATAATTTTTAGTTTTTTTTT |  | 190 |
| 93 | F788 | TTTCGAGTTTTTA | 169 | 211 |
|  | R17 | TAAACACTTCGTTT |  | 212 |
|  | P17 | TTGGGGATAATTTTTAGTTTTTTTTT |  | 190 |
| 94 | F789 | TTCGAGTTTTTAC | 168 | 213 |
|  | R17 | TAAACACTTCGTTT |  | 214 |
|  | P17 | TTGGGGATAATTTTTAGTTTTTTTTT |  | 190 |
| 95 | F790 | TCGAGTTTTTACG | 167 | 215 |
|  | R17 | TAAACACTTCGTTT |  | 216 |
|  | P17 | TTGGGGATAATTTTTAGTTTTTTTTT |  | 190 |
| 96 | F791 | CGAGTTTTTACGT | 166 | 217 |
|  | R17 | TAAACACTTCGTTT |  | 218 |
|  | P17 | TTGGGGATAATTTTTAGTTTTTTTTT |  | 190 |
| 97 | F792 | GAGTTTTTACGTT | 165 | 219 |
|  | R17 | TAAACACTTCGTTT |  | 220 |
|  | P17 | TTGGGGATAATTTTTAGTTTTTTTTT |  | 190 |
| 98 | F793 | AGTTTTTACGTTT | 164 | 221 |
|  | R17 | TAAACACTTCGTTT |  | 222 |
|  | P17 | TTGGGGATAATTTTTAGTTTTTTTTT |  | 190 |
| 99 | F794 | GTTTTTACGTTTT | 163 | 223 |
|  | R17 | TAAACACTTCGTTT |  | 224 |
|  | P17 | TTGGGGATAATTTTTAGTTTTTTTTT |  | 190 |
| 100 | F795 | TTTTTACGTTTTT | 162 | 225 |
|  | R17 | TAAACACTTCGTTT |  | 226 |
|  | P17 | TTGGGGATAATTTTTAGTTTTTTTTT |  | 190 |

TABLE 7-continued

Sequences of primer and probes for GPM6A gene qMSP

| Set | Primer | Sequence (5'→3') | Size of amplified product (bp) | Sequence No. |
|---|---|---|---|---|
| 101 | F796 | TTTTTACGTTTTTA | 161 | 227 |
| | R17 | TAAACACTTCGTTT | | 228 |
| | P17 | TTGGGGATAATTTTTAGTTTTTTTTT | | 190 |
| 102 | F797 | TTTTACGTTTTTAT | 160 | 229 |
| | R17 | TAAACACTTCGTTT | | 230 |
| | P17 | TTGGGGATAATTTTTAGTTTTTTTTT | | 190 |
| 103 | F798 | TTTACGTTTTTATG | 159 | 231 |
| | R17 | TAAACACTTCGTTT | | 232 |
| | P17 | TTGGGGATAATTTTTAGTTTTTTTTT | | 190 |
| 104 | F799 | TTACGTTTTTATGT | 158 | 233 |
| | R17 | TAAACACTTCGTTT | | 234 |
| | P17 | TTGGGGATAATTTTTAGTTTTTTTTT | | 190 |
| 105 | F800 | TACGTTTTTATGTT | 157 | 235 |
| | R17 | TAAACACTTCGTTT | | 236 |
| | P17 | TTGGGGATAATTTTTAGTTTTTTTTT | | 190 |
| 106 | F801 | ACGTTTTTATGTTT | 156 | 237 |
| | R17 | TAAACACTTCGTTT | | 238 |
| | P17 | TTGGGGATAATTTTTAGTTTTTTTTT | | 190 |
| 107 | F802 | CGTTTTTATGTTTT | 155 | 239 |
| | R17 | TAAACACTTCGTTT | | 240 |
| | P17 | TTGGGGATAATTTTTAGTTTTTTTTT | | 190 |
| 108 | F803 | GTTTTTATGTTTTT | 154 | 241 |
| | R17 | TAAACACTTCGTTT | | 242 |
| | P17 | TTGGGGATAATTTTTAGTTTTTTTTT | | 190 |
| 109 | F804 | TTTTTATGTTTTTT | 153 | 243 |
| | R17 | TAAACACTTCGTTT | | 244 |
| | P17 | TTGGGGATAATTTTTAGTTTTTTTTT | | 190 |
| 110 | F805 | TTTTATGTTTTTTT | 152 | 245 |
| | R17 | TAAACACTTCGTTT | | 246 |
| | P17 | TTGGGGATAATTTTTAGTTTTTTTTT | | 190 |
| 111 | F806 | TTTATGTTTTTTTT | 151 | 247 |
| | R17 | TAAACACTTCGTTT | | 248 |
| | P17 | TTGGGGATAATTTTTAGTTTTTTTTT | | 190 |
| 112 | F807 | TTATGTTTTTTTTG | 150 | 249 |
| | R17 | TAAACACTTCGTTT | | 250 |
| | P17 | TTGGGGATAATTTTTAGTTTTTTTTT | | 190 |
| 113 | F808 | TATGTTTTTTTTGG | 149 | 251 |
| | R17 | TAAACACTTCGTTT | | 252 |
| | P17 | TTGGGGATAATTTTTAGTTTTTTTTT | | 190 |
| 114 | F809 | ATGTTTTTTTTGGG | 148 | 253 |
| | R17 | TAAACACTTCGTTT | | 254 |
| | P17 | TTGGGGATAATTTTTAGTTTTTTTTT | | 190 |
| 115 | F810 | TGTTTTTTTTGGGG | 147 | 255 |
| | R17 | TAAACACTTCGTTT | | 256 |
| | P17 | TTGGGGATAATTTTTAGTTTTTTTTT | | 190 |
| 116 | F811 | GTTTTTTTTGGGGA | 146 | 257 |
| | R17 | TAAACACTTCGTTT | | 258 |
| | P17 | TTGGGGATAATTTTTAGTTTTTTTTT | | 190 |
| 117 | F812 | TTTTTTTTGGGGAG | 145 | 259 |
| | R17 | TAAACACTTCGTTT | | 260 |
| | P17 | TTGGGGATAATTTTTAGTTTTTTTTT | | 190 |
| 118 | F813 | TTTTTTTGGGGAGT | 144 | 261 |
| | R17 | TAAACACTTCGTTT | | 262 |
| | P17 | TTGGGGATAATTTTTAGTTTTTTTTT | | 190 |

TABLE 7-continued

Sequences of primer and probes for GPM6A gene qMSP

| Set | Primer | Sequence (5'→3') | Size of amplified product (bp) | Sequence No. |
|---|---|---|---|---|
| 119 | F814 | TTTTTTGGGGAGTA | 143 | 263 |
|  | R17 | TAAACACTTCGTTT |  | 264 |
|  | P17 | TTGGGGATAATTTTTAGTTTTTTTTT |  | 190 |
| 120 | F815 | TTTTTGGGGAGTAA | 142 | 265 |
|  | R17 | TAAACACTTCGTTT |  | 266 |
|  | P17 | TTGGGGATAATTTTTAGTTTTTTTTT |  | 190 |
| 121 | F816 | TTTTGGGGAGTAAG | 141 | 267 |
|  | R17 | TAAACACTTCGTTT |  | 268 |
|  | P17 | TTGGGGATAATTTTTAGTTTTTTTTT |  | 190 |
| 122 | F817 | TTTGGGGAGTAAGT | 140 | 269 |
|  | R17 | TAAACACTTCGTTT |  | 270 |
|  | P17 | TTGGGGATAATTTTTAGTTTTTTTTT |  | 190 |
| 123 | F818 | TTGGGGAGTAAGTT | 139 | 271 |
|  | R17 | TAAACACTTCGTTT |  | 272 |
|  | P17 | TTGGGGATAATTTTTAGTTTTTTTTT |  | 190 |
| 124 | F819 | TGGGGAGTAAGTTG | 138 | 273 |
|  | R17 | TAAACACTTCGTTT |  | 274 |
|  | P17 | TTGGGGATAATTTTTAGTTTTTTTTT |  | 190 |
| 125 | F820 | GGGGAGTAAGTTGA | 137 | 275 |
|  | R17 | TAAACACTTCGTTT |  | 276 |
|  | P17 | TTGGGGATAATTTTTAGTTTTTTTTT |  | 190 |
| 126 | F821 | GGGAGTAAGTTGAA | 136 | 277 |
|  | R17 | TAAACACTTCGTTT |  | 278 |
|  | P17 | TTGGGGATAATTTTTAGTTTTTTTTT |  | 190 |
| 127 | F822 | GGAGTAAGTTGAAA | 135 | 279 |
|  | R17 | TAAACACTTCGTTT |  | 280 |
|  | P17 | TTGGGGATAATTTTTAGTTTTTTTTT |  | 190 |
| 128 | F823 | GAGTAAGTTGAAAC | 134 | 281 |
|  | R17 | TAAACACTTCGTTT |  | 282 |
|  | P17 | TTGGGGATAATTTTTAGTTTTTTTTT |  | 190 |
| 129 | F824 | AGTAAGTTGAAACG | 133 | 283 |
|  | R17 | TAAACACTTCGTTT |  | 284 |
|  | P17 | TTGGGGATAATTTTTAGTTTTTTTTT |  | 190 |
| 130 | F825 | GTAAGTTGAAACGG | 132 | 285 |
|  | R17 | TAAACACTTCGTTT |  | 286 |
|  | P17 | TTGGGGATAATTTTTAGTTTTTTTTT |  | 190 |
| 131 | F826 | TAAGTTGAAACGGG | 131 | 287 |
|  | R17 | TAAACACTTCGTTT |  | 288 |
|  | P17 | TTGGGGATAATTTTTAGTTTTTTTTT |  | 190 |
| 132 | F827 | AAGTTGAAACGGGG | 130 | 289 |
|  | R17 | TAAACACTTCGTTT |  | 290 |
|  | P17 | TTGGGGATAATTTTTAGTTTTTTTTT |  | 190 |
| 133 | F828 | AGTTGAAACGGGGT | 129 | 291 |
|  | R17 | TAAACACTTCGTTT |  | 292 |
|  | P17 | TTGGGGATAATTTTTAGTTTTTTTTT |  | 190 |
| 134 | F829 | GTTGAAACGGGGTA | 128 | 293 |
|  | R17 | TAAACACTTCGTTT |  | 294 |
|  | P17 | TTGGGGATAATTTTTAGTTTTTTTTT |  | 190 |
| 135 | F830 | TTGAAACGGGGTAC | 127 | 295 |
|  | R17 | TAAACACTTCGTTT |  | 296 |
|  | P17 | TTGGGGATAATTTTTAGTTTTTTTTT |  | 190 |
| 136 | F831 | TGAAACGGGGTACG | 126 | 297 |
|  | R17 | TAAACACTTCGTTT |  | 298 |
|  | P17 | TTGGGGATAATTTTTAGTTTTTTTTT |  | 190 |

TABLE 7-continued

Sequences of primer and probes for GPM6A gene qMSP

| Set | Primer | Sequence (5'→3') | Size of amplified product (bp) | Sequence No. |
|---|---|---|---|---|
| 137 | F832 | GAAACGGGGTACGA | 125 | 299 |
|  | R17 | TAAACACTTCGTTT |  | 300 |
|  | P17 | TTGGGGATAATTTTTAGTTTTTTTTT |  | 190 |
| 138 | F833 | AAACGGGGTACGAG | 124 | 301 |
|  | R17 | TAAACACTTCGTTT |  | 302 |
|  | P17 | TTGGGGATAATTTTTAGTTTTTTTTT |  | 190 |
| 139 | F834 | AACGGGGTACGAGA | 123 | 303 |
|  | R17 | TAAACACTTCGTTT |  | 304 |
|  | P17 | TTGGGGATAATTTTTAGTTTTTTTTT |  | 190 |
| 140 | F835 | ACGGGGTACGAGAA | 122 | 305 |
|  | R17 | TAAACACTTCGTTT |  | 306 |
|  | P17 | TTGGGGATAATTTTTAGTTTTTTTTT |  | 190 |
| 141 | F836 | CGGGGTACGAGAAA | 121 | 307 |
|  | R17 | TAAACACTTCGTTT |  | 308 |
|  | P17 | TTGGGGATAATTTTTAGTTTTTTTTT |  | 190 |
| 142 | F837 | GGGGTACGAGAAAT | 120 | 309 |
|  | R17 | TAAACACTTCGTTT |  | 310 |
|  | P17 | TTGGGGATAATTTTTAGTTTTTTTTT |  | 190 |
| 143 | F838 | GGGTACGAGAAATG | 119 | 311 |
|  | R17 | TAAACACTTCGTTT |  | 312 |
|  | P17 | TTGGGGATAATTTTTAGTTTTTTTTT |  | 190 |
| 144 | F839 | GGTACGAGAAATGG | 118 | 313 |
|  | R17 | TAAACACTTCGTTT |  | 314 |
|  | P17 | TTGGGGATAATTTTTAGTTTTTTTTT |  | 190 |
| 145 | F840 | GTACGAGAAATGGA | 117 | 315 |
|  | R17 | TAAACACTTCGTTT |  | 316 |
|  | P17 | TTGGGGATAATTTTTAGTTTTTTTTT |  | 190 |
| 146 | F841 | TACGAGAAATGGAA | 116 | 317 |
|  | R17 | TAAACACTTCGTTT |  | 318 |
|  | P17 | TTGGGGATAATTTTTAGTTTTTTTTT |  | 190 |
| 147 | F842 | ACGAGAAATGGAAA | 115 | 319 |
|  | R17 | TAAACACTTCGTTT |  | 320 |
|  | P17 | TTGGGGATAATTTTTAGTTTTTTTTT |  | 190 |
| 148 | F843 | CGAGAAATGGAAAT | 114 | 321 |
|  | R17 | TAAACACTTCGTTT |  | 322 |
|  | P17 | TTGGGGATAATTTTTAGTTTTTTTTT |  | 190 |
| 149 | F844 | GAGAAATGGAAATT | 113 | 323 |
|  | R17 | TAAACACTTCGTTT |  | 324 |
|  | P17 | TTGGGGATAATTTTTAGTTTTTTTTT |  | 190 |
| 150 | F845 | AGAAATGGAAATTT | 112 | 325 |
|  | R17 | TAAACACTTCGTTT |  | 326 |
|  | P17 | TTGGGGATAATTTTTAGTTTTTTTTT |  | 190 |
| 151 | F846 | GAAATGGAAATTTT | 111 | 327 |
|  | R17 | TAAACACTTCGTTT |  | 328 |
|  | P17 | TTGGGGATAATTTTTAGTTTTTTTTT |  | 190 |
| 152 | F847 | AAATGGAAATTTTT | 110 | 329 |
|  | R17 | TAAACACTTCGTTT |  | 330 |
|  | P17 | TTGGGGATAATTTTTAGTTTTTTTTT |  | 190 |
| 153 | F848 | AATGGAAATTTTTT | 109 | 331 |
|  | R17 | TAAACACTTCGTTT |  | 332 |
|  | P17 | TTGGGGATAATTTTTAGTTTTTTTTT |  | 190 |
| 154 | F849 | ATGGAAATTTTTTA | 108 | 333 |
|  | R17 | TAAACACTTCGTTT |  | 334 |
|  | P17 | TTGGGGATAATTTTTAGTTTTTTTTT |  | 190 |

TABLE 7-continued

Sequences of primer and probes for GPM6A gene qMSP

| Set | Primer | Sequence (5'→3') | Size of amplified product (bp) | Sequence No. |
|---|---|---|---|---|
| 155 | F850 | TGGAAATTTTTTAA | 107 | 335 |
|  | R17 | TAAACACTTCGTTT |  | 336 |
|  | P17 | TTGGGGATAATTTTTAGTTTTTTTTT |  | 190 |
| 156 | F851 | GGAAATTTTTTAAA | 106 | 337 |
|  | R17 | TAAACACTTCGTTT |  | 338 |
|  | P17 | TTGGGGATAATTTTTAGTTTTTTTTT |  | 190 |
| 157 | F852 | GAAATTTTTTAAAA | 105 | 339 |
|  | R17 | TAAACACTTCGTTT |  | 340 |
|  | P17 | TTGGGGATAATTTTTAGTTTTTTTTT |  | 190 |
| 158 | F853 | AAATTTTTTAAAAT | 104 | 341 |
|  | R17 | TAAACACTTCGTTT |  | 342 |
|  | P17 | TTGGGGATAATTTTTAGTTTTTTTTT |  | 190 |
| 159 | F854 | AATTTTTTAAAATT | 103 | 343 |
|  | R17 | TAAACACTTCGTTT |  | 344 |
|  | P17 | TTGGGGATAATTTTTAGTTTTTTTTT |  | 190 |
| 160 | F855 | ATTTTTTAAAATTT | 102 | 345 |
|  | R17 | TAAACACTTCGTTT |  | 346 |
|  | P17 | TTGGGGATAATTTTTAGTTTTTTTTT |  | 190 |
| 161 | F856 | TTTTTTAAAATTTT | 101 | 347 |
|  | R17 | TAAACACTTCGTTT |  | 348 |
|  | P17 | TTGGGGATAATTTTTAGTTTTTTTTT |  | 190 |
| 162 | F857 | TTTTTAAAATTTTT | 100 | 349 |
|  | R17 | TAAACACTTCGTTT |  | 350 |
|  | P17 | TTGGGGATAATTTTTAGTTTTTTTTT |  | 190 |
| 163 | F858 | TTTTAAAATTTTTA | 99 | 351 |
|  | R17 | TAAACACTTCGTTT |  | 352 |
|  | P17 | TTGGGGATAATTTTTAGTTTTTTTTT |  | 190 |
| 164 | F859 | TTTAAAATTTTTAT | 98 | 353 |
|  | R17 | TAAACACTTCGTTT |  | 354 |
|  | P17 | TTGGGGATAATTTTTAGTTTTTTTTT |  | 190 |
| 165 | F860 | TTAAAATTTTTATT | 97 | 355 |
|  | R17 | TAAACACTTCGTTT |  | 356 |
|  | P17 | TTGGGGATAATTTTTAGTTTTTTTTT |  | 190 |
| 166 | F861 | TAAAATTTTTATTT | 96 | 357 |
|  | R17 | TAAACACTTCGTTT |  | 358 |
|  | P17 | TTGGGGATAATTTTTAGTTTTTTTTT |  | 190 |
| 167 | F862 | AAAATTTTTATTTT | 95 | 359 |
|  | R17 | TAAACACTTCGTTT |  | 360 |
|  | P17 | TTGGGGATAATTTTTAGTTTTTTTTT |  | 190 |
| 168 | F863 | AAATTTTTATTTTG | 94 | 361 |
|  | R17 | TAAACACTTCGTTT |  | 362 |
|  | P17 | TTGGGGATAATTTTTAGTTTTTTTTT |  | 190 |
| 169 | F864 | AATTTTTATTTTGT | 93 | 363 |
|  | R17 | TAAACACTTCGTTT |  | 364 |
|  | P17 | TTGGGGATAATTTTTAGTTTTTTTTT |  | 190 |
| 170 | F865 | ATTTTTATTTTGTA | 92 | 365 |
|  | R17 | TAAACACTTCGTTT |  | 366 |
|  | P17 | TTGGGGATAATTTTTAGTTTTTTTTT |  | 190 |
| 171 | F866 | TTTTTATTTTGTAT | 91 | 367 |
|  | R17 | TAAACACTTCGTTT |  | 368 |
|  | P17 | TTGGGGATAATTTTTAGTTTTTTTTT |  | 190 |
| 172 | F867 | TTTTATTTTGTATA | 90 | 369 |
|  | R17 | TAAACACTTCGTTT |  | 370 |
|  | P17 | TTGGGGATAATTTTTAGTTTTTTTTT |  | 190 |

TABLE 7-continued

Sequences of primer and probes for GPM6A gene qMSP

| Set | Primer | Sequence (5'→3') | Size of amplified product (bp) | Sequence No. |
|---|---|---|---|---|
| 173 | F868 | TTTATTTTGTATAG | 89 | 371 |
| | R17 | TAAACACTTCGTTT | | 372 |
| | P17 | TTGGGGATAATTTTTAGTTTTTTTTT | | 190 |
| 174 | F869 | TTATTTTGTATAGG | 88 | 373 |
| | R17 | TAAACACTTCGTTT | | 374 |
| | P17 | TTGGGGATAATTTTTAGTTTTTTTTT | | 190 |
| 175 | F870 | TATTTTGTATAGGT | 87 | 375 |
| | R17 | TAAACACTTCGTTT | | 376 |
| | P17 | TTGGGGATAATTTTTAGTTTTTTTTT | | 190 |
| 176 | F871 | ATTTTGTATAGGTT | 86 | 377 |
| | R17 | TAAACACTTCGTTT | | 378 |
| | P17 | TTGGGGATAATTTTTAGTTTTTTTTT | | 190 |
| 177 | F872 | TTTTGTATAGGTTT | 85 | 379 |
| | R17 | TAAACACTTCGTTT | | 380 |
| | P17 | TTGGGGATAATTTTTAGTTTTTTTTT | | 190 |
| 178 | F873 | TTTGTATAGGTTTG | 84 | 381 |
| | R17 | TAAACACTTCGTTT | | 382 |
| | P17 | TTGGGGATAATTTTTAGTTTTTTTTT | | 190 |
| 179 | F874 | TTGTATAGGTTTGA | 83 | 383 |
| | R17 | TAAACACTTCGTTT | | 384 |
| | P17 | TTGGGGATAATTTTTAGTTTTTTTTT | | 190 |
| 180 | F875 | TGTATAGGTTTGAG | 82 | 385 |
| | R17 | TAAACACTTCGTTT | | 386 |
| | P17 | TTGGGGATAATTTTTAGTTTTTTTTT | | 190 |
| 181 | F876 | GTATAGGTTTGAGT | 81 | 387 |
| | R17 | TAAACACTTCGTTT | | 388 |
| | P17 | TTGGGGATAATTTTTAGTTTTTTTTT | | 190 |
| 182 | F877 | TATAGGTTTGAGTA | 80 | 389 |
| | R17 | TAAACACTTCGTTT | | 390 |
| | P17 | TTGGGGATAATTTTTAGTTTTTTTTT | | 190 |
| 183 | F878 | ATAGGTTTGAGTAG | 150 | 391 |
| | R18 | TCACGCTATTTACC | | 392 |
| | P18 | TTGATTTTTTTTAAATTTTATTTG | | 393 |
| 184 | F879 | TAGGTTTGAGTAGA | 149 | 394 |
| | R18 | TCACGCTATTTACC | | 395 |
| | P18 | TTGATTTTTTTTAAATTTTATTTG | | 393 |
| 185 | F880 | AGGTTTGAGTAGAG | 148 | 396 |
| | R18 | TCACGCTATTTACC | | 397 |
| | P18 | TTGATTTTTTTTAAATTTTATTTG | | 393 |
| 186 | F881 | GGTTTGAGTAGAGG | 147 | 398 |
| | R18 | TCACGCTATTTACC | | 399 |
| | P18 | TTGATTTTTTTTAAATTTTATTTG | | 393 |
| 187 | F882 | GTTTGAGTAGAGGA | 146 | 400 |
| | R18 | TCACGCTATTTACC | | 401 |
| | P18 | TTGATTTTTTTTAAATTTTATTTG | | 393 |
| 188 | F883 | TTTGAGTAGAGGAA | 145 | 402 |
| | R18 | TCACGCTATTTACC | | 403 |
| | P18 | TTGATTTTTTTTAAATTTTATTTG | | 393 |
| 189 | F884 | TTGAGTAGAGGAAG | 144 | 404 |
| | R18 | TCACGCTATTTACC | | 405 |
| | P18 | TTGATTTTTTTTAAATTTTATTTG | | 393 |
| 190 | F885 | TGAGTAGAGGAAGG | 143 | 406 |
| | R18 | TCACGCTATTTACC | | 407 |
| | P18 | TTGATTTTTTTTAAATTTTATTTG | | 393 |

TABLE 7-continued

Sequences of primer and probes for GPM6A gene qMSP

| Set | Primer | Sequence (5'→3') | Size of amplified product (bp) | Sequence No. |
|---|---|---|---|---|
| 191 | F886 | GAGTAGAGGAAGGT | 142 | 408 |
|  | R18 | TCACGCTATTTACC |  | 409 |
|  | P18 | TTGATTTTTTTTAAATTTTATTTG |  | 393 |
| 192 | F887 | AGTAGAGGAAGGTG | 141 | 410 |
|  | R18 | TCACGCTATTTACC |  | 411 |
|  | P18 | TTGATTTTTTTTAAATTTTATTTG |  | 393 |
| 193 | F888 | GTAGAGGAAGGTGT | 140 | 412 |
|  | R18 | TCACGCTATTTACC |  | 413 |
|  | P18 | TTGATTTTTTTTAAATTTTATTTG |  | 393 |
| 194 | F889 | TAGAGGAAGGTGTT | 139 | 414 |
|  | R18 | TCACGCTATTTACC |  | 415 |
|  | P18 | TTGATTTTTTTTAAATTTTATTTG |  | 393 |
| 195 | F890 | AGAGGAAGGTGTTG | 138 | 416 |
|  | R18 | TCACGCTATTTACC |  | 417 |
|  | P18 | TTGATTTTTTTTAAATTTTATTTG |  | 393 |
| 196 | F891 | GAGGAAGGTGTTGG | 137 | 418 |
|  | R18 | TCACGCTATTTACC |  | 419 |
|  | P18 | TTGATTTTTTTTAAATTTTATTTG |  | 393 |
| 197 | F892 | AGGAAGGTGTTGGT | 136 | 420 |
|  | R18 | TCACGCTATTTACC |  | 421 |
|  | P18 | TTGATTTTTTTTAAATTTTATTTG |  | 393 |
| 198 | F893 | GGAAGGTGTTGGTG | 135 | 422 |
|  | R18 | TCACGCTATTTACC |  | 423 |
|  | P18 | TTGATTTTTTTTAAATTTTATTTG |  | 393 |
| 199 | F894 | GAAGGTGTTGGTGT | 134 | 424 |
|  | R18 | TCACGCTATTTACC |  | 425 |
|  | P18 | TTGATTTTTTTTAAATTTTATTTG |  | 393 |
| 200 | F895 | AAGGTGTTGGTGTA | 133 | 426 |
|  | R18 | TCACGCTATTTACC |  | 427 |
|  | P18 | TTGATTTTTTTTAAATTTTATTTG |  | 393 |
| 201 | F896 | AGGTGTTGGTGTAG | 132 | 428 |
|  | R18 | TCACGCTATTTACC |  | 429 |
|  | P18 | TTGATTTTTTTTAAATTTTATTTG |  | 393 |
| 202 | F897 | GGTGTTGGTGTAGG | 131 | 430 |
|  | R18 | TCACGCTATTTACC |  | 431 |
|  | P18 | TTGATTTTTTTTAAATTTTATTTG |  | 393 |
| 203 | F898 | GTGTTGGTGTAGGG | 130 | 432 |
|  | R18 | TCACGCTATTTACC |  | 433 |
|  | P18 | TTGATTTTTTTTAAATTTTATTTG |  | 393 |
| 204 | F899 | TGTTGGTGTAGGGT | 129 | 434 |
|  | R18 | TCACGCTATTTACC |  | 435 |
|  | P18 | TTGATTTTTTTTAAATTTTATTTG |  | 393 |
| 205 | F900 | GTTGGTGTAGGGTT | 128 | 436 |
|  | R18 | TCACGCTATTTACC |  | 437 |
|  | P18 | TTGATTTTTTTTAAATTTTATTTG |  | 393 |
| 206 | F901 | TTGGTGTAGGGTTA | 127 | 438 |
|  | R18 | TCACGCTATTTACC |  | 439 |
|  | P18 | TTGATTTTTTTTAAATTTTATTTG |  | 393 |
| 207 | F902 | TGGTGTAGGGTTAG | 126 | 440 |
|  | R18 | TCACGCTATTTACC |  | 441 |
|  | P18 | TTGATTTTTTTTAAATTTTATTTG |  | 393 |
| 208 | F903 | GGTGTAGGGTTAGA | 125 | 442 |
|  | R18 | TCACGCTATTTACC |  | 443 |
|  | P18 | TTGATTTTTTTTAAATTTTATTTG |  | 393 |

TABLE 7-continued

Sequences of primer and probes for GPM6A gene qMSP

| Set | Primer | Sequence (5'→3') | Size of amplified product (bp) | Sequence No. |
|---|---|---|---|---|
| 209 | F904 | GTGTAGGGTTAGAT | 124 | 444 |
|  | R18 | TCACGCTATTTACC |  | 445 |
|  | P18 | TTGATTTTTTTAAATTTTATTTG |  | 393 |
| 210 | F905 | TGTAGGGTTAGATT | 123 | 446 |
|  | R18 | TCACGCTATTTACC |  | 447 |
|  | P18 | TTGATTTTTTTAAATTTTATTTG |  | 393 |
| 211 | F906 | GTAGGGTTAGATTG | 122 | 448 |
|  | R18 | TCACGCTATTTACC |  | 449 |
|  | P18 | TTGATTTTTTTAAATTTTATTTG |  | 393 |
| 212 | F907 | TAGGGTTAGATTGG | 121 | 450 |
|  | R18 | TCACGCTATTTACC |  | 451 |
|  | P18 | TTGATTTTTTTAAATTTTATTTG |  | 393 |
| 213 | F908 | AGGGTTAGATTGGG | 120 | 452 |
|  | R18 | TCACGCTATTTACC |  | 453 |
|  | P18 | TTGATTTTTTTAAATTTTATTTG |  | 393 |
| 214 | F909 | GGGTTAGATTGGGG | 119 | 454 |
|  | R18 | TCACGCTATTTACC |  | 455 |
|  | P18 | TTGATTTTTTTAAATTTTATTTG |  | 393 |
| 215 | F910 | GGTTAGATTGGGGA | 118 | 456 |
|  | R18 | TCACGCTATTTACC |  | 457 |
|  | P18 | TTGATTTTTTTAAATTTTATTTG |  | 393 |
| 216 | F911 | GTTAGATTGGGGAT | 117 | 458 |
|  | R18 | TCACGCTATTTACC |  | 459 |
|  | P18 | TTGATTTTTTTAAATTTTATTTG |  | 393 |
| 217 | F912 | TTAGATTGGGGATA | 116 | 460 |
|  | R18 | TCACGCTATTTACC |  | 461 |
|  | P18 | TTGATTTTTTTAAATTTTATTTG |  | 393 |
| 218 | F913 | TAGATTGGGGATAA | 115 | 462 |
|  | R18 | TCACGCTATTTACC |  | 463 |
|  | P18 | TTGATTTTTTTAAATTTTATTTG |  | 393 |
| 219 | F914 | AGATTGGGGATAAT | 114 | 464 |
|  | R18 | TCACGCTATTTACC |  | 465 |
|  | P18 | TTGATTTTTTTAAATTTTATTTG |  | 393 |
| 220 | F915 | GATTGGGGATAATT | 113 | 466 |
|  | R18 | TCACGCTATTTACC |  | 467 |
|  | P18 | TTGATTTTTTTAAATTTTATTTG |  | 393 |
| 221 | F916 | ATTGGGGATAATTT | 112 | 468 |
|  | R18 | TCACGCTATTTACC |  | 469 |
|  | P18 | TTGATTTTTTTAAATTTTATTTG |  | 393 |
| 222 | F917 | TTGGGGATAATTTT | 111 | 470 |
|  | R18 | TCACGCTATTTACC |  | 471 |
|  | P18 | TTGATTTTTTTAAATTTTATTTG |  | 393 |
| 223 | F918 | TGGGGATAATTTTT | 110 | 472 |
|  | R18 | TCACGCTATTTACC |  | 473 |
|  | P18 | TTGATTTTTTTAAATTTTATTTG |  | 393 |
| 224 | F919 | GGGGATAATTTTTA | 109 | 474 |
|  | R18 | TCACGCTATTTACC |  | 475 |
|  | P18 | TTGATTTTTTTAAATTTTATTTG |  | 393 |
| 225 | F920 | GGGATAATTTTTAG | 108 | 476 |
|  | R18 | TCACGCTATTTACC |  | 477 |
|  | P18 | TTGATTTTTTTAAATTTTATTTG |  | 393 |
| 226 | F921 | GGATAATTTTTAGT | 107 | 478 |
|  | R18 | TCACGCTATTTACC |  | 479 |
|  | P18 | TTGATTTTTTTAAATTTTATTTG |  | 393 |

TABLE 7-continued

Sequences of primer and probes for GPM6A gene qMSP

| Set | Primer | Sequence (5'→3') | Size of amplified product (bp) | Sequence No. |
|---|---|---|---|---|
| 227 | F922 | GATAATTTTTAGTT | 106 | 480 |
|  | R18 | TCACGCTATTTACC |  | 481 |
|  | P18 | TTGATTTTTTTTAAATTTTATTTG |  | 393 |
| 228 | F923 | ATAATTTTTAGTTT | 105 | 482 |
|  | R18 | TCACGCTATTTACC |  | 483 |
|  | P18 | TTGATTTTTTTTAAATTTTATTTG |  | 393 |
| 229 | F924 | TAATTTTTAGTTTT | 104 | 484 |
|  | R18 | TCACGCTATTTACC |  | 485 |
|  | P18 | TTGATTTTTTTTAAATTTTATTTG |  | 393 |
| 230 | F925 | AATTTTTAGTTTTT | 103 | 486 |
|  | R18 | TCACGCTATTTACC |  | 487 |
|  | P18 | TTGATTTTTTTTAAATTTTATTTG |  | 393 |
| 231 | F926 | ATTTTTAGTTTTTT | 102 | 488 |
|  | R18 | TCACGCTATTTACC |  | 489 |
|  | P18 | TTGATTTTTTTTAAATTTTATTTG |  | 393 |
| 232 | F927 | TTTTTAGTTTTTTT | 101 | 490 |
|  | R18 | TCACGCTATTTACC |  | 491 |
|  | P18 | TTGATTTTTTTTAAATTTTATTTG |  | 393 |
| 233 | F928 | TTTTAGTTTTTTTT | 100 | 492 |
|  | R18 | TCACGCTATTTACC |  | 493 |
|  | P18 | TTGATTTTTTTTAAATTTTATTTG |  | 393 |
| 234 | F929 | TTTAGTTTTTTTTT | 99 | 494 |
|  | R18 | TCACGCTATTTACC |  | 495 |
|  | P18 | TTGATTTTTTTTAAATTTTATTTG |  | 393 |
| 235 | F930 | TTAGTTTTTTTTA | 98 | 496 |
|  | R18 | TCACGCTATTTACC |  | 497 |
|  | P18 | TTGATTTTTTTTAAATTTTATTTG |  | 393 |
| 236 | F931 | TAGTTTTTTTTAA | 97 | 498 |
|  | R18 | TCACGCTATTTACC |  | 499 |
|  | P18 | TTGATTTTTTTTAAATTTTATTTG |  | 393 |
| 237 | F932 | AGTTTTTTTTAAA | 96 | 500 |
|  | R18 | TCACGCTATTTACC |  | 501 |
|  | P18 | TTGATTTTTTTTAAATTTTATTTG |  | 393 |
| 238 | F933 | GTTTTTTTTAAAC | 95 | 502 |
|  | R18 | TCACGCTATTTACC |  | 503 |
|  | P18 | TTGATTTTTTTTAAATTTTATTTG |  | 393 |
| 239 | F934 | TTTTTTTTAAACG | 94 | 504 |
|  | R18 | TCACGCTATTTACC |  | 505 |
|  | P18 | TTGATTTTTTTTAAATTTTATTTG |  | 393 |
| 240 | F935 | TTTTTTTAAACGA | 93 | 506 |
|  | R18 | TCACGCTATTTACC |  | 507 |
|  | P18 | TTGATTTTTTTTAAATTTTATTTG |  | 393 |
| 241 | F936 | TTTTTTAAACGAA | 92 | 508 |
|  | R18 | TCACGCTATTTACC |  | 509 |
|  | P18 | TTGATTTTTTTTAAATTTTATTTG |  | 393 |
| 242 | F937 | TTTTTAAACGAAG | 91 | 510 |
|  | R18 | TCACGCTATTTACC |  | 511 |
|  | P18 | TTGATTTTTTTTAAATTTTATTTG |  | 393 |
| 243 | F938 | TTTTAAACGAAGT | 90 | 512 |
|  | R18 | TCACGCTATTTACC |  | 513 |
|  | P18 | TTGATTTTTTTTAAATTTTATTTG |  | 393 |
| 244 | F939 | TTTAAACGAAGTG | 89 | 514 |
|  | R18 | TCACGCTATTTACC |  | 515 |
|  | P18 | TTGATTTTTTTTAAATTTTATTTG |  | 393 |

TABLE 7-continued

Sequences of primer and probes for GPM6A gene qMSP

| Set | Primer | Sequence (5'→3') | Size of amplified product (bp) | Sequence No. |
|---|---|---|---|---|
| 245 | F940 | TTTAAACGAAGTGT | 88 | 516 |
| | R18 | TCACGCTATTTACC | | 517 |
| | P18 | TTGATTTTTTTAAATTTTATTTG | | 393 |
| 246 | F941 | TTAAACGAAGTGTT | 87 | 518 |
| | R18 | TCACGCTATTTACC | | 519 |
| | P18 | TTGATTTTTTTAAATTTTATTTG | | 393 |
| 247 | F942 | TAAACGAAGTGTTT | 86 | 520 |
| | R18 | TCACGCTATTTACC | | 521 |
| | P18 | TTGATTTTTTTAAATTTTATTTG | | 393 |
| 248 | F943 | AAACGAAGTGTTTA | 85 | 522 |
| | R18 | TCACGCTATTTACC | | 523 |
| | P18 | TTGATTTTTTTAAATTTTATTTG | | 393 |
| 249 | F944 | AACGAAGTGTTTAT | 84 | 524 |
| | R18 | TCACGCTATTTACC | | 525 |
| | P18 | TTGATTTTTTTAAATTTTATTTG | | 393 |
| 250 | F945 | ACGAAGTGTTTATT | 83 | 526 |
| | R18 | TCACGCTATTTACC | | 527 |
| | P18 | TTGATTTTTTTAAATTTTATTTG | | 393 |
| 251 | F946 | CGAAGTGTTTATTT | 82 | 528 |
| | R18 | TCACGCTATTTACC | | 529 |
| | P18 | TTGATTTTTTTAAATTTTATTTG | | 393 |
| 252 | F947 | GAAGTGTTTATTTG | 81 | 530 |
| | R18 | TCACGCTATTTACC | | 531 |
| | P18 | TTGATTTTTTTAAATTTTATTTG | | 393 |
| 253 | F948 | AAGTGTTTATTTGT | 80 | 532 |
| | R18 | TCACGCTATTTACC | | 533 |
| | P18 | TTGATTTTTTTAAATTTTATTTG | | 393 |
| 254 | F949 | AGTGTTTATTTGTA | 140 | 534 |
| | R19 | AAACTAAACTACGC | | 535 |
| | P19 | CGGGTTATTGGACGGTGGAGTTCG | | 536 |
| 255 | F950 | GTGTTTATTTGTAT | 139 | 537 |
| | R19 | AAACTAAACTACGC | | 538 |
| | P19 | CGGGTTATTGGACGGTGGAGTTCG | | 536 |
| 256 | F951 | TGTTTATTTGTATA | 138 | 539 |
| | R19 | AAACTAAACTACGC | | 540 |
| | P19 | CGGGTTATTGGACGGTGGAGTTCG | | 536 |
| 257 | F952 | GTTTATTTGTATAA | 137 | 541 |
| | R19 | AAACTAAACTACGC | | 542 |
| | P19 | CGGGTTATTGGACGGTGGAGTTCG | | 536 |
| 258 | F953 | TTTATTTGTATAAA | 136 | 543 |
| | R19 | AAACTAAACTACGC | | 544 |
| | P19 | CGGGTTATTGGACGGTGGAGTTCG | | 536 |
| 259 | F954 | TTATTTGTATAAAA | 135 | 545 |
| | R19 | AAACTAAACTACGC | | 546 |
| | P19 | CGGGTTATTGGACGGTGGAGTTCG | | 536 |
| 260 | F955 | TATTTGTATAAAAG | 134 | 547 |
| | R19 | AAACTAAACTACGC | | 548 |
| | P19 | CGGGTTATTGGACGGTGGAGTTCG | | 536 |
| 261 | F956 | ATTTGTATAAAAGG | 133 | 549 |
| | R19 | AAACTAAACTACGC | | 550 |
| | P19 | CGGGTTATTGGACGGTGGAGTTCG | | 536 |
| 262 | F957 | TTTGTATAAAAGGT | 132 | 551 |
| | R19 | AAACTAAACTACGC | | 552 |
| | P19 | CGGGTTATTGGACGGTGGAGTTCG | | 536 |

TABLE 7-continued

Sequences of primer and probes for GPM6A gene qMSP

| Set | Primer | Sequence (5'→3') | Size of amplified product (bp) | Sequence No. |
|---|---|---|---|---|
| 263 | F958 | TTGTATAAAAGGTT | 131 | 553 |
|  | R19 | AAACTAAACTACGC |  | 554 |
|  | P19 | CGGGTTATTGGACGGTGGAGTTCG |  | 536 |
| 264 | F959 | TGTATAAAAGGTTT | 130 | 555 |
|  | R19 | AAACTAAACTACGC |  | 556 |
|  | P19 | CGGGTTATTGGACGGTGGAGTTCG |  | 536 |
| 265 | F960 | GTATAAAAGGTTTG | 129 | 557 |
|  | R19 | AAACTAAACTACGC |  | 558 |
|  | P19 | CGGGTTATTGGACGGTGGAGTTCG |  | 536 |
| 266 | F961 | TATAAAAGGTTTGA | 128 | 559 |
|  | R19 | AAACTAAACTACGC |  | 560 |
|  | P19 | CGGGTTATTGGACGGTGGAGTTCG |  | 536 |
| 267 | F962 | ATAAAAGGTTTGAG | 127 | 561 |
|  | R19 | AAACTAAACTACGC |  | 562 |
|  | P19 | CGGGTTATTGGACGGTGGAGTTCG |  | 536 |
| 268 | F963 | TAAAAGGTTTGAGG | 126 | 563 |
|  | R19 | AAACTAAACTACGC |  | 564 |
|  | P19 | CGGGTTATTGGACGGTGGAGTTCG |  | 536 |
| 269 | F964 | AAAAGGTTTGAGGT | 125 | 565 |
|  | R19 | AAACTAAACTACGC |  | 566 |
|  | P19 | CGGGTTATTGGACGGTGGAGTTCG |  | 536 |
| 270 | F965 | AAAGGTTTGAGGTT | 124 | 567 |
|  | R19 | AAACTAAACTACGC |  | 568 |
|  | P19 | CGGGTTATTGGACGGTGGAGTTCG |  | 536 |
| 271 | F966 | AAGGTTTGAGGTTG | 123 | 569 |
|  | R19 | AAACTAAACTACGC |  | 570 |
|  | P19 | CGGGTTATTGGACGGTGGAGTTCG |  | 536 |
| 272 | F967 | AGGTTTGAGGTTGA | 122 | 571 |
|  | R19 | AAACTAAACTACGC |  | 572 |
|  | P19 | CGGGTTATTGGACGGTGGAGTTCG |  | 536 |
| 273 | F968 | GGTTTGAGGTTGAG | 121 | 573 |
|  | R19 | AAACTAAACTACGC |  | 574 |
|  | P19 | CGGGTTATTGGACGGTGGAGTTCG |  | 536 |
| 274 | F969 | GTTTGAGGTTGAGG | 120 | 575 |
|  | R19 | AAACTAAACTACGC |  | 576 |
|  | P19 | CGGGTTATTGGACGGTGGAGTTCG |  | 536 |
| 275 | F970 | TTTGAGGTTGAGGT | 119 | 577 |
|  | R19 | AAACTAAACTACGC |  | 578 |
|  | P19 | CGGGTTATTGGACGGTGGAGTTCG |  | 536 |
| 276 | F971 | TTGAGGTTGAGGTT | 118 | 579 |
|  | R19 | AAACTAAACTACGC |  | 580 |
|  | P19 | CGGGTTATTGGACGGTGGAGTTCG |  | 536 |
| 277 | F972 | TGAGGTTGAGGTTG | 117 | 581 |
|  | R19 | AAACTAAACTACGC |  | 582 |
|  | P19 | CGGGTTATTGGACGGTGGAGTTCG |  | 536 |
| 278 | F973 | GAGGTTGAGGTTGA | 116 | 583 |
|  | R19 | AAACTAAACTACGC |  | 584 |
|  | P19 | CGGGTTATTGGACGGTGGAGTTCG |  | 536 |
| 279 | F974 | AGGTTGAGGTTGAA | 115 | 585 |
|  | R19 | AAACTAAACTACGC |  | 586 |
|  | P19 | CGGGTTATTGGACGGTGGAGTTCG |  | 536 |
| 280 | F975 | GGTTGAGGTTGAAG | 114 | 587 |
|  | R19 | AAACTAAACTACGC |  | 588 |
|  | P19 | CGGGTTATTGGACGGTGGAGTTCG |  | 536 |

TABLE 7-continued

Sequences of primer and probes for GPM6A gene qMSP

| Set | Primer | Sequence (5'→3') | Size of amplified product (bp) | Sequence No. |
|---|---|---|---|---|
| 281 | F976 | GTTGAGGTTGAAGG | 113 | 589 |
|  | R19 | AAACTAAACTACGC |  | 590 |
|  | P19 | CGGGTTATTGGACGGTGGAGTTCG |  | 536 |
| 282 | F977 | TTGAGGTTGAAGGT | 112 | 591 |
|  | R19 | AAACTAAACTACGC |  | 592 |
|  | P19 | CGGGTTATTGGACGGTGGAGTTCG |  | 536 |
| 283 | F978 | TGAGGTTGAAGGTT | 111 | 593 |
|  | R19 | AAACTAAACTACGC |  | 594 |
|  | P19 | CGGGTTATTGGACGGTGGAGTTCG |  | 536 |
| 284 | F979 | GAGGTTGAAGGTTG | 110 | 595 |
|  | R19 | AAACTAAACTACGC |  | 596 |
|  | P19 | CGGGTTATTGGACGGTGGAGTTCG |  | 536 |
| 285 | F980 | AGGTTGAAGGTTGA | 109 | 597 |
|  | R19 | AAACTAAACTACGC |  | 598 |
|  | P19 | CGGGTTATTGGACGGTGGAGTTCG |  | 536 |
| 286 | F981 | GGTTGAAGGTTGAT | 108 | 599 |
|  | R19 | AAACTAAACTACGC |  | 600 |
|  | P19 | CGGGTTATTGGACGGTGGAGTTCG |  | 536 |
| 287 | F982 | GTTGAAGGTTGATT | 107 | 601 |
|  | R19 | AAACTAAACTACGC |  | 602 |
|  | P19 | CGGGTTATTGGACGGTGGAGTTCG |  | 536 |
| 288 | F983 | TTGAAGGTTGATTT | 106 | 603 |
|  | R19 | AAACTAAACTACGC |  | 604 |
|  | P19 | CGGGTTATTGGACGGTGGAGTTCG |  | 536 |
| 289 | F984 | TGAAGGTTGATTTT | 105 | 605 |
|  | R19 | AAACTAAACTACGC |  | 606 |
|  | P19 | CGGGTTATTGGACGGTGGAGTTCG |  | 536 |
| 290 | F985 | GAAGGTTGATTTTT | 104 | 607 |
|  | R19 | AAACTAAACTACGC |  | 608 |
|  | P19 | CGGGTTATTGGACGGTGGAGTTCG |  | 536 |
| 291 | F986 | AAGGTTGATTTTTT | 103 | 609 |
|  | R19 | AAACTAAACTACGC |  | 610 |
|  | P19 | CGGGTTATTGGACGGTGGAGTTCG |  | 536 |
| 292 | F987 | AGGTTGATTTTTTT | 102 | 611 |
|  | R19 | AAACTAAACTACGC |  | 612 |
|  | P19 | CGGGTTATTGGACGGTGGAGTTCG |  | 536 |
| 293 | F988 | GGTTGATTTTTTTT | 101 | 613 |
|  | R19 | AAACTAAACTACGC |  | 614 |
|  | P19 | CGGGTTATTGGACGGTGGAGTTCG |  | 536 |
| 294 | F989 | GTTGATTTTTTTA | 100 | 615 |
|  | R19 | AAACTAAACTACGC |  | 616 |
|  | P19 | CGGGTTATTGGACGGTGGAGTTCG |  | 536 |
| 295 | F990 | TTGATTTTTTTAA | 99 | 617 |
|  | R19 | AAACTAAACTACGC |  | 618 |
|  | P19 | CGGGTTATTGGACGGTGGAGTTCG |  | 536 |
| 296 | F991 | TGATTTTTTTAAA | 98 | 619 |
|  | R19 | AAACTAAACTACGC |  | 620 |
|  | P19 | CGGGTTATTGGACGGTGGAGTTCG |  | 536 |
| 297 | F992 | GATTTTTTTAAAT | 97 | 621 |
|  | R19 | AAACTAAACTACGC |  | 622 |
|  | P19 | CGGGTTATTGGACGGTGGAGTTCG |  | 536 |
| 298 | F993 | ATTTTTTTAAATT | 96 | 623 |
|  | R19 | AAACTAAACTACGC |  | 624 |
|  | P19 | CGGGTTATTGGACGGTGGAGTTCG |  | 536 |

TABLE 7-continued

Sequences of primer and probes for GPM6A gene qMSP

| Set | Primer | Sequence (5'→3') | Size of amplified product (bp) | Sequence No. |
|---|---|---|---|---|
| 299 | F994 | TTTTTTTAAATTT | 95 | 625 |
|  | R19 | AAACTAAACTACGC |  | 626 |
|  | P19 | CGGGTTATTGGACGGTGGAGTTCG |  | 536 |
| 300 | F995 | TTTTTTAAATTTT | 94 | 627 |
|  | R19 | AAACTAAACTACGC |  | 628 |
|  | P19 | CGGGTTATTGGACGGTGGAGTTCG |  | 536 |
| 301 | F996 | TTTTTAAATTTTA | 93 | 629 |
|  | R19 | AAACTAAACTACGC |  | 630 |
|  | P19 | CGGGTTATTGGACGGTGGAGTTCG |  | 536 |
| 302 | F997 | TTTTAAATTTTAT | 92 | 631 |
|  | R19 | AAACTAAACTACGC |  | 632 |
|  | P19 | CGGGTTATTGGACGGTGGAGTTCG |  | 536 |
| 303 | F998 | TTTAAATTTTATT | 91 | 633 |
|  | R19 | AAACTAAACTACGC |  | 634 |
|  | P19 | CGGGTTATTGGACGGTGGAGTTCG |  | 536 |
| 304 | F999 | TTAAATTTTATTT | 90 | 635 |
|  | R19 | AAACTAAACTACGC |  | 636 |
|  | P19 | CGGGTTATTGGACGGTGGAGTTCG |  | 536 |
| 305 | F1000 | TAAATTTTATTTG | 89 | 637 |
|  | R19 | AAACTAAACTACGC |  | 638 |
|  | P19 | CGGGTTATTGGACGGTGGAGTTCG |  | 536 |
| 306 | F1001 | AAATTTTATTTGG | 88 | 639 |
|  | R19 | AAACTAAACTACGC |  | 640 |
|  | P19 | CGGGTTATTGGACGGTGGAGTTCG |  | 536 |
| 307 | F1002 | AATTTTATTTGGG | 87 | 641 |
|  | R19 | AAACTAAACTACGC |  | 642 |
|  | P19 | CGGGTTATTGGACGGTGGAGTTCG |  | 536 |
| 308 | F1003 | ATTTTATTTGGGT | 86 | 643 |
|  | R19 | AAACTAAACTACGC |  | 644 |
|  | P19 | CGGGTTATTGGACGGTGGAGTTCG |  | 536 |
| 309 | F1004 | TTTTATTTGGGTA | 85 | 645 |
|  | R19 | AAACTAAACTACGC |  | 646 |
|  | P19 | CGGGTTATTGGACGGTGGAGTTCG |  | 536 |
| 310 | F1005 | TTTATTTGGGTAA | 84 | 647 |
|  | R19 | AAACTAAACTACGC |  | 648 |
|  | P19 | CGGGTTATTGGACGGTGGAGTTCG |  | 536 |
| 311 | F1006 | TTATTTGGGTAAA | 83 | 649 |
|  | R19 | AAACTAAACTACGC |  | 650 |
|  | P19 | CGGGTTATTGGACGGTGGAGTTCG |  | 536 |
| 312 | F1007 | TATTTGGGTAAAT | 82 | 651 |
|  | R19 | AAACTAAACTACGC |  | 652 |
|  | P19 | CGGGTTATTGGACGGTGGAGTTCG |  | 536 |
| 313 | F1008 | ATTTGGGTAAATA | 81 | 653 |
|  | R19 | AAACTAAACTACGC |  | 654 |
|  | P19 | CGGGTTATTGGACGGTGGAGTTCG |  | 536 |
| 314 | F1009 | TTTGGGTAAATAG | 80 | 655 |
|  | R19 | AAACTAAACTACGC |  | 656 |
|  | P19 | CGGGTTATTGGACGGTGGAGTTCG |  | 536 |
| 315 | F1010 | TTGGGTAAATAGC | 130 | 657 |
|  | R20 | ACTACCTCCGCTAA |  | 658 |
|  | P20 | AGGTAGGGTTCGTTTATTCGGTGT |  | 659 |
| 316 | F1011 | TGGGTAAATAGCG | 129 | 660 |
|  | R20 | ACTACCTCCGCTAA |  | 661 |
|  | P20 | AGGTAGGGTTCGTTTATTCGGTGT |  | 659 |

TABLE 7-continued

Sequences of primer and probes for GPM6A gene qMSP

| Set | Primer | Sequence (5'→3') | Size of amplified product (bp) | Sequence No. |
|---|---|---|---|---|
| 317 | F1012 | TGGGTAAATAGCGT | 128 | 662 |
|  | R20 | ACTACCTCCGCTAA |  | 663 |
|  | P20 | AGGTAGGGTTCGTTTATTCGGTGT |  | 659 |
| 318 | F1013 | GGGTAAATAGCGTG | 127 | 664 |
|  | R20 | ACTACCTCCGCTAA |  | 665 |
|  | P20 | AGGTAGGGTTCGTTTATTCGGTGT |  | 659 |
| 319 | F1014 | GGTAAATAGCGTGA | 126 | 666 |
|  | R20 | ACTACCTCCGCTAA |  | 667 |
|  | P20 | AGGTAGGGTTCGTTTATTCGGTGT |  | 659 |
| 320 | F1015 | GTAAATAGCGTGAT | 125 | 668 |
|  | R20 | ACTACCTCCGCTAA |  | 669 |
|  | P20 | AGGTAGGGTTCGTTTATTCGGTGT |  | 659 |
| 321 | F1016 | TAAATAGCGTGATT | 124 | 670 |
|  | R20 | ACTACCTCCGCTAA |  | 671 |
|  | P20 | AGGTAGGGTTCGTTTATTCGGTGT |  | 659 |
| 322 | F1017 | AAATAGCGTGATTA | 123 | 672 |
|  | R20 | ACTACCTCCGCTAA |  | 673 |
|  | P20 | AGGTAGGGTTCGTTTATTCGGTGT |  | 659 |
| 323 | F1018 | AATAGCGTGATTAA | 122 | 674 |
|  | R20 | ACTACCTCCGCTAA |  | 675 |
|  | P20 | AGGTAGGGTTCGTTTATTCGGTGT |  | 659 |
| 324 | F1019 | ATAGCGTGATTAAA | 121 | 676 |
|  | R20 | ACTACCTCCGCTAA |  | 677 |
|  | P20 | AGGTAGGGTTCGTTTATTCGGTGT |  | 659 |
| 325 | F1020 | TAGCGTGATTAAAA | 120 | 678 |
|  | R20 | ACTACCTCCGCTAA |  | 679 |
|  | P20 | AGGTAGGGTTCGTTTATTCGGTGT |  | 659 |
| 326 | F1021 | AGCGTGATTAAAAG | 119 | 680 |
|  | R20 | ACTACCTCCGCTAA |  | 681 |
|  | P20 | AGGTAGGGTTCGTTTATTCGGTGT |  | 659 |
| 327 | F1022 | GCGTGATTAAAAGG | 118 | 682 |
|  | R20 | ACTACCTCCGCTAA |  | 683 |
|  | P20 | AGGTAGGGTTCGTTTATTCGGTGT |  | 659 |
| 328 | F1023 | CGTGATTAAAAGGG | 117 | 684 |
|  | R20 | ACTACCTCCGCTAA |  | 685 |
|  | P20 | AGGTAGGGTTCGTTTATTCGGTGT |  | 659 |
| 329 | F1024 | GTGATTAAAAGGGC | 116 | 686 |
|  | R20 | ACTACCTCCGCTAA |  | 687 |
|  | P20 | AGGTAGGGTTCGTTTATTCGGTGT |  | 659 |
| 330 | F1025 | TGATTAAAAGGGCG | 115 | 688 |
|  | R20 | ACTACCTCCGCTAA |  | 689 |
|  | P20 | AGGTAGGGTTCGTTTATTCGGTGT |  | 659 |
| 331 | F1026 | GATTAAAAGGGCGT | 114 | 690 |
|  | R20 | ACTACCTCCGCTAA |  | 691 |
|  | P20 | AGGTAGGGTTCGTTTATTCGGTGT |  | 659 |
| 332 | F1027 | ATTAAAAGGGCGTT | 113 | 692 |
|  | R20 | ACTACCTCCGCTAA |  | 693 |
|  | P20 | AGGTAGGGTTCGTTTATTCGGTGT |  | 659 |
| 333 | F1028 | TTAAAAGGGCGTTT | 112 | 694 |
|  | R20 | ACTACCTCCGCTAA |  | 695 |
|  | P20 | AGGTAGGGTTCGTTTATTCGGTGT |  | 659 |
| 334 | F1029 | TAAAAGGGCGTTTA | 111 | 696 |
|  | R20 | ACTACCTCCGCTAA |  | 697 |
|  | P20 | AGGTAGGGTTCGTTTATTCGGTGT |  | 659 |

TABLE 7-continued

Sequences of primer and probes for GPM6A gene qMSP

| Set | Primer | Sequence (5'→3') | Size of amplified product (bp) | Sequence No. |
|---|---|---|---|---|
| 335 | F1030 | AAAAGGGCGTTTAT | 110 | 698 |
|  | R20 | ACTACCTCCGCTAA |  | 699 |
|  | P20 | AGGTAGGGTTCGTTTATTCGGTGT |  | 659 |
| 336 | F1031 | AAAGGGCGTTTATA | 109 | 700 |
|  | R20 | ACTACCTCCGCTAA |  | 701 |
|  | P20 | AGGTAGGGTTCGTTTATTCGGTGT |  | 659 |
| 337 | F1032 | AAGGGCGTTTATAT | 108 | 702 |
|  | R20 | ACTACCTCCGCTAA |  | 703 |
|  | P20 | AGGTAGGGTTCGTTTATTCGGTGT |  | 659 |
| 338 | F1033 | AGGGCGTTTATATT | 107 | 704 |
|  | R20 | ACTACCTCCGCTAA |  | 705 |
|  | P20 | AGGTAGGGTTCGTTTATTCGGTGT |  | 659 |
| 339 | F1034 | GGGCGTTTATATTG | 106 | 706 |
|  | R20 | ACTACCTCCGCTAA |  | 707 |
|  | P20 | AGGTAGGGTTCGTTTATTCGGTGT |  | 659 |
| 340 | F1035 | GGCGTTTATATTGG | 105 | 708 |
|  | R20 | ACTACCTCCGCTAA |  | 709 |
|  | P20 | AGGTAGGGTTCGTTTATTCGGTGT |  | 659 |
| 341 | F1036 | GCGTTTATATTGGT | 104 | 710 |
|  | R20 | ACTACCTCCGCTAA |  | 711 |
|  | P20 | AGGTAGGGTTCGTTTATTCGGTGT |  | 659 |
| 342 | F1037 | CGTTTATATTGGTT | 103 | 712 |
|  | R20 | ACTACCTCCGCTAA |  | 713 |
|  | P20 | AGGTAGGGTTCGTTTATTCGGTGT |  | 659 |
| 343 | F1038 | GTTTATATTGGTTC | 102 | 714 |
|  | R20 | ACTACCTCCGCTAA |  | 715 |
|  | P20 | AGGTAGGGTTCGTTTATTCGGTGT |  | 659 |
| 344 | F1039 | TTTATATTGGTTCG | 101 | 716 |
|  | R20 | ACTACCTCCGCTAA |  | 717 |
|  | P20 | AGGTAGGGTTCGTTTATTCGGTGT |  | 659 |
| 345 | F1040 | TTATATTGGTTCGG | 100 | 718 |
|  | R20 | ACTACCTCCGCTAA |  | 719 |
|  | P20 | AGGTAGGGTTCGTTTATTCGGTGT |  | 659 |
| 346 | F1041 | TATATTGGTTCGGG | 99 | 720 |
|  | R20 | ACTACCTCCGCTAA |  | 721 |
|  | P20 | AGGTAGGGTTCGTTTATTCGGTGT |  | 659 |
| 347 | F1042 | ATATTGGTTCGGGT | 98 | 722 |
|  | R20 | ACTACCTCCGCTAA |  | 723 |
|  | P20 | AGGTAGGGTTCGTTTATTCGGTGT |  | 659 |
| 348 | F1043 | TATTGGTTCGGGTT | 97 | 724 |
|  | R20 | ACTACCTCCGCTAA |  | 725 |
|  | P20 | AGGTAGGGTTCGTTTATTCGGTGT |  | 659 |
| 349 | F1044 | ATTGGTTCGGGTTA | 96 | 726 |
|  | R20 | ACTACCTCCGCTAA |  | 727 |
|  | P20 | AGGTAGGGTTCGTTTATTCGGTGT |  | 659 |
| 350 | F1045 | TTGGTTCGGGTTAT | 95 | 728 |
|  | R20 | ACTACCTCCGCTAA |  | 729 |
|  | P20 | AGGTAGGGTTCGTTTATTCGGTGT |  | 659 |
| 351 | F1046 | TGGTTCGGGTTATT | 94 | 730 |
|  | R20 | ACTACCTCCGCTAA |  | 731 |
|  | P20 | AGGTAGGGTTCGTTTATTCGGTGT |  | 659 |
| 352 | F1047 | GGTTCGGGTTATTG | 93 | 732 |
|  | R20 | ACTACCTCCGCTAA |  | 733 |
|  | P20 | AGGTAGGGTTCGTTTATTCGGTGT |  | 659 |

TABLE 7-continued

Sequences of primer and probes for GPM6A gene qMSP

| Set | Primer | Sequence (5'→3') | Size of amplified product (bp) | Sequence No. |
|---|---|---|---|---|
| 353 | F1048 | GTTCGGGTTATTGG | 92 | 734 |
|  | R20 | ACTACCTCCGCTAA |  | 735 |
|  | P20 | AGGTAGGGTTCGTTTATTCGGTGT |  | 659 |
| 354 | F1049 | TTCGGGTTATTGGA | 91 | 736 |
|  | R20 | ACTACCTCCGCTAA |  | 737 |
|  | P20 | AGGTAGGGTTCGTTTATTCGGTGT |  | 659 |
| 355 | F1050 | TCGGGTTATTGGAC | 90 | 738 |
|  | R20 | ACTACCTCCGCTAA |  | 739 |
|  | P20 | AGGTAGGGTTCGTTTATTCGGTGT |  | 659 |
| 356 | F1051 | CGGGTTATTGGACG | 89 | 740 |
|  | R20 | ACTACCTCCGCTAA |  | 741 |
|  | P20 | AGGTAGGGTTCGTTTATTCGGTGT |  | 659 |
| 357 | F1052 | GGGTTATTGGACGG | 88 | 742 |
|  | R20 | ACTACCTCCGCTAA |  | 743 |
|  | P20 | AGGTAGGGTTCGTTTATTCGGTGT |  | 659 |
| 358 | F1053 | GGTTATTGGACGGT | 87 | 744 |
|  | R20 | ACTACCTCCGCTAA |  | 745 |
|  | P20 | AGGTAGGGTTCGTTTATTCGGTGT |  | 659 |
| 359 | F1054 | GTTATTGGACGGTG | 86 | 746 |
|  | R20 | ACTACCTCCGCTAA |  | 747 |
|  | P20 | AGGTAGGGTTCGTTTATTCGGTGT |  | 659 |
| 360 | F1055 | TTATTGGACGGTGG | 85 | 748 |
|  | R20 | ACTACCTCCGCTAA |  | 749 |
|  | P20 | AGGTAGGGTTCGTTTATTCGGTGT |  | 659 |
| 361 | F1056 | TATTGGACGGTGGA | 84 | 750 |
|  | R20 | ACTACCTCCGCTAA |  | 751 |
|  | P20 | AGGTAGGGTTCGTTTATTCGGTGT |  | 659 |
| 362 | F1057 | ATTGGACGGTGGAG | 83 | 752 |
|  | R20 | ACTACCTCCGCTAA |  | 753 |
|  | P20 | AGGTAGGGTTCGTTTATTCGGTGT |  | 659 |
| 363 | F1058 | TTGGACGGTGGAGT | 82 | 754 |
|  | R20 | ACTACCTCCGCTAA |  | 755 |
|  | P20 | AGGTAGGGTTCGTTTATTCGGTGT |  | 659 |
| 364 | F1059 | TGGACGGTGGAGTT | 81 | 756 |
|  | R20 | ACTACCTCCGCTAA |  | 757 |
|  | P20 | AGGTAGGGTTCGTTTATTCGGTGT |  | 659 |
| 365 | F1060 | GGACGGTGGAGTTC | 80 | 758 |
|  | R20 | ACTACCTCCGCTAA |  | 759 |
|  | P20 | AGGTAGGGTTCGTTTATTCGGTGT |  | 659 |
| 366 | F1061 | GACGGTGGAGTTCG | 120 | 760 |
|  | R21 | CCCCTCCGCCACAC |  | 761 |
|  | P21 | GGAATAGTTTTAGGAATGTGATTGC |  | 762 |
| 367 | F1062 | ACGGTGGAGTTCGG | 119 | 763 |
|  | R21 | CCCCTCCGCCACAC |  | 764 |
|  | P21 | GGAATAGTTTTAGGAATGTGATTGC |  | 762 |
| 368 | F1063 | CGGTGGAGTTCGGC | 118 | 765 |
|  | R21 | CCCCTCCGCCACAC |  | 766 |
|  | P21 | GGAATAGTTTTAGGAATGTGATTGC |  | 762 |
| 369 | F1064 | GGTGGAGTTCGGCG | 117 | 767 |
|  | R21 | CCCCTCCGCCACAC |  | 768 |
|  | P21 | GGAATAGTTTTAGGAATGTGATTGC |  | 762 |
| 370 | F1065 | GTGGAGTTCGGCGT | 116 | 769 |
|  | R21 | CCCCTCCGCCACAC |  | 770 |
|  | P21 | GGAATAGTTTTAGGAATGTGATTGC |  | 762 |

TABLE 7-continued

Sequences of primer and probes for GPM6A gene qMSP

| Set | Primer | Sequence (5'→3') | Size of amplified product (bp) | Sequence No. |
|---|---|---|---|---|
| 371 | F1066 | TGGAGTTCGGCGTA | 115 | 771 |
|  | R21 | CCCCTCCGCCACAC |  | 772 |
|  | P21 | GGAATAGTTTTAGGAATGTGATTGC |  | 762 |
| 372 | F1067 | GGAGTTCGGCGTAG | 114 | 773 |
|  | R21 | CCCCTCCGCCACAC |  | 774 |
|  | P21 | GGAATAGTTTTAGGAATGTGATTGC |  | 762 |
| 373 | F1068 | GAGTTCGGCGTAGT | 113 | 775 |
|  | R21 | CCCCTCCGCCACAC |  | 776 |
|  | P21 | GGAATAGTTTTAGGAATGTGATTGC |  | 762 |
| 374 | F1069 | AGTTCGGCGTAGTT | 112 | 777 |
|  | R21 | CCCCTCCGCCACAC |  | 778 |
|  | P21 | GGAATAGTTTTAGGAATGTGATTGC |  | 762 |
| 375 | F1070 | GTTCGGCGTAGTTT | 111 | 779 |
|  | R21 | CCCCTCCGCCACAC |  | 780 |
|  | P21 | GGAATAGTTTTAGGAATGTGATTGC |  | 762 |
| 376 | F1071 | TTCGGCGTAGTTTA | 110 | 781 |
|  | R21 | CCCCTCCGCCACAC |  | 782 |
|  | P21 | GGAATAGTTTTAGGAATGTGATTGC |  | 762 |
| 377 | F1072 | TCGGCGTAGTTTAG | 109 | 783 |
|  | R21 | CCCCTCCGCCACAC |  | 784 |
|  | P21 | GGAATAGTTTTAGGAATGTGATTGC |  | 762 |
| 378 | F1073 | CGGCGTAGTTTAGT | 108 | 785 |
|  | R21 | CCCCTCCGCCACAC |  | 786 |
|  | P21 | GGAATAGTTTTAGGAATGTGATTGC |  | 762 |
| 379 | F1074 | GGCGTAGTTTAGTT | 107 | 787 |
|  | R21 | CCCCTCCGCCACAC |  | 788 |
|  | P21 | GGAATAGTTTTAGGAATGTGATTGC |  | 762 |
| 380 | F1075 | GCGTAGTTTAGTTT | 106 | 789 |
|  | R21 | CCCCTCCGCCACAC |  | 790 |
|  | P21 | GGAATAGTTTTAGGAATGTGATTGC |  | 762 |
| 381 | F1076 | CGTAGTTTAGTTTC | 105 | 791 |
|  | R21 | CCCCTCCGCCACAC |  | 792 |
|  | P21 | GGAATAGTTTTAGGAATGTGATTGC |  | 762 |
| 382 | F1077 | GTAGTTTAGTTTCG | 104 | 793 |
|  | R21 | CCCCTCCGCCACAC |  | 794 |
|  | P21 | GGAATAGTTTTAGGAATGTGATTGC |  | 762 |
| 383 | F1078 | TAGTTTAGTTTCGT | 103 | 795 |
|  | R21 | CCCCTCCGCCACAC |  | 796 |
|  | P21 | GGAATAGTTTTAGGAATGTGATTGC |  | 762 |
| 384 | F1079 | AGTTTAGTTTCGTT | 102 | 797 |
|  | R21 | CCCCTCCGCCACAC |  | 798 |
|  | P21 | GGAATAGTTTTAGGAATGTGATTGC |  | 762 |
| 385 | F1080 | GTTTAGTTTCGTTT | 101 | 799 |
|  | R21 | CCCCTCCGCCACAC |  | 800 |
|  | P21 | GGAATAGTTTTAGGAATGTGATTGC |  | 762 |
| 386 | F1081 | TTTAGTTTCGTTTA | 100 | 801 |
|  | R21 | CCCCTCCGCCACAC |  | 802 |
|  | P21 | GGAATAGTTTTAGGAATGTGATTGC |  | 762 |
| 387 | F1082 | TTAGTTTCGTTTAA | 99 | 803 |
|  | R21 | CCCCTCCGCCACAC |  | 804 |
|  | P21 | GGAATAGTTTTAGGAATGTGATTGC |  | 762 |
| 388 | F1083 | TAGTTTCGTTTAAG | 98 | 805 |
|  | R21 | CCCCTCCGCCACAC |  | 806 |
|  | P21 | GGAATAGTTTTAGGAATGTGATTGC |  | 762 |

TABLE 7-continued

Sequences of primer and probes for GPM6A gene qMSP

| Set | Primer | Sequence (5'→3') | Size of amplified product (bp) | Sequence No. |
|---|---|---|---|---|
| 389 | F1084 | AGTTTCGTTTAAGT | 97 | 807 |
|  | R21 | CCCCTCCGCCACAC |  | 808 |
|  | P21 | GGAATAGTTTTAGGAATGTGATTGC |  | 762 |
| 390 | F1085 | GTTTCGTTTAAGTT | 96 | 809 |
|  | R21 | CCCCTCCGCCACAC |  | 810 |
|  | P21 | GGAATAGTTTTAGGAATGTGATTGC |  | 762 |
| 391 | F1086 | TTTCGTTTAAGTTT | 95 | 811 |
|  | R21 | CCCCTCCGCCACAC |  | 812 |
|  | P21 | GGAATAGTTTTAGGAATGTGATTGC |  | 762 |
| 392 | F1087 | TTCGTTTAAGTTTT | 94 | 813 |
|  | R21 | CCCCTCCGCCACAC |  | 814 |
|  | P21 | GGAATAGTTTTAGGAATGTGATTGC |  | 762 |
| 393 | F1088 | TCGTTTAAGTTTTT | 93 | 815 |
|  | R21 | CCCCTCCGCCACAC |  | 816 |
|  | P21 | GGAATAGTTTTAGGAATGTGATTGC |  | 762 |
| 394 | F1089 | CGTTTAAGTTTTTA | 92 | 817 |
|  | R21 | CCCCTCCGCCACAC |  | 818 |
|  | P21 | GGAATAGTTTTAGGAATGTGATTGC |  | 762 |
| 395 | F1090 | GTTTAAGTTTTTAG | 91 | 819 |
|  | R21 | CCCCTCCGCCACAC |  | 820 |
|  | P21 | GGAATAGTTTTAGGAATGTGATTGC |  | 762 |
| 396 | F1091 | TTTAAGTTTTTAGG | 90 | 821 |
|  | R21 | CCCCTCCGCCACAC |  | 822 |
|  | P21 | GGAATAGTTTTAGGAATGTGATTGC |  | 762 |
| 397 | F1092 | TTAAGTTTTTAGGT | 89 | 823 |
|  | R21 | CCCCTCCGCCACAC |  | 824 |
|  | P21 | GGAATAGTTTTAGGAATGTGATTGC |  | 762 |
| 398 | F1093 | TAAGTTTTTAGGTA | 88 | 825 |
|  | R21 | CCCCTCCGCCACAC |  | 826 |
|  | P21 | GGAATAGTTTTAGGAATGTGATTGC |  | 762 |
| 399 | F1094 | AAGTTTTTAGGTAG | 87 | 827 |
|  | R21 | CCCCTCCGCCACAC |  | 828 |
|  | P21 | GGAATAGTTTTAGGAATGTGATTGC |  | 762 |
| 400 | F1095 | AGTTTTTAGGTAGG | 86 | 829 |
|  | R21 | CCCCTCCGCCACAC |  | 830 |
|  | P21 | GGAATAGTTTTAGGAATGTGATTGC |  | 762 |
| 401 | F1096 | GTTTTTAGGTAGGG | 85 | 831 |
|  | R21 | CCCCTCCGCCACAC |  | 832 |
|  | P21 | GGAATAGTTTTAGGAATGTGATTGC |  | 762 |
| 402 | F1097 | TTTTTAGGTAGGGT | 84 | 833 |
|  | R21 | CCCCTCCGCCACAC |  | 834 |
|  | P21 | GGAATAGTTTTAGGAATGTGATTGC |  | 762 |
| 403 | F1098 | TTTTAGGTAGGGTT | 83 | 835 |
|  | R21 | CCCCTCCGCCACAC |  | 836 |
|  | P21 | GGAATAGTTTTAGGAATGTGATTGC |  | 762 |
| 404 | F1099 | TTTAGGTAGGGTTC | 82 | 837 |
|  | R21 | CCCCTCCGCCACAC |  | 838 |
|  | P21 | GGAATAGTTTTAGGAATGTGATTGC |  | 762 |
| 405 | F1100 | TTAGGTAGGGTTCG | 81 | 839 |
|  | R21 | CCCCTCCGCCACAC |  | 840 |
|  | P21 | GGAATAGTTTTAGGAATGTGATTGC |  | 762 |
| 406 | F1101 | TAGGTAGGGTTCGT | 80 | 841 |
|  | R21 | CCCCTCCGCCACAC |  | 842 |
|  | P21 | GGAATAGTTTTAGGAATGTGATTGC |  | 762 |

TABLE 7-continued

Sequences of primer and probes for GPM6A gene qMSP

| Set | Primer | Sequence (5'→3') | Size of amplified product (bp) | Sequence No. |
|---|---|---|---|---|
| 407 | F1102 | AGGTAGGGTTCGTT | 140 | 843 |
|  | R22 | TCGTAAAACCCTAC |  | 844 |
|  | P22 | TCGATTTATATTTAGTATTAGGAC |  | 845 |
| 408 | F1103 | GGTAGGGTTCGTTT | 139 | 846 |
|  | R22 | TCGTAAAACCCTAC |  | 847 |
|  | P22 | TCGATTTATATTTAGTATTAGGAC |  | 845 |
| 409 | F1104 | GTAGGGTTCGTTTA | 138 | 848 |
|  | R22 | TCGTAAAACCCTAC |  | 849 |
|  | P22 | TCGATTTATATTTAGTATTAGGAC |  | 845 |
| 410 | F1105 | TAGGGTTCGTTTAT | 137 | 850 |
|  | R22 | TCGTAAAACCCTAC |  | 851 |
|  | P22 | TCGATTTATATTTAGTATTAGGAC |  | 845 |
| 411 | F1106 | AGGGTTCGTTTATT | 136 | 852 |
|  | R22 | TCGTAAAACCCTAC |  | 853 |
|  | P22 | TCGATTTATATTTAGTATTAGGAC |  | 845 |
| 412 | F1107 | GGGTTCGTTTATTC | 135 | 854 |
|  | R22 | TCGTAAAACCCTAC |  | 855 |
|  | P22 | TCGATTTATATTTAGTATTAGGAC |  | 845 |
| 413 | F1108 | GGTTCGTTTATTCG | 134 | 856 |
|  | R22 | TCGTAAAACCCTAC |  | 857 |
|  | P22 | TCGATTTATATTTAGTATTAGGAC |  | 845 |
| 414 | F1109 | GTTCGTTTATTCGG | 133 | 858 |
|  | R22 | TCGTAAAACCCTAC |  | 859 |
|  | P22 | TCGATTTATATTTAGTATTAGGAC |  | 845 |
| 415 | F1110 | TTCGTTTATTCGGT | 132 | 860 |
|  | R22 | TCGTAAAACCCTAC |  | 861 |
|  | P22 | TCGATTTATATTTAGTATTAGGAC |  | 845 |
| 416 | F1111 | TCGTTTATTCGGTG | 131 | 862 |
|  | R22 | TCGTAAAACCCTAC |  | 863 |
|  | P22 | TCGATTTATATTTAGTATTAGGAC |  | 845 |
| 417 | F1112 | CGTTTATTCGGTGT | 130 | 864 |
|  | R22 | TCGTAAAACCCTAC |  | 865 |
|  | P22 | TCGATTTATATTTAGTATTAGGAC |  | 845 |
| 418 | F1113 | GTTTATTCGGTGTT | 129 | 866 |
|  | R22 | TCGTAAAACCCTAC |  | 867 |
|  | P22 | TCGATTTATATTTAGTATTAGGAC |  | 845 |
| 419 | F1114 | TTTATTCGGTGTTT | 128 | 868 |
|  | R22 | TCGTAAAACCCTAC |  | 869 |
|  | P22 | TCGATTTATATTTAGTATTAGGAC |  | 845 |
| 420 | F1115 | TTATTCGGTGTTTA | 127 | 870 |
|  | R22 | TCGTAAAACCCTAC |  | 871 |
|  | P22 | TCGATTTATATTTAGTATTAGGAC |  | 845 |
| 421 | F1116 | TATTCGGTGTTTAG | 126 | 872 |
|  | R22 | TCGTAAAACCCTAC |  | 873 |
|  | P22 | TCGATTTATATTTAGTATTAGGAC |  | 845 |
| 422 | F1117 | ATTCGGTGTTTAGC | 125 | 874 |
|  | R22 | TCGTAAAACCCTAC |  | 875 |
|  | P22 | TCGATTTATATTTAGTATTAGGAC |  | 845 |
| 423 | F1118 | TTCGGTGTTTAGCG | 124 | 876 |
|  | R22 | TCGTAAAACCCTAC |  | 877 |
|  | P22 | TCGATTTATATTTAGTATTAGGAC |  | 845 |
| 424 | F1119 | TCGGTGTTTAGCGG | 123 | 878 |
|  | R22 | TCGTAAAACCCTAC |  | 879 |
|  | P22 | TCGATTTATATTTAGTATTAGGAC |  | 845 |

TABLE 7-continued

Sequences of primer and probes for GPM6A gene qMSP

| Set | Primer | Sequence (5'→3') | Size of amplified product (bp) | Sequence No. |
|---|---|---|---|---|
| 425 | F1120 | CGGTGTTTAGCGGA | 122 | 880 |
|  | R22 | TCGTAAAACCCTAC |  | 881 |
|  | P22 | TCGATTTATATTTAGTATTAGGAC |  | 845 |
| 426 | F1121 | GGTGTTTAGCGGAG | 121 | 882 |
|  | R22 | TCGTAAAACCCTAC |  | 883 |
|  | P22 | TCGATTTATATTTAGTATTAGGAC |  | 845 |
| 427 | F1122 | GTGTTTAGCGGAGG | 120 | 884 |
|  | R22 | TCGTAAAACCCTAC |  | 885 |
|  | P22 | TCGATTTATATTTAGTATTAGGAC |  | 845 |
| 428 | F1123 | TGTTTAGCGGAGGT | 119 | 886 |
|  | R22 | TCGTAAAACCCTAC |  | 887 |
|  | P22 | TCGATTTATATTTAGTATTAGGAC |  | 845 |
| 429 | F1124 | GTTTAGCGGAGGTA | 118 | 888 |
|  | R22 | TCGTAAAACCCTAC |  | 889 |
|  | P22 | TCGATTTATATTTAGTATTAGGAC |  | 845 |
| 430 | F1125 | TTTAGCGGAGGTAG | 117 | 890 |
|  | R22 | TCGTAAAACCCTAC |  | 891 |
|  | P22 | TCGATTTATATTTAGTATTAGGAC |  | 845 |
| 431 | F1126 | TTAGCGGAGGTAGT | 116 | 892 |
|  | R22 | TCGTAAAACCCTAC |  | 893 |
|  | P22 | TCGATTTATATTTAGTATTAGGAC |  | 845 |
| 432 | F1127 | TAGCGGAGGTAGTT | 115 | 894 |
|  | R22 | TCGTAAAACCCTAC |  | 895 |
|  | P22 | TCGATTTATATTTAGTATTAGGAC |  | 845 |
| 433 | F1128 | AGCGGAGGTAGTTT | 114 | 896 |
|  | R22 | TCGTAAAACCCTAC |  | 897 |
|  | P22 | TCGATTTATATTTAGTATTAGGAC |  | 845 |
| 434 | F1129 | GCGGAGGTAGTTTG | 113 | 898 |
|  | R22 | TCGTAAAACCCTAC |  | 899 |
|  | P22 | TCGATTTATATTTAGTATTAGGAC |  | 845 |
| 435 | F1130 | CGGAGGTAGTTTGG | 112 | 900 |
|  | R22 | TCGTAAAACCCTAC |  | 901 |
|  | P22 | TCGATTTATATTTAGTATTAGGAC |  | 845 |
| 436 | F1131 | GGAGGTAGTTTGGA | 111 | 902 |
|  | R22 | TCGTAAAACCCTAC |  | 903 |
|  | P22 | TCGATTTATATTTAGTATTAGGAC |  | 845 |
| 437 | F1132 | GAGGTAGTTTGGAA | 110 | 904 |
|  | R22 | TCGTAAAACCCTAC |  | 905 |
|  | P22 | TCGATTTATATTTAGTATTAGGAC |  | 845 |
| 438 | F1133 | AGGTAGTTTGGAAT | 109 | 906 |
|  | R22 | TCGTAAAACCCTAC |  | 907 |
|  | P22 | TCGATTTATATTTAGTATTAGGAC |  | 845 |
| 439 | F1134 | GGTAGTTTGGAATA | 108 | 908 |
|  | R22 | TCGTAAAACCCTAC |  | 909 |
|  | P22 | TCGATTTATATTTAGTATTAGGAC |  | 845 |
| 440 | F1135 | GTAGTTTGGAATAG | 107 | 910 |
|  | R22 | TCGTAAAACCCTAC |  | 911 |
|  | P22 | TCGATTTATATTTAGTATTAGGAC |  | 845 |
| 441 | F1136 | TAGTTTGGAATAGT | 106 | 912 |
|  | R22 | TCGTAAAACCCTAC |  | 913 |
|  | P22 | TCGATTTATATTTAGTATTAGGAC |  | 845 |
| 442 | F1137 | AGTTTGGAATAGTT | 105 | 914 |
|  | R22 | TCGTAAAACCCTAC |  | 915 |
|  | P22 | TCGATTTATATTTAGTATTAGGAC |  | 845 |

TABLE 7-continued

Sequences of primer and probes for GPM6A gene qMSP

| Set | Primer | Sequence (5'→3') | Size of amplified product (bp) | Sequence No. |
|---|---|---|---|---|
| 443 | F1138 | GTTTGGAATAGTTTT | 104 | 916 |
|  | R22 | TCGTAAAACCCTAC |  | 917 |
|  | P22 | TCGATTTATATTTAGTATTAGGAC |  | 845 |
| 444 | F1139 | TTTGGAATAGTTTTA | 103 | 918 |
|  | R22 | TCGTAAAACCCTAC |  | 919 |
|  | P22 | TCGATTTATATTTAGTATTAGGAC |  | 845 |
| 445 | F1140 | TTGGAATAGTTTTAG | 102 | 920 |
|  | R22 | TCGTAAAACCCTAC |  | 921 |
|  | P22 | TCGATTTATATTTAGTATTAGGAC |  | 845 |
| 446 | F1141 | TGGAATAGTTTTAG | 101 | 922 |
|  | R22 | TCGTAAAACCCTAC |  | 923 |
|  | P22 | TCGATTTATATTTAGTATTAGGAC |  | 845 |
| 447 | F1142 | GGAATAGTTTTAGG | 100 | 924 |
|  | R22 | TCGTAAAACCCTAC |  | 925 |
|  | P22 | TCGATTTATATTTAGTATTAGGAC |  | 845 |
| 448 | F1143 | GAATAGTTTTAGGA | 99 | 926 |
|  | R22 | TCGTAAAACCCTAC |  | 927 |
|  | P22 | TCGATTTATATTTAGTATTAGGAC |  | 845 |
| 449 | F1144 | AATAGTTTTAGGAA | 98 | 928 |
|  | R22 | TCGTAAAACCCTAC |  | 929 |
|  | P22 | TCGATTTATATTTAGTATTAGGAC |  | 845 |
| 450 | F1145 | ATAGTTTTAGGAAT | 97 | 930 |
|  | R22 | TCGTAAAACCCTAC |  | 931 |
|  | P22 | TCGATTTATATTTAGTATTAGGAC |  | 845 |
| 451 | F1146 | TAGTTTTAGGAATG | 96 | 932 |
|  | R22 | TCGTAAAACCCTAC |  | 933 |
|  | P22 | TCGATTTATATTTAGTATTAGGAC |  | 845 |
| 452 | F1147 | AGTTTTAGGAATGT | 95 | 934 |
|  | R22 | TCGTAAAACCCTAC |  | 935 |
|  | P22 | TCGATTTATATTTAGTATTAGGAC |  | 845 |
| 453 | F1148 | GTTTTAGGAATGTG | 94 | 936 |
|  | R22 | TCGTAAAACCCTAC |  | 937 |
|  | P22 | TCGATTTATATTTAGTATTAGGAC |  | 845 |
| 454 | F1149 | TTTTAGGAATGTGA | 93 | 938 |
|  | R22 | TCGTAAAACCCTAC |  | 939 |
|  | P22 | TCGATTTATATTTAGTATTAGGAC |  | 845 |
| 455 | F1150 | TTTAGGAATGTGAT | 92 | 940 |
|  | R22 | TCGTAAAACCCTAC |  | 941 |
|  | P22 | TCGATTTATATTTAGTATTAGGAC |  | 845 |
| 456 | F1151 | TTAGGAATGTGATT | 91 | 942 |
|  | R22 | TCGTAAAACCCTAC |  | 943 |
|  | P22 | TCGATTTATATTTAGTATTAGGAC |  | 845 |
| 457 | F1152 | TAGGAATGTGATTG | 90 | 944 |
|  | R22 | TCGTAAAACCCTAC |  | 945 |
|  | P22 | TCGATTTATATTTAGTATTAGGAC |  | 845 |
| 458 | F1153 | AGGAATGTGATTGC | 89 | 946 |
|  | R22 | TCGTAAAACCCTAC |  | 947 |
|  | P22 | TCGATTTATATTTAGTATTAGGAC |  | 845 |
| 459 | F1154 | GGAATGTGATTGCG | 88 | 948 |
|  | R22 | TCGTAAAACCCTAC |  | 949 |
|  | P22 | TCGATTTATATTTAGTATTAGGAC |  | 845 |
| 460 | F1155 | GAATGTGATTGCGT | 87 | 950 |
|  | R22 | TCGTAAAACCCTAC |  | 951 |
|  | P22 | TCGATTTATATTTAGTATTAGGAC |  | 845 |

TABLE 7-continued

Sequences of primer and probes for GPM6A gene qMSP

| Set | Primer | Sequence (5'→3') | Size of amplified product (bp) | Sequence No. |
|---|---|---|---|---|
| 461 | F1156 | AATGTGATTGCGTG | 86 | 952 |
|  | R22 | TCGTAAAACCCTAC |  | 953 |
|  | P22 | TCGATTTATATTTAGTATTAGGAC |  | 845 |
| 462 | F1157 | ATGTGATTGCGTGT | 85 | 954 |
|  | R22 | TCGTAAAACCCTAC |  | 955 |
|  | P22 | TCGATTTATATTTAGTATTAGGAC |  | 845 |
| 463 | F1158 | TGTGATTGCGTGTG | 84 | 956 |
|  | R22 | TCGTAAAACCCTAC |  | 957 |
|  | P22 | TCGATTTATATTTAGTATTAGGAC |  | 845 |
| 464 | F1159 | GTGATTGCGTGTGG | 83 | 958 |
|  | R22 | TCGTAAAACCCTAC |  | 959 |
|  | P22 | TCGATTTATATTTAGTATTAGGAC |  | 845 |
| 465 | F1160 | TGATTGCGTGTGGC | 82 | 960 |
|  | R22 | TCGTAAAACCCTAC |  | 961 |
|  | P22 | TCGATTTATATTTAGTATTAGGAC |  | 845 |
| 466 | F1161 | GATTGCGTGTGGCG | 81 | 962 |
|  | R22 | TCGTAAAACCCTAC |  | 963 |
|  | P22 | TCGATTTATATTTAGTATTAGGAC |  | 845 |
| 467 | F1162 | ATTGCGTGTGGCGG | 80 | 964 |
|  | R22 | TCGTAAAACCCTAC |  | 965 |
|  | P22 | TCGATTTATATTTAGTATTAGGAC |  | 845 |
| 468 | F1163 | TTGCGTGTGGCGGA | 130 | 966 |
|  | R23 | AATAACGAATACTT |  | 967 |
|  | P23 | GAGCGAGGGAGAAGTTGGGGAGGAGA |  | 968 |
| 469 | F1164 | TGCGTGTGGCGGAG | 129 | 969 |
|  | R23 | AATAACGAATACTT |  | 970 |
|  | P23 | GAGCGAGGGAGAAGTTGGGGAGGAGA |  | 968 |
| 470 | F1165 | GCGTGTGGCGGAGG | 128 | 971 |
|  | R23 | AATAACGAATACTT |  | 972 |
|  | P23 | GAGCGAGGGAGAAGTTGGGGAGGAGA |  | 968 |
| 471 | F1166 | CGTGTGGCGGAGGG | 127 | 973 |
|  | R23 | AATAACGAATACTT |  | 974 |
|  | P23 | GAGCGAGGGAGAAGTTGGGGAGGAGA |  | 968 |
| 472 | F1167 | GTGTGGCGGAGGGG | 126 | 975 |
|  | R23 | AATAACGAATACTT |  | 976 |
|  | P23 | GAGCGAGGGAGAAGTTGGGGAGGAGA |  | 968 |
| 473 | F1168 | TGTGGCGGAGGGGA | 125 | 977 |
|  | R23 | AATAACGAATACTT |  | 978 |
|  | P23 | GAGCGAGGGAGAAGTTGGGGAGGAGA |  | 968 |
| 474 | F1169 | GTGGCGGAGGGGAG | 124 | 979 |
|  | R23 | AATAACGAATACTT |  | 980 |
|  | P23 | GAGCGAGGGAGAAGTTGGGGAGGAGA |  | 968 |
| 475 | F1170 | TGGCGGAGGGGAGG | 123 | 981 |
|  | R23 | AATAACGAATACTT |  | 982 |
|  | P23 | GAGCGAGGGAGAAGTTGGGGAGGAGA |  | 968 |
| 476 | F1171 | GGCGGAGGGGAGGA | 122 | 983 |
|  | R23 | AATAACGAATACTT |  | 984 |
|  | P23 | GAGCGAGGGAGAAGTTGGGGAGGAGA |  | 968 |
| 477 | F1172 | GCGGAGGGGAGGAA | 121 | 985 |
|  | R23 | AATAACGAATACTT |  | 986 |
|  | P23 | GAGCGAGGGAGAAGTTGGGGAGGAGA |  | 968 |
| 478 | F1173 | CGGAGGGGAGGAAG | 120 | 987 |
|  | R23 | AATAACGAATACTT |  | 988 |
|  | P23 | GAGCGAGGGAGAAGTTGGGGAGGAGA |  | 968 |

TABLE 7-continued

Sequences of primer and probes for GPM6A gene qMSP

| Set | Primer | Sequence (5'→3') | Size of amplified product (bp) | Sequence No. |
|---|---|---|---|---|
| 479 | F1174 | GGAGGGGAGGAAGA | 119 | 989 |
|  | R23 | AATAACGAATACTT |  | 990 |
|  | P23 | GAGCGAGGGAGAAGTTGGGGAGGAGA |  | 968 |
| 480 | F1175 | GAGGGGAGGAAGAA | 118 | 991 |
|  | R23 | AATAACGAATACTT |  | 992 |
|  | P23 | GAGCGAGGGAGAAGTTGGGGAGGAGA |  | 968 |
| 481 | F1176 | AGGGGAGGAAGAAT | 117 | 993 |
|  | R23 | AATAACGAATACTT |  | 994 |
|  | P23 | GAGCGAGGGAGAAGTTGGGGAGGAGA |  | 968 |
| 482 | F1177 | GGGGAGGAAGAATT | 116 | 995 |
|  | R23 | AATAACGAATACTT |  | 996 |
|  | P23 | GAGCGAGGGAGAAGTTGGGGAGGAGA |  | 968 |
| 483 | F1178 | GGGAGGAAGAATTG | 115 | 997 |
|  | R23 | AATAACGAATACTT |  | 998 |
|  | P23 | GAGCGAGGGAGAAGTTGGGGAGGAGA |  | 968 |
| 484 | F1179 | GGAGGAAGAATTGG | 114 | 999 |
|  | R23 | AATAACGAATACTT |  | 1000 |
|  | P23 | GAGCGAGGGAGAAGTTGGGGAGGAGA |  | 968 |
| 485 | F1180 | GAGGAAGAATTGGG | 113 | 1001 |
|  | R23 | AATAACGAATACTT |  | 1002 |
|  | P23 | GAGCGAGGGAGAAGTTGGGGAGGAGA |  | 968 |
| 486 | F1181 | AGGAAGAATTGGGT | 112 | 1003 |
|  | R23 | AATAACGAATACTT |  | 1004 |
|  | P23 | GAGCGAGGGAGAAGTTGGGGAGGAGA |  | 968 |
| 487 | F1182 | GGAAGAATTGGGTG | 111 | 1005 |
|  | R23 | AATAACGAATACTT |  | 1006 |
|  | P23 | GAGCGAGGGAGAAGTTGGGGAGGAGA |  | 968 |
| 488 | F1183 | GAAGAATTGGGTGT | 110 | 1007 |
|  | R23 | AATAACGAATACTT |  | 1008 |
|  | P23 | GAGCGAGGGAGAAGTTGGGGAGGAGA |  | 968 |
| 489 | F1184 | AAGAATTGGGTGTG | 109 | 1009 |
|  | R23 | AATAACGAATACTT |  | 1010 |
|  | P23 | GAGCGAGGGAGAAGTTGGGGAGGAGA |  | 968 |
| 490 | F1185 | AGAATTGGGTGTGA | 108 | 1011 |
|  | R23 | AATAACGAATACTT |  | 1012 |
|  | P23 | GAGCGAGGGAGAAGTTGGGGAGGAGA |  | 968 |
| 491 | F1186 | GAATTGGGTGTGAA | 107 | 1013 |
|  | R23 | AATAACGAATACTT |  | 1014 |
|  | P23 | GAGCGAGGGAGAAGTTGGGGAGGAGA |  | 968 |
| 492 | F1187 | AATTGGGTGTGAAA | 106 | 1015 |
|  | R23 | AATAACGAATACTT |  | 1016 |
|  | P23 | GAGCGAGGGAGAAGTTGGGGAGGAGA |  | 968 |
| 493 | F1188 | ATTGGGTGTGAAAT | 105 | 1017 |
|  | R23 | AATAACGAATACTT |  | 1018 |
|  | P23 | GAGCGAGGGAGAAGTTGGGGAGGAGA |  | 968 |
| 494 | F1189 | TTGGGTGTGAAATA | 104 | 1019 |
|  | R23 | AATAACGAATACTT |  | 1020 |
|  | P23 | GAGCGAGGGAGAAGTTGGGGAGGAGA |  | 968 |
| 495 | F1190 | TGGGTGTGAAATAG | 103 | 1021 |
|  | R23 | AATAACGAATACTT |  | 1022 |
|  | P23 | GAGCGAGGGAGAAGTTGGGGAGGAGA |  | 968 |
| 496 | F1191 | GGGTGTGAAATAGT | 102 | 1023 |
|  | R23 | AATAACGAATACTT |  | 1024 |
|  | P23 | GAGCGAGGGAGAAGTTGGGGAGGAGA |  | 968 |

TABLE 7-continued

Sequences of primer and probes for GPM6A gene qMSP

| Set | Primer | Sequence (5'→3') | Size of amplified product (bp) | Sequence No. |
|---|---|---|---|---|
| 497 | F1192 | GGTGTGAAATAGTC | 101 | 1025 |
|  | R23 | AATAACGAATACTT |  | 1026 |
|  | P23 | GAGCGAGGGAGAAGTTGGGGAGGAGA |  | 968 |
| 498 | F1193 | GTGTGAAATAGTCG | 100 | 1027 |
|  | R23 | AATAACGAATACTT |  | 1028 |
|  | P23 | GAGCGAGGGAGAAGTTGGGGAGGAGA |  | 968 |
| 499 | F1194 | TGTGAAATAGTCGA | 99 | 1029 |
|  | R23 | AATAACGAATACTT |  | 1030 |
|  | P23 | GAGCGAGGGAGAAGTTGGGGAGGAGA |  | 968 |
| 500 | F1195 | GTGAAATAGTCGAT | 98 | 1031 |
|  | R23 | AATAACGAATACTT |  | 1032 |
|  | P23 | GAGCGAGGGAGAAGTTGGGGAGGAGA |  | 968 |
| 501 | F1196 | TGAAATAGTCGATT | 97 | 1033 |
|  | R23 | AATAACGAATACTT |  | 1034 |
|  | P23 | GAGCGAGGGAGAAGTTGGGGAGGAGA |  | 968 |
| 502 | F1197 | GAAATAGTCGATTT | 96 | 1035 |
|  | R23 | AATAACGAATACTT |  | 1036 |
|  | P23 | GAGCGAGGGAGAAGTTGGGGAGGAGA |  | 968 |
| 503 | F1198 | AAATAGTCGATTTA | 95 | 1037 |
|  | R23 | AATAACGAATACTT |  | 1038 |
|  | P23 | GAGCGAGGGAGAAGTTGGGGAGGAGA |  | 968 |
| 504 | F1199 | AATAGTCGATTTAT | 94 | 1039 |
|  | R23 | AATAACGAATACTT |  | 1040 |
|  | P23 | GAGCGAGGGAGAAGTTGGGGAGGAGA |  | 968 |
| 505 | F1200 | ATAGTCGATTTATA | 93 | 1041 |
|  | R23 | AATAACGAATACTT |  | 1042 |
|  | P23 | GAGCGAGGGAGAAGTTGGGGAGGAGA |  | 968 |
| 506 | F1201 | TAGTCGATTTATAT | 92 | 1043 |
|  | R23 | AATAACGAATACTT |  | 1044 |
|  | P23 | GAGCGAGGGAGAAGTTGGGGAGGAGA |  | 968 |
| 507 | F1202 | AGTCGATTTATATT | 91 | 1045 |
|  | R23 | AATAACGAATACTT |  | 1046 |
|  | P23 | GAGCGAGGGAGAAGTTGGGGAGGAGA |  | 968 |
| 508 | F1203 | GTCGATTTATATTT | 90 | 1047 |
|  | R23 | AATAACGAATACTT |  | 1048 |
|  | P23 | GAGCGAGGGAGAAGTTGGGGAGGAGA |  | 968 |
| 509 | F1204 | TCGATTTATATTTA | 89 | 1049 |
|  | R23 | AATAACGAATACTT |  | 1050 |
|  | P23 | GAGCGAGGGAGAAGTTGGGGAGGAGA |  | 968 |
| 510 | F1205 | CGATTTATATTTAG | 88 | 1051 |
|  | R23 | AATAACGAATACTT |  | 1052 |
|  | P23 | GAGCGAGGGAGAAGTTGGGGAGGAGA |  | 968 |
| 511 | F1206 | GATTTATATTTAGT | 87 | 1053 |
|  | R23 | AATAACGAATACTT |  | 1054 |
|  | P23 | GAGCGAGGGAGAAGTTGGGGAGGAGA |  | 968 |
| 512 | F1207 | ATTTATATTTAGTA | 86 | 1055 |
|  | R23 | AATAACGAATACTT |  | 1056 |
|  | P23 | GAGCGAGGGAGAAGTTGGGGAGGAGA |  | 968 |
| 513 | F1208 | TTTATATTTAGTAT | 85 | 1057 |
|  | R23 | AATAACGAATACTT |  | 1058 |
|  | P23 | GAGCGAGGGAGAAGTTGGGGAGGAGA |  | 968 |
| 514 | F1209 | TTATATTTAGTATT | 84 | 1059 |
|  | R23 | AATAACGAATACTT |  | 1060 |
|  | P23 | GAGCGAGGGAGAAGTTGGGGAGGAGA |  | 968 |

TABLE 7-continued

Sequences of primer and probes for GPM6A gene qMSP

| Set | Primer | Sequence (5'→3') | Size of amplified product (bp) | Sequence No. |
|---|---|---|---|---|
| 515 | F1210 | TATATTTAGTATTA | 83 | 1061 |
|  | R23 | AATAACGAATACTT |  | 1062 |
|  | P23 | GAGCGAGGGAGAAGTTGGGGAGGAGA |  | 968 |
| 516 | F1211 | ATATTTAGTATTAG | 82 | 1063 |
|  | R23 | AATAACGAATACTT |  | 1064 |
|  | P23 | GAGCGAGGGAGAAGTTGGGGAGGAGA |  | 968 |
| 517 | F1212 | TATTTAGTATTAGG | 81 | 1065 |
|  | R23 | AATAACGAATACTT |  | 1066 |
|  | P23 | GAGCGAGGGAGAAGTTGGGGAGGAGA |  | 968 |
| 518 | F1213 | ATTTAGTATTAGGA | 80 | 1067 |
|  | R23 | AATAACGAATACTT |  | 1068 |
|  | P23 | GAGCGAGGGAGAAGTTGGGGAGGAGA |  | 968 |
| 519 | F1214 | TTTAGTATTAGGAC | 140 | 1069 |
|  | R24 | CGCAATCGACAACC |  | 1070 |
|  | P24 | GTAGGGGAGATGTTGTTTTTCGC |  | 1071 |
| 520 | F1215 | TTAGTATTAGGACG | 139 | 1072 |
|  | R24 | CGCAATCGACAACC |  | 1073 |
|  | P24 | GTAGGGGAGATGTTGTTTTTCGC |  | 1071 |
| 521 | F1216 | TAGTATTAGGACGT | 138 | 1074 |
|  | R24 | CGCAATCGACAACC |  | 1075 |
|  | P24 | GTAGGGGAGATGTTGTTTTTCGC |  | 1071 |
| 522 | F1217 | AGTATTAGGACGTA | 137 | 1076 |
|  | R24 | CGCAATCGACAACC |  | 1077 |
|  | P24 | GTAGGGGAGATGTTGTTTTTCGC |  | 1071 |
| 523 | F1218 | GTATTAGGACGTAG | 136 | 1078 |
|  | R24 | CGCAATCGACAACC |  | 1079 |
|  | P24 | GTAGGGGAGATGTTGTTTTTCGC |  | 1071 |
| 524 | F1219 | TATTAGGACGTAGG | 135 | 1080 |
|  | R24 | CGCAATCGACAACC |  | 1081 |
|  | P24 | GTAGGGGAGATGTTGTTTTTCGC |  | 1071 |
| 525 | F1220 | ATTAGGACGTAGGG | 134 | 1082 |
|  | R24 | CGCAATCGACAACC |  | 1083 |
|  | P24 | GTAGGGGAGATGTTGTTTTTCGC |  | 1071 |
| 526 | F1221 | TTAGGACGTAGGGT | 133 | 1084 |
|  | R24 | CGCAATCGACAACC |  | 1085 |
|  | P24 | GTAGGGGAGATGTTGTTTTTCGC |  | 1071 |
| 527 | F1222 | TAGGACGTAGGGTT | 132 | 1086 |
|  | R24 | CGCAATCGACAACC |  | 1087 |
|  | P24 | GTAGGGGAGATGTTGTTTTTCGC |  | 1071 |
| 528 | F1223 | AGGACGTAGGGTTT | 131 | 1088 |
|  | R24 | CGCAATCGACAACC |  | 1089 |
|  | P24 | GTAGGGGAGATGTTGTTTTTCGC |  | 1071 |
| 529 | F1224 | GGACGTAGGGTTTT | 130 | 1090 |
|  | R24 | CGCAATCGACAACC |  | 1091 |
|  | P24 | GTAGGGGAGATGTTGTTTTTCGC |  | 1071 |
| 530 | F1225 | GACGTAGGGTTTTA | 129 | 1092 |
|  | R24 | CGCAATCGACAACC |  | 1093 |
|  | P24 | GTAGGGGAGATGTTGTTTTTCGC |  | 1071 |
| 531 | F1226 | ACGTAGGGTTTTAC | 128 | 1094 |
|  | R24 | CGCAATCGACAACC |  | 1095 |
|  | P24 | GTAGGGGAGATGTTGTTTTTCGC |  | 1071 |
| 532 | F1227 | CGTAGGGTTTTACG | 127 | 1096 |
|  | R24 | CGCAATCGACAACC |  | 1097 |
|  | P24 | GTAGGGGAGATGTTGTTTTTCGC |  | 1071 |

TABLE 7-continued

Sequences of primer and probes for GPM6A gene qMSP

| Set | Primer | Sequence (5'→3') | Size of amplified product (bp) | Sequence No. |
|---|---|---|---|---|
| 533 | F1228 | GTAGGGTTTTACGA | 126 | 1098 |
|  | R24 | CGCAATCGACAACC |  | 1099 |
|  | P24 | GTAGGGGAGATGTTGTTTTTCGC |  | 1071 |
| 534 | F1229 | TAGGGTTTTACGAG | 125 | 1100 |
|  | R24 | CGCAATCGACAACC |  | 1101 |
|  | P24 | GTAGGGGAGATGTTGTTTTTCGC |  | 1071 |
| 535 | F1230 | AGGGTTTTACGAGT | 124 | 1102 |
|  | R24 | CGCAATCGACAACC |  | 1103 |
|  | P24 | GTAGGGGAGATGTTGTTTTTCGC |  | 1071 |
| 536 | F1231 | GGGTTTTACGAGTT | 123 | 1104 |
|  | R24 | CGCAATCGACAACC |  | 1105 |
|  | P24 | GTAGGGGAGATGTTGTTTTTCGC |  | 1071 |
| 537 | F1232 | GGTTTTACGAGTTA | 122 | 1106 |
|  | R24 | CGCAATCGACAACC |  | 1107 |
|  | P24 | GTAGGGGAGATGTTGTTTTTCGC |  | 1071 |
| 538 | F1233 | GTTTTACGAGTTAT | 121 | 1108 |
|  | R24 | CGCAATCGACAACC |  | 1109 |
|  | P24 | GTAGGGGAGATGTTGTTTTTCGC |  | 1071 |
| 539 | F1234 | TTTTACGAGTTATT | 120 | 1110 |
|  | R24 | CGCAATCGACAACC |  | 1111 |
|  | P24 | GTAGGGGAGATGTTGTTTTTCGC |  | 1071 |
| 540 | F1235 | TTTACGAGTTATTT | 119 | 1112 |
|  | R24 | CGCAATCGACAACC |  | 1113 |
|  | P24 | GTAGGGGAGATGTTGTTTTTCGC |  | 1071 |
| 541 | F1236 | TTACGAGTTATTTC | 118 | 1114 |
|  | R24 | CGCAATCGACAACC |  | 1115 |
|  | P24 | GTAGGGGAGATGTTGTTTTTCGC |  | 1071 |
| 542 | F1237 | TACGAGTTATTTCG | 117 | 1116 |
|  | R24 | CGCAATCGACAACC |  | 1117 |
|  | P24 | GTAGGGGAGATGTTGTTTTTCGC |  | 1071 |
| 543 | F1238 | ACGAGTTATTTCGA | 116 | 1118 |
|  | R24 | CGCAATCGACAACC |  | 1119 |
|  | P24 | GTAGGGGAGATGTTGTTTTTCGC |  | 1071 |
| 544 | F1239 | CGAGTTATTTCGAA | 115 | 1120 |
|  | R24 | CGCAATCGACAACC |  | 1121 |
|  | P24 | GTAGGGGAGATGTTGTTTTTCGC |  | 1071 |
| 545 | F1240 | GAGTTATTTCGAAG | 114 | 1122 |
|  | R24 | CGCAATCGACAACC |  | 1123 |
|  | P24 | GTAGGGGAGATGTTGTTTTTCGC |  | 1071 |
| 546 | F1241 | AGTTATTTCGAAGA | 113 | 1124 |
|  | R24 | CGCAATCGACAACC |  | 1125 |
|  | P24 | GTAGGGGAGATGTTGTTTTTCGC |  | 1071 |
| 547 | F1242 | GTTATTTCGAAGAG | 112 | 1126 |
|  | R24 | CGCAATCGACAACC |  | 1127 |
|  | P24 | GTAGGGGAGATGTTGTTTTTCGC |  | 1071 |
| 548 | F1243 | TTATTTCGAAGAGC | 111 | 1128 |
|  | R24 | CGCAATCGACAACC |  | 1129 |
|  | P24 | GTAGGGGAGATGTTGTTTTTCGC |  | 1071 |
| 549 | F1244 | TATTTCGAAGAGCG | 110 | 1130 |
|  | R24 | CGCAATCGACAACC |  | 1131 |
|  | P24 | GTAGGGGAGATGTTGTTTTTCGC |  | 1071 |
| 550 | F1245 | ATTTCGAAGAGCGA | 109 | 1132 |
|  | R24 | CGCAATCGACAACC |  | 1133 |
|  | P24 | GTAGGGGAGATGTTGTTTTTCGC |  | 1071 |

TABLE 7-continued

Sequences of primer and probes for GPM6A gene qMSP

| Set | Primer | Sequence (5'→3') | Size of amplified product (bp) | Sequence No. |
|---|---|---|---|---|
| 551 | F1246 | TTTCGAAGAGCGAG | 108 | 1134 |
| | R24 | CGCAATCGACAACC | | 1135 |
| | P24 | GTAGGGGAGATGTTGTTTTTCGC | | 1071 |
| 552 | F1247 | TTCGAAGAGCGAGG | 107 | 1136 |
| | R24 | CGCAATCGACAACC | | 1137 |
| | P24 | GTAGGGGAGATGTTGTTTTTCGC | | 1071 |
| 553 | F1248 | TCGAAGAGCGAGGG | 106 | 1138 |
| | R24 | CGCAATCGACAACC | | 1139 |
| | P24 | GTAGGGGAGATGTTGTTTTTCGC | | 1071 |
| 554 | F1249 | CGAAGAGCGAGGGA | 105 | 1140 |
| | R24 | CGCAATCGACAACC | | 1141 |
| | P24 | GTAGGGGAGATGTTGTTTTTCGC | | 1071 |
| 555 | F1250 | GAAGAGCGAGGGAG | 104 | 1142 |
| | R24 | CGCAATCGACAACC | | 1143 |
| | P24 | GTAGGGGAGATGTTGTTTTTCGC | | 1071 |
| 556 | F1251 | AAGAGCGAGGGAGA | 103 | 1144 |
| | R24 | CGCAATCGACAACC | | 1145 |
| | P24 | GTAGGGGAGATGTTGTTTTTCGC | | 1071 |
| 557 | F1252 | AGAGCGAGGGAGAA | 102 | 1146 |
| | R24 | CGCAATCGACAACC | | 1147 |
| | P24 | GTAGGGGAGATGTTGTTTTTCGC | | 1071 |
| 558 | F1253 | GAGCGAGGGAGAAG | 101 | 1148 |
| | R24 | CGCAATCGACAACC | | 1149 |
| | P24 | GTAGGGGAGATGTTGTTTTTCGC | | 1071 |
| 559 | F1254 | AGCGAGGGAGAAGT | 100 | 1150 |
| | R24 | CGCAATCGACAACC | | 1151 |
| | P24 | GTAGGGGAGATGTTGTTTTTCGC | | 1071 |
| 560 | F1255 | GCGAGGGAGAAGTT | 99 | 1152 |
| | R24 | CGCAATCGACAACC | | 1153 |
| | P24 | GTAGGGGAGATGTTGTTTTTCGC | | 1071 |
| 561 | F1256 | CGAGGGAGAAGTTG | 98 | 1154 |
| | R24 | CGCAATCGACAACC | | 1155 |
| | P24 | GTAGGGGAGATGTTGTTTTTCGC | | 1071 |
| 562 | F1257 | GAGGGAGAAGTTGG | 97 | 1156 |
| | R24 | CGCAATCGACAACC | | 1157 |
| | P24 | GTAGGGGAGATGTTGTTTTTCGC | | 1071 |
| 563 | F1258 | AGGGAGAAGTTGGG | 96 | 1158 |
| | R24 | CGCAATCGACAACC | | 1159 |
| | P24 | GTAGGGGAGATGTTGTTTTTCGC | | 1071 |
| 564 | F1259 | GGGAGAAGTTGGGG | 95 | 1160 |
| | R24 | CGCAATCGACAACC | | 1161 |
| | P24 | GTAGGGGAGATGTTGTTTTTCGC | | 1071 |
| 565 | F1260 | GGAGAAGTTGGGGA | 94 | 1162 |
| | R24 | CGCAATCGACAACC | | 1163 |
| | P24 | GTAGGGGAGATGTTGTTTTTCGC | | 1071 |
| 566 | F1261 | GAGAAGTTGGGGAG | 93 | 1164 |
| | R24 | CGCAATCGACAACC | | 1165 |
| | P24 | GTAGGGGAGATGTTGTTTTTCGC | | 1071 |
| 567 | F1262 | AGAAGTTGGGGAGG | 92 | 1166 |
| | R24 | CGCAATCGACAACC | | 1167 |
| | P24 | GTAGGGGAGATGTTGTTTTTCGC | | 1071 |
| 568 | F1263 | GAAGTTGGGGAGGA | 91 | 1168 |
| | R24 | CGCAATCGACAACC | | 1169 |
| | P24 | GTAGGGGAGATGTTGTTTTTCGC | | 1071 |

TABLE 7-continued

Sequences of primer and probes for GPM6A gene qMSP

| Set | Primer | Sequence (5'→3') | Size of amplified product (bp) | Sequence No. |
|---|---|---|---|---|
| 569 | F1264 | AAGTTGGGGAGGAG | 90 | 1170 |
| | R24 | CGCAATCGACAACC | | 1171 |
| | P24 | GTAGGGGAGATGTTGTTTTTCGC | | 1071 |
| 570 | F1265 | AGTTGGGGAGGAGA | 89 | 1172 |
| | R24 | CGCAATCGACAACC | | 1173 |
| | P24 | GTAGGGGAGATGTTGTTTTTCGC | | 1071 |
| 571 | F1266 | GTTGGGGAGGAGAA | 88 | 1174 |
| | R24 | CGCAATCGACAACC | | 1175 |
| | P24 | GTAGGGGAGATGTTGTTTTTCGC | | 1071 |
| 572 | F1267 | TTGGGGAGGAGAAA | 87 | 1176 |
| | R24 | CGCAATCGACAACC | | 1177 |
| | P24 | GTAGGGGAGATGTTGTTTTTCGC | | 1071 |
| 573 | F1268 | TGGGGAGGAGAAAG | 86 | 1178 |
| | R24 | CGCAATCGACAACC | | 1179 |
| | P24 | GTAGGGGAGATGTTGTTTTTCGC | | 1071 |
| 574 | F1269 | GGGGAGGAGAAAGT | 85 | 1180 |
| | R24 | CGCAATCGACAACC | | 1181 |
| | P24 | GTAGGGGAGATGTTGTTTTTCGC | | 1071 |
| 575 | F1270 | GGGAGGAGAAAGTA | 84 | 1182 |
| | R24 | CGCAATCGACAACC | | 1183 |
| | P24 | GTAGGGGAGATGTTGTTTTTCGC | | 1071 |
| 576 | F1271 | GGAGGAGAAAGTAT | 83 | 1184 |
| | R24 | CGCAATCGACAACC | | 1185 |
| | P24 | GTAGGGGAGATGTTGTTTTTCGC | | 1071 |
| 577 | F1272 | GAGGAGAAAGTATT | 82 | 1186 |
| | R24 | CGCAATCGACAACC | | 1187 |
| | P24 | GTAGGGGAGATGTTGTTTTTCGC | | 1071 |
| 578 | F1273 | AGGAGAAAGTATTC | 81 | 1188 |
| | R24 | CGCAATCGACAACC | | 1189 |
| | P24 | GTAGGGGAGATGTTGTTTTTCGC | | 1071 |
| 579 | F1274 | GGAGAAAGTATTCG | 80 | 1190 |
| | R24 | CGCAATCGACAACC | | 1191 |
| | P24 | GTAGGGGAGATGTTGTTTTTCGC | | 1071 |
| 580 | F1275 | GAGAAAGTATTCGT | 120 | 1192 |
| | R25 | ACGAACTAAAATTA | | 1193 |
| | P25 | AGTTCGTAGTTCGAGTTATTTTT | | 1194 |
| 581 | F1276 | AGAAAGTATTCGTT | 119 | 1195 |
| | R25 | ACGAACTAAAATTA | | 1196 |
| | P25 | AGTTCGTAGTTCGAGTTATTTTT | | 1194 |
| 582 | F1277 | GAAAGTATTCGTTA | 118 | 1197 |
| | R25 | ACGAACTAAAATTA | | 1198 |
| | P25 | AGTTCGTAGTTCGAGTTATTTTT | | 1194 |
| 583 | F1278 | AAAGTATTCGTTAT | 117 | 1199 |
| | R25 | ACGAACTAAAATTA | | 1200 |
| | P25 | AGTTCGTAGTTCGAGTTATTTTT | | 1194 |
| 584 | F1279 | AAGTATTCGTTATT | 116 | 1201 |
| | R25 | ACGAACTAAAATTA | | 1202 |
| | P25 | AGTTCGTAGTTCGAGTTATTTTT | | 1194 |
| 585 | F1280 | AGTATTCGTTATTT | 115 | 1203 |
| | R25 | ACGAACTAAAATTA | | 1204 |
| | P25 | AGTTCGTAGTTCGAGTTATTTTT | | 1194 |
| 586 | F1281 | GTATTCGTTATTTT | 114 | 1205 |
| | R25 | ACGAACTAAAATTA | | 1206 |
| | P25 | AGTTCGTAGTTCGAGTTATTTTT | | 1194 |

TABLE 7-continued

Sequences of primer and probes for GPM6A gene qMSP

| Set | Primer | Sequence (5'→3') | Size of amplified product (bp) | Sequence No. |
|---|---|---|---|---|
| 587 | F1282 | TATTCGTTATTTTT | 113 | 1207 |
|  | R25 | ACGAACTAAAATTA |  | 1208 |
|  | P25 | AGTTCGTAGTTCGAGTTATTTTTT |  | 1194 |
| 588 | F1283 | ATTCGTTATTTTTG | 112 | 1209 |
|  | R25 | ACGAACTAAAATTA |  | 1210 |
|  | P25 | AGTTCGTAGTTCGAGTTATTTTTT |  | 1194 |
| 589 | F1284 | TTCGTTATTTTTGG | 111 | 1211 |
|  | R25 | ACGAACTAAAATTA |  | 1212 |
|  | P25 | AGTTCGTAGTTCGAGTTATTTTTT |  | 1194 |
| 590 | F1285 | TCGTTATTTTTGGA | 110 | 1213 |
|  | R25 | ACGAACTAAAATTA |  | 1214 |
|  | P25 | AGTTCGTAGTTCGAGTTATTTTTT |  | 1194 |
| 591 | F1286 | CGTTATTTTTGGAT | 109 | 1215 |
|  | R25 | ACGAACTAAAATTA |  | 1216 |
|  | P25 | AGTTCGTAGTTCGAGTTATTTTTT |  | 1194 |
| 592 | F1287 | GTTATTTTTGGATT | 108 | 1217 |
|  | R25 | ACGAACTAAAATTA |  | 1218 |
|  | P25 | AGTTCGTAGTTCGAGTTATTTTTT |  | 1194 |
| 593 | F1288 | TTATTTTTGGATTG | 107 | 1219 |
|  | R25 | ACGAACTAAAATTA |  | 1220 |
|  | P25 | AGTTCGTAGTTCGAGTTATTTTTT |  | 1194 |
| 594 | F1289 | TATTTTTGGATTGG | 106 | 1221 |
|  | R25 | ACGAACTAAAATTA |  | 1222 |
|  | P25 | AGTTCGTAGTTCGAGTTATTTTTT |  | 1194 |
| 595 | F1290 | ATTTTTGGATTGGC | 105 | 1223 |
|  | R25 | ACGAACTAAAATTA |  | 1224 |
|  | P25 | AGTTCGTAGTTCGAGTTATTTTTT |  | 1194 |
| 596 | F1291 | TTTTTGGATTGGCG | 104 | 1225 |
|  | R25 | ACGAACTAAAATTA |  | 1226 |
|  | P25 | AGTTCGTAGTTCGAGTTATTTTTT |  | 1194 |
| 597 | F1292 | TTTTGGATTGGCGT | 103 | 1227 |
|  | R25 | ACGAACTAAAATTA |  | 1228 |
|  | P25 | AGTTCGTAGTTCGAGTTATTTTTT |  | 1194 |
| 598 | F1293 | TTTGGATTGGCGTA | 102 | 1229 |
|  | R25 | ACGAACTAAAATTA |  | 1230 |
|  | P25 | AGTTCGTAGTTCGAGTTATTTTTT |  | 1194 |
| 599 | F1294 | TTGGATTGGCGTAT | 101 | 1231 |
|  | R25 | ACGAACTAAAATTA |  | 1232 |
|  | P25 | AGTTCGTAGTTCGAGTTATTTTTT |  | 1194 |
| 600 | F1295 | TGGATTGGCGTATT | 100 | 1233 |
|  | R25 | ACGAACTAAAATTA |  | 1234 |
|  | P25 | AGTTCGTAGTTCGAGTTATTTTTT |  | 1194 |
| 601 | F1296 | GGATTGGCGTATTT | 99 | 1235 |
|  | R25 | ACGAACTAAAATTA |  | 1236 |
|  | P25 | AGTTCGTAGTTCGAGTTATTTTTT |  | 1194 |
| 602 | F1297 | GATTGGCGTATTTA | 98 | 1237 |
|  | R25 | ACGAACTAAAATTA |  | 1238 |
|  | P25 | AGTTCGTAGTTCGAGTTATTTTTT |  | 1194 |
| 603 | F1298 | ATTGGCGTATTTAT | 97 | 1239 |
|  | R25 | ACGAACTAAAATTA |  | 1240 |
|  | P25 | AGTTCGTAGTTCGAGTTATTTTTT |  | 1194 |
| 604 | F1299 | TTGGCGTATTTATA | 96 | 1241 |
|  | R25 | ACGAACTAAAATTA |  | 1242 |
|  | P25 | AGTTCGTAGTTCGAGTTATTTTTT |  | 1194 |

TABLE 7-continued

Sequences of primer and probes for GPM6A gene qMSP

| Set | Primer | Sequence (5'→3') | Size of amplified product (bp) | Sequence No. |
|---|---|---|---|---|
| 605 | F1300 | TGGCGTATTTATAG | 95 | 1243 |
|  | R25 | ACGAACTAAAATTA |  | 1244 |
|  | P25 | AGTTCGTAGTTCGAGTTATTTTTT |  | 1194 |
| 606 | F1301 | GGCGTATTTATAGG | 94 | 1245 |
|  | R25 | ACGAACTAAAATTA |  | 1246 |
|  | P25 | AGTTCGTAGTTCGAGTTATTTTTT |  | 1194 |
| 607 | F1302 | GCGTATTTATAGGC | 93 | 1247 |
|  | R25 | ACGAACTAAAATTA |  | 1248 |
|  | P25 | AGTTCGTAGTTCGAGTTATTTTTT |  | 1194 |
| 608 | F1303 | CGTATTTATAGGCG | 92 | 1249 |
|  | R25 | ACGAACTAAAATTA |  | 1250 |
|  | P25 | AGTTCGTAGTTCGAGTTATTTTTT |  | 1194 |
| 609 | F1304 | GTATTTATAGGCGT | 91 | 1251 |
|  | R25 | ACGAACTAAAATTA |  | 1252 |
|  | P25 | AGTTCGTAGTTCGAGTTATTTTTT |  | 1194 |
| 610 | F1305 | TATTTATAGGCGTA | 90 | 1253 |
|  | R25 | ACGAACTAAAATTA |  | 1254 |
|  | P25 | AGTTCGTAGTTCGAGTTATTTTTT |  | 1194 |
| 611 | F1306 | ATTTATAGGCGTAG | 89 | 1255 |
|  | R25 | ACGAACTAAAATTA |  | 1256 |
|  | P25 | AGTTCGTAGTTCGAGTTATTTTTT |  | 1194 |
| 612 | F1307 | TTTATAGGCGTAGG | 88 | 1257 |
|  | R25 | ACGAACTAAAATTA |  | 1258 |
|  | P25 | AGTTCGTAGTTCGAGTTATTTTTT |  | 1194 |
| 613 | F1308 | TTATAGGCGTAGGG | 87 | 1259 |
|  | R25 | ACGAACTAAAATTA |  | 1260 |
|  | P25 | AGTTCGTAGTTCGAGTTATTTTTT |  | 1194 |
| 614 | F1309 | TATAGGCGTAGGGG | 86 | 1261 |
|  | R25 | ACGAACTAAAATTA |  | 1262 |
|  | P25 | AGTTCGTAGTTCGAGTTATTTTTT |  | 1194 |
| 615 | F1310 | ATAGGCGTAGGGGA | 85 | 1263 |
|  | R25 | ACGAACTAAAATTA |  | 1264 |
|  | P25 | AGTTCGTAGTTCGAGTTATTTTTT |  | 1194 |
| 616 | F1311 | TAGGCGTAGGGGAG | 84 | 1265 |
|  | R25 | ACGAACTAAAATTA |  | 1266 |
|  | P25 | AGTTCGTAGTTCGAGTTATTTTTT |  | 1194 |
| 617 | F1312 | AGGCGTAGGGGAGA | 83 | 1267 |
|  | R25 | ACGAACTAAAATTA |  | 1268 |
|  | P25 | AGTTCGTAGTTCGAGTTATTTTTT |  | 1194 |
| 618 | F1313 | GGCGTAGGGGAGAT | 82 | 1269 |
|  | R25 | ACGAACTAAAATTA |  | 1270 |
|  | P25 | AGTTCGTAGTTCGAGTTATTTTTT |  | 1194 |
| 619 | F1314 | GCGTAGGGGAGATG | 81 | 1271 |
|  | R25 | ACGAACTAAAATTA |  | 1272 |
|  | P25 | AGTTCGTAGTTCGAGTTATTTTTT |  | 1194 |
| 620 | F1315 | CGTAGGGGAGATGT | 80 | 1273 |
|  | R25 | ACGAACTAAAATTA |  | 1274 |
|  | P25 | AGTTCGTAGTTCGAGTTATTTTTT |  | 1194 |
| 621 | F1316 | GTAGGGGAGATGTT | 120 | 1275 |
|  | R26 | AAAAAAAAAAAACG |  | 1276 |
|  | P26 | ATTTTTTTTAGTTAAGTTTATTGGG |  | 1277 |
| 622 | F1317 | TAGGGGAGATGTTG | 119 | 1278 |
|  | R26 | AAAAAAAAAAAACG |  | 1279 |
|  | P26 | ATTTTTTTTAGTTAAGTTTATTGGG |  | 1277 |

TABLE 7-continued

Sequences of primer and probes for GPM6A gene qMSP

| Set | Primer | Sequence (5'→3') | Size of amplified product (bp) | Sequence No. |
|---|---|---|---|---|
| 623 | F1318 | AGGGGAGATGTTGT | 118 | 1280 |
|  | R26 | AAAAAAAAAAAACG |  | 1281 |
|  | P26 | ATTTTTTTAGTTAAGTTTATTGGG |  | 1277 |
| 624 | F1319 | GGGGAGATGTTGTT | 117 | 1282 |
|  | R26 | AAAAAAAAAAAACG |  | 1283 |
|  | P26 | ATTTTTTTAGTTAAGTTTATTGGG |  | 1277 |
| 625 | F1320 | GGGAGATGTTGTTT | 116 | 1284 |
|  | R26 | AAAAAAAAAAAACG |  | 1285 |
|  | P26 | ATTTTTTTAGTTAAGTTTATTGGG |  | 1277 |
| 626 | F1321 | GGAGATGTTGTTTT | 115 | 1286 |
|  | R26 | AAAAAAAAAAAACG |  | 1287 |
|  | P26 | ATTTTTTTAGTTAAGTTTATTGGG |  | 1277 |
| 627 | F1322 | GAGATGTTGTTTTT | 114 | 1288 |
|  | R26 | AAAAAAAAAAAACG |  | 1289 |
|  | P26 | ATTTTTTTAGTTAAGTTTATTGGG |  | 1277 |
| 628 | F1323 | AGATGTTGTTTTTT | 113 | 1290 |
|  | R26 | AAAAAAAAAAAACG |  | 1291 |
|  | P26 | ATTTTTTTAGTTAAGTTTATTGGG |  | 1277 |
| 629 | F1324 | GATGTTGTTTTTTC | 112 | 1292 |
|  | R26 | AAAAAAAAAAAACG |  | 1293 |
|  | P26 | ATTTTTTTAGTTAAGTTTATTGGG |  | 1277 |
| 630 | F1325 | ATGTTGTTTTTTCG | 111 | 1294 |
|  | R26 | AAAAAAAAAAAACG |  | 1295 |
|  | P26 | ATTTTTTTAGTTAAGTTTATTGGG |  | 1277 |
| 631 | F1326 | TGTTGTTTTTTCGC | 110 | 1296 |
|  | R26 | AAAAAAAAAAAACG |  | 1297 |
|  | P26 | ATTTTTTTAGTTAAGTTTATTGGG |  | 1277 |
| 632 | F1327 | GTTGTTTTTTCGCG | 109 | 1298 |
|  | R26 | AAAAAAAAAAAACG |  | 1299 |
|  | P26 | ATTTTTTTAGTTAAGTTTATTGGG |  | 1277 |
| 633 | F1328 | TTGTTTTTTCGCGG | 108 | 1300 |
|  | R26 | AAAAAAAAAAAACG |  | 1301 |
|  | P26 | ATTTTTTTAGTTAAGTTTATTGGG |  | 1277 |
| 634 | F1329 | TGTTTTTTCGCGGT | 107 | 1302 |
|  | R26 | AAAAAAAAAAAACG |  | 1303 |
|  | P26 | ATTTTTTTAGTTAAGTTTATTGGG |  | 1277 |
| 635 | F1330 | GTTTTTTCGCGGTT | 106 | 1304 |
|  | R26 | AAAAAAAAAAAACG |  | 1305 |
|  | P26 | ATTTTTTTAGTTAAGTTTATTGGG |  | 1277 |
| 636 | F1331 | TTTTTTCGCGGTTG | 105 | 1306 |
|  | R26 | AAAAAAAAAAAACG |  | 1307 |
|  | P26 | ATTTTTTTAGTTAAGTTTATTGGG |  | 1277 |
| 637 | F1332 | TTTTTCGCGGTTGT | 104 | 1308 |
|  | R26 | AAAAAAAAAAAACG |  | 1309 |
|  | P26 | ATTTTTTTAGTTAAGTTTATTGGG |  | 1277 |
| 638 | F1333 | TTTTCGCGGTTGTC | 103 | 1310 |
|  | R26 | AAAAAAAAAAAACG |  | 1311 |
|  | P26 | ATTTTTTTAGTTAAGTTTATTGGG |  | 1277 |
| 639 | F1334 | TTTCGCGGTTGTCG | 102 | 1312 |
|  | R26 | AAAAAAAAAAAACG |  | 1313 |
|  | P26 | ATTTTTTTAGTTAAGTTTATTGGG |  | 1277 |
| 640 | F1335 | TTCGCGGTTGTCGA | 101 | 1314 |
|  | R26 | AAAAAAAAAAAACG |  | 1315 |
|  | P26 | ATTTTTTTAGTTAAGTTTATTGGG |  | 1277 |

TABLE 7-continued

Sequences of primer and probes for GPM6A gene qMSP

| Set | Primer | Sequence (5'→3') | Size of amplified product (bp) | Sequence No. |
|---|---|---|---|---|
| 641 | F1336 | TCGCGGTTGTCGAT | 100 | 1316 |
|  | R26 | AAAAAAAAAAAACG |  | 1317 |
|  | P26 | ATTTTTTTAGTTAAGTTTATTGGG |  | 1277 |
| 642 | F1337 | CGCGGTTGTCGATT | 99 | 1318 |
|  | R26 | AAAAAAAAAAAACG |  | 1319 |
|  | P26 | ATTTTTTTAGTTAAGTTTATTGGG |  | 1277 |
| 643 | F1338 | GCGGTTGTCGATTG | 98 | 1320 |
|  | R26 | AAAAAAAAAAAACG |  | 1321 |
|  | P26 | ATTTTTTTAGTTAAGTTTATTGGG |  | 1277 |
| 644 | F1339 | CGGTTGTCGATTGC | 97 | 1322 |
|  | R26 | AAAAAAAAAAAACG |  | 1323 |
|  | P26 | ATTTTTTTAGTTAAGTTTATTGGG |  | 1277 |
| 645 | F1340 | GGTTGTCGATTGCG | 96 | 1324 |
|  | R26 | AAAAAAAAAAAACG |  | 1325 |
|  | P26 | ATTTTTTTAGTTAAGTTTATTGGG |  | 1277 |
| 646 | F1341 | GTTGTCGATTGCGT | 95 | 1326 |
|  | R26 | AAAAAAAAAAAACG |  | 1327 |
|  | P26 | ATTTTTTTAGTTAAGTTTATTGGG |  | 1277 |
| 647 | F1342 | TTGTCGATTGCGTT | 94 | 1328 |
|  | R26 | AAAAAAAAAAAACG |  | 1329 |
|  | P26 | ATTTTTTTAGTTAAGTTTATTGGG |  | 1277 |
| 648 | F1343 | TGTCGATTGCGTTT | 93 | 1330 |
|  | R26 | AAAAAAAAAAAACG |  | 1331 |
|  | P26 | ATTTTTTTAGTTAAGTTTATTGGG |  | 1277 |
| 649 | F1344 | GTCGATTGCGTTTA | 92 | 1332 |
|  | R26 | AAAAAAAAAAAACG |  | 1333 |
|  | P26 | ATTTTTTTAGTTAAGTTTATTGGG |  | 1277 |
| 650 | F1345 | TCGATTGCGTTTAG | 91 | 1334 |
|  | R26 | AAAAAAAAAAAACG |  | 1335 |
|  | P26 | ATTTTTTTAGTTAAGTTTATTGGG |  | 1277 |
| 651 | F1346 | CGATTGCGTTTAGT | 90 | 1336 |
|  | R26 | AAAAAAAAAAAACG |  | 1337 |
|  | P26 | ATTTTTTTAGTTAAGTTTATTGGG |  | 1277 |
| 652 | F1347 | GATTGCGTTTAGTT | 89 | 1338 |
|  | R26 | AAAAAAAAAAAACG |  | 1339 |
|  | P26 | ATTTTTTTAGTTAAGTTTATTGGG |  | 1277 |
| 653 | F1348 | ATTGCGTTTAGTTC | 88 | 1340 |
|  | R26 | AAAAAAAAAAAACG |  | 1341 |
|  | P26 | ATTTTTTTAGTTAAGTTTATTGGG |  | 1277 |
| 654 | F1349 | TTGCGTTTAGTTCG | 87 | 1342 |
|  | R26 | AAAAAAAAAAAACG |  | 1343 |
|  | P26 | ATTTTTTTAGTTAAGTTTATTGGG |  | 1277 |
| 655 | F1350 | TGCGTTTAGTTCGT | 86 | 1344 |
|  | R26 | AAAAAAAAAAAACG |  | 1345 |
|  | P26 | ATTTTTTTAGTTAAGTTTATTGGG |  | 1277 |
| 656 | F1351 | GCGTTTAGTTCGTA | 85 | 1346 |
|  | R26 | AAAAAAAAAAAACG |  | 1347 |
|  | P26 | ATTTTTTTAGTTAAGTTTATTGGG |  | 1277 |
| 657 | F1352 | CGTTTAGTTCGTAG | 84 | 1348 |
|  | R26 | AAAAAAAAAAAACG |  | 1349 |
|  | P26 | ATTTTTTTAGTTAAGTTTATTGGG |  | 1277 |
| 658 | F1353 | GTTTAGTTCGTAGT | 83 | 1350 |
|  | R26 | AAAAAAAAAAAACG |  | 1351 |
|  | P26 | ATTTTTTTAGTTAAGTTTATTGGG |  | 1277 |

TABLE 7-continued

Sequences of primer and probes for GPM6A gene qMSP

| Set | Primer | Sequence (5'→3') | Size of amplified product (bp) | Sequence No. |
|---|---|---|---|---|
| 659 | F1354 | TTTAGTTCGTAGTT | 82 | 1352 |
|  | R26 | AAAAAAAAAAAACG |  | 1353 |
|  | P26 | ATTTTTTTTAGTTAAGTTTATTGGG |  | 1277 |
| 660 | F1355 | TTAGTTCGTAGTTC | 81 | 1354 |
|  | R26 | AAAAAAAAAAAACG |  | 1355 |
|  | P26 | ATTTTTTTTAGTTAAGTTTATTGGG |  | 1277 |
| 661 | F1356 | TAGTTCGTAGTTCG | 80 | 1356 |
|  | R26 | AAAAAAAAAAAACG |  | 1357 |
|  | P26 | ATTTTTTTTAGTTAAGTTTATTGGG |  | 1277 |
| 662 | F1357 | AGTTCGTAGTTCGA | 150 | 1358 |
|  | R27 | CGAACACGTCAATC |  | 1359 |
|  | P27 | TTTAAGAGTAAAGGAGGTTTTGGG |  | 1360 |
| 663 | F1358 | GTTCGTAGTTCGAG | 149 | 1361 |
|  | R27 | CGAACACGTCAATC |  | 1362 |
|  | P27 | TTTAAGAGTAAAGGAGGTTTTGGG |  | 1360 |
| 664 | F1359 | TTCGTAGTTCGAGT | 148 | 1363 |
|  | R27 | CGAACACGTCAATC |  | 1364 |
|  | P27 | TTTAAGAGTAAAGGAGGTTTTGGG |  | 1360 |
| 665 | F1360 | TCGTAGTTCGAGTT | 147 | 1365 |
|  | R27 | CGAACACGTCAATC |  | 1366 |
|  | P27 | TTTAAGAGTAAAGGAGGTTTTGGG |  | 1360 |
| 666 | F1361 | CGTAGTTCGAGTTA | 146 | 1367 |
|  | R27 | CGAACACGTCAATC |  | 1368 |
|  | P27 | TTTAAGAGTAAAGGAGGTTTTGGG |  | 1360 |
| 667 | F1362 | GTAGTTCGAGTTAT | 145 | 1369 |
|  | R27 | CGAACACGTCAATC |  | 1370 |
|  | P27 | TTTAAGAGTAAAGGAGGTTTTGGG |  | 1360 |
| 668 | F1363 | TAGTTCGAGTTATT | 144 | 1371 |
|  | R27 | CGAACACGTCAATC |  | 1372 |
|  | P27 | TTTAAGAGTAAAGGAGGTTTTGGG |  | 1360 |
| 669 | F1364 | AGTTCGAGTTATTT | 143 | 1373 |
|  | R27 | CGAACACGTCAATC |  | 1374 |
|  | P27 | TTTAAGAGTAAAGGAGGTTTTGGG |  | 1360 |
| 670 | F1365 | GTTCGAGTTATTTT | 142 | 1375 |
|  | R27 | CGAACACGTCAATC |  | 1376 |
|  | P27 | TTTAAGAGTAAAGGAGGTTTTGGG |  | 1360 |
| 671 | F1366 | TTCGAGTTATTTTT | 141 | 1377 |
|  | R27 | CGAACACGTCAATC |  | 1378 |
|  | P27 | TTTAAGAGTAAAGGAGGTTTTGGG |  | 1360 |
| 672 | F1367 | TCGAGTTATTTTTT | 140 | 1379 |
|  | R27 | CGAACACGTCAATC |  | 1380 |
|  | P27 | TTTAAGAGTAAAGGAGGTTTTGGG |  | 1360 |
| 673 | F1368 | CGAGTTATTTTTTT | 139 | 1381 |
|  | R27 | CGAACACGTCAATC |  | 1382 |
|  | P27 | TTTAAGAGTAAAGGAGGTTTTGGG |  | 1360 |
| 674 | F1369 | GAGTTATTTTTTTA | 138 | 1383 |
|  | R27 | CGAACACGTCAATC |  | 1384 |
|  | P27 | TTTAAGAGTAAAGGAGGTTTTGGG |  | 1360 |
| 675 | F1370 | AGTTATTTTTTTAA | 137 | 1385 |
|  | R27 | CGAACACGTCAATC |  | 1386 |
|  | P27 | TTTAAGAGTAAAGGAGGTTTTGGG |  | 1360 |
| 676 | F1371 | GTTATTTTTTTAAT | 136 | 1387 |
|  | R27 | CGAACACGTCAATC |  | 1388 |
|  | P27 | TTTAAGAGTAAAGGAGGTTTTGGG |  | 1360 |

TABLE 7-continued

Sequences of primer and probes for GPM6A gene qMSP

| Set | Primer | Sequence (5'→3') | Size of amplified product (bp) | Sequence No. |
|---|---|---|---|---|
| 677 | F1372 | TTATTTTTTAATT | 135 | 1389 |
|  | R27 | CGAACACGTCAATC |  | 1390 |
|  | P27 | TTTAAGAGTAAAGGAGGTTTTGGG |  | 1360 |
| 678 | F1373 | TATTTTTTAATTT | 134 | 1391 |
|  | R27 | CGAACACGTCAATC |  | 1392 |
|  | P27 | TTTAAGAGTAAAGGAGGTTTTGGG |  | 1360 |
| 679 | F1374 | ATTTTTTAATTTT | 133 | 1393 |
|  | R27 | CGAACACGTCAATC |  | 1394 |
|  | P27 | TTTAAGAGTAAAGGAGGTTTTGGG |  | 1360 |
| 680 | F1375 | TTTTTTAATTTTA | 132 | 1395 |
|  | R27 | CGAACACGTCAATC |  | 1396 |
|  | P27 | TTTAAGAGTAAAGGAGGTTTTGGG |  | 1360 |
| 681 | F1376 | TTTTTTAATTTTAG | 131 | 1397 |
|  | R27 | CGAACACGTCAATC |  | 1398 |
|  | P27 | TTTAAGAGTAAAGGAGGTTTTGGG |  | 1360 |
| 682 | F1377 | TTTTTAATTTTAGT | 130 | 1399 |
|  | R27 | CGAACACGTCAATC |  | 1400 |
|  | P27 | TTTAAGAGTAAAGGAGGTTTTGGG |  | 1360 |
| 683 | F1378 | TTTTAATTTTAGTT | 129 | 1401 |
|  | R27 | CGAACACGTCAATC |  | 1402 |
|  | P27 | TTTAAGAGTAAAGGAGGTTTTGGG |  | 1360 |
| 684 | F1379 | TTTAATTTTAGTTC | 128 | 1403 |
|  | R27 | CGAACACGTCAATC |  | 1404 |
|  | P27 | TTTAAGAGTAAAGGAGGTTTTGGG |  | 1360 |
| 685 | F1380 | TTAATTTTAGTTCG | 127 | 1405 |
|  | R27 | CGAACACGTCAATC |  | 1406 |
|  | P27 | TTTAAGAGTAAAGGAGGTTTTGGG |  | 1360 |
| 686 | F1381 | TAATTTTAGTTCGT | 126 | 1407 |
|  | R27 | CGAACACGTCAATC |  | 1408 |
|  | P27 | TTTAAGAGTAAAGGAGGTTTTGGG |  | 1360 |

As a result of evaluating methylation of GPM6A gene using DNA from colorectal cancer tissues and normal tissues adjacent to cancer tissues, it was found that the sensitivity of GPM6A gene for colorectal cancer diagnosis was 70% (14/20)~90.0% (18/20) and the specificity of the GPM6A gene was 80% (4/20)~95% (1/20). Such results suggest that the GPM6A methylation biomarker gene is useful for diagnosis of colorectal cancer.

TABLE 8

Evaluation of ability to diagnose colorectal cancer using GPM6A gene

| Set of primers and probes | Cut-off (Ct) | Sensitivity (%), n = 20 | Specificity (%), n = 20 |
|---|---|---|---|
| 1 | >3.3 | 90 | 85 |
| 2 | >2.4 | 85 | 90 |
| 3 | >5.7 | 90 | 85 |
| 4 | >3.3 | 85 | 90 |
| 5 | >1.2 | 85 | 85 |
| 6 | >0.4 | 80 | 90 |
| 7 | >2.1 | 85 | 85 |
| 8 | >5.7 | 80 | 90 |
| 9 | >2.3 | 75 | 90 |
| 10 | >0.5 | 75 | 80 |
| 11 | >1.2 | 80 | 85 |
| 12 | >2.1 | 90 | 85 |
| 13 | >3.0 | 80 | 90 |
| 14 | >3.2 | 85 | 90 |
| 15 | >0.6 | 85 | 85 |
| 16 | >1.2 | 85 | 85 |
| 17 | >5.7 | 90 | 80 |
| 18 | >2.9 | 80 | 95 |
| 19 | >0.4 | 75 | 90 |
| 20 | >3.5 | 80 | 85 |
| 21 | >0.7 | 90 | 85 |
| 22 | >4.2 | 85 | 85 |
| 23 | >3.0 | 80 | 90 |
| 24 | >0.4 | 90 | 90 |
| 25 | >2.9 | 80 | 90 |
| 26 | >3.6 | 85 | 90 |
| 27 | >1.2 | 85 | 90 |
| 28 | >2.2 | 80 | 95 |
| 29 | >3.8 | 75 | 95 |
| 30 | >2.9 | 80 | 90 |
| 31 | >0.7 | 85 | 85 |
| 32 | >3.6 | 80 | 95 |
| 33 | >2.2 | 80 | 90 |
| 34 | >3.3 | 75 | 90 |
| 35 | >2.1 | 90 | 85 |
| 36 | >0.4 | 90 | 80 |

TABLE 8-continued

Evaluation of ability to diagnose colorectal cancer using GPM6A gene

| Set of primers and probes | Cut-off (Ct) | Sensitivity (%), n = 20 | Specificity (%), n = 20 |
|---|---|---|---|
| 37 | >2.2 | 75 | 95 |
| 38 | >0.4 | 85 | 90 |
| 39 | >2.2 | 80 | 90 |
| 40 | >2.7 | 75 | 95 |
| 41 | >1.2 | 75 | 90 |
| 42 | >0.4 | 85 | 85 |
| 43 | >0.4 | 90 | 85 |
| 44 | >0.7 | 90 | 80 |
| 45 | >1.2 | 80 | 90 |
| 46 | >2.0 | 80 | 90 |
| 47 | >2.1 | 80 | 90 |
| 48 | >2.1 | 80 | 85 |
| 49 | >2.2 | 80 | 90 |
| 50 | >2.3 | 90 | 80 |
| 51 | >2.3 | 75 | 95 |
| 52 | >2.7 | 85 | 90 |
| 53 | >2.7 | 80 | 90 |
| 54 | >3.2 | 85 | 85 |
| 55 | >3.3 | 85 | 90 |
| 56 | >3.6 | 85 | 85 |
| 57 | >4.2 | 85 | 90 |
| 58 | >4.5 | 80 | 85 |
| 59 | >5.7 | 80 | 95 |
| 60 | >2.1 | 90 | 85 |
| 61 | >2.1 | 85 | 90 |
| 62 | >0.4 | 85 | 90 |
| 63 | >5.7 | 85 | 90 |
| 64 | >2.3 | 85 | 90 |
| 65 | >4.3 | 90 | 90 |
| 66 | >2.1 | 85 | 90 |
| 67 | >0.7 | 80 | 90 |
| 68 | >0.5 | 75 | 90 |
| 69 | >3.3 | 75 | 95 |
| 70 | >0.4 | 75 | 95 |
| 71 | >0.5 | 85 | 90 |
| 72 | >0.7 | 85 | 90 |
| 73 | >1.2 | 75 | 90 |
| 74 | >2.0 | 75 | 90 |
| 75 | >2.1 | 75 | 85 |
| 76 | >2.2 | 85 | 90 |
| 77 | >2.2 | 80 | 90 |
| 78 | >2.3 | 80 | 90 |
| 79 | >2.3 | 85 | 90 |
| 80 | >2.7 | 85 | 90 |
| 81 | >2.9 | 80 | 90 |
| 82 | >3.2 | 90 | 80 |
| 83 | >3.3 | 85 | 90 |
| 84 | >3.6 | 75 | 95 |
| 85 | >4.2 | 80 | 85 |
| 86 | >4.5 | 75 | 90 |
| 87 | >5.7 | 80 | 90 |
| 88 | >0.5 | 85 | 90 |
| 89 | >1.2 | 80 | 85 |
| 90 | >2.4 | 90 | 85 |
| 91 | >2.1 | 80 | 95 |
| 92 | >4.2 | 80 | 85 |
| 93 | >0.5 | 80 | 95 |
| 94 | >0.7 | 85 | 90 |
| 95 | >3.5 | 80 | 90 |
| 96 | >2.4 | 80 | 90 |
| 97 | >2.7 | 85 | 85 |
| 98 | >2.4 | 75 | 90 |
| 99 | >2.1 | 80 | 90 |
| 100 | >4.2 | 90 | 80 |
| 101 | >4.5 | 80 | 85 |
| 102 | >4.2 | 85 | 90 |
| 103 | >3.6 | 85 | 90 |
| 104 | >0.7 | 90 | 85 |
| 105 | >2.1 | 85 | 90 |
| 106 | >2.7 | 85 | 90 |
| 107 | >3.2 | 80 | 95 |
| 108 | >2.9 | 85 | 90 |
| 109 | >2.2 | 75 | 90 |
| 110 | >1.2 | 85 | 90 |
| 111 | >0.4 | 85 | 90 |
| 112 | >2.7 | 80 | 85 |
| 113 | >0.4 | 90 | 85 |
| 114 | >2.3 | 75 | 95 |
| 115 | >2.3 | 85 | 85 |
| 116 | >1.2 | 75 | 95 |
| 117 | >2.1 | 90 | 80 |
| 118 | >0.4 | 80 | 95 |
| 119 | >2.3 | 75 | 90 |
| 120 | >2.3 | 80 | 85 |
| 121 | >2.3 | 85 | 90 |
| 122 | >2.3 | 80 | 85 |
| 123 | >0.5 | 80 | 85 |
| 124 | >2.3 | 85 | 85 |
| 125 | >2.2 | 85 | 85 |
| 126 | >2.7 | 75 | 90 |
| 127 | >2.3 | 85 | 95 |
| 128 | >3.2 | 80 | 90 |
| 129 | >2.1 | 85 | 85 |
| 130 | >5.7 | 80 | 90 |
| 131 | >3.3 | 85 | 90 |
| 132 | >2.4 | 75 | 90 |
| 133 | >0.4 | 80 | 85 |
| 134 | >0.5 | 85 | 90 |
| 135 | >2.3 | 85 | 90 |
| 136 | >2.3 | 75 | 90 |
| 137 | >5.7 | 80 | 95 |
| 138 | >2.3 | 90 | 85 |
| 139 | >2.0 | 80 | 85 |
| 140 | >3.3 | 85 | 95 |
| 141 | >0.4 | 85 | 90 |
| 142 | >0.4 | 80 | 90 |
| 143 | >0.4 | 80 | 85 |
| 144 | >0.5 | 85 | 90 |
| 145 | >0.7 | 85 | 90 |
| 146 | >1.2 | 80 | 95 |
| 147 | >1.2 | 80 | 90 |
| 148 | >2.0 | 80 | 95 |
| 149 | >2.1 | 75 | 90 |
| 150 | >4.1 | 90 | 85 |
| 151 | >2.1 | 80 | 90 |
| 152 | >2.2 | 85 | 85 |
| 153 | >2.3 | 80 | 90 |
| 154 | >3.2 | 80 | 90 |
| 155 | >4.7 | 80 | 90 |
| 156 | >2.3 | 80 | 85 |
| 157 | >2.4 | 90 | 85 |
| 158 | >2.7 | 90 | 85 |
| 159 | >2.7 | 80 | 95 |
| 160 | >2.9 | 80 | 90 |
| 161 | >3.0 | 85 | 85 |
| 162 | >3.2 | 85 | 90 |
| 163 | >3.5 | 90 | 85 |
| 164 | >3.5 | 80 | 90 |
| 165 | >3.6 | 75 | 90 |
| 166 | >4.2 | 80 | 95 |
| 167 | >4.3 | 85 | 90 |
| 168 | >4.5 | 75 | 90 |
| 169 | >5.7 | 80 | 90 |
| 170 | >2.2 | 75 | 90 |
| 171 | >3.6 | 80 | 90 |
| 172 | >2.9 | 85 | 85 |
| 173 | >4.3 | 80 | 90 |
| 174 | >3.0 | 90 | 80 |
| 175 | >4.3 | 75 | 90 |
| 176 | >3.3 | 85 | 90 |
| 177 | >2.0 | 90 | 85 |
| 178 | >2.3 | 85 | 90 |
| 179 | >2.4 | 75 | 95 |
| 180 | >3.3 | 90 | 85 |
| 181 | >2.3 | 85 | 90 |
| 182 | >2.3 | 75 | 95 |
| 183 | >0.7 | 75 | 90 |
| 184 | >2.1 | 80 | 90 |

TABLE 8-continued

Evaluation of ability to diagnose colorectal cancer using GPM6A gene

| Set of primers and probes | Cut-off (Ct) | Sensitivity (%), n = 20 | Specificity (%), n = 20 |
|---|---|---|---|
| 185 | >4.5 | 75 | 90 |
| 186 | >0.4 | 80 | 90 |
| 187 | >0.4 | 85 | 90 |
| 188 | >0.4 | 80 | 90 |
| 189 | >0.5 | 80 | 85 |
| 190 | >0.7 | 80 | 85 |
| 191 | >1.2 | 85 | 90 |
| 192 | >1.2 | 90 | 85 |
| 193 | >2.3 | 85 | 90 |
| 194 | >2.1 | 80 | 90 |
| 195 | >5.1 | 85 | 90 |
| 196 | >2.1 | 90 | 85 |
| 197 | >2.1 | 85 | 90 |
| 198 | >2.2 | 90 | 85 |
| 199 | >2.3 | 85 | 85 |
| 200 | >3.6 | 85 | 90 |
| 201 | >2.3 | 85 | 90 |
| 202 | >2.4 | 80 | 90 |
| 203 | >2.7 | 75 | 90 |
| 204 | >2.7 | 80 | 85 |
| 205 | >2.9 | 80 | 85 |
| 206 | >3.0 | 85 | 85 |
| 207 | >3.2 | 80 | 90 |
| 208 | >3.3 | 90 | 85 |
| 209 | >3.5 | 80 | 90 |
| 210 | >3.6 | 90 | 85 |
| 211 | >4.2 | 85 | 90 |
| 212 | >4.3 | 75 | 90 |
| 213 | >4.5 | 85 | 90 |
| 214 | >5.7 | 85 | 95 |
| 215 | >2.1 | 75 | 90 |
| 216 | >2.3 | 75 | 95 |
| 217 | >1.2 | 80 | 90 |
| 218 | >2.1 | 80 | 90 |
| 219 | >3.0 | 85 | 85 |
| 220 | >4.3 | 75 | 90 |
| 221 | >2.7 | 80 | 90 |
| 222 | >2.3 | 85 | 90 |
| 223 | >2.3 | 75 | 90 |
| 224 | >2.9 | 85 | 90 |
| 225 | >3.0 | 85 | 90 |
| 226 | >2.9 | 85 | 90 |
| 227 | >0.5 | 80 | 90 |
| 228 | >4.3 | 75 | 95 |
| 229 | >2.7 | 90 | 90 |
| 230 | >1.2 | 85 | 90 |
| 231 | >5.7 | 85 | 90 |
| 232 | >2.3 | 75 | 95 |
| 233 | >0.4 | 85 | 85 |
| 234 | >2.3 | 85 | 90 |
| 235 | >4.2 | 85 | 90 |
| 236 | >1.2 | 80 | 90 |
| 237 | >4.2 | 85 | 90 |
| 238 | >2.2 | 80 | 90 |
| 239 | >0.5 | 90 | 85 |
| 240 | >3.0 | 75 | 90 |
| 241 | >2.9 | 85 | 90 |
| 242 | >2.3 | 75 | 90 |
| 243 | >2.3 | 85 | 85 |
| 244 | >2.7 | 85 | 90 |
| 245 | >3.3 | 80 | 85 |
| 246 | >2.0 | 90 | 85 |
| 247 | >4.2 | 85 | 90 |
| 248 | >3.5 | 90 | 85 |
| 249 | >3.2 | 80 | 90 |
| 250 | >0.4 | 75 | 90 |
| 251 | >3.6 | 85 | 90 |
| 252 | >0.5 | 85 | 85 |
| 253 | >4.5 | 90 | 85 |
| 254 | >2.3 | 85 | 90 |
| 255 | >2.0 | 75 | 95 |
| 256 | >3.5 | 90 | 85 |
| 257 | >0.5 | 80 | 90 |
| 258 | >2.7 | 85 | 90 |
| 259 | >3.0 | 85 | 85 |
| 260 | >2.9 | 80 | 90 |
| 261 | >3.2 | 85 | 85 |
| 262 | >3.5 | 75 | 95 |
| 263 | >4.3 | 85 | 85 |
| 264 | >2.1 | 75 | 95 |
| 265 | >1.2 | 80 | 95 |
| 266 | >4.3 | 80 | 90 |
| 267 | >4.3 | 85 | 90 |
| 268 | >2.1 | 80 | 90 |
| 269 | >2.3 | 75 | 95 |
| 270 | >4.5 | 80 | 90 |
| 271 | >3.0 | 85 | 90 |
| 272 | >2.1 | 80 | 90 |
| 273 | >0.4 | 80 | 85 |
| 274 | >0.4 | 80 | 90 |
| 275 | >2.1 | 90 | 80 |
| 276 | >0.6 | 80 | 90 |
| 277 | >0.5 | 85 | 85 |
| 278 | >0.5 | 90 | 85 |
| 279 | >1.2 | 80 | 90 |
| 280 | >1.2 | 85 | 90 |
| 281 | >2.0 | 90 | 80 |
| 282 | >2.1 | 80 | 95 |
| 283 | >2.1 | 80 | 90 |
| 284 | >2.1 | 80 | 90 |
| 285 | >2.3 | 85 | 90 |
| 286 | >2.3 | 80 | 95 |
| 287 | >2.4 | 75 | 90 |
| 288 | >2.4 | 85 | 85 |
| 289 | >2.8 | 75 | 90 |
| 290 | >2.9 | 85 | 90 |
| 291 | >3.2 | 75 | 95 |
| 292 | >3.3 | 85 | 85 |
| 293 | >3.6 | 90 | 80 |
| 294 | >3.8 | 75 | 90 |
| 295 | >4.3 | 85 | 90 |
| 296 | >4.5 | 90 | 85 |
| 297 | >2.1 | 80 | 90 |
| 298 | >1.2 | 80 | 95 |
| 299 | >4.5 | 90 | 85 |
| 300 | >2.4 | 85 | 90 |
| 301 | >2.1 | 80 | 90 |
| 302 | >2.1 | 75 | 90 |
| 303 | >5.7 | 80 | 90 |
| 304 | >4.5 | 90 | 80 |
| 305 | >2.7 | 85 | 90 |
| 306 | >4.3 | 85 | 85 |
| 307 | >0.4 | 85 | 90 |
| 308 | >2.1 | 75 | 90 |
| 309 | >4.5 | 75 | 85 |
| 310 | >0.4 | 75 | 95 |
| 311 | >0.5 | 75 | 85 |
| 312 | >0.5 | 80 | 90 |
| 313 | >1.2 | 75 | 90 |
| 314 | >1.2 | 80 | 90 |
| 315 | >2.0 | 80 | 90 |
| 316 | >2.1 | 85 | 95 |
| 317 | >2.1 | 80 | 90 |
| 318 | >2.2 | 85 | 90 |
| 319 | >2.3 | 75 | 90 |
| 320 | >5.2 | 85 | 85 |
| 321 | >2.4 | 75 | 85 |
| 322 | >2.4 | 90 | 85 |
| 323 | >2.7 | 80 | 90 |
| 324 | >2.9 | 85 | 90 |
| 325 | >3.2 | 85 | 90 |
| 326 | >3.3 | 85 | 85 |
| 327 | >3.6 | 80 | 90 |
| 328 | >3.8 | 75 | 80 |
| 329 | >4.3 | 85 | 85 |
| 330 | >4.5 | 80 | 90 |
| 331 | >0.7 | 90 | 85 |
| 332 | >3.3 | 90 | 85 |

TABLE 8-continued

Evaluation of ability to diagnose colorectal cancer using GPM6A gene

| Set of primers and probes | Cut-off (Ct) | Sensitivity (%), n = 20 | Specificity (%), n = 20 |
|---|---|---|---|
| 333 | >4.5 | 85 | 90 |
| 334 | >2.3 | 80 | 90 |
| 335 | >1.2 | 85 | 90 |
| 336 | >2.4 | 90 | 80 |
| 337 | >2.1 | 85 | 85 |
| 338 | >2.7 | 85 | 90 |
| 339 | >1.2 | 85 | 90 |
| 340 | >1.2 | 85 | 95 |
| 341 | >2.7 | 85 | 85 |
| 342 | >2.3 | 80 | 85 |
| 343 | >3.5 | 90 | 85 |
| 344 | >2.1 | 85 | 90 |
| 345 | >3.3 | 75 | 85 |
| 346 | >4.3 | 90 | 85 |
| 347 | >0.5 | 75 | 90 |
| 348 | >2.3 | 80 | 85 |
| 349 | >2.0 | 75 | 90 |
| 350 | >0.4 | 80 | 85 |
| 351 | >0.7 | 80 | 90 |
| 352 | >0.7 | 85 | 85 |
| 353 | >3.2 | 90 | 80 |
| 354 | >3.6 | 85 | 85 |
| 355 | >2.3 | 85 | 85 |
| 356 | >0.4 | 75 | 90 |
| 357 | >3.6 | 75 | 90 |
| 358 | >4.3 | 75 | 95 |
| 359 | >2.4 | 75 | 95 |
| 360 | >4.5 | 80 | 90 |
| 361 | >2.9 | 75 | 95 |
| 362 | >5.6 | 75 | 90 |
| 363 | >2.3 | 75 | 95 |
| 364 | >0.5 | 85 | 85 |
| 365 | >2.1 | 85 | 90 |
| 366 | >4.2 | 85 | 85 |
| 367 | >2.7 | 90 | 85 |
| 368 | >2.1 | 75 | 90 |
| 369 | >2.0 | 85 | 85 |
| 370 | >5.7 | 90 | 90 |
| 371 | >4.5 | 80 | 90 |
| 372 | >1.2 | 80 | 85 |
| 373 | >4.2 | 85 | 85 |
| 374 | >3.3 | 85 | 90 |
| 375 | >1.2 | 90 | 85 |
| 376 | >0.7 | 75 | 90 |
| 377 | >2.3 | 75 | 95 |
| 378 | >3.6 | 90 | 85 |
| 379 | >0.4 | 75 | 90 |
| 380 | >0.5 | 85 | 90 |
| 381 | >0.7 | 80 | 90 |
| 382 | >1.2 | 85 | 95 |
| 383 | >2.0 | 85 | 90 |
| 384 | >2.1 | 85 | 90 |
| 385 | >2.2 | 80 | 90 |
| 386 | >2.3 | 85 | 90 |
| 387 | >2.3 | 85 | 90 |
| 388 | >2.7 | 85 | 85 |
| 389 | >2.9 | 80 | 90 |
| 390 | >3.2 | 85 | 95 |
| 391 | >3.5 | 90 | 85 |
| 392 | >4.2 | 90 | 80 |
| 393 | >4.3 | 80 | 90 |
| 394 | >5.7 | 85 | 90 |
| 395 | >2.1 | 75 | 95 |
| 396 | >2.3 | 80 | 85 |
| 397 | >0.4 | 75 | 90 |
| 398 | >1.2 | 80 | 85 |
| 399 | >2.4 | 75 | 90 |
| 400 | >2.7 | 85 | 90 |
| 401 | >0.4 | 80 | 90 |
| 402 | >0.4 | 80 | 90 |
| 403 | >1.2 | 85 | 85 |
| 404 | >0.4 | 90 | 85 |
| 405 | >0.4 | 85 | 85 |
| 406 | >0.7 | 85 | 85 |
| 407 | >1.2 | 75 | 95 |
| 408 | >2.0 | 85 | 95 |
| 409 | >2.1 | 80 | 90 |
| 410 | >2.2 | 85 | 85 |
| 411 | >2.3 | 85 | 90 |
| 412 | >2.3 | 75 | 80 |
| 413 | >2.4 | 90 | 85 |
| 414 | >2.7 | 90 | 85 |
| 415 | >3.0 | 75 | 90 |
| 416 | >3.5 | 80 | 90 |
| 417 | >3.6 | 90 | 85 |
| 418 | >4.3 | 75 | 90 |
| 419 | >4.5 | 85 | 90 |
| 420 | >0.4 | 90 | 80 |
| 421 | >2.1 | 80 | 85 |
| 422 | >5.7 | 85 | 85 |
| 423 | >2.3 | 75 | 95 |
| 424 | >2.4 | 75 | 95 |
| 425 | >5.7 | 85 | 85 |
| 426 | >2.1 | 75 | 90 |
| 427 | >0.5 | 80 | 90 |
| 428 | >2.1 | 90 | 85 |
| 429 | >3.6 | 85 | 90 |
| 430 | >4.3 | 75 | 95 |
| 431 | >1.2 | 75 | 90 |
| 432 | >2.3 | 75 | 90 |
| 433 | >0.4 | 85 | 90 |
| 434 | >2.7 | 90 | 80 |
| 435 | >2.2 | 85 | 85 |
| 436 | >2.7 | 75 | 95 |
| 437 | >4.5 | 75 | 90 |
| 438 | >2.7 | 80 | 90 |
| 439 | >3.5 | 75 | 95 |
| 440 | >5.4 | 80 | 90 |
| 441 | >2.3 | 85 | 85 |
| 442 | >3.2 | 90 | 85 |
| 443 | >2.3 | 75 | 90 |
| 444 | >0.4 | 85 | 90 |
| 445 | >2.9 | 80 | 85 |
| 446 | >1.2 | 90 | 85 |
| 447 | >3.6 | 90 | 80 |
| 448 | >2.3 | 85 | 90 |
| 449 | >2.1 | 85 | 85 |
| 450 | >3.0 | 80 | 95 |
| 451 | >5.7 | 90 | 80 |
| 452 | >2.1 | 85 | 85 |
| 453 | >2.7 | 90 | 85 |
| 454 | >0.4 | 75 | 95 |
| 455 | >0.7 | 85 | 90 |
| 456 | >2.3 | 85 | 85 |
| 457 | >2.1 | 75 | 95 |
| 458 | >2.3 | 75 | 95 |
| 459 | >2.4 | 85 | 85 |
| 460 | >3.0 | 85 | 85 |
| 461 | >3.3 | 80 | 85 |
| 462 | >4.2 | 90 | 80 |
| 463 | >5.7 | 75 | 95 |
| 464 | >5.7 | 75 | 95 |
| 465 | >2.3 | 80 | 90 |
| 466 | >4.2 | 85 | 90 |
| 467 | >3.0 | 75 | 95 |
| 468 | >0.4 | 90 | 80 |
| 469 | >0.5 | 80 | 85 |
| 470 | >0.5 | 75 | 90 |
| 471 | >1.2 | 85 | 90 |
| 472 | >2.1 | 85 | 85 |
| 473 | >2.3 | 90 | 80 |
| 474 | >2.3 | 90 | 85 |
| 475 | >2.7 | 85 | 90 |
| 476 | >3.2 | 75 | 90 |
| 477 | >3.6 | 85 | 90 |
| 478 | >5.6 | 75 | 90 |
| 479 | >2.0 | 85 | 90 |
| 480 | >2.1 | 75 | 95 |

TABLE 8-continued

Evaluation of ability to diagnose colorectal cancer using GPM6A gene

| Set of primers and probes | Cut-off (Ct) | Sensitivity (%), n = 20 | Specificity (%), n = 20 |
| --- | --- | --- | --- |
| 481 | >3.3 | 85 | 90 |
| 482 | >2.1 | 75 | 90 |
| 483 | >0.5 | 85 | 95 |
| 484 | >2.7 | 85 | 90 |
| 485 | >3.0 | 80 | 90 |
| 486 | >3.0 | 75 | 90 |
| 487 | >3.3 | 80 | 95 |
| 488 | >0.4 | 80 | 90 |
| 489 | >4.5 | 90 | 85 |
| 490 | >4.2 | 75 | 95 |
| 491 | >2.2 | 80 | 95 |
| 492 | >2.2 | 80 | 85 |
| 493 | >3.3 | 85 | 90 |
| 494 | >2.4 | 75 | 90 |
| 495 | >4.5 | 80 | 90 |
| 496 | >0.5 | 75 | 90 |
| 497 | >3.6 | 75 | 90 |
| 498 | >0.4 | 85 | 85 |
| 499 | >2.0 | 75 | 95 |
| 500 | >0.5 | 85 | 90 |
| 501 | >3.3 | 75 | 90 |
| 502 | >4.5 | 80 | 90 |
| 503 | >0.5 | 85 | 90 |
| 504 | >2.1 | 75 | 90 |
| 505 | >2.2 | 75 | 95 |
| 506 | >2.7 | 75 | 95 |
| 507 | >3.0 | 80 | 90 |
| 508 | >4.3 | 85 | 90 |
| 509 | >4.3 | 85 | 90 |
| 510 | >4.2 | 90 | 85 |
| 511 | >2.2 | 90 | 85 |
| 512 | >2.1 | 80 | 95 |
| 513 | >0.4 | 90 | 80 |
| 514 | >2.1 | 85 | 85 |
| 515 | >2.1 | 75 | 95 |
| 516 | >2.7 | 75 | 90 |
| 517 | >3.0 | 85 | 90 |
| 518 | >4.3 | 90 | 85 |
| 519 | >5.7 | 80 | 90 |
| 520 | >2.7 | 80 | 90 |
| 521 | >3.3 | 85 | 90 |
| 522 | >1.2 | 80 | 90 |
| 523 | >0.5 | 75 | 90 |
| 524 | >4.3 | 80 | 85 |
| 525 | >2.1 | 90 | 85 |
| 526 | >0.5 | 80 | 85 |
| 527 | >2.3 | 80 | 90 |
| 528 | >3.6 | 80 | 90 |
| 529 | >2.3 | 80 | 90 |
| 530 | >2.4 | 80 | 95 |
| 531 | >0.4 | 85 | 90 |
| 532 | >2.3 | 85 | 90 |
| 533 | >0.4 | 90 | 85 |
| 534 | >1.2 | 85 | 85 |
| 535 | >2.1 | 75 | 90 |
| 536 | >2.4 | 80 | 90 |
| 537 | >2.7 | 85 | 90 |
| 538 | >4.2 | 80 | 85 |
| 539 | >5.7 | 85 | 85 |
| 540 | >3.0 | 75 | 95 |
| 541 | >3.3 | 85 | 85 |
| 542 | >2.7 | 85 | 85 |
| 543 | >0.5 | 85 | 90 |
| 544 | >2.1 | 90 | 90 |
| 545 | >2.3 | 90 | 80 |
| 546 | >3.0 | 85 | 90 |
| 547 | >3.5 | 75 | 90 |
| 548 | >4.2 | 80 | 95 |
| 549 | >2.9 | 75 | 90 |
| 550 | >5.7 | 80 | 90 |
| 551 | >2.1 | 85 | 85 |
| 552 | >3.0 | 80 | 90 |
| 553 | >2.3 | 80 | 90 |
| 554 | >0.4 | 85 | 90 |
| 555 | >2.7 | 75 | 95 |
| 556 | >2.2 | 90 | 80 |
| 557 | >3.6 | 80 | 90 |
| 558 | >2.3 | 85 | 85 |
| 559 | >3.5 | 80 | 90 |
| 560 | >3.2 | 85 | 90 |
| 561 | >4.5 | 85 | 90 |
| 562 | >0.4 | 85 | 90 |
| 563 | >2.2 | 85 | 90 |
| 564 | >2.3 | 80 | 85 |
| 565 | >3.5 | 80 | 95 |
| 566 | >4.3 | 85 | 85 |
| 567 | >1.2 | 85 | 85 |
| 568 | >4.2 | 85 | 85 |
| 569 | >0.4 | 90 | 80 |
| 570 | >1.2 | 80 | 95 |
| 571 | >2.3 | 85 | 90 |
| 572 | >2.7 | 80 | 90 |
| 573 | >4.2 | 90 | 80 |
| 574 | >5.7 | 80 | 95 |
| 575 | >4.5 | 80 | 90 |
| 576 | >2.3 | 90 | 90 |
| 577 | >2.1 | 80 | 90 |
| 578 | >2.4 | 85 | 90 |
| 579 | >0.4 | 85 | 90 |
| 580 | >3.6 | 85 | 85 |
| 581 | >0.5 | 70 | 85 |
| 582 | >2.1 | 85 | 90 |
| 583 | >4.3 | 85 | 90 |
| 584 | >2.4 | 85 | 90 |
| 585 | >0.4 | 80 | 90 |
| 586 | >1.2 | 75 | 95 |
| 587 | >2.3 | 75 | 90 |
| 588 | >3.0 | 85 | 95 |
| 589 | >4.5 | 85 | 90 |
| 590 | >1.2 | 75 | 90 |
| 591 | >2.1 | 90 | 85 |
| 592 | >0.4 | 75 | 90 |
| 593 | >2.0 | 80 | 90 |
| 594 | >2.3 | 75 | 90 |
| 595 | >3.3 | 80 | 90 |
| 596 | >4.3 | 80 | 95 |
| 597 | >0.4 | 75 | 95 |
| 598 | >3.6 | 85 | 85 |
| 599 | >4.2 | 85 | 90 |
| 600 | >2.1 | 80 | 90 |
| 601 | >2.1 | 85 | 90 |
| 602 | >2.7 | 80 | 90 |
| 603 | >3.6 | 80 | 90 |
| 604 | >4.5 | 85 | 90 |
| 605 | >1.2 | 80 | 90 |
| 606 | >3.0 | 80 | 90 |
| 607 | >3.3 | 80 | 90 |
| 608 | >0.5 | 80 | 90 |
| 609 | >2.7 | 75 | 90 |
| 610 | >4.3 | 85 | 85 |
| 611 | >2.1 | 80 | 90 |
| 612 | >2.3 | 75 | 95 |
| 613 | >2.7 | 90 | 85 |
| 614 | >2.7 | 85 | 90 |
| 615 | >0.7 | 80 | 90 |
| 616 | >0.5 | 80 | 90 |
| 617 | >2.1 | 80 | 90 |
| 618 | >2.4 | 85 | 90 |
| 619 | >3.6 | 85 | 90 |
| 620 | >2.7 | 75 | 95 |
| 621 | >0.4 | 80 | 85 |
| 622 | >0.7 | 80 | 90 |
| 623 | >1.2 | 75 | 90 |
| 624 | >2.1 | 80 | 90 |
| 625 | >2.9 | 80 | 90 |
| 626 | >3.6 | 75 | 90 |
| 627 | >4.2 | 85 | 85 |
| 628 | >4.3 | 80 | 85 |

TABLE 8-continued

Evaluation of ability to diagnose colorectal cancer using GPM6A gene

| Set of primers and probes | Cut-off (Ct) | Sensitivity (%), n = 20 | Specificity (%), n = 20 |
|---|---|---|---|
| 629 | >4.3 | 85 | 95 |
| 630 | >5.7 | 90 | 85 |
| 631 | >0.7 | 90 | 85 |
| 632 | >2.3 | 85 | 90 |
| 633 | >5.6 | 85 | 90 |
| 634 | >2.2 | 80 | 90 |
| 635 | >2.3 | 80 | 90 |
| 636 | >3.6 | 85 | 90 |
| 637 | >0.4 | 75 | 85 |
| 638 | >2.3 | 80 | 90 |
| 639 | >2.7 | 90 | 85 |
| 640 | >2.1 | 85 | 90 |
| 641 | >2.2 | 75 | 90 |
| 642 | >2.4 | 90 | 85 |
| 643 | >2.0 | 85 | 90 |
| 644 | >5.7 | 90 | 85 |
| 645 | >0.7 | 85 | 90 |
| 646 | >3.5 | 80 | 90 |
| 647 | >0.5 | 80 | 90 |
| 648 | >2.3 | 85 | 90 |
| 649 | >5.7 | 85 | 90 |
| 650 | >2.7 | 85 | 90 |
| 651 | >2.0 | 90 | 85 |
| 652 | >2.4 | 85 | 90 |
| 653 | >2.4 | 85 | 90 |
| 654 | >2.7 | 85 | 90 |
| 655 | >2.1 | 90 | 80 |
| 656 | >3.3 | 75 | 90 |
| 657 | >2.7 | 90 | 85 |
| 658 | >0.6 | 80 | 85 |
| 659 | >5.7 | 90 | 80 |
| 660 | >3.2 | 80 | 85 |
| 661 | >2.2 | 80 | 90 |
| 662 | >2.3 | 80 | 90 |
| 663 | >2.3 | 85 | 85 |
| 664 | >3.5 | 90 | 80 |
| 665 | >2.1 | 85 | 90 |
| 666 | >2.9 | 75 | 90 |
| 667 | >2.1 | 75 | 95 |
| 668 | >2.1 | 90 | 85 |
| 669 | >3.5 | 80 | 90 |
| 670 | >5.7 | 75 | 95 |
| 671 | >1.2 | 85 | 85 |
| 672 | >4.2 | 75 | 95 |
| 673 | >2.3 | 75 | 90 |
| 674 | >4.5 | 80 | 90 |
| 675 | >2.3 | 80 | 90 |
| 676 | >3.5 | 80 | 95 |
| 677 | >0.4 | 75 | 90 |
| 678 | >2.2 | 75 | 95 |
| 679 | >5.7 | 85 | 90 |
| 680 | >3.3 | 85 | 90 |
| 681 | >0.5 | 85 | 90 |
| 682 | >2.3 | 80 | 90 |
| 683 | >2.2 | 85 | 90 |
| 684 | >0.7 | 85 | 90 |
| 685 | >3.2 | 80 | 90 |
| 686 | >0.7 | 80 | 90 |

INDUSTRIAL APPLICABILITY

As described above, the present disclosure enables the methylation of the CpG island of a colorectal cancer-specific marker gene to be detected to thereby provide information for diagnosing colorectal cancer. The use of the inventive method for detecting methylation and the inventive composition, kit and nucleic acid chip for diagnosing colorectal cancer makes it possible to diagnose colorectal cancer at an early transformation stage, thus enabling the early diagnosis of colorectal cancer. In addition, the inventive method enables colorectal cancer to be effectively diagnosed in an accurate and rapid manner compared to conventional methods.

Although the present disclosure has been described in detail with reference to the specific features, it will be apparent to those skilled in the art that this description is only for a preferred embodiment and does not limit the scope of the present disclosure. Thus, the substantial scope of the present disclosure will be defined by the appended claims and equivalents thereof.

What is claimed is:

1. A method for detecting CpG methylation of GPM6A (glycoprotein M6A) gene, the method comprising the steps of:
   (a) isolating genomic DNA from a clinical sample;
   (b) treating the genomic DNA or a fragment thereof with bisulfite;
   (c) amplifying a methylated CpG of GPM6A gene in the bisulfite-treated genomic DNA or fragment thereof from step (b) by using primer pair comprising:
   a primer comprising the sequence of SEQ ID NO: 25, and a primer comprising the sequence of SEQ ID NO: 24, 27, 29, 31, 33, 35, 37, 39, 41, 43, 45, 47, 49, 51, 53, 55, 57 or 59 to amplify a methylated CpG of the bisulfite-treated GPM6A gene; and
   (d) determining whether the CpG of GPM6A was methylated based on whether the DNA was amplified in step (c).

2. The method of claim 1, wherein the detection of methylation is performed by real-time methylation-specific PCR.

3. The method of claim 1, wherein the clinical sample is selected from the group consisting of a tissue, cell, blood, blood plasma, serum, feces, and urine from a patient suspected of cancer or a subject to be diagnosed.

4. The method of claim 1, wherein step (d) is performed by using probe(s) capable of hybridizing with a methylated CpG of GPM6A comprising at least one or more CpG dinucleotide in a region which hybridizes to the methylated CpG of GPM6A.

5. The method of claim 4, wherein the probe(s) comprise sequence(s) of SEQ ID NO: 26, 107, 190, 393, 536, 659, 762, 815, 968, 1071, 1191, 1277 and 1360.

* * * * *

SEQUENCE LISTING

<160> NUMBER OF SEQ ID NOS: 1408

<210> SEQ ID NO 1
<211> LENGTH: 700
<212> TYPE: DNA
<213> ORGANISM: Artificial Sequence
<220> FEATURE:
<223> OTHER INFORMATION: Synthetic Construct

<400> SEQUENCE: 1

```
ggtctaccgt gctgggggcg gtatttggga aataaagaaa gactaagaga cccaggatcc      60
gaatagcgag gcgattacag ggagatctct gtcctcccga gttcccacgt tttcatgttc     120
tctttgggga gcaagttgaa acggggcacg agaaatggaa acttcctaaa acttccactt     180
tgtacaggtt tgagcagagg aaggtgctgg tgcagggcca gactggggac aatttctagt     240 cccttttccaa acgaagtgcc catttgcaca aaaggtttga ggttgaggct gaaggctgat     300
tcttcctaaa ttccacctgg gtaaacagcg tgattaaaag ggcgtccaca ctggctcggg     360
tcactggacg gtggagttcg gcgcagttca gcttcgctca agtttccagg cagggtccgc     420
```

```
ttattcggtg cttagcggag gcagcttgga atagctccag gaatgtgact gcgtgtggcg      480 gagggagga agaactgggt gtgaaatagc cgattcacac ccagcactag gacgcagggt      540
cccacgagtc acctcgaaga gcgagggaga agctgggag gagaaagcac tcgccatccc      600
tggactggcg tatccacagg cgcaggggag atgctgctct tccgcggttg ccgactgcgt      660
tcagcccgca gcccgagtta ctcttccaac cccagcccgc                            700

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
gtatttggga aataaagaaa                                                  20

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
gactaagaga cccaggatcc gaatagcgag                                       30

<210> SEQ ID NO 4
<211> LENGTH: 40
<212> TYPE: DNA
<213> ORGANISM: Artificial Sequence
<220> FEATURE:
<223> OTHER INFORMATION: Synthetic Construct

<400> SEQUENCE: 4
gttcccacgt tttcatgttc tctttgggga gcaagttgaa                            40

<210> SEQ ID NO 5
<211> LENGTH: 50
<212> TYPE: DNA
<213> ORGANISM: Artificial Sequence
<220> FEATURE:
<223> OTHER INFORMATION: Synthetic Construct

<400> SEQUENCE: 5
ggcgtccaca ctggctcggg tcactggacg gtggagttcg gcgcagttca                 50

<210> SEQ ID NO 6
<211> LENGTH: 60
<212> TYPE: DNA
<213> ORGANISM: Artificial Sequence
<220> FEATURE:
<223> OTHER INFORMATION: Synthetic Construct

<400> SEQUENCE: 6
agtttccagg cagggtccgc ttattcggtg cttagcggag gcagcttgga atagctccag      60

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
```

-continued tgttgatttt tggtgtattg a                    21

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
aacacatcaa crtcctaatt acata                25

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tgtttggtgt aggggggaagt                     20

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct

<400> SEQUENCE: 10
cccraaaaaa ttattttacc tcca                 24

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11
gggaaataaa gaaagattaa gaga                 24

<210> SEQ ID NO 12
<211> LENGTH: 19
<212> TYPE: DNA
<213> ORGANISM: Artificial Sequence
<220> FEATURE:
<223> OTHER INFORMATION: Synthetic Construct

<400> SEQUENCE: 12
accccrtttc aacttactc                       19

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
attttagtgg tttaaagatg                      20

<210> SEQ ID NO 14
<211> LENGTH: 19
<212> TYPE: DNA

-continued

```
<213> ORGANISM: Artificial Sequence
<220> FEATURE:
<223> OTHER INFORMATION: Synthetic Construct

<400> SEQUENCE: 14
tgggtgtatt gagagattt                                                19

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
aagattaaga gatttaggat                                               20

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16 ttaaagggc gtttatattg gttcg                                          25

<210> SEQ ID NO 17
<211> LENGTH: 24
<212> TYPE: DNA
<213> ORGANISM: Artificial Sequence
<220> FEATURE:
<223> OTHER INFORMATION: Synthetic Construct

<400> SEQUENCE: 17
cctcgctctt cgaaataact cgta                                          24

<210> SEQ ID NO 18
<211> LENGTH: 26
<212> TYPE: DNA
<213> ORGANISM: Artificial Sequence
<220> FEATURE:
<223> OTHER INFORMATION: Synthetic Construct

<400> SEQUENCE: 18
tagggttcgt ttattcggtg tttagc                                        26

<210> SEQ ID NO 19
<211> LENGTH: 24
<212> TYPE: DNA
<213> ORGANISM: Artificial Sequence
<220> FEATURE:
<223> OTHER INFORMATION: Synthetic Construct

<400> SEQUENCE: 19
cctcgctctt cgaaataact cgta                                          24

<210> SEQ ID NO 20
<211> LENGTH: 25
<212> TYPE: DNA
<213> ORGANISM: Artificial Sequence
<220> FEATURE:
<223> OTHER INFORMATION: Synthetic Construct

<400> SEQUENCE: 20
taaaagggtg tttatattgg tttgg                                         25
```

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct

<400> SEQUENCE: 21
ccctcactct tcaaaataac tcata                                           25

<210> SEQ ID NO 22
<211> LENGTH: 29
<212> TYPE: DNA
<213> ORGANISM: Artificial Sequence
<220> FEATURE:
<223> OTHER INFORMATION: Synthetic Construct

<400> SEQUENCE: 22
ggtagggttt gtttatttgg tgtttagtg                                       29

<210> SEQ ID NO 23
<211> LENGTH: 26
<212> TYPE: DNA
<213> ORGANISM: Artificial Sequence
<220> FEATURE:
<223> OTHER INFORMATION: Synthetic Construct

<400> SEQUENCE: 23
tccctcactc ttcaaaataa ctcata                                          26

<210> SEQ ID NO 24
<211> LENGTH: 14
<212> TYPE: DNA
<213> ORGANISM: Artificial Sequence
<220> FEATURE:
<223> OTHER INFORMATION: Synthetic Construct

<400> SEQUENCE: 24
gtttatcgtg ttgg                                                       14

<210> SEQ ID NO 25
<211> LENGTH: 14
<212> TYPE: DNA
<213> ORGANISM: Artificial Sequence
<220> FEATURE:
<223> OTHER INFORMATION: Synthetic Construct

<400> SEQUENCE: 25
aaacataaaa acgt                                                       14

<210> SEQ ID NO 26
<211> LENGTH: 27
<212> TYPE: DNA
<213> ORGANISM: Artificial Sequence
<220> FEATURE:
<223> OTHER INFORMATION: Synthetic Construct

<400> SEQUENCE: 26
gggagatttt tgtttttcg agttttt                                          27

<210> SEQ ID NO 27
<211> LENGTH: 14
<212> TYPE: DNA
<213> ORGANISM: Artificial Sequence
<220> FEATURE:

<223> OTHER INFORMATION: Synthetic Construct

<400> SEQUENCE: 27
tttatcgtgt tggg                                                      14

<210> SEQ ID NO 28
<211> LENGTH: 14
<212> TYPE: DNA
<213> ORGANISM: Artificial Sequence
<220> FEATURE:
<223> OTHER INFORMATION: Synthetic Construct

<400> SEQUENCE: 28
aaacataaaa acgt                                                      14

<210> SEQ ID NO 29
<211> LENGTH: 14
<212> TYPE: DNA
<213> ORGANISM: Artificial Sequence
<220> FEATURE:
<223> OTHER INFORMATION: Synthetic Construct

<400> SEQUENCE: 29
ttatcgtgtt gggg                                                      14

<210> SEQ ID NO 30
<211> LENGTH: 14
<212> TYPE: DNA
<213> ORGANISM: Artificial Sequence
<220> FEATURE:
<223> OTHER INFORMATION: Synthetic Construct

<400> SEQUENCE: 30
aaacataaaa acgt                                                      14

<210> SEQ ID NO 31
<211> LENGTH: 14
<212> TYPE: DNA
<213> ORGANISM: Artificial Sequence
<220> FEATURE:
<223> OTHER INFORMATION: Synthetic Construct

<400> SEQUENCE: 31
tatcgtgttg gggg                                                      14

<210> SEQ ID NO 32
<211> LENGTH: 14
<212> TYPE: DNA
<213> ORGANISM: Artificial Sequence
<220> FEATURE:
<223> OTHER INFORMATION: Synthetic Construct

<400> SEQUENCE: 32
aaacataaaa acgt                                                      14

<210> SEQ ID NO 33
<211> LENGTH: 14
<212> TYPE: DNA
<213> ORGANISM: Artificial Sequence
<220> FEATURE:
<223> OTHER INFORMATION: Synthetic Construct

<400> SEQUENCE: 33
atcgtgttgg gggc                                                      14

```
<210> SEQ ID NO 34
<211> LENGTH: 14
<212> TYPE: DNA
<213> ORGANISM: Artificial Sequence
<220> FEATURE:
<223> OTHER INFORMATION: Synthetic Construct

<400> SEQUENCE: 34
aaacataaaa acgt                                                       14

<210> SEQ ID NO 35
<211> LENGTH: 14
<212> TYPE: DNA
<213> ORGANISM: Artificial Sequence
<220> FEATURE:
<223> OTHER INFORMATION: Synthetic Construct

<400> SEQUENCE: 35
tcgtgttggg ggcg                                                       14

<210> SEQ ID NO 36
<211> LENGTH: 14
<212> TYPE: DNA
<213> ORGANISM: Artificial Sequence
<220> FEATURE:
<223> OTHER INFORMATION: Synthetic Construct

<400> SEQUENCE: 36
aaacataaaa acgt                                                       14

<210> SEQ ID NO 37
<211> LENGTH: 14
<212> TYPE: DNA
<213> ORGANISM: Artificial Sequence
<220> FEATURE:
<223> OTHER INFORMATION: Synthetic Construct

<400> SEQUENCE: 37
cgtgttgggg gcgg                                                       14

<210> SEQ ID NO 38
<211> LENGTH: 14
<212> TYPE: DNA
<213> ORGANISM: Artificial Sequence
<220> FEATURE:
<223> OTHER INFORMATION: Synthetic Construct

<400> SEQUENCE: 38
aaacataaaa acgt                                                       14

<210> SEQ ID NO 39
<211> LENGTH: 14
<212> TYPE: DNA
<213> ORGANISM: Artificial Sequence
<220> FEATURE:
<223> OTHER INFORMATION: Synthetic Construct

<400> SEQUENCE: 39
gtgttggggg cggt                                                       14

<210> SEQ ID NO 40
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 40
aaacataaaa acgt                                                         14

<210> SEQ ID NO 41
<211> LENGTH: 14
<212> TYPE: DNA
<213> ORGANISM: Artificial Sequence
<220> FEATURE:
<223> OTHER INFORMATION: Synthetic Construct

<400> SEQUENCE: 41
tgttgggggc ggta                                                         14

<210> SEQ ID NO 42
<211> LENGTH: 14
<212> TYPE: DNA
<213> ORGANISM: Artificial Sequence
<220> FEATURE:
<223> OTHER INFORMATION: Synthetic Construct

<400> SEQUENCE: 42
aaacataaaa acgt                                                         14

<210> SEQ ID NO 43
<211> LENGTH: 14
<212> TYPE: DNA
<213> ORGANISM: Artificial Sequence
<220> FEATURE:
<223> OTHER INFORMATION: Synthetic Construct

<400> SEQUENCE: 43 gttggggcg gtat                                                          14

<210> SEQ ID NO 44
<211> LENGTH: 14
<212> TYPE: DNA
<213> ORGANISM: Artificial Sequence
<220> FEATURE:
<223> OTHER INFORMATION: Synthetic Construct

<400> SEQUENCE: 44
aaacataaaa acgt                                                         14

<210> SEQ ID NO 45
<211> LENGTH: 14
<212> TYPE: DNA
<213> ORGANISM: Artificial Sequence
<220> FEATURE:
<223> OTHER INFORMATION: Synthetic Construct

<400> SEQUENCE: 45 ttggggcgg tatt                                                          14

<210> SEQ ID NO 46
<211> LENGTH: 14
<212> TYPE: DNA
<213> ORGANISM: Artificial Sequence
<220> FEATURE:
<223> OTHER INFORMATION: Synthetic Construct

<400> SEQUENCE: 46
aaacataaaa acgt                                                         14

<210> SEQ ID NO 47
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 47
tgggggcggt attt                                                         14

<210> SEQ ID NO 48
<211> LENGTH: 14
<212> TYPE: DNA
<213> ORGANISM: Artificial Sequence
<220> FEATURE:
<223> OTHER INFORMATION: Synthetic Construct

<400> SEQUENCE: 48
aaacataaaa acgt                                                         14

<210> SEQ ID NO 49
<211> LENGTH: 14
<212> TYPE: DNA
<213> ORGANISM: Artificial Sequence
<220> FEATURE:
<223> OTHER INFORMATION: Synthetic Construct

<400> SEQUENCE: 49 ggggcggta tttg                                                          14

<210> SEQ ID NO 50
<211> LENGTH: 14
<212> TYPE: DNA
<213> ORGANISM: Artificial Sequence
<220> FEATURE:
<223> OTHER INFORMATION: Synthetic Construct

<400> SEQUENCE: 50
aaacataaaa acgt                                                         14

<210> SEQ ID NO 51
<211> LENGTH: 14
<212> TYPE: DNA
<213> ORGANISM: Artificial Sequence
<220> FEATURE:
<223> OTHER INFORMATION: Synthetic Construct

<400> SEQUENCE: 51
ggggcggtat ttgg                                                         14

<210> SEQ ID NO 52
<211> LENGTH: 14
<212> TYPE: DNA
<213> ORGANISM: Artificial Sequence
<220> FEATURE:
<223> OTHER INFORMATION: Synthetic Construct

<400> SEQUENCE: 52
aaacataaaa acgt                                                         14

<210> SEQ ID NO 53
<211> LENGTH: 14
<212> TYPE: DNA
<213> ORGANISM: Artificial Sequence
<220> FEATURE:
<223> OTHER INFORMATION: Synthetic Construct

<400> SEQUENCE: 53
```
gggcggtatt tggg                                                         14

<210> SEQ ID NO 54
<211> LENGTH: 14
<212> TYPE: DNA
<213> ORGANISM: Artificial Sequence
<220> FEATURE:
<223> OTHER INFORMATION: Synthetic Construct

<400> SEQUENCE: 54
aaacataaaa acgt                                                         14

<210> SEQ ID NO 55
<211> LENGTH: 14
<212> TYPE: DNA
<213> ORGANISM: Artificial Sequence
<220> FEATURE:
<223> OTHER INFORMATION: Synthetic Construct

<400> SEQUENCE: 55
ggcggtattt ggga                                                         14

<210> SEQ ID NO 56
<211> LENGTH: 14
<212> TYPE: DNA
<213> ORGANISM: Artificial Sequence
<220> FEATURE:
<223> OTHER INFORMATION: Synthetic Construct

<400> SEQUENCE: 56
aaacataaaa acgt                                                         14

<210> SEQ ID NO 57
<211> LENGTH: 14
<212> TYPE: DNA
<213> ORGANISM: Artificial Sequence
<220> FEATURE:
<223> OTHER INFORMATION: Synthetic Construct

<400> SEQUENCE: 57
gcggtatttg ggaa                                                         14

<210> SEQ ID NO 58
<211> LENGTH: 14
<212> TYPE: DNA
<213> ORGANISM: Artificial Sequence
<220> FEATURE:
<223> OTHER INFORMATION: Synthetic Construct

<400> SEQUENCE: 58
aaacataaaa acgt                                                         14

<210> SEQ ID NO 59
<211> LENGTH: 14
<212> TYPE: DNA
<213> ORGANISM: Artificial Sequence
<220> FEATURE:
<223> OTHER INFORMATION: Synthetic Construct

<400> SEQUENCE: 59
cggtatttgg gaaa                                                         14

<210> SEQ ID NO 60
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 60
aaacataaaa acgt                                                         14

<210> SEQ ID NO 61
<211> LENGTH: 14
<212> TYPE: DNA
<213> ORGANISM: Artificial Sequence
<220> FEATURE:
<223> OTHER INFORMATION: Synthetic Construct

<400> SEQUENCE: 61
ggtatttggg aaat                                                         14

<210> SEQ ID NO 62
<211> LENGTH: 14
<212> TYPE: DNA
<213> ORGANISM: Artificial Sequence
<220> FEATURE:
<223> OTHER INFORMATION: Synthetic Construct

<400> SEQUENCE: 62
aaacataaaa acgt                                                         14

<210> SEQ ID NO 63
<211> LENGTH: 14
<212> TYPE: DNA
<213> ORGANISM: Artificial Sequence
<220> FEATURE:
<223> OTHER INFORMATION: Synthetic Construct

<400> SEQUENCE: 63
gtatttggga aata                                                         14

<210> SEQ ID NO 64
<211> LENGTH: 14
<212> TYPE: DNA
<213> ORGANISM: Artificial Sequence
<220> FEATURE:
<223> OTHER INFORMATION: Synthetic Construct

<400> SEQUENCE: 64
aaacataaaa acgt                                                         14

<210> SEQ ID NO 65
<211> LENGTH: 14
<212> TYPE: DNA
<213> ORGANISM: Artificial Sequence
<220> FEATURE:
<223> OTHER INFORMATION: Synthetic Construct

<400> SEQUENCE: 65
tatttgggaa ataa                                                         14

<210> SEQ ID NO 66
<211> LENGTH: 14
<212> TYPE: DNA
<213> ORGANISM: Artificial Sequence
<220> FEATURE:
<223> OTHER INFORMATION: Synthetic Construct

<400> SEQUENCE: 66
aaacataaaa acgt                                                         14
```

<210> SEQ ID NO 67
<211> LENGTH: 14
<212> TYPE: DNA
<213> ORGANISM: Artificial Sequence
<220> FEATURE:
<223> OTHER INFORMATION: Synthetic Construct

<400> SEQUENCE: 67
atttgggaaa taaa                                                          14

<210> SEQ ID NO 68
<211> LENGTH: 14
<212> TYPE: DNA
<213> ORGANISM: Artificial Sequence
<220> FEATURE:
<223> OTHER INFORMATION: Synthetic Construct

<400> SEQUENCE: 68
aaacataaaa acgt                                                          14

<210> SEQ ID NO 69
<211> LENGTH: 14
<212> TYPE: DNA
<213> ORGANISM: Artificial Sequence
<220> FEATURE:
<223> OTHER INFORMATION: Synthetic Construct

<400> SEQUENCE: 69
tttgggaaat aaag                                                          14

<210> SEQ ID NO 70
<211> LENGTH: 14
<212> TYPE: DNA
<213> ORGANISM: Artificial Sequence
<220> FEATURE:
<223> OTHER INFORMATION: Synthetic Construct

<400> SEQUENCE: 70
aaacataaaa acgt                                                          14

<210> SEQ ID NO 71
<211> LENGTH: 14
<212> TYPE: DNA
<213> ORGANISM: Artificial Sequence
<220> FEATURE:
<223> OTHER INFORMATION: Synthetic Construct

<400> SEQUENCE: 71
ttgggaaata aaga                                                          14

<210> SEQ ID NO 72
<211> LENGTH: 14
<212> TYPE: DNA
<213> ORGANISM: Artificial Sequence
<220> FEATURE:
<223> OTHER INFORMATION: Synthetic Construct

<400> SEQUENCE: 72
aaacataaaa acgt                                                          14

<210> SEQ ID NO 73
<211> LENGTH: 14
<212> TYPE: DNA
<213> ORGANISM: Artificial Sequence
<220> FEATURE:
<223> OTHER INFORMATION: Synthetic Construct

<400> SEQUENCE: 73
tgggaaataa agaa                                                              14

<210> SEQ ID NO 74
<211> LENGTH: 14
<212> TYPE: DNA
<213> ORGANISM: Artificial Sequence
<220> FEATURE:
<223> OTHER INFORMATION: Synthetic Construct

<400> SEQUENCE: 74
aaacataaaa acgt                                                              14

<210> SEQ ID NO 75
<211> LENGTH: 14
<212> TYPE: DNA
<213> ORGANISM: Artificial Sequence
<220> FEATURE:
<223> OTHER INFORMATION: Synthetic Construct

<400> SEQUENCE: 75
gggaaataaa gaaa                                                              14

<210> SEQ ID NO 76
<211> LENGTH: 14
<212> TYPE: DNA
<213> ORGANISM: Artificial Sequence
<220> FEATURE:
<223> OTHER INFORMATION: Synthetic Construct

<400> SEQUENCE: 76
aaacataaaa acgt                                                              14

<210> SEQ ID NO 77
<211> LENGTH: 14
<212> TYPE: DNA
<213> ORGANISM: Artificial Sequence
<220> FEATURE:
<223> OTHER INFORMATION: Synthetic Construct

<400> SEQUENCE: 77
ggaaataaag aaag                                                              14

<210> SEQ ID NO 78
<211> LENGTH: 14
<212> TYPE: DNA
<213> ORGANISM: Artificial Sequence
<220> FEATURE:
<223> OTHER INFORMATION: Synthetic Construct

<400> SEQUENCE: 78
aaacataaaa acgt                                                              14

<210> SEQ ID NO 79
<211> LENGTH: 14
<212> TYPE: DNA
<213> ORGANISM: Artificial Sequence
<220> FEATURE:
<223> OTHER INFORMATION: Synthetic Construct

<400> SEQUENCE: 79
gaaataaaga aaga                                                              14

<210> SEQ ID NO 80

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 80
aaacataaaa acgt                                                     14

<210> SEQ ID NO 81
<211> LENGTH: 14
<212> TYPE: DNA
<213> ORGANISM: Artificial Sequence
<220> FEATURE:
<223> OTHER INFORMATION: Synthetic Construct

<400> SEQUENCE: 81
aaataaagaa agat                                                     14

<210> SEQ ID NO 82
<211> LENGTH: 14
<212> TYPE: DNA
<213> ORGANISM: Artificial Sequence
<220> FEATURE:
<223> OTHER INFORMATION: Synthetic Construct

<400> SEQUENCE: 82
aaacataaaa acgt                                                     14

<210> SEQ ID NO 83
<211> LENGTH: 14
<212> TYPE: DNA
<213> ORGANISM: Artificial Sequence
<220> FEATURE:
<223> OTHER INFORMATION: Synthetic Construct

<400> SEQUENCE: 83
aataaagaaa gatt                                                     14

<210> SEQ ID NO 84
<211> LENGTH: 14
<212> TYPE: DNA
<213> ORGANISM: Artificial Sequence
<220> FEATURE:
<223> OTHER INFORMATION: Synthetic Construct

<400> SEQUENCE: 84
aaacataaaa acgt                                                     14

<210> SEQ ID NO 85
<211> LENGTH: 14
<212> TYPE: DNA
<213> ORGANISM: Artificial Sequence
<220> FEATURE:
<223> OTHER INFORMATION: Synthetic Construct

<400> SEQUENCE: 85
ataaagaaag atta                                                     14

<210> SEQ ID NO 86
<211> LENGTH: 14
<212> TYPE: DNA
<213> ORGANISM: Artificial Sequence
<220> FEATURE:
<223> OTHER INFORMATION: Synthetic Construct

<400> SEQUENCE: 86
```
aaacataaaa acgt                                        14

<210> SEQ ID NO 87
<211> LENGTH: 14
<212> TYPE: DNA
<213> ORGANISM: Artificial Sequence
<220> FEATURE:
<223> OTHER INFORMATION: Synthetic Construct

<400> SEQUENCE: 87
taaagaaaga ttaa                                        14

<210> SEQ ID NO 88
<211> LENGTH: 14
<212> TYPE: DNA
<213> ORGANISM: Artificial Sequence
<220> FEATURE:
<223> OTHER INFORMATION: Synthetic Construct

<400> SEQUENCE: 88
aaacataaaa acgt                                        14

<210> SEQ ID NO 89
<211> LENGTH: 14
<212> TYPE: DNA
<213> ORGANISM: Artificial Sequence
<220> FEATURE:
<223> OTHER INFORMATION: Synthetic Construct

<400> SEQUENCE: 89
aaagaaagat taag                                        14

<210> SEQ ID NO 90
<211> LENGTH: 14
<212> TYPE: DNA
<213> ORGANISM: Artificial Sequence
<220> FEATURE:
<223> OTHER INFORMATION: Synthetic Construct

<400> SEQUENCE: 90
aaacataaaa acgt                                        14

<210> SEQ ID NO 91
<211> LENGTH: 14
<212> TYPE: DNA
<213> ORGANISM: Artificial Sequence
<220> FEATURE:
<223> OTHER INFORMATION: Synthetic Construct

<400> SEQUENCE: 91
aagaaagatt aaga                                        14

<210> SEQ ID NO 92
<211> LENGTH: 14
<212> TYPE: DNA
<213> ORGANISM: Artificial Sequence
<220> FEATURE:
<223> OTHER INFORMATION: Synthetic Construct

<400> SEQUENCE: 92
aaacataaaa acgt                                        14

<210> SEQ ID NO 93
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 93
agaaagatta agag                                                          14

<210> SEQ ID NO 94
<211> LENGTH: 14
<212> TYPE: DNA
<213> ORGANISM: Artificial Sequence
<220> FEATURE:
<223> OTHER INFORMATION: Synthetic Construct

<400> SEQUENCE: 94
aaacataaaa acgt                                                          14

<210> SEQ ID NO 95
<211> LENGTH: 14
<212> TYPE: DNA
<213> ORGANISM: Artificial Sequence
<220> FEATURE:
<223> OTHER INFORMATION: Synthetic Construct

<400> SEQUENCE: 95
gaaagattaa gaga                                                          14

<210> SEQ ID NO 96
<211> LENGTH: 14
<212> TYPE: DNA
<213> ORGANISM: Artificial Sequence
<220> FEATURE:
<223> OTHER INFORMATION: Synthetic Construct

<400> SEQUENCE: 96
aaacataaaa acgt                                                          14

<210> SEQ ID NO 97
<211> LENGTH: 14
<212> TYPE: DNA
<213> ORGANISM: Artificial Sequence
<220> FEATURE:
<223> OTHER INFORMATION: Synthetic Construct

<400> SEQUENCE: 97
aaagattaag agat                                                          14

<210> SEQ ID NO 98
<211> LENGTH: 14
<212> TYPE: DNA
<213> ORGANISM: Artificial Sequence
<220> FEATURE:
<223> OTHER INFORMATION: Synthetic Construct

<400> SEQUENCE: 98
aaacataaaa acgt                                                          14

<210> SEQ ID NO 99
<211> LENGTH: 14
<212> TYPE: DNA
<213> ORGANISM: Artificial Sequence
<220> FEATURE:
<223> OTHER INFORMATION: Synthetic Construct

<400> SEQUENCE: 99
aagattaaga gatt                                                          14
```

```
<210> SEQ ID NO 100
<211> LENGTH: 14
<212> TYPE: DNA
<213> ORGANISM: Artificial Sequence
<220> FEATURE:
<223> OTHER INFORMATION: Synthetic Construct

<400> SEQUENCE: 100
aaacataaaa acgt                                                          14

<210> SEQ ID NO 101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 101
agattaagag attt                                                          14

<210> SEQ ID NO 102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 102
aaacataaaa acgt                                                          14

<210> SEQ ID NO 103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 103
gattaagaga ttta                                                          14

<210> SEQ ID NO 104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 104
aaacataaaa acgt                                                          14

<210> SEQ ID NO 105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 105
attaagagat ttag                                                          14

<210> SEQ ID NO 106
<211> LENGTH: 14
<212> TYPE: DNA
<213> ORGANISM: Artificial Sequence
<220> FEATURE:
```

```
<223> OTHER INFORMATION: Synthetic Construct

<400> SEQUENCE: 106
tttccatttc tcgt                                                     14

<210> SEQ ID NO 107
<211> LENGTH: 21
<212> TYPE: DNA
<213> ORGANISM: Artificial Sequence
<220> FEATURE:
<223> OTHER INFORMATION: Synthetic Construct

<400> SEQUENCE: 107
gggagtaagt tgaaacgggg t                                             21

<210> SEQ ID NO 108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 108
ttaagagatt tagg                                                     14

<210> SEQ ID NO 109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 109
tttccatttc tcgt                                                     14

<210> SEQ ID NO 110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 110
taagagattt agga                                                     14

<210> SEQ ID NO 111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 111
tttccatttc tcgt                                                     14

<210> SEQ ID NO 112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 112
aagagattta ggat                                                     14
```

```
<210> SEQ ID NO 113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 113
tttccatttc tcgt                                                        14

<210> SEQ ID NO 114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 114
agagatttag gatt                                                        14

<210> SEQ ID NO 115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 115
tttccatttc tcgt                                                        14

<210> SEQ ID NO 116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 116
gagatttagg attc                                                        14

<210> SEQ ID NO 117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 117
tttccatttc tcgt                                                        14

<210> SEQ ID NO 118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 118
agatttagga ttcg                                                        14

<210> SEQ ID NO 119
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 119
tttccatttc tcgt                                                      14

<210> SEQ ID NO 120
<211> LENGTH: 14
<212> TYPE: DNA
<213> ORGANISM: Artificial Sequence
<220> FEATURE:
<223> OTHER INFORMATION: Synthetic Construct

<400> SEQUENCE: 120
gatttaggat tcga                                                      14

<210> SEQ ID NO 121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 121
tttccatttc tcgt                                                      14

<210> SEQ ID NO 122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 122
atttaggatt cgaa                                                      14

<210> SEQ ID NO 123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 123
tttccatttc tcgt                                                      14

<210> SEQ ID NO 124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 124
tttaggattc gaat                                                      14

<210> SEQ ID NO 125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 125
tttccatttc tcgt                                                      14

<210> SEQ ID NO 126
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 126
ttaggattcg aata                                                           14

<210> SEQ ID NO 127
<211> LENGTH: 14
<212> TYPE: DNA
<213> ORGANISM: Artificial Sequence
<220> FEATURE:
<223> OTHER INFORMATION: Synthetic Construct

<400> SEQUENCE: 127
tttccatttc tcgt                                                           14

<210> SEQ ID NO 128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 128
taggattcga atag                                                           14

<210> SEQ ID NO 129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 129
tttccatttc tcgt                                                           14

<210> SEQ ID NO 130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 130
aggattcgaa tagc                                                           14

<210> SEQ ID NO 131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 131
tttccatttc tcgt                                                           14

<210> SEQ ID NO 132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 132
```
ggattcgaat agcg                                                        14

<210> SEQ ID NO 133
<211> LENGTH: 14
<212> TYPE: DNA
<213> ORGANISM: Artificial Sequence
<220> FEATURE:
<223> OTHER INFORMATION: Synthetic Construct

<400> SEQUENCE: 133
tttccatttc tcgt                                                        14

<210> SEQ ID NO 134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 134
gattcgaata gcga                                                        14

<210> SEQ ID NO 135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 135
tttccatttc tcgt                                                        14

<210> SEQ ID NO 136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 136
attcgaatag cgag                                                        14

<210> SEQ ID NO 137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 137
tttccatttc tcgt                                                        14

<210> SEQ ID NO 138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 138
ttcgaatagc gagg                                                        14

<210> SEQ ID NO 139
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 139
tttccatttc tcgt                                                         14

<210> SEQ ID NO 140
<211> LENGTH: 14
<212> TYPE: DNA
<213> ORGANISM: Artificial Sequence
<220> FEATURE:
<223> OTHER INFORMATION: Synthetic Construct

<400> SEQUENCE: 140
tcgaatagcg aggc                                                         14

<210> SEQ ID NO 141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 141
tttccatttc tcgt                                                         14

<210> SEQ ID NO 142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 142
cgaatagcga ggcg                                                         14

<210> SEQ ID NO 143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 143
tttccatttc tcgt                                                         14

<210> SEQ ID NO 144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 144
gaatagcgag gcga                                                         14

<210> SEQ ID NO 145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 145
tttccatttc tcgt                                                         14
```

<210> SEQ ID NO 146
<211> LENGTH: 14
<212> TYPE: DNA
<213> ORGANISM: Artificial Sequence
<220> FEATURE:
<223> OTHER INFORMATION: Synthetic Construct

<400> SEQUENCE: 146
aatagcgagg cgat                                                        14

<210> SEQ ID NO 147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 147
tttccatttc tcgt                                                        14

<210> SEQ ID NO 148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 148
atagcgaggc gatt                                                        14

<210> SEQ ID NO 149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 149
tttccatttc tcgt                                                        14

<210> SEQ ID NO 150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 150
tagcgaggcg atta                                                        14

<210> SEQ ID NO 151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 151
tttccatttc tcgt                                                        14

<210> SEQ ID NO 152
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 152
agcgaggcga ttat                                              14

<210> SEQ ID NO 153
<211> LENGTH: 14
<212> TYPE: DNA
<213> ORGANISM: Artificial Sequence
<220> FEATURE:
<223> OTHER INFORMATION: Synthetic Construct

<400> SEQUENCE: 153
tttccatttc tcgt                                              14

<210> SEQ ID NO 154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 154
gcgaggcgat tata                                              14

<210> SEQ ID NO 155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 155
tttccatttc tcgt                                              14

<210> SEQ ID NO 156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 156
cgaggcgatt atag                                              14

<210> SEQ ID NO 157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 157
tttccatttc tcgt                                              14

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 158
gaggcgatta tagg                                              14

<210> SEQ ID NO 159
```

```
<210> SEQ ID NO 159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 159
tttccatttc tcgt                                                     14

<210> SEQ ID NO 160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 160
aggcgattat aggg                                                     14

<210> SEQ ID NO 161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 161
tttccatttc tcgt                                                     14

<210> SEQ ID NO 162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 162
ggcgattata ggga                                                     14

<210> SEQ ID NO 163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 163
tttccatttc tcgt                                                     14

<210> SEQ ID NO 164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 164
gcgattatag ggag                                                     14

<210> SEQ ID NO 165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 165
```

```
tttccatttc tcgt                                                    14

<210> SEQ ID NO 166
<211> LENGTH: 14
<212> TYPE: DNA
<213> ORGANISM: Artificial Sequence
<220> FEATURE:
<223> OTHER INFORMATION: Synthetic Construct

<400> SEQUENCE: 166
cgattatagg gaga                                                    14

<210> SEQ ID NO 167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 167
tttccatttc tcgt                                                    14

<210> SEQ ID NO 168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 168
gattataggg agat                                                    14

<210> SEQ ID NO 169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 169
tttccatttc tcgt                                                    14

<210> SEQ ID NO 170
<211> LENGTH: 14
<212> TYPE: DNA
<213> ORGANISM: Artificial Sequence
<220> FEATURE:
<223> OTHER INFORMATION: Synthetic Construct

<400> SEQUENCE: 170
attataggga gatt                                                    14

<210> SEQ ID NO 171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 171
tttccatttc tcgt                                                    14

<210> SEQ ID NO 172
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 172
ttatagggag attt                                                        14

<210> SEQ ID NO 173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 173
tttccatttc tcgt                                                        14

<210> SEQ ID NO 174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 174
tatagggaga tttt                                                        14

<210> SEQ ID NO 175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 175
tttccatttc tcgt                                                        14

<210> SEQ ID NO 176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 176
atagggagat tttt                                                        14

<210> SEQ ID NO 177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 177
tttccatttc tcgt                                                        14

<210> SEQ ID NO 178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 178
tagggagatt tttg                                                        14
```

```
<210> SEQ ID NO 179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 179
tttccatttc tcgt                                                     14

<210> SEQ ID NO 180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 180
agggagattt ttgt                                                     14

<210> SEQ ID NO 181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 181
tttccatttc tcgt                                                     14

<210> SEQ ID NO 182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 182
gggagatttt tgtt                                                     14

<210> SEQ ID NO 183
<211> LENGTH: 14
<212> TYPE: DNA
<213> ORGANISM: Artificial Sequence
<220> FEATURE:
<223> OTHER INFORMATION: Synthetic Construct

<400> SEQUENCE: 183
tttccatttc tcgt                                                     14

<210> SEQ ID NO 184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 184
ggagattttt gttt                                                     14

<210> SEQ ID NO 185
<211> LENGTH: 14
<212> TYPE: DNA
<213> ORGANISM: Artificial Sequence
<220> FEATURE:
```

```
<223> OTHER INFORMATION: Synthetic Construct

<400> SEQUENCE: 185
tttccatttc tcgt                                                      14

<210> SEQ ID NO 186
<211> LENGTH: 14
<212> TYPE: DNA
<213> ORGANISM: Artificial Sequence
<220> FEATURE:
<223> OTHER INFORMATION: Synthetic Construct

<400> SEQUENCE: 186
gagatttttg tttt                                                      14

<210> SEQ ID NO 187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 187
tttccatttc tcgt                                                      14

<210> SEQ ID NO 188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 188
agatttttgt tttt                                                      14

<210> SEQ ID NO 189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 189
taaacacttc gttt                                                      14

<210> SEQ ID NO 190
<211> LENGTH: 26
<212> TYPE: DNA
<213> ORGANISM: Artificial Sequence
<220> FEATURE:
<223> OTHER INFORMATION: Synthetic Construct

<400> SEQUENCE: 190
ttggggataa tttttagttt tttttt                                         26

<210> SEQ ID NO 191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 191 gattttttgtt tttt                                                     14
```

```
<210> SEQ ID NO 192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 192
taaacacttc gttt                                                        14

<210> SEQ ID NO 193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 193
atttttgttt tttc                                                        14

<210> SEQ ID NO 194
<211> LENGTH: 14
<212> TYPE: DNA
<213> ORGANISM: Artificial Sequence
<220> FEATURE:
<223> OTHER INFORMATION: Synthetic Construct

<400> SEQUENCE: 194
taaacacttc gttt                                                        14

<210> SEQ ID NO 195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 195
tttttgtttt ttcg                                                        14

<210> SEQ ID NO 196
<211> LENGTH: 14
<212> TYPE: DNA
<213> ORGANISM: Artificial Sequence
<220> FEATURE:
<223> OTHER INFORMATION: Synthetic Construct

<400> SEQUENCE: 196
taaacacttc gttt                                                        14

<210> SEQ ID NO 197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 197
ttttgttttt tcga                                                        14

<210> SEQ ID NO 198
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 198
taaacacttc gttt                                                 14

<210> SEQ ID NO 199
<211> LENGTH: 14
<212> TYPE: DNA
<213> ORGANISM: Artificial Sequence
<220> FEATURE:
<223> OTHER INFORMATION: Synthetic Construct

<400> SEQUENCE: 199 tttgttttttt cgag                                                14

<210> SEQ ID NO 200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 200
taaacacttc gttt                                                 14

<210> SEQ ID NO 201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 201 ttgtttttttc gagt                                                14

<210> SEQ ID NO 202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 202
taaacacttc gttt                                                 14

<210> SEQ ID NO 203
<211> LENGTH: 14
<212> TYPE: DNA
<213> ORGANISM: Artificial Sequence
<220> FEATURE:
<223> OTHER INFORMATION: Synthetic Construct

<400> SEQUENCE: 203
tgttttttcg agtt                                                 14

<210> SEQ ID NO 204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 204
taaacacttc gttt                                                 14

<210> SEQ ID NO 205
<211> LENGTH: 14
```

-continued

```
<212> TYPE: DNA
<213> ORGANISM: Artificial Sequence
<220> FEATURE:
<223> OTHER INFORMATION: Synthetic Construct

<400> SEQUENCE: 205 gtttttcga gttt                                                          14

<210> SEQ ID NO 206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 206
taaacacttc gttt                                                         14

<210> SEQ ID NO 207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 207 tttttcgag tttt                                                          14

<210> SEQ ID NO 208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 208
taaacacttc gttt                                                         14

<210> SEQ ID NO 209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 209 ttttcgagt tttt                                                          14

<210> SEQ ID NO 210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 210
taaacacttc gttt                                                         14

<210> SEQ ID NO 211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 211
```
ttttcgagtt ttta                                         14

<210> SEQ ID NO 212
<211> LENGTH: 14
<212> TYPE: DNA
<213> ORGANISM: Artificial Sequence
<220> FEATURE:
<223> OTHER INFORMATION: Synthetic Construct

<400> SEQUENCE: 212
taaacacttc gttt                                         14

<210> SEQ ID NO 213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 213
tttcgagttt ttac                                         14

<210> SEQ ID NO 214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 214
taaacacttc gttt                                         14

<210> SEQ ID NO 215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 215
ttcgagtttt tacg                                         14

<210> SEQ ID NO 216
<211> LENGTH: 14
<212> TYPE: DNA
<213> ORGANISM: Artificial Sequence
<220> FEATURE:
<223> OTHER INFORMATION: Synthetic Construct

<400> SEQUENCE: 216
taaacacttc gttt                                         14

<210> SEQ ID NO 217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 217
tcgagttttt acgt                                         14

<210> SEQ ID NO 218
<211> LENGTH: 14
<212> TYPE: DNA
<213> ORGANISM: Artificial Sequence -continued

```
<220> FEATURE:
<223> OTHER INFORMATION: Synthetic Construct

<400> SEQUENCE: 218
taaacacttc gttt                                                        14

<210> SEQ ID NO 219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 219
cgagttttta cgtt                                                        14

<210> SEQ ID NO 220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 220
taaacacttc gttt                                                        14

<210> SEQ ID NO 221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 221
gagtttttac gttt                                                        14

<210> SEQ ID NO 222
<211> LENGTH: 14
<212> TYPE: DNA
<213> ORGANISM: Artificial Sequence
<220> FEATURE:
<223> OTHER INFORMATION: Synthetic Construct

<400> SEQUENCE: 222
taaacacttc gttt                                                        14

<210> SEQ ID NO 223
<211> LENGTH: 14
<212> TYPE: DNA
<213> ORGANISM: Artificial Sequence
<220> FEATURE:
<223> OTHER INFORMATION: Synthetic Construct

<400> SEQUENCE: 223 agttttacg tttt                                                         14

<210> SEQ ID NO 224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 224
taaacacttc gttt                                                        14
```

```
<210> SEQ ID NO 225
<211> LENGTH: 14
<212> TYPE: DNA
<213> ORGANISM: Artificial Sequence
<220> FEATURE:
<223> OTHER INFORMATION: Synthetic Construct

<400> SEQUENCE: 225
gtttttacgt tttt                                                       14

<210> SEQ ID NO 226
<211> LENGTH: 14
<212> TYPE: DNA
<213> ORGANISM: Artificial Sequence
<220> FEATURE:
<223> OTHER INFORMATION: Synthetic Construct

<400> SEQUENCE: 226
taaacacttc gttt                                                       14

<210> SEQ ID NO 227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 227
tttttacgtt ttta                                                       14

<210> SEQ ID NO 228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 228
taaacacttc gttt                                                       14

<210> SEQ ID NO 229
<211> LENGTH: 14
<212> TYPE: DNA
<213> ORGANISM: Artificial Sequence
<220> FEATURE:
<223> OTHER INFORMATION: Synthetic Construct

<400> SEQUENCE: 229
ttttacgttt ttat                                                       14

<210> SEQ ID NO 230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 230
taaacacttc gttt                                                       14

<210> SEQ ID NO 231
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 231
tttacgtttt tatg                                                       14

<210> SEQ ID NO 232
<211> LENGTH: 14
<212> TYPE: DNA
<213> ORGANISM: Artificial Sequence
<220> FEATURE:
<223> OTHER INFORMATION: Synthetic Construct

<400> SEQUENCE: 232
taaacacttc gttt                                                       14

<210> SEQ ID NO 233
<211> LENGTH: 14
<212> TYPE: DNA
<213> ORGANISM: Artificial Sequence
<220> FEATURE:
<223> OTHER INFORMATION: Synthetic Construct

<400> SEQUENCE: 233
ttacgttttt atgt                                                       14

<210> SEQ ID NO 234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 234
taaacacttc gttt                                                       14

<210> SEQ ID NO 235
<211> LENGTH: 14
<212> TYPE: DNA
<213> ORGANISM: Artificial Sequence
<220> FEATURE:
<223> OTHER INFORMATION: Synthetic Construct

<400> SEQUENCE: 235
tacgttttta tgtt                                                       14

<210> SEQ ID NO 236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 236
taaacacttc gttt                                                       14

<210> SEQ ID NO 237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 237 acgttttat gttt                                                        14

<210> SEQ ID NO 238
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 238
taaacacttc gttt                                                       14

<210> SEQ ID NO 239
<211> LENGTH: 14
<212> TYPE: DNA
<213> ORGANISM: Artificial Sequence
<220> FEATURE:
<223> OTHER INFORMATION: Synthetic Construct

<400> SEQUENCE: 239
cgtttttatg tttt                                                       14

<210> SEQ ID NO 240
<211> LENGTH: 14
<212> TYPE: DNA
<213> ORGANISM: Artificial Sequence
<220> FEATURE:
<223> OTHER INFORMATION: Synthetic Construct

<400> SEQUENCE: 240
taaacacttc gttt                                                       14

<210> SEQ ID NO 241
<211> LENGTH: 14
<212> TYPE: DNA
<213> ORGANISM: Artificial Sequence
<220> FEATURE:
<223> OTHER INFORMATION: Synthetic Construct

<400> SEQUENCE: 241
gtttttatgt tttt                                                       14

<210> SEQ ID NO 242
<211> LENGTH: 14
<212> TYPE: DNA
<213> ORGANISM: Artificial Sequence
<220> FEATURE:
<223> OTHER INFORMATION: Synthetic Construct

<400> SEQUENCE: 242
taaacacttc gttt                                                       14

<210> SEQ ID NO 243
<211> LENGTH: 14
<212> TYPE: DNA
<213> ORGANISM: Artificial Sequence
<220> FEATURE:
<223> OTHER INFORMATION: Synthetic Construct

<400> SEQUENCE: 243
tttttatgtt tttt                                                       14

<210> SEQ ID NO 244
<211> LENGTH: 14
<212> TYPE: DNA
<213> ORGANISM: Artificial Sequence
<220> FEATURE:
<223> OTHER INFORMATION: Synthetic Construct

<400> SEQUENCE: 244
```
taaacacttc gttt                                                    14

<210> SEQ ID NO 245
<211> LENGTH: 14
<212> TYPE: DNA
<213> ORGANISM: Artificial Sequence
<220> FEATURE:
<223> OTHER INFORMATION: Synthetic Construct

<400> SEQUENCE: 245
ttttatgttt tttt                                                    14

<210> SEQ ID NO 246
<211> LENGTH: 14
<212> TYPE: DNA
<213> ORGANISM: Artificial Sequence
<220> FEATURE:
<223> OTHER INFORMATION: Synthetic Construct

<400> SEQUENCE: 246
taaacacttc gttt                                                    14

<210> SEQ ID NO 247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 247
tttatgtttt tttt                                                    14

<210> SEQ ID NO 248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 248
taaacacttc gttt                                                    14

<210> SEQ ID NO 249
<211> LENGTH: 14
<212> TYPE: DNA
<213> ORGANISM: Artificial Sequence
<220> FEATURE:
<223> OTHER INFORMATION: Synthetic Construct

<400> SEQUENCE: 249
ttatgttttt tttg                                                    14

<210> SEQ ID NO 250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 250
taaacacttc gttt                                                    14

<210> SEQ ID NO 251
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 251 tatgttttt ttgg                                                        14

<210> SEQ ID NO 252
<211> LENGTH: 14
<212> TYPE: DNA
<213> ORGANISM: Artificial Sequence
<220> FEATURE:
<223> OTHER INFORMATION: Synthetic Construct

<400> SEQUENCE: 252
taaacacttc gttt                                                       14

<210> SEQ ID NO 253
<211> LENGTH: 14
<212> TYPE: DNA
<213> ORGANISM: Artificial Sequence
<220> FEATURE:
<223> OTHER INFORMATION: Synthetic Construct

<400> SEQUENCE: 253
atgttttttt tggg                                                       14

<210> SEQ ID NO 254
<211> LENGTH: 14
<212> TYPE: DNA
<213> ORGANISM: Artificial Sequence
<220> FEATURE:
<223> OTHER INFORMATION: Synthetic Construct

<400> SEQUENCE: 254
taaacacttc gttt                                                       14

<210> SEQ ID NO 255
<211> LENGTH: 14
<212> TYPE: DNA
<213> ORGANISM: Artificial Sequence
<220> FEATURE:
<223> OTHER INFORMATION: Synthetic Construct

<400> SEQUENCE: 255 tgttttttt gggg                                                        14

<210> SEQ ID NO 256
<211> LENGTH: 14
<212> TYPE: DNA
<213> ORGANISM: Artificial Sequence
<220> FEATURE:
<223> OTHER INFORMATION: Synthetic Construct

<400> SEQUENCE: 256
taaacacttc gttt                                                       14

<210> SEQ ID NO 257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 257 gtttttttg ggga                                                        14
```

```
<210> SEQ ID NO 258
<211> LENGTH: 14
<212> TYPE: DNA
<213> ORGANISM: Artificial Sequence
<220> FEATURE:
<223> OTHER INFORMATION: Synthetic Construct

<400> SEQUENCE: 258
taaacacttc gttt                                                      14

<210> SEQ ID NO 259
<211> LENGTH: 14
<212> TYPE: DNA
<213> ORGANISM: Artificial Sequence
<220> FEATURE:
<223> OTHER INFORMATION: Synthetic Construct

<400> SEQUENCE: 259
ttttttttgg ggag                                                      14

<210> SEQ ID NO 260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 260
taaacacttc gttt                                                      14

<210> SEQ ID NO 261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 261
tttttttggg gagt                                                      14

<210> SEQ ID NO 262
<211> LENGTH: 14
<212> TYPE: DNA
<213> ORGANISM: Artificial Sequence
<220> FEATURE:
<223> OTHER INFORMATION: Synthetic Construct

<400> SEQUENCE: 262
taaacacttc gttt                                                      14

<210> SEQ ID NO 263
<211> LENGTH: 14
<212> TYPE: DNA
<213> ORGANISM: Artificial Sequence
<220> FEATURE:
<223> OTHER INFORMATION: Synthetic Construct

<400> SEQUENCE: 263 tttttgggg agta                                                       14

<210> SEQ ID NO 264
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 264
taaacacttc gttt                                                          14

<210> SEQ ID NO 265
<211> LENGTH: 14
<212> TYPE: DNA
<213> ORGANISM: Artificial Sequence
<220> FEATURE:
<223> OTHER INFORMATION: Synthetic Construct

<400> SEQUENCE: 265
tttttgggga gtaa                                                          14

<210> SEQ ID NO 266
<211> LENGTH: 14
<212> TYPE: DNA
<213> ORGANISM: Artificial Sequence
<220> FEATURE:
<223> OTHER INFORMATION: Synthetic Construct

<400> SEQUENCE: 266
taaacacttc gttt                                                          14

<210> SEQ ID NO 267
<211> LENGTH: 14
<212> TYPE: DNA
<213> ORGANISM: Artificial Sequence
<220> FEATURE:
<223> OTHER INFORMATION: Synthetic Construct

<400> SEQUENCE: 267
ttttggggag taag                                                          14

<210> SEQ ID NO 268
<211> LENGTH: 14
<212> TYPE: DNA
<213> ORGANISM: Artificial Sequence
<220> FEATURE:
<223> OTHER INFORMATION: Synthetic Construct

<400> SEQUENCE: 268
taaacacttc gttt                                                          14

<210> SEQ ID NO 269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 269
tttggggagt aagt                                                          14

<210> SEQ ID NO 270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 270
taaacacttc gttt                                                          14

```
<210> SEQ ID NO 271
<211> LENGTH: 14
<212> TYPE: DNA
<213> ORGANISM: Artificial Sequence
<220> FEATURE:
<223> OTHER INFORMATION: Synthetic Construct

<400> SEQUENCE: 271
ttggggagta agtt                                                       14

<210> SEQ ID NO 272
<211> LENGTH: 14
<212> TYPE: DNA
<213> ORGANISM: Artificial Sequence
<220> FEATURE:
<223> OTHER INFORMATION: Synthetic Construct

<400> SEQUENCE: 272
taaacacttc gttt                                                       14

<210> SEQ ID NO 273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 273
tggggagtaa gttg                                                       14

<210> SEQ ID NO 274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 274
taaacacttc gttt                                                       14

<210> SEQ ID NO 275
<211> LENGTH: 14
<212> TYPE: DNA
<213> ORGANISM: Artificial Sequence
<220> FEATURE:
<223> OTHER INFORMATION: Synthetic Construct

<400> SEQUENCE: 275
ggggagtaag ttga                                                       14

<210> SEQ ID NO 276
<211> LENGTH: 14
<212> TYPE: DNA
<213> ORGANISM: Artificial Sequence
<220> FEATURE:
<223> OTHER INFORMATION: Synthetic Construct

<400> SEQUENCE: 276
taaacacttc gttt                                                       14

<210> SEQ ID NO 277
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 277
gggagtaagt tgaa                                                    14

<210> SEQ ID NO 278
<211> LENGTH: 14
<212> TYPE: DNA
<213> ORGANISM: Artificial Sequence
<220> FEATURE:
<223> OTHER INFORMATION: Synthetic Construct

<400> SEQUENCE: 278
taaacacttc gttt                                                    14

<210> SEQ ID NO 279
<211> LENGTH: 14
<212> TYPE: DNA
<213> ORGANISM: Artificial Sequence
<220> FEATURE:
<223> OTHER INFORMATION: Synthetic Construct

<400> SEQUENCE: 279
ggagtaagtt gaaa                                                    14

<210> SEQ ID NO 280
<211> LENGTH: 14
<212> TYPE: DNA
<213> ORGANISM: Artificial Sequence
<220> FEATURE:
<223> OTHER INFORMATION: Synthetic Construct

<400> SEQUENCE: 280
taaacacttc gttt                                                    14

<210> SEQ ID NO 281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 281
gagtaagttg aaac                                                    14

<210> SEQ ID NO 282
<211> LENGTH: 14
<212> TYPE: DNA
<213> ORGANISM: Artificial Sequence
<220> FEATURE:
<223> OTHER INFORMATION: Synthetic Construct

<400> SEQUENCE: 282
taaacacttc gttt                                                    14

<210> SEQ ID NO 283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 283
agtaagttga aacg                                                    14

<210> SEQ ID NO 284
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 284
taaacacttc gttt                                              14

<210> SEQ ID NO 285
<211> LENGTH: 14
<212> TYPE: DNA
<213> ORGANISM: Artificial Sequence
<220> FEATURE:
<223> OTHER INFORMATION: Synthetic Construct

<400> SEQUENCE: 285
gtaagttgaa acgg                                              14

<210> SEQ ID NO 286
<211> LENGTH: 14
<212> TYPE: DNA
<213> ORGANISM: Artificial Sequence
<220> FEATURE:
<223> OTHER INFORMATION: Synthetic Construct

<400> SEQUENCE: 286
taaacacttc gttt                                              14

<210> SEQ ID NO 287
<211> LENGTH: 14
<212> TYPE: DNA
<213> ORGANISM: Artificial Sequence
<220> FEATURE:
<223> OTHER INFORMATION: Synthetic Construct

<400> SEQUENCE: 287
taagttgaaa cggg                                              14

<210> SEQ ID NO 288
<211> LENGTH: 14
<212> TYPE: DNA
<213> ORGANISM: Artificial Sequence
<220> FEATURE:
<223> OTHER INFORMATION: Synthetic Construct

<400> SEQUENCE: 288
taaacacttc gttt                                              14

<210> SEQ ID NO 289
<211> LENGTH: 14
<212> TYPE: DNA
<213> ORGANISM: Artificial Sequence
<220> FEATURE:
<223> OTHER INFORMATION: Synthetic Construct

<400> SEQUENCE: 289
aagttgaaac gggg                                              14

<210> SEQ ID NO 290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 290
```

```
taaacacttc gttt                                                          14

<210> SEQ ID NO 291
<211> LENGTH: 14
<212> TYPE: DNA
<213> ORGANISM: Artificial Sequence
<220> FEATURE:
<223> OTHER INFORMATION: Synthetic Construct

<400> SEQUENCE: 291
agttgaaacg gggt                                                          14

<210> SEQ ID NO 292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 292
taaacacttc gttt                                                          14

<210> SEQ ID NO 293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 293
gttgaaacgg ggta                                                          14

<210> SEQ ID NO 294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 294
taaacacttc gttt                                                          14

<210> SEQ ID NO 295
<211> LENGTH: 14
<212> TYPE: DNA
<213> ORGANISM: Artificial Sequence
<220> FEATURE:
<223> OTHER INFORMATION: Synthetic Construct

<400> SEQUENCE: 295
ttgaaacggg gtac                                                          14

<210> SEQ ID NO 296
<211> LENGTH: 14
<212> TYPE: DNA
<213> ORGANISM: Artificial Sequence
<220> FEATURE:
<223> OTHER INFORMATION: Synthetic Construct

<400> SEQUENCE: 296
taaacacttc gttt                                                          14

<210> SEQ ID NO 297
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 297
tgaaacgggg tacg                                                         14

<210> SEQ ID NO 298
<211> LENGTH: 14
<212> TYPE: DNA
<213> ORGANISM: Artificial Sequence
<220> FEATURE:
<223> OTHER INFORMATION: Synthetic Construct

<400> SEQUENCE: 298
taaacacttc gttt                                                         14

<210> SEQ ID NO 299
<211> LENGTH: 14
<212> TYPE: DNA
<213> ORGANISM: Artificial Sequence
<220> FEATURE:
<223> OTHER INFORMATION: Synthetic Construct

<400> SEQUENCE: 299
gaaacggggt acga                                                         14

<210> SEQ ID NO 300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 300
taaacacttc gttt                                                         14

<210> SEQ ID NO 301
<211> LENGTH: 14
<212> TYPE: DNA
<213> ORGANISM: Artificial Sequence
<220> FEATURE:
<223> OTHER INFORMATION: Synthetic Construct

<400> SEQUENCE: 301
aaacggggta cgag                                                         14

<210> SEQ ID NO 302
<211> LENGTH: 14
<212> TYPE: DNA
<213> ORGANISM: Artificial Sequence
<220> FEATURE:
<223> OTHER INFORMATION: Synthetic Construct

<400> SEQUENCE: 302
taaacacttc gttt                                                         14

<210> SEQ ID NO 303
<211> LENGTH: 14
<212> TYPE: DNA
<213> ORGANISM: Artificial Sequence
<220> FEATURE:
<223> OTHER INFORMATION: Synthetic Construct

<400> SEQUENCE: 303
aacggggtac gaga                                                         14
```

<210> SEQ ID NO 304
<211> LENGTH: 14
<212> TYPE: DNA
<213> ORGANISM: Artificial Sequence
<220> FEATURE:
<223> OTHER INFORMATION: Synthetic Construct

<400> SEQUENCE: 304
taaacacttc gttt                                                        14

<210> SEQ ID NO 305
<211> LENGTH: 14
<212> TYPE: DNA
<213> ORGANISM: Artificial Sequence
<220> FEATURE:
<223> OTHER INFORMATION: Synthetic Construct

<400> SEQUENCE: 305
acggggtacg agaa                                                        14

<210> SEQ ID NO 306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 306
taaacacttc gttt                                                        14

<210> SEQ ID NO 307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 307
cggggtacga gaaa                                                        14

<210> SEQ ID NO 308
<211> LENGTH: 14
<212> TYPE: DNA
<213> ORGANISM: Artificial Sequence
<220> FEATURE:
<223> OTHER INFORMATION: Synthetic Construct

<400> SEQUENCE: 308
taaacacttc gttt                                                        14

<210> SEQ ID NO 309
<211> LENGTH: 14
<212> TYPE: DNA
<213> ORGANISM: Artificial Sequence
<220> FEATURE:
<223> OTHER INFORMATION: Synthetic Construct

<400> SEQUENCE: 309
ggggtacgag aaat                                                        14

<210> SEQ ID NO 310
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 310
taaacacttc gttt                                                    14

<210> SEQ ID NO 311
<211> LENGTH: 14
<212> TYPE: DNA
<213> ORGANISM: Artificial Sequence
<220> FEATURE:
<223> OTHER INFORMATION: Synthetic Construct

<400> SEQUENCE: 311
gggtacgaga aatg                                                    14

<210> SEQ ID NO 312
<211> LENGTH: 14
<212> TYPE: DNA
<213> ORGANISM: Artificial Sequence
<220> FEATURE:
<223> OTHER INFORMATION: Synthetic Construct

<400> SEQUENCE: 312
taaacacttc gttt                                                    14

<210> SEQ ID NO 313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 313
ggtacgagaa atgg                                                    14

<210> SEQ ID NO 314
<211> LENGTH: 14
<212> TYPE: DNA
<213> ORGANISM: Artificial Sequence
<220> FEATURE:
<223> OTHER INFORMATION: Synthetic Construct

<400> SEQUENCE: 314
taaacacttc gttt                                                    14

<210> SEQ ID NO 315
<211> LENGTH: 14
<212> TYPE: DNA
<213> ORGANISM: Artificial Sequence
<220> FEATURE:
<223> OTHER INFORMATION: Synthetic Construct

<400> SEQUENCE: 315
gtacgagaaa tgga                                                    14

<210> SEQ ID NO 316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 316
taaacacttc gttt                                                    14

<210> SEQ ID NO 317
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 317
tacgagaaat ggaa                                                    14

<210> SEQ ID NO 318
<211> LENGTH: 14
<212> TYPE: DNA
<213> ORGANISM: Artificial Sequence
<220> FEATURE:
<223> OTHER INFORMATION: Synthetic Construct

<400> SEQUENCE: 318
taaacacttc gttt                                                    14

<210> SEQ ID NO 319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 319
acgagaaatg gaaa                                                    14

<210> SEQ ID NO 320
<211> LENGTH: 14
<212> TYPE: DNA
<213> ORGANISM: Artificial Sequence
<220> FEATURE:
<223> OTHER INFORMATION: Synthetic Construct

<400> SEQUENCE: 320
taaacacttc gttt                                                    14

<210> SEQ ID NO 321
<211> LENGTH: 14
<212> TYPE: DNA
<213> ORGANISM: Artificial Sequence
<220> FEATURE:
<223> OTHER INFORMATION: Synthetic Construct

<400> SEQUENCE: 321
cgagaaatgg aaat                                                    14

<210> SEQ ID NO 322
<211> LENGTH: 14
<212> TYPE: DNA
<213> ORGANISM: Artificial Sequence
<220> FEATURE:
<223> OTHER INFORMATION: Synthetic Construct

<400> SEQUENCE: 322
taaacacttc gttt                                                    14

<210> SEQ ID NO 323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 323
```
gagaaatgga aatt                                           14

<210> SEQ ID NO 324
<211> LENGTH: 14
<212> TYPE: DNA
<213> ORGANISM: Artificial Sequence
<220> FEATURE:
<223> OTHER INFORMATION: Synthetic Construct

<400> SEQUENCE: 324
taaacacttc gttt                                           14

<210> SEQ ID NO 325
<211> LENGTH: 14
<212> TYPE: DNA
<213> ORGANISM: Artificial Sequence
<220> FEATURE:
<223> OTHER INFORMATION: Synthetic Construct

<400> SEQUENCE: 325
agaaatggaa attt                                           14

<210> SEQ ID NO 326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 326
taaacacttc gttt                                           14

<210> SEQ ID NO 327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 327
gaaatggaaa tttt                                           14

<210> SEQ ID NO 328
<211> LENGTH: 14
<212> TYPE: DNA
<213> ORGANISM: Artificial Sequence
<220> FEATURE:
<223> OTHER INFORMATION: Synthetic Construct

<400> SEQUENCE: 328
taaacacttc gttt                                           14

<210> SEQ ID NO 329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 329
aaatggaaat tttt                                           14

<210> SEQ ID NO 330
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 330
taaacacttc gttt                                                      14

<210> SEQ ID NO 331
<211> LENGTH: 14
<212> TYPE: DNA
<213> ORGANISM: Artificial Sequence
<220> FEATURE:
<223> OTHER INFORMATION: Synthetic Construct

<400> SEQUENCE: 331
aatggaaatt tttt                                                      14

<210> SEQ ID NO 332
<211> LENGTH: 14
<212> TYPE: DNA
<213> ORGANISM: Artificial Sequence
<220> FEATURE:
<223> OTHER INFORMATION: Synthetic Construct

<400> SEQUENCE: 332
taaacacttc gttt                                                      14

<210> SEQ ID NO 333
<211> LENGTH: 14
<212> TYPE: DNA
<213> ORGANISM: Artificial Sequence
<220> FEATURE:
<223> OTHER INFORMATION: Synthetic Construct

<400> SEQUENCE: 333
atggaaattt ttta                                                      14

<210> SEQ ID NO 334
<211> LENGTH: 14
<212> TYPE: DNA
<213> ORGANISM: Artificial Sequence
<220> FEATURE:
<223> OTHER INFORMATION: Synthetic Construct

<400> SEQUENCE: 334
taaacacttc gttt                                                      14

<210> SEQ ID NO 335
<211> LENGTH: 14
<212> TYPE: DNA
<213> ORGANISM: Artificial Sequence
<220> FEATURE:
<223> OTHER INFORMATION: Synthetic Construct

<400> SEQUENCE: 335
tggaaatttt ttaa                                                      14

<210> SEQ ID NO 336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 336
taaacacttc gttt                                                      14
```

```
<210> SEQ ID NO 337
<211> LENGTH: 14
<212> TYPE: DNA
<213> ORGANISM: Artificial Sequence
<220> FEATURE:
<223> OTHER INFORMATION: Synthetic Construct

<400> SEQUENCE: 337
ggaaattttt taaa                                                      14

<210> SEQ ID NO 338
<211> LENGTH: 14
<212> TYPE: DNA
<213> ORGANISM: Artificial Sequence
<220> FEATURE:
<223> OTHER INFORMATION: Synthetic Construct

<400> SEQUENCE: 338
taaacacttc gttt                                                      14

<210> SEQ ID NO 339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 339 gaaattttt aaaa                                                       14

<210> SEQ ID NO 340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 340
taaacacttc gttt                                                      14

<210> SEQ ID NO 341
<211> LENGTH: 14
<212> TYPE: DNA
<213> ORGANISM: Artificial Sequence
<220> FEATURE:
<223> OTHER INFORMATION: Synthetic Construct

<400> SEQUENCE: 341 aaattttta aaat                                                       14

<210> SEQ ID NO 342
<211> LENGTH: 14
<212> TYPE: DNA
<213> ORGANISM: Artificial Sequence
<220> FEATURE:
<223> OTHER INFORMATION: Synthetic Construct

<400> SEQUENCE: 342
taaacacttc gttt                                                      14

<210> SEQ ID NO 343
<211> LENGTH: 14
<212> TYPE: DNA
<213> ORGANISM: Artificial Sequence
<220> FEATURE:
```

```
<223> OTHER INFORMATION: Synthetic Construct

<400> SEQUENCE: 343 aatttttaa aatt                                                          14

<210> SEQ ID NO 344
<211> LENGTH: 14
<212> TYPE: DNA
<213> ORGANISM: Artificial Sequence
<220> FEATURE:
<223> OTHER INFORMATION: Synthetic Construct

<400> SEQUENCE: 344
taaacacttc gttt                                                         14

<210> SEQ ID NO 345
<211> LENGTH: 14
<212> TYPE: DNA
<213> ORGANISM: Artificial Sequence
<220> FEATURE:
<223> OTHER INFORMATION: Synthetic Construct

<400> SEQUENCE: 345 atttttaaa attt                                                          14

<210> SEQ ID NO 346
<211> LENGTH: 14
<212> TYPE: DNA
<213> ORGANISM: Artificial Sequence
<220> FEATURE:
<223> OTHER INFORMATION: Synthetic Construct

<400> SEQUENCE: 346
taaacacttc gttt                                                         14

<210> SEQ ID NO 347
<211> LENGTH: 14
<212> TYPE: DNA
<213> ORGANISM: Artificial Sequence
<220> FEATURE:
<223> OTHER INFORMATION: Synthetic Construct

<400> SEQUENCE: 347 tttttaaaa tttt                                                          14

<210> SEQ ID NO 348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 348
taaacacttc gttt                                                         14

<210> SEQ ID NO 349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 349 ttttaaaat tttt                                                          14
```

```
<210> SEQ ID NO 350
<211> LENGTH: 14
<212> TYPE: DNA
<213> ORGANISM: Artificial Sequence
<220> FEATURE:
<223> OTHER INFORMATION: Synthetic Construct

<400> SEQUENCE: 350
taaacacttc gttt                                                        14

<210> SEQ ID NO 351
<211> LENGTH: 14
<212> TYPE: DNA
<213> ORGANISM: Artificial Sequence
<220> FEATURE:
<223> OTHER INFORMATION: Synthetic Construct

<400> SEQUENCE: 351
ttttaaaatt ttta                                                        14

<210> SEQ ID NO 352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 352
taaacacttc gttt                                                        14

<210> SEQ ID NO 353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 353
tttaaaattt ttat                                                        14

<210> SEQ ID NO 354
<211> LENGTH: 14
<212> TYPE: DNA
<213> ORGANISM: Artificial Sequence
<220> FEATURE:
<223> OTHER INFORMATION: Synthetic Construct

<400> SEQUENCE: 354
taaacacttc gttt                                                        14

<210> SEQ ID NO 355
<211> LENGTH: 14
<212> TYPE: DNA
<213> ORGANISM: Artificial Sequence
<220> FEATURE:
<223> OTHER INFORMATION: Synthetic Construct

<400> SEQUENCE: 355
ttaaaatttt tatt                                                        14

<210> SEQ ID NO 356
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 356
taaacacttc gttt                                                        14

<210> SEQ ID NO 357
<211> LENGTH: 14
<212> TYPE: DNA
<213> ORGANISM: Artificial Sequence
<220> FEATURE:
<223> OTHER INFORMATION: Synthetic Construct

<400> SEQUENCE: 357
taaaattttt attt                                                        14

<210> SEQ ID NO 358
<211> LENGTH: 14
<212> TYPE: DNA
<213> ORGANISM: Artificial Sequence
<220> FEATURE:
<223> OTHER INFORMATION: Synthetic Construct

<400> SEQUENCE: 358
taaacacttc gttt                                                        14

<210> SEQ ID NO 359
<211> LENGTH: 14
<212> TYPE: DNA
<213> ORGANISM: Artificial Sequence
<220> FEATURE:
<223> OTHER INFORMATION: Synthetic Construct

<400> SEQUENCE: 359
aaaattttta tttt                                                        14

<210> SEQ ID NO 360
<211> LENGTH: 14
<212> TYPE: DNA
<213> ORGANISM: Artificial Sequence
<220> FEATURE:
<223> OTHER INFORMATION: Synthetic Construct

<400> SEQUENCE: 360
taaacacttc gttt                                                        14

<210> SEQ ID NO 361
<211> LENGTH: 14
<212> TYPE: DNA
<213> ORGANISM: Artificial Sequence
<220> FEATURE:
<223> OTHER INFORMATION: Synthetic Construct

<400> SEQUENCE: 361 aaattttat tttg                                                         14

<210> SEQ ID NO 362
<211> LENGTH: 14
<212> TYPE: DNA
<213> ORGANISM: Artificial Sequence
<220> FEATURE:
<223> OTHER INFORMATION: Synthetic Construct

<400> SEQUENCE: 362
taaacacttc gttt                                                        14

<210> SEQ ID NO 363
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 363
aatttttatt ttgt                                                    14

<210> SEQ ID NO 364
<211> LENGTH: 14
<212> TYPE: DNA
<213> ORGANISM: Artificial Sequence
<220> FEATURE:
<223> OTHER INFORMATION: Synthetic Construct

<400> SEQUENCE: 364
taaacacttc gttt                                                    14

<210> SEQ ID NO 365
<211> LENGTH: 14
<212> TYPE: DNA
<213> ORGANISM: Artificial Sequence
<220> FEATURE:
<223> OTHER INFORMATION: Synthetic Construct

<400> SEQUENCE: 365 attttttattt tgta                                                   14

<210> SEQ ID NO 366
<211> LENGTH: 14
<212> TYPE: DNA
<213> ORGANISM: Artificial Sequence
<220> FEATURE:
<223> OTHER INFORMATION: Synthetic Construct

<400> SEQUENCE: 366
taaacacttc gttt                                                    14

<210> SEQ ID NO 367
<211> LENGTH: 14
<212> TYPE: DNA
<213> ORGANISM: Artificial Sequence
<220> FEATURE:
<223> OTHER INFORMATION: Synthetic Construct

<400> SEQUENCE: 367
tttttatttt gtat                                                    14

<210> SEQ ID NO 368
<211> LENGTH: 14
<212> TYPE: DNA
<213> ORGANISM: Artificial Sequence
<220> FEATURE:
<223> OTHER INFORMATION: Synthetic Construct

<400> SEQUENCE: 368
taaacacttc gttt                                                    14

<210> SEQ ID NO 369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 369
```
ttttattttg tata                                               14

<210> SEQ ID NO 370
<211> LENGTH: 14
<212> TYPE: DNA
<213> ORGANISM: Artificial Sequence
<220> FEATURE:
<223> OTHER INFORMATION: Synthetic Construct

<400> SEQUENCE: 370
taaacacttc gttt                                               14

<210> SEQ ID NO 371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 371
tttattttgt atag                                               14

<210> SEQ ID NO 372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 372
taaacacttc gttt                                               14

<210> SEQ ID NO 373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 373
ttattttgta tagg                                               14

<210> SEQ ID NO 374
<211> LENGTH: 14
<212> TYPE: DNA
<213> ORGANISM: Artificial Sequence
<220> FEATURE:
<223> OTHER INFORMATION: Synthetic Construct

<400> SEQUENCE: 374
taaacacttc gttt                                               14

<210> SEQ ID NO 375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 375
tattttgtat aggt                                               14

<210> SEQ ID NO 376
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 376
taaacacttc gttt                                                        14

<210> SEQ ID NO 377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 377
attttgtata ggtt                                                        14

<210> SEQ ID NO 378
<211> LENGTH: 14
<212> TYPE: DNA
<213> ORGANISM: Artificial Sequence
<220> FEATURE:
<223> OTHER INFORMATION: Synthetic Construct

<400> SEQUENCE: 378
taaacacttc gttt                                                        14

<210> SEQ ID NO 379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 379
ttttgtatag gttt                                                        14

<210> SEQ ID NO 380
<211> LENGTH: 14
<212> TYPE: DNA
<213> ORGANISM: Artificial Sequence
<220> FEATURE:
<223> OTHER INFORMATION: Synthetic Construct

<400> SEQUENCE: 380
taaacacttc gttt                                                        14

<210> SEQ ID NO 381
<211> LENGTH: 14
<212> TYPE: DNA
<213> ORGANISM: Artificial Sequence
<220> FEATURE:
<223> OTHER INFORMATION: Synthetic Construct

<400> SEQUENCE: 381
tttgtatagg tttg                                                        14

<210> SEQ ID NO 382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 382
taaacacttc gttt                                                        14
```

<210> SEQ ID NO 383
<211> LENGTH: 14
<212> TYPE: DNA
<213> ORGANISM: Artificial Sequence
<220> FEATURE:
<223> OTHER INFORMATION: Synthetic Construct

<400> SEQUENCE: 383
ttgtataggt ttga                                                     14

<210> SEQ ID NO 384
<211> LENGTH: 14
<212> TYPE: DNA
<213> ORGANISM: Artificial Sequence
<220> FEATURE:
<223> OTHER INFORMATION: Synthetic Construct

<400> SEQUENCE: 384
taaacacttc gttt                                                     14

<210> SEQ ID NO 385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 385
tgtataggtt tgag                                                     14

<210> SEQ ID NO 386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 386
taaacacttc gttt                                                     14

<210> SEQ ID NO 387
<211> LENGTH: 14
<212> TYPE: DNA
<213> ORGANISM: Artificial Sequence
<220> FEATURE:
<223> OTHER INFORMATION: Synthetic Construct

<400> SEQUENCE: 387
gtataggttt gagt                                                     14

<210> SEQ ID NO 388
<211> LENGTH: 14
<212> TYPE: DNA
<213> ORGANISM: Artificial Sequence
<220> FEATURE:
<223> OTHER INFORMATION: Synthetic Construct

<400> SEQUENCE: 388
taaacacttc gttt                                                     14

<210> SEQ ID NO 389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 389
tataggtttg agta                                                                14

<210> SEQ ID NO 390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 390
taaacacttc gttt                                                                14

<210> SEQ ID NO 391
<211> LENGTH: 14
<212> TYPE: DNA
<213> ORGANISM: Artificial Sequence
<220> FEATURE:
<223> OTHER INFORMATION: Synthetic Construct

<400> SEQUENCE: 391
ataggtttga gtag                                                                14

<210> SEQ ID NO 392
<211> LENGTH: 14
<212> TYPE: DNA
<213> ORGANISM: Artificial Sequence
<220> FEATURE:
<223> OTHER INFORMATION: Synthetic Construct

<400> SEQUENCE: 392
tcacgctatt tacc                                                                14

<210> SEQ ID NO 393
<211> LENGTH: 24
<212> TYPE: DNA
<213> ORGANISM: Artificial Sequence
<220> FEATURE:
<223> OTHER INFORMATION: Synthetic Construct

<400> SEQUENCE: 393
ttgatttttt ttaaatttta tttg                                                     24

<210> SEQ ID NO 394
<211> LENGTH: 14
<212> TYPE: DNA
<213> ORGANISM: Artificial Sequence
<220> FEATURE:
<223> OTHER INFORMATION: Synthetic Construct

<400> SEQUENCE: 394
taggtttgag taga                                                                14

<210> SEQ ID NO 395
<211> LENGTH: 14
<212> TYPE: DNA
<213> ORGANISM: Artificial Sequence
<220> FEATURE:
<223> OTHER INFORMATION: Synthetic Construct

<400> SEQUENCE: 395
tcacgctatt tacc                                                                14

<210> SEQ ID NO 396

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 396
aggtttgagt agag                                                        14

<210> SEQ ID NO 397
<211> LENGTH: 14
<212> TYPE: DNA
<213> ORGANISM: Artificial Sequence
<220> FEATURE:
<223> OTHER INFORMATION: Synthetic Construct

<400> SEQUENCE: 397
tcacgctatt tacc                                                        14

<210> SEQ ID NO 398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 398
ggtttgagta gagg                                                        14

<210> SEQ ID NO 399
<211> LENGTH: 14
<212> TYPE: DNA
<213> ORGANISM: Artificial Sequence
<220> FEATURE:
<223> OTHER INFORMATION: Synthetic Construct

<400> SEQUENCE: 399
tcacgctatt tacc                                                        14

<210> SEQ ID NO 400
<211> LENGTH: 14
<212> TYPE: DNA
<213> ORGANISM: Artificial Sequence
<220> FEATURE:
<223> OTHER INFORMATION: Synthetic Construct

<400> SEQUENCE: 400
gtttgagtag agga                                                        14

<210> SEQ ID NO 401
<211> LENGTH: 14
<212> TYPE: DNA
<213> ORGANISM: Artificial Sequence
<220> FEATURE:
<223> OTHER INFORMATION: Synthetic Construct

<400> SEQUENCE: 401
tcacgctatt tacc                                                        14

<210> SEQ ID NO 402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 402
```
tttgagtaga ggaa                                             14

<210> SEQ ID NO 403
<211> LENGTH: 14
<212> TYPE: DNA
<213> ORGANISM: Artificial Sequence
<220> FEATURE:
<223> OTHER INFORMATION: Synthetic Construct

<400> SEQUENCE: 403
tcacgctatt tacc                                             14

<210> SEQ ID NO 404
<211> LENGTH: 14
<212> TYPE: DNA
<213> ORGANISM: Artificial Sequence
<220> FEATURE:
<223> OTHER INFORMATION: Synthetic Construct

<400> SEQUENCE: 404
ttgagtagag gaag                                             14

<210> SEQ ID NO 405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 405
tcacgctatt tacc                                             14

<210> SEQ ID NO 406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 406
tgagtagagg aagg                                             14

<210> SEQ ID NO 407
<211> LENGTH: 14
<212> TYPE: DNA
<213> ORGANISM: Artificial Sequence
<220> FEATURE:
<223> OTHER INFORMATION: Synthetic Construct

<400> SEQUENCE: 407
tcacgctatt tacc                                             14

<210> SEQ ID NO 408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 408
gagtagagga aggt                                             14

<210> SEQ ID NO 409
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 409
tcacgctatt tacc                                                        14

<210> SEQ ID NO 410
<211> LENGTH: 14
<212> TYPE: DNA
<213> ORGANISM: Artificial Sequence
<220> FEATURE:
<223> OTHER INFORMATION: Synthetic Construct

<400> SEQUENCE: 410
agtagaggaa ggtg                                                        14

<210> SEQ ID NO 411
<211> LENGTH: 14
<212> TYPE: DNA
<213> ORGANISM: Artificial Sequence
<220> FEATURE:
<223> OTHER INFORMATION: Synthetic Construct

<400> SEQUENCE: 411
tcacgctatt tacc                                                        14

<210> SEQ ID NO 412
<211> LENGTH: 14
<212> TYPE: DNA
<213> ORGANISM: Artificial Sequence
<220> FEATURE:
<223> OTHER INFORMATION: Synthetic Construct

<400> SEQUENCE: 412
gtagaggaag gtgt                                                        14

<210> SEQ ID NO 413
<211> LENGTH: 14
<212> TYPE: DNA
<213> ORGANISM: Artificial Sequence
<220> FEATURE:
<223> OTHER INFORMATION: Synthetic Construct

<400> SEQUENCE: 413
tcacgctatt tacc                                                        14

<210> SEQ ID NO 414
<211> LENGTH: 14
<212> TYPE: DNA
<213> ORGANISM: Artificial Sequence
<220> FEATURE:
<223> OTHER INFORMATION: Synthetic Construct

<400> SEQUENCE: 414
tagaggaagg tgtt                                                        14

<210> SEQ ID NO 415
<211> LENGTH: 14
<212> TYPE: DNA
<213> ORGANISM: Artificial Sequence
<220> FEATURE:
<223> OTHER INFORMATION: Synthetic Construct

<400> SEQUENCE: 415
tcacgctatt tacc                                                        14
```

```
<210> SEQ ID NO 416
<211> LENGTH: 14
<212> TYPE: DNA
<213> ORGANISM: Artificial Sequence
<220> FEATURE:
<223> OTHER INFORMATION: Synthetic Construct

<400> SEQUENCE: 416
agaggaaggt gttg                                                        14

<210> SEQ ID NO 417
<211> LENGTH: 14
<212> TYPE: DNA
<213> ORGANISM: Artificial Sequence
<220> FEATURE:
<223> OTHER INFORMATION: Synthetic Construct

<400> SEQUENCE: 417
tcacgctatt tacc                                                        14

<210> SEQ ID NO 418
<211> LENGTH: 14
<212> TYPE: DNA
<213> ORGANISM: Artificial Sequence
<220> FEATURE:
<223> OTHER INFORMATION: Synthetic Construct

<400> SEQUENCE: 418
gaggaaggtg ttgg                                                        14

<210> SEQ ID NO 419
<211> LENGTH: 14
<212> TYPE: DNA
<213> ORGANISM: Artificial Sequence
<220> FEATURE:
<223> OTHER INFORMATION: Synthetic Construct

<400> SEQUENCE: 419
tcacgctatt tacc                                                        14

<210> SEQ ID NO 420
<211> LENGTH: 14
<212> TYPE: DNA
<213> ORGANISM: Artificial Sequence
<220> FEATURE:
<223> OTHER INFORMATION: Synthetic Construct

<400> SEQUENCE: 420
aggaaggtgt tggt                                                        14

<210> SEQ ID NO 421
<211> LENGTH: 14
<212> TYPE: DNA
<213> ORGANISM: Artificial Sequence
<220> FEATURE:
<223> OTHER INFORMATION: Synthetic Construct

<400> SEQUENCE: 421
tcacgctatt tacc                                                        14

<210> SEQ ID NO 422
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 422
ggaaggtgtt ggtg                                             14

<210> SEQ ID NO 423
<211> LENGTH: 14
<212> TYPE: DNA
<213> ORGANISM: Artificial Sequence
<220> FEATURE:
<223> OTHER INFORMATION: Synthetic Construct

<400> SEQUENCE: 423
tcacgctatt tacc                                             14

<210> SEQ ID NO 424
<211> LENGTH: 14
<212> TYPE: DNA
<213> ORGANISM: Artificial Sequence
<220> FEATURE:
<223> OTHER INFORMATION: Synthetic Construct

<400> SEQUENCE: 424
gaaggtgttg gtgt                                             14

<210> SEQ ID NO 425
<211> LENGTH: 14
<212> TYPE: DNA
<213> ORGANISM: Artificial Sequence
<220> FEATURE:
<223> OTHER INFORMATION: Synthetic Construct

<400> SEQUENCE: 425
tcacgctatt tacc                                             14

<210> SEQ ID NO 426
<211> LENGTH: 14
<212> TYPE: DNA
<213> ORGANISM: Artificial Sequence
<220> FEATURE:
<223> OTHER INFORMATION: Synthetic Construct

<400> SEQUENCE: 426
aaggtgttgg tgta                                             14

<210> SEQ ID NO 427
<211> LENGTH: 14
<212> TYPE: DNA
<213> ORGANISM: Artificial Sequence
<220> FEATURE:
<223> OTHER INFORMATION: Synthetic Construct

<400> SEQUENCE: 427
tcacgctatt tacc                                             14

<210> SEQ ID NO 428
<211> LENGTH: 14
<212> TYPE: DNA
<213> ORGANISM: Artificial Sequence
<220> FEATURE:
<223> OTHER INFORMATION: Synthetic Construct

<400> SEQUENCE: 428
aggtgttggt gtag                                             14

```
<210> SEQ ID NO 429
<211> LENGTH: 14
<212> TYPE: DNA
<213> ORGANISM: Artificial Sequence
<220> FEATURE:
<223> OTHER INFORMATION: Synthetic Construct

<400> SEQUENCE: 429
tcacgctatt tacc                                                       14

<210> SEQ ID NO 430
<211> LENGTH: 14
<212> TYPE: DNA
<213> ORGANISM: Artificial Sequence
<220> FEATURE:
<223> OTHER INFORMATION: Synthetic Construct

<400> SEQUENCE: 430
ggtgttggtg tagg                                                       14

<210> SEQ ID NO 431
<211> LENGTH: 14
<212> TYPE: DNA
<213> ORGANISM: Artificial Sequence
<220> FEATURE:
<223> OTHER INFORMATION: Synthetic Construct

<400> SEQUENCE: 431
tcacgctatt tacc                                                       14

<210> SEQ ID NO 432
<211> LENGTH: 14
<212> TYPE: DNA
<213> ORGANISM: Artificial Sequence
<220> FEATURE:
<223> OTHER INFORMATION: Synthetic Construct

<400> SEQUENCE: 432
gtgttggtgt aggg                                                       14

<210> SEQ ID NO 433
<211> LENGTH: 14
<212> TYPE: DNA
<213> ORGANISM: Artificial Sequence
<220> FEATURE:
<223> OTHER INFORMATION: Synthetic Construct

<400> SEQUENCE: 433
tcacgctatt tacc                                                       14

<210> SEQ ID NO 434
<211> LENGTH: 14
<212> TYPE: DNA
<213> ORGANISM: Artificial Sequence
<220> FEATURE:
<223> OTHER INFORMATION: Synthetic Construct

<400> SEQUENCE: 434
tgttggtgta gggt                                                       14

<210> SEQ ID NO 435
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 435
tcacgctatt tacc                                                    14

<210> SEQ ID NO 436
<211> LENGTH: 14
<212> TYPE: DNA
<213> ORGANISM: Artificial Sequence
<220> FEATURE:
<223> OTHER INFORMATION: Synthetic Construct

<400> SEQUENCE: 436
gttggtgtag ggtt                                                    14

<210> SEQ ID NO 437
<211> LENGTH: 14
<212> TYPE: DNA
<213> ORGANISM: Artificial Sequence
<220> FEATURE:
<223> OTHER INFORMATION: Synthetic Construct

<400> SEQUENCE: 437
tcacgctatt tacc                                                    14

<210> SEQ ID NO 438
<211> LENGTH: 14
<212> TYPE: DNA
<213> ORGANISM: Artificial Sequence
<220> FEATURE:
<223> OTHER INFORMATION: Synthetic Construct

<400> SEQUENCE: 438
ttggtgtagg gtta                                                    14

<210> SEQ ID NO 439
<211> LENGTH: 14
<212> TYPE: DNA
<213> ORGANISM: Artificial Sequence
<220> FEATURE:
<223> OTHER INFORMATION: Synthetic Construct

<400> SEQUENCE: 439
tcacgctatt tacc                                                    14

<210> SEQ ID NO 440
<211> LENGTH: 14
<212> TYPE: DNA
<213> ORGANISM: Artificial Sequence
<220> FEATURE:
<223> OTHER INFORMATION: Synthetic Construct

<400> SEQUENCE: 440
tggtgtaggg ttag                                                    14

<210> SEQ ID NO 441
<211> LENGTH: 14
<212> TYPE: DNA
<213> ORGANISM: Artificial Sequence
<220> FEATURE:
<223> OTHER INFORMATION: Synthetic Construct

<400> SEQUENCE: 441
tcacgctatt tacc                                                    14

<210> SEQ ID NO 442
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 442
ggtgtagggt taga                                                         14

<210> SEQ ID NO 443
<211> LENGTH: 14
<212> TYPE: DNA
<213> ORGANISM: Artificial Sequence
<220> FEATURE:
<223> OTHER INFORMATION: Synthetic Construct

<400> SEQUENCE: 443
tcacgctatt tacc                                                         14

<210> SEQ ID NO 444
<211> LENGTH: 14
<212> TYPE: DNA
<213> ORGANISM: Artificial Sequence
<220> FEATURE:
<223> OTHER INFORMATION: Synthetic Construct

<400> SEQUENCE: 444
gtgtagggtt agat                                                         14

<210> SEQ ID NO 445
<211> LENGTH: 14
<212> TYPE: DNA
<213> ORGANISM: Artificial Sequence
<220> FEATURE:
<223> OTHER INFORMATION: Synthetic Construct

<400> SEQUENCE: 445
tcacgctatt tacc                                                         14

<210> SEQ ID NO 446
<211> LENGTH: 14
<212> TYPE: DNA
<213> ORGANISM: Artificial Sequence
<220> FEATURE:
<223> OTHER INFORMATION: Synthetic Construct

<400> SEQUENCE: 446
tgtagggtta gatt                                                         14

<210> SEQ ID NO 447
<211> LENGTH: 14
<212> TYPE: DNA
<213> ORGANISM: Artificial Sequence
<220> FEATURE:
<223> OTHER INFORMATION: Synthetic Construct

<400> SEQUENCE: 447
tcacgctatt tacc                                                         14

<210> SEQ ID NO 448
<211> LENGTH: 14
<212> TYPE: DNA
<213> ORGANISM: Artificial Sequence
<220> FEATURE:
<223> OTHER INFORMATION: Synthetic Construct

<400> SEQUENCE: 448
```
gtagggttag attg                                                    14

<210> SEQ ID NO 449
<211> LENGTH: 14
<212> TYPE: DNA
<213> ORGANISM: Artificial Sequence
<220> FEATURE:
<223> OTHER INFORMATION: Synthetic Construct

<400> SEQUENCE: 449
tcacgctatt tacc                                                    14

<210> SEQ ID NO 450
<211> LENGTH: 14
<212> TYPE: DNA
<213> ORGANISM: Artificial Sequence
<220> FEATURE:
<223> OTHER INFORMATION: Synthetic Construct

<400> SEQUENCE: 450
tagggttaga ttgg                                                    14

<210> SEQ ID NO 451
<211> LENGTH: 14
<212> TYPE: DNA
<213> ORGANISM: Artificial Sequence
<220> FEATURE:
<223> OTHER INFORMATION: Synthetic Construct

<400> SEQUENCE: 451
tcacgctatt tacc                                                    14

<210> SEQ ID NO 452
<211> LENGTH: 14
<212> TYPE: DNA
<213> ORGANISM: Artificial Sequence
<220> FEATURE:
<223> OTHER INFORMATION: Synthetic Construct

<400> SEQUENCE: 452
agggttagat tggg                                                    14

<210> SEQ ID NO 453
<211> LENGTH: 14
<212> TYPE: DNA
<213> ORGANISM: Artificial Sequence
<220> FEATURE:
<223> OTHER INFORMATION: Synthetic Construct

<400> SEQUENCE: 453
tcacgctatt tacc                                                    14

<210> SEQ ID NO 454
<211> LENGTH: 14
<212> TYPE: DNA
<213> ORGANISM: Artificial Sequence
<220> FEATURE:
<223> OTHER INFORMATION: Synthetic Construct

<400> SEQUENCE: 454
gggttagatt gggg                                                    14

<210> SEQ ID NO 455
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 455
tcacgctatt tacc                                                        14

<210> SEQ ID NO 456
<211> LENGTH: 14
<212> TYPE: DNA
<213> ORGANISM: Artificial Sequence
<220> FEATURE:
<223> OTHER INFORMATION: Synthetic Construct

<400> SEQUENCE: 456
ggttagattg ggga                                                        14

<210> SEQ ID NO 457
<211> LENGTH: 14
<212> TYPE: DNA
<213> ORGANISM: Artificial Sequence
<220> FEATURE:
<223> OTHER INFORMATION: Synthetic Construct

<400> SEQUENCE: 457
tcacgctatt tacc                                                        14

<210> SEQ ID NO 458
<211> LENGTH: 14
<212> TYPE: DNA
<213> ORGANISM: Artificial Sequence
<220> FEATURE:
<223> OTHER INFORMATION: Synthetic Construct

<400> SEQUENCE: 458
gttagattgg ggat                                                        14

<210> SEQ ID NO 459
<211> LENGTH: 14
<212> TYPE: DNA
<213> ORGANISM: Artificial Sequence
<220> FEATURE:
<223> OTHER INFORMATION: Synthetic Construct

<400> SEQUENCE: 459
tcacgctatt tacc                                                        14

<210> SEQ ID NO 460
<211> LENGTH: 14
<212> TYPE: DNA
<213> ORGANISM: Artificial Sequence
<220> FEATURE:
<223> OTHER INFORMATION: Synthetic Construct

<400> SEQUENCE: 460
ttagattggg gata                                                        14

<210> SEQ ID NO 461
<211> LENGTH: 14
<212> TYPE: DNA
<213> ORGANISM: Artificial Sequence
<220> FEATURE:
<223> OTHER INFORMATION: Synthetic Construct

<400> SEQUENCE: 461
tcacgctatt tacc                                                        14
```

```
<210> SEQ ID NO 462
<211> LENGTH: 14
<212> TYPE: DNA
<213> ORGANISM: Artificial Sequence
<220> FEATURE:
<223> OTHER INFORMATION: Synthetic Construct

<400> SEQUENCE: 462
tagattgggg ataa                                                     14

<210> SEQ ID NO 463
<211> LENGTH: 14
<212> TYPE: DNA
<213> ORGANISM: Artificial Sequence
<220> FEATURE:
<223> OTHER INFORMATION: Synthetic Construct

<400> SEQUENCE: 463
tcacgctatt tacc                                                     14

<210> SEQ ID NO 464
<211> LENGTH: 14
<212> TYPE: DNA
<213> ORGANISM: Artificial Sequence
<220> FEATURE:
<223> OTHER INFORMATION: Synthetic Construct

<400> SEQUENCE: 464 agattggggga taat                                                    14

<210> SEQ ID NO 465
<211> LENGTH: 14
<212> TYPE: DNA
<213> ORGANISM: Artificial Sequence
<220> FEATURE:
<223> OTHER INFORMATION: Synthetic Construct

<400> SEQUENCE: 465
tcacgctatt tacc                                                     14

<210> SEQ ID NO 466
<211> LENGTH: 14
<212> TYPE: DNA
<213> ORGANISM: Artificial Sequence
<220> FEATURE:
<223> OTHER INFORMATION: Synthetic Construct

<400> SEQUENCE: 466
gattggggat aatt                                                     14

<210> SEQ ID NO 467
<211> LENGTH: 14
<212> TYPE: DNA
<213> ORGANISM: Artificial Sequence
<220> FEATURE:
<223> OTHER INFORMATION: Synthetic Construct

<400> SEQUENCE: 467
tcacgctatt tacc                                                     14

<210> SEQ ID NO 468
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 468
attggggata attt                                                14

<210> SEQ ID NO 469
<211> LENGTH: 14
<212> TYPE: DNA
<213> ORGANISM: Artificial Sequence
<220> FEATURE:
<223> OTHER INFORMATION: Synthetic Construct

<400> SEQUENCE: 469
tcacgctatt tacc                                                14

<210> SEQ ID NO 470
<211> LENGTH: 14
<212> TYPE: DNA
<213> ORGANISM: Artificial Sequence
<220> FEATURE:
<223> OTHER INFORMATION: Synthetic Construct

<400> SEQUENCE: 470
ttggggataa tttt                                                14

<210> SEQ ID NO 471
<211> LENGTH: 14
<212> TYPE: DNA
<213> ORGANISM: Artificial Sequence
<220> FEATURE:
<223> OTHER INFORMATION: Synthetic Construct

<400> SEQUENCE: 471
tcacgctatt tacc                                                14

<210> SEQ ID NO 472
<211> LENGTH: 14
<212> TYPE: DNA
<213> ORGANISM: Artificial Sequence
<220> FEATURE:
<223> OTHER INFORMATION: Synthetic Construct

<400> SEQUENCE: 472
tggggataat tttt                                                14

<210> SEQ ID NO 473
<211> LENGTH: 14
<212> TYPE: DNA
<213> ORGANISM: Artificial Sequence
<220> FEATURE:
<223> OTHER INFORMATION: Synthetic Construct

<400> SEQUENCE: 473
tcacgctatt tacc                                                14

<210> SEQ ID NO 474
<211> LENGTH: 14
<212> TYPE: DNA
<213> ORGANISM: Artificial Sequence
<220> FEATURE:
<223> OTHER INFORMATION: Synthetic Construct

<400> SEQUENCE: 474
ggggataatt ttta                                                14

<210> SEQ ID NO 475
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 475
tcacgctatt tacc                                                       14

<210> SEQ ID NO 476
<211> LENGTH: 14
<212> TYPE: DNA
<213> ORGANISM: Artificial Sequence
<220> FEATURE:
<223> OTHER INFORMATION: Synthetic Construct

<400> SEQUENCE: 476
gggataattt ttag                                                       14

<210> SEQ ID NO 477
<211> LENGTH: 14
<212> TYPE: DNA
<213> ORGANISM: Artificial Sequence
<220> FEATURE:
<223> OTHER INFORMATION: Synthetic Construct

<400> SEQUENCE: 477
tcacgctatt tacc                                                       14

<210> SEQ ID NO 478
<211> LENGTH: 14
<212> TYPE: DNA
<213> ORGANISM: Artificial Sequence
<220> FEATURE:
<223> OTHER INFORMATION: Synthetic Construct

<400> SEQUENCE: 478
ggataatttt tagt                                                       14

<210> SEQ ID NO 479
<211> LENGTH: 14
<212> TYPE: DNA
<213> ORGANISM: Artificial Sequence
<220> FEATURE:
<223> OTHER INFORMATION: Synthetic Construct

<400> SEQUENCE: 479
tcacgctatt tacc                                                       14

<210> SEQ ID NO 480
<211> LENGTH: 14
<212> TYPE: DNA
<213> ORGANISM: Artificial Sequence
<220> FEATURE:
<223> OTHER INFORMATION: Synthetic Construct

<400> SEQUENCE: 480
gataattttt agtt                                                       14

<210> SEQ ID NO 481
<211> LENGTH: 14
<212> TYPE: DNA
<213> ORGANISM: Artificial Sequence
<220> FEATURE:
<223> OTHER INFORMATION: Synthetic Construct

<400> SEQUENCE: 481
```
tcacgctatt tacc                                                    14

<210> SEQ ID NO 482
<211> LENGTH: 14
<212> TYPE: DNA
<213> ORGANISM: Artificial Sequence
<220> FEATURE:
<223> OTHER INFORMATION: Synthetic Construct

<400> SEQUENCE: 482
ataattttta gttt                                                    14

<210> SEQ ID NO 483
<211> LENGTH: 14
<212> TYPE: DNA
<213> ORGANISM: Artificial Sequence
<220> FEATURE:
<223> OTHER INFORMATION: Synthetic Construct

<400> SEQUENCE: 483
tcacgctatt tacc                                                    14

<210> SEQ ID NO 484
<211> LENGTH: 14
<212> TYPE: DNA
<213> ORGANISM: Artificial Sequence
<220> FEATURE:
<223> OTHER INFORMATION: Synthetic Construct

<400> SEQUENCE: 484
taatttttag tttt                                                    14

<210> SEQ ID NO 485
<211> LENGTH: 14
<212> TYPE: DNA
<213> ORGANISM: Artificial Sequence
<220> FEATURE:
<223> OTHER INFORMATION: Synthetic Construct

<400> SEQUENCE: 485
tcacgctatt tacc                                                    14

<210> SEQ ID NO 486
<211> LENGTH: 14
<212> TYPE: DNA
<213> ORGANISM: Artificial Sequence
<220> FEATURE:
<223> OTHER INFORMATION: Synthetic Construct

<400> SEQUENCE: 486
aatttttagt tttt                                                    14

<210> SEQ ID NO 487
<211> LENGTH: 14
<212> TYPE: DNA
<213> ORGANISM: Artificial Sequence
<220> FEATURE:
<223> OTHER INFORMATION: Synthetic Construct

<400> SEQUENCE: 487
tcacgctatt tacc                                                    14

<210> SEQ ID NO 488
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 488 attttagtt tttt                                                           14

<210> SEQ ID NO 489
<211> LENGTH: 14
<212> TYPE: DNA
<213> ORGANISM: Artificial Sequence
<220> FEATURE:
<223> OTHER INFORMATION: Synthetic Construct

<400> SEQUENCE: 489
tcacgctatt tacc                                                          14

<210> SEQ ID NO 490
<211> LENGTH: 14
<212> TYPE: DNA
<213> ORGANISM: Artificial Sequence
<220> FEATURE:
<223> OTHER INFORMATION: Synthetic Construct

<400> SEQUENCE: 490
tttttagttt tttt                                                          14

<210> SEQ ID NO 491
<211> LENGTH: 14
<212> TYPE: DNA
<213> ORGANISM: Artificial Sequence
<220> FEATURE:
<223> OTHER INFORMATION: Synthetic Construct

<400> SEQUENCE: 491
tcacgctatt tacc                                                          14

<210> SEQ ID NO 492
<211> LENGTH: 14
<212> TYPE: DNA
<213> ORGANISM: Artificial Sequence
<220> FEATURE:
<223> OTHER INFORMATION: Synthetic Construct

<400> SEQUENCE: 492
ttttagtttt tttt                                                          14

<210> SEQ ID NO 493
<211> LENGTH: 14
<212> TYPE: DNA
<213> ORGANISM: Artificial Sequence
<220> FEATURE:
<223> OTHER INFORMATION: Synthetic Construct

<400> SEQUENCE: 493
tcacgctatt tacc                                                          14

<210> SEQ ID NO 494
<211> LENGTH: 14
<212> TYPE: DNA
<213> ORGANISM: Artificial Sequence
<220> FEATURE:
<223> OTHER INFORMATION: Synthetic Construct

<400> SEQUENCE: 494
tttagttttt tttt                                                          14
```

```
<210> SEQ ID NO 495
<211> LENGTH: 14
<212> TYPE: DNA
<213> ORGANISM: Artificial Sequence
<220> FEATURE:
<223> OTHER INFORMATION: Synthetic Construct

<400> SEQUENCE: 495
tcacgctatt tacc                                                    14

<210> SEQ ID NO 496
<211> LENGTH: 14
<212> TYPE: DNA
<213> ORGANISM: Artificial Sequence
<220> FEATURE:
<223> OTHER INFORMATION: Synthetic Construct

<400> SEQUENCE: 496 ttagttttt ttta                                                     14

<210> SEQ ID NO 497
<211> LENGTH: 14
<212> TYPE: DNA
<213> ORGANISM: Artificial Sequence
<220> FEATURE:
<223> OTHER INFORMATION: Synthetic Construct

<400> SEQUENCE: 497
tcacgctatt tacc                                                    14

<210> SEQ ID NO 498
<211> LENGTH: 14
<212> TYPE: DNA
<213> ORGANISM: Artificial Sequence
<220> FEATURE:
<223> OTHER INFORMATION: Synthetic Construct

<400> SEQUENCE: 498 tagtttttt ttaa                                                     14

<210> SEQ ID NO 499
<211> LENGTH: 14
<212> TYPE: DNA
<213> ORGANISM: Artificial Sequence
<220> FEATURE:
<223> OTHER INFORMATION: Synthetic Construct

<400> SEQUENCE: 499
tcacgctatt tacc                                                    14

<210> SEQ ID NO 500
<211> LENGTH: 14
<212> TYPE: DNA
<213> ORGANISM: Artificial Sequence
<220> FEATURE:
<223> OTHER INFORMATION: Synthetic Construct

<400> SEQUENCE: 500 agttttttt taaa                                                     14

<210> SEQ ID NO 501
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 501
tcacgctatt tacc                                                          14

<210> SEQ ID NO 502
<211> LENGTH: 14
<212> TYPE: DNA
<213> ORGANISM: Artificial Sequence
<220> FEATURE:
<223> OTHER INFORMATION: Synthetic Construct

<400> SEQUENCE: 502 gtttttttt aaac                                                           14

<210> SEQ ID NO 503
<211> LENGTH: 14
<212> TYPE: DNA
<213> ORGANISM: Artificial Sequence
<220> FEATURE:
<223> OTHER INFORMATION: Synthetic Construct

<400> SEQUENCE: 503
tcacgctatt tacc                                                          14

<210> SEQ ID NO 504
<211> LENGTH: 14
<212> TYPE: DNA
<213> ORGANISM: Artificial Sequence
<220> FEATURE:
<223> OTHER INFORMATION: Synthetic Construct

<400> SEQUENCE: 504
ttttttttta aacg                                                          14

<210> SEQ ID NO 505
<211> LENGTH: 14
<212> TYPE: DNA
<213> ORGANISM: Artificial Sequence
<220> FEATURE:
<223> OTHER INFORMATION: Synthetic Construct

<400> SEQUENCE: 505
tcacgctatt tacc                                                          14

<210> SEQ ID NO 506
<211> LENGTH: 14
<212> TYPE: DNA
<213> ORGANISM: Artificial Sequence
<220> FEATURE:
<223> OTHER INFORMATION: Synthetic Construct

<400> SEQUENCE: 506
ttttttttaa acga                                                          14

<210> SEQ ID NO 507
<211> LENGTH: 14
<212> TYPE: DNA
<213> ORGANISM: Artificial Sequence
<220> FEATURE:
<223> OTHER INFORMATION: Synthetic Construct

<400> SEQUENCE: 507
tcacgctatt tacc                                                          14

```
<210> SEQ ID NO 508
<211> LENGTH: 14
<212> TYPE: DNA
<213> ORGANISM: Artificial Sequence
<220> FEATURE:
<223> OTHER INFORMATION: Synthetic Construct

<400> SEQUENCE: 508
tttttttaaa cgaa                                                        14

<210> SEQ ID NO 509
<211> LENGTH: 14
<212> TYPE: DNA
<213> ORGANISM: Artificial Sequence
<220> FEATURE:
<223> OTHER INFORMATION: Synthetic Construct

<400> SEQUENCE: 509
tcacgctatt tacc                                                        14

<210> SEQ ID NO 510
<211> LENGTH: 14
<212> TYPE: DNA
<213> ORGANISM: Artificial Sequence
<220> FEATURE:
<223> OTHER INFORMATION: Synthetic Construct

<400> SEQUENCE: 510 tttttttaaac gaag                                                       14

<210> SEQ ID NO 511
<211> LENGTH: 14
<212> TYPE: DNA
<213> ORGANISM: Artificial Sequence
<220> FEATURE:
<223> OTHER INFORMATION: Synthetic Construct

<400> SEQUENCE: 511
tcacgctatt tacc                                                        14

<210> SEQ ID NO 512
<211> LENGTH: 14
<212> TYPE: DNA
<213> ORGANISM: Artificial Sequence
<220> FEATURE:
<223> OTHER INFORMATION: Synthetic Construct

<400> SEQUENCE: 512 ttttttaaacg aagt                                                       14

<210> SEQ ID NO 513
<211> LENGTH: 14
<212> TYPE: DNA
<213> ORGANISM: Artificial Sequence
<220> FEATURE:
<223> OTHER INFORMATION: Synthetic Construct

<400> SEQUENCE: 513
tcacgctatt tacc                                                        14

<210> SEQ ID NO 514
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 514
ttttaaacga agtg                                                        14

<210> SEQ ID NO 515
<211> LENGTH: 14
<212> TYPE: DNA
<213> ORGANISM: Artificial Sequence
<220> FEATURE:
<223> OTHER INFORMATION: Synthetic Construct

<400> SEQUENCE: 515
tcacgctatt tacc                                                        14

<210> SEQ ID NO 516
<211> LENGTH: 14
<212> TYPE: DNA
<213> ORGANISM: Artificial Sequence
<220> FEATURE:
<223> OTHER INFORMATION: Synthetic Construct

<400> SEQUENCE: 516
tttaaacgaa gtgt                                                        14

<210> SEQ ID NO 517
<211> LENGTH: 14
<212> TYPE: DNA
<213> ORGANISM: Artificial Sequence
<220> FEATURE:
<223> OTHER INFORMATION: Synthetic Construct

<400> SEQUENCE: 517
tcacgctatt tacc                                                        14

<210> SEQ ID NO 518
<211> LENGTH: 14
<212> TYPE: DNA
<213> ORGANISM: Artificial Sequence
<220> FEATURE:
<223> OTHER INFORMATION: Synthetic Construct

<400> SEQUENCE: 518
ttaaacgaag tgtt                                                        14

<210> SEQ ID NO 519
<211> LENGTH: 14
<212> TYPE: DNA
<213> ORGANISM: Artificial Sequence
<220> FEATURE:
<223> OTHER INFORMATION: Synthetic Construct

<400> SEQUENCE: 519
tcacgctatt tacc                                                        14

<210> SEQ ID NO 520
<211> LENGTH: 14
<212> TYPE: DNA
<213> ORGANISM: Artificial Sequence
<220> FEATURE:
<223> OTHER INFORMATION: Synthetic Construct

<400> SEQUENCE: 520
taaacgaagt gttt                                                        14

<210> SEQ ID NO 521
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 521
tcacgctatt tacc                                                         14

<210> SEQ ID NO 522
<211> LENGTH: 14
<212> TYPE: DNA
<213> ORGANISM: Artificial Sequence
<220> FEATURE:
<223> OTHER INFORMATION: Synthetic Construct

<400> SEQUENCE: 522
aaacgaagtg ttta                                                         14

<210> SEQ ID NO 523
<211> LENGTH: 14
<212> TYPE: DNA
<213> ORGANISM: Artificial Sequence
<220> FEATURE:
<223> OTHER INFORMATION: Synthetic Construct

<400> SEQUENCE: 523
tcacgctatt tacc                                                         14

<210> SEQ ID NO 524
<211> LENGTH: 14
<212> TYPE: DNA
<213> ORGANISM: Artificial Sequence
<220> FEATURE:
<223> OTHER INFORMATION: Synthetic Construct

<400> SEQUENCE: 524
aacgaagtgt ttat                                                         14

<210> SEQ ID NO 525
<211> LENGTH: 14
<212> TYPE: DNA
<213> ORGANISM: Artificial Sequence
<220> FEATURE:
<223> OTHER INFORMATION: Synthetic Construct

<400> SEQUENCE: 525
tcacgctatt tacc                                                         14

<210> SEQ ID NO 526
<211> LENGTH: 14
<212> TYPE: DNA
<213> ORGANISM: Artificial Sequence
<220> FEATURE:
<223> OTHER INFORMATION: Synthetic Construct

<400> SEQUENCE: 526
acgaagtgtt tatt                                                         14

<210> SEQ ID NO 527
<211> LENGTH: 14
<212> TYPE: DNA
<213> ORGANISM: Artificial Sequence
<220> FEATURE:
<223> OTHER INFORMATION: Synthetic Construct

<400> SEQUENCE: 527
```

-continued tcacgctatt tacc                                              14

<210> SEQ ID NO 528
<211> LENGTH: 14
<212> TYPE: DNA
<213> ORGANISM: Artificial Sequence
<220> FEATURE:
<223> OTHER INFORMATION: Synthetic Construct

<400> SEQUENCE: 528
cgaagtgttt attt                                              14

<210> SEQ ID NO 529
<211> LENGTH: 14
<212> TYPE: DNA
<213> ORGANISM: Artificial Sequence
<220> FEATURE:
<223> OTHER INFORMATION: Synthetic Construct

<400> SEQUENCE: 529
tcacgctatt tacc                                              14

<210> SEQ ID NO 530
<211> LENGTH: 14
<212> TYPE: DNA
<213> ORGANISM: Artificial Sequence
<220> FEATURE:
<223> OTHER INFORMATION: Synthetic Construct

<400> SEQUENCE: 530
gaagtgttta tttg                                              14

<210> SEQ ID NO 531
<211> LENGTH: 14
<212> TYPE: DNA
<213> ORGANISM: Artificial Sequence
<220> FEATURE:
<223> OTHER INFORMATION: Synthetic Construct

<400> SEQUENCE: 531
tcacgctatt tacc                                              14

<210> SEQ ID NO 532
<211> LENGTH: 14
<212> TYPE: DNA
<213> ORGANISM: Artificial Sequence
<220> FEATURE:
<223> OTHER INFORMATION: Synthetic Construct

<400> SEQUENCE: 532
aagtgtttat ttgt                                              14

<210> SEQ ID NO 533
<211> LENGTH: 14
<212> TYPE: DNA
<213> ORGANISM: Artificial Sequence
<220> FEATURE:
<223> OTHER INFORMATION: Synthetic Construct

<400> SEQUENCE: 533
tcacgctatt tacc                                              14

<210> SEQ ID NO 534
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 534
agtgtttatt tgta                                                         14

<210> SEQ ID NO 535
<211> LENGTH: 14
<212> TYPE: DNA
<213> ORGANISM: Artificial Sequence
<220> FEATURE:
<223> OTHER INFORMATION: Synthetic Construct

<400> SEQUENCE: 535
aaactaaact acgc                                                         14

<210> SEQ ID NO 536
<211> LENGTH: 24
<212> TYPE: DNA
<213> ORGANISM: Artificial Sequence
<220> FEATURE:
<223> OTHER INFORMATION: Synthetic Construct

<400> SEQUENCE: 536
cgggttattg gacggtggag ttcg                                              24

<210> SEQ ID NO 537
<211> LENGTH: 14
<212> TYPE: DNA
<213> ORGANISM: Artificial Sequence
<220> FEATURE:
<223> OTHER INFORMATION: Synthetic Construct

<400> SEQUENCE: 537
gtgtttattt gtat                                                         14

<210> SEQ ID NO 538
<211> LENGTH: 14
<212> TYPE: DNA
<213> ORGANISM: Artificial Sequence
<220> FEATURE:
<223> OTHER INFORMATION: Synthetic Construct

<400> SEQUENCE: 538
aaactaaact acgc                                                         14

<210> SEQ ID NO 539
<211> LENGTH: 14
<212> TYPE: DNA
<213> ORGANISM: Artificial Sequence
<220> FEATURE:
<223> OTHER INFORMATION: Synthetic Construct

<400> SEQUENCE: 539
tgtttatttg tata                                                         14

<210> SEQ ID NO 540
<211> LENGTH: 14
<212> TYPE: DNA
<213> ORGANISM: Artificial Sequence
<220> FEATURE:
<223> OTHER INFORMATION: Synthetic Construct

<400> SEQUENCE: 540
aaactaaact acgc                                                         14
```

```
<210> SEQ ID NO 541
<211> LENGTH: 14
<212> TYPE: DNA
<213> ORGANISM: Artificial Sequence
<220> FEATURE:
<223> OTHER INFORMATION: Synthetic Construct

<400> SEQUENCE: 541
gtttatttgt ataa                                                    14

<210> SEQ ID NO 542
<211> LENGTH: 14
<212> TYPE: DNA
<213> ORGANISM: Artificial Sequence
<220> FEATURE:
<223> OTHER INFORMATION: Synthetic Construct

<400> SEQUENCE: 542
aaactaaact acgc                                                    14

<210> SEQ ID NO 543
<211> LENGTH: 14
<212> TYPE: DNA
<213> ORGANISM: Artificial Sequence
<220> FEATURE:
<223> OTHER INFORMATION: Synthetic Construct

<400> SEQUENCE: 543
tttatttgta taaa                                                    14

<210> SEQ ID NO 544
<211> LENGTH: 14
<212> TYPE: DNA
<213> ORGANISM: Artificial Sequence
<220> FEATURE:
<223> OTHER INFORMATION: Synthetic Construct

<400> SEQUENCE: 544
aaactaaact acgc                                                    14

<210> SEQ ID NO 545
<211> LENGTH: 14
<212> TYPE: DNA
<213> ORGANISM: Artificial Sequence
<220> FEATURE:
<223> OTHER INFORMATION: Synthetic Construct

<400> SEQUENCE: 545
ttatttgtat aaaa                                                    14

<210> SEQ ID NO 546
<211> LENGTH: 14
<212> TYPE: DNA
<213> ORGANISM: Artificial Sequence
<220> FEATURE:
<223> OTHER INFORMATION: Synthetic Construct

<400> SEQUENCE: 546
aaactaaact acgc                                                    14

<210> SEQ ID NO 547
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 547
tatttgtata aaag                                                14

<210> SEQ ID NO 548
<211> LENGTH: 14
<212> TYPE: DNA
<213> ORGANISM: Artificial Sequence
<220> FEATURE:
<223> OTHER INFORMATION: Synthetic Construct

<400> SEQUENCE: 548
aaactaaact acgc                                                14

<210> SEQ ID NO 549
<211> LENGTH: 14
<212> TYPE: DNA
<213> ORGANISM: Artificial Sequence
<220> FEATURE:
<223> OTHER INFORMATION: Synthetic Construct

<400> SEQUENCE: 549
atttgtataa aagg                                                14

<210> SEQ ID NO 550
<211> LENGTH: 14
<212> TYPE: DNA
<213> ORGANISM: Artificial Sequence
<220> FEATURE:
<223> OTHER INFORMATION: Synthetic Construct

<400> SEQUENCE: 550
aaactaaact acgc                                                14

<210> SEQ ID NO 551
<211> LENGTH: 14
<212> TYPE: DNA
<213> ORGANISM: Artificial Sequence
<220> FEATURE:
<223> OTHER INFORMATION: Synthetic Construct

<400> SEQUENCE: 551
tttgtataaa aggt                                                14

<210> SEQ ID NO 552
<211> LENGTH: 14
<212> TYPE: DNA
<213> ORGANISM: Artificial Sequence
<220> FEATURE:
<223> OTHER INFORMATION: Synthetic Construct

<400> SEQUENCE: 552
aaactaaact acgc                                                14

<210> SEQ ID NO 553
<211> LENGTH: 14
<212> TYPE: DNA
<213> ORGANISM: Artificial Sequence
<220> FEATURE:
<223> OTHER INFORMATION: Synthetic Construct

<400> SEQUENCE: 553
ttgtataaaa ggtt                                                14

<210> SEQ ID NO 554
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 554
aaactaaact acgc                                                         14

<210> SEQ ID NO 555
<211> LENGTH: 14
<212> TYPE: DNA
<213> ORGANISM: Artificial Sequence
<220> FEATURE:
<223> OTHER INFORMATION: Synthetic Construct

<400> SEQUENCE: 555
tgtataaaag gttt                                                         14

<210> SEQ ID NO 556
<211> LENGTH: 14
<212> TYPE: DNA
<213> ORGANISM: Artificial Sequence
<220> FEATURE:
<223> OTHER INFORMATION: Synthetic Construct

<400> SEQUENCE: 556
aaactaaact acgc                                                         14

<210> SEQ ID NO 557
<211> LENGTH: 14
<212> TYPE: DNA
<213> ORGANISM: Artificial Sequence
<220> FEATURE:
<223> OTHER INFORMATION: Synthetic Construct

<400> SEQUENCE: 557
gtataaaagg tttg                                                         14

<210> SEQ ID NO 558
<211> LENGTH: 14
<212> TYPE: DNA
<213> ORGANISM: Artificial Sequence
<220> FEATURE:
<223> OTHER INFORMATION: Synthetic Construct

<400> SEQUENCE: 558
aaactaaact acgc                                                         14

<210> SEQ ID NO 559
<211> LENGTH: 14
<212> TYPE: DNA
<213> ORGANISM: Artificial Sequence
<220> FEATURE:
<223> OTHER INFORMATION: Synthetic Construct

<400> SEQUENCE: 559 tataaaggt ttga                                                          14

<210> SEQ ID NO 560
<211> LENGTH: 14
<212> TYPE: DNA
<213> ORGANISM: Artificial Sequence
<220> FEATURE:
<223> OTHER INFORMATION: Synthetic Construct

<400> SEQUENCE: 560
```

```
aaactaaaact acgc                                               14

<210> SEQ ID NO 561
<211> LENGTH: 14
<212> TYPE: DNA
<213> ORGANISM: Artificial Sequence
<220> FEATURE:
<223> OTHER INFORMATION: Synthetic Construct

<400> SEQUENCE: 561
ataaaaggtt tgag                                                14

<210> SEQ ID NO 562
<211> LENGTH: 14
<212> TYPE: DNA
<213> ORGANISM: Artificial Sequence
<220> FEATURE:
<223> OTHER INFORMATION: Synthetic Construct

<400> SEQUENCE: 562 aaactaaaact acgc                                               14

<210> SEQ ID NO 563
<211> LENGTH: 14
<212> TYPE: DNA
<213> ORGANISM: Artificial Sequence
<220> FEATURE:
<223> OTHER INFORMATION: Synthetic Construct

<400> SEQUENCE: 563
taaaaggttt gagg                                                14

<210> SEQ ID NO 564
<211> LENGTH: 14
<212> TYPE: DNA
<213> ORGANISM: Artificial Sequence
<220> FEATURE:
<223> OTHER INFORMATION: Synthetic Construct

<400> SEQUENCE: 564 aaactaaaact acgc                                               14

<210> SEQ ID NO 565
<211> LENGTH: 14
<212> TYPE: DNA
<213> ORGANISM: Artificial Sequence
<220> FEATURE:
<223> OTHER INFORMATION: Synthetic Construct

<400> SEQUENCE: 565 aaaggtttg aggt                                                 14

<210> SEQ ID NO 566
<211> LENGTH: 14
<212> TYPE: DNA
<213> ORGANISM: Artificial Sequence
<220> FEATURE:
<223> OTHER INFORMATION: Synthetic Construct

<400> SEQUENCE: 566 aaactaaaact acgc                                               14

<210> SEQ ID NO 567
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 567
aaaggtttga ggtt                                                    14

<210> SEQ ID NO 568
<211> LENGTH: 14
<212> TYPE: DNA
<213> ORGANISM: Artificial Sequence
<220> FEATURE:
<223> OTHER INFORMATION: Synthetic Construct

<400> SEQUENCE: 568
aaactaaact acgc                                                    14

<210> SEQ ID NO 569
<211> LENGTH: 14
<212> TYPE: DNA
<213> ORGANISM: Artificial Sequence
<220> FEATURE:
<223> OTHER INFORMATION: Synthetic Construct

<400> SEQUENCE: 569
aaggtttgag gttg                                                    14

<210> SEQ ID NO 570
<211> LENGTH: 14
<212> TYPE: DNA
<213> ORGANISM: Artificial Sequence
<220> FEATURE:
<223> OTHER INFORMATION: Synthetic Construct

<400> SEQUENCE: 570
aaactaaact acgc                                                    14

<210> SEQ ID NO 571
<211> LENGTH: 14
<212> TYPE: DNA
<213> ORGANISM: Artificial Sequence
<220> FEATURE:
<223> OTHER INFORMATION: Synthetic Construct

<400> SEQUENCE: 571
aggtttgagg ttga                                                    14

<210> SEQ ID NO 572
<211> LENGTH: 14
<212> TYPE: DNA
<213> ORGANISM: Artificial Sequence
<220> FEATURE:
<223> OTHER INFORMATION: Synthetic Construct

<400> SEQUENCE: 572
aaactaaact acgc                                                    14

<210> SEQ ID NO 573
<211> LENGTH: 14
<212> TYPE: DNA
<213> ORGANISM: Artificial Sequence
<220> FEATURE:
<223> OTHER INFORMATION: Synthetic Construct

<400> SEQUENCE: 573
ggtttgaggt tgag                                                    14
```

<210> SEQ ID NO 574
<211> LENGTH: 14
<212> TYPE: DNA
<213> ORGANISM: Artificial Sequence
<220> FEATURE:
<223> OTHER INFORMATION: Synthetic Construct

<400> SEQUENCE: 574
aaactaaact acgc                                                        14

<210> SEQ ID NO 575
<211> LENGTH: 14
<212> TYPE: DNA
<213> ORGANISM: Artificial Sequence
<220> FEATURE:
<223> OTHER INFORMATION: Synthetic Construct

<400> SEQUENCE: 575
gtttgaggtt gagg                                                        14

<210> SEQ ID NO 576
<211> LENGTH: 14
<212> TYPE: DNA
<213> ORGANISM: Artificial Sequence
<220> FEATURE:
<223> OTHER INFORMATION: Synthetic Construct

<400> SEQUENCE: 576
aaactaaact acgc                                                        14

<210> SEQ ID NO 577
<211> LENGTH: 14
<212> TYPE: DNA
<213> ORGANISM: Artificial Sequence
<220> FEATURE:
<223> OTHER INFORMATION: Synthetic Construct

<400> SEQUENCE: 577
tttgaggttg aggt                                                        14

<210> SEQ ID NO 578
<211> LENGTH: 14
<212> TYPE: DNA
<213> ORGANISM: Artificial Sequence
<220> FEATURE:
<223> OTHER INFORMATION: Synthetic Construct

<400> SEQUENCE: 578
aaactaaact acgc                                                        14

<210> SEQ ID NO 579
<211> LENGTH: 14
<212> TYPE: DNA
<213> ORGANISM: Artificial Sequence
<220> FEATURE:
<223> OTHER INFORMATION: Synthetic Construct

<400> SEQUENCE: 579
ttgaggttga ggtt                                                        14

<210> SEQ ID NO 580
<211> LENGTH: 14
<212> TYPE: DNA
<213> ORGANISM: Artificial Sequence
<220> FEATURE:

<223> OTHER INFORMATION: Synthetic Construct

<400> SEQUENCE: 580
aaactaaact acgc                                                             14

<210> SEQ ID NO 581
<211> LENGTH: 14
<212> TYPE: DNA
<213> ORGANISM: Artificial Sequence
<220> FEATURE:
<223> OTHER INFORMATION: Synthetic Construct

<400> SEQUENCE: 581
tgaggttgag gttg                                                             14

<210> SEQ ID NO 582
<211> LENGTH: 14
<212> TYPE: DNA
<213> ORGANISM: Artificial Sequence
<220> FEATURE:
<223> OTHER INFORMATION: Synthetic Construct

<400> SEQUENCE: 582
aaactaaact acgc                                                             14

<210> SEQ ID NO 583
<211> LENGTH: 14
<212> TYPE: DNA
<213> ORGANISM: Artificial Sequence
<220> FEATURE:
<223> OTHER INFORMATION: Synthetic Construct

<400> SEQUENCE: 583
gaggttgagg ttga                                                             14

<210> SEQ ID NO 584
<211> LENGTH: 14
<212> TYPE: DNA
<213> ORGANISM: Artificial Sequence
<220> FEATURE:
<223> OTHER INFORMATION: Synthetic Construct

<400> SEQUENCE: 584
aaactaaact acgc                                                             14

<210> SEQ ID NO 585
<211> LENGTH: 14
<212> TYPE: DNA
<213> ORGANISM: Artificial Sequence
<220> FEATURE:
<223> OTHER INFORMATION: Synthetic Construct

<400> SEQUENCE: 585
aggttgaggt tgaa                                                             14

<210> SEQ ID NO 586
<211> LENGTH: 14
<212> TYPE: DNA
<213> ORGANISM: Artificial Sequence
<220> FEATURE:
<223> OTHER INFORMATION: Synthetic Construct

<400> SEQUENCE: 586
aaactaaact acgc                                                             14

```
<210> SEQ ID NO 587
<211> LENGTH: 14
<212> TYPE: DNA
<213> ORGANISM: Artificial Sequence
<220> FEATURE:
<223> OTHER INFORMATION: Synthetic Construct

<400> SEQUENCE: 587
ggttgaggtt gaag                                                      14

<210> SEQ ID NO 588
<211> LENGTH: 14
<212> TYPE: DNA
<213> ORGANISM: Artificial Sequence
<220> FEATURE:
<223> OTHER INFORMATION: Synthetic Construct

<400> SEQUENCE: 588
aaactaaact acgc                                                      14

<210> SEQ ID NO 589
<211> LENGTH: 14
<212> TYPE: DNA
<213> ORGANISM: Artificial Sequence
<220> FEATURE:
<223> OTHER INFORMATION: Synthetic Construct

<400> SEQUENCE: 589
gttgaggttg aagg                                                      14

<210> SEQ ID NO 590
<211> LENGTH: 14
<212> TYPE: DNA
<213> ORGANISM: Artificial Sequence
<220> FEATURE:
<223> OTHER INFORMATION: Synthetic Construct

<400> SEQUENCE: 590
aaactaaact acgc                                                      14

<210> SEQ ID NO 591
<211> LENGTH: 14
<212> TYPE: DNA
<213> ORGANISM: Artificial Sequence
<220> FEATURE:
<223> OTHER INFORMATION: Synthetic Construct

<400> SEQUENCE: 591
ttgaggttga aggt                                                      14

<210> SEQ ID NO 592
<211> LENGTH: 14
<212> TYPE: DNA
<213> ORGANISM: Artificial Sequence
<220> FEATURE:
<223> OTHER INFORMATION: Synthetic Construct

<400> SEQUENCE: 592
aaactaaact acgc                                                      14

<210> SEQ ID NO 593
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 593
tgaggttgaa ggtt                                                    14

<210> SEQ ID NO 594
<211> LENGTH: 14
<212> TYPE: DNA
<213> ORGANISM: Artificial Sequence
<220> FEATURE:
<223> OTHER INFORMATION: Synthetic Construct

<400> SEQUENCE: 594
aaactaaact acgc                                                    14

<210> SEQ ID NO 595
<211> LENGTH: 14
<212> TYPE: DNA
<213> ORGANISM: Artificial Sequence
<220> FEATURE:
<223> OTHER INFORMATION: Synthetic Construct

<400> SEQUENCE: 595
gaggttgaag gttg                                                    14

<210> SEQ ID NO 596
<211> LENGTH: 14
<212> TYPE: DNA
<213> ORGANISM: Artificial Sequence
<220> FEATURE:
<223> OTHER INFORMATION: Synthetic Construct

<400> SEQUENCE: 596
aaactaaact acgc                                                    14

<210> SEQ ID NO 597
<211> LENGTH: 14
<212> TYPE: DNA
<213> ORGANISM: Artificial Sequence
<220> FEATURE:
<223> OTHER INFORMATION: Synthetic Construct

<400> SEQUENCE: 597
aggttgaagg ttga                                                    14

<210> SEQ ID NO 598
<211> LENGTH: 14
<212> TYPE: DNA
<213> ORGANISM: Artificial Sequence
<220> FEATURE:
<223> OTHER INFORMATION: Synthetic Construct

<400> SEQUENCE: 598
aaactaaact acgc                                                    14

<210> SEQ ID NO 599
<211> LENGTH: 14
<212> TYPE: DNA
<213> ORGANISM: Artificial Sequence
<220> FEATURE:
<223> OTHER INFORMATION: Synthetic Construct

<400> SEQUENCE: 599
ggttgaaggt tgat                                                    14

<210> SEQ ID NO 600
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 600
aaactaaact acgc                                                      14

<210> SEQ ID NO 601
<211> LENGTH: 14
<212> TYPE: DNA
<213> ORGANISM: Artificial Sequence
<220> FEATURE:
<223> OTHER INFORMATION: Synthetic Construct

<400> SEQUENCE: 601
gttgaaggtt gatt                                                      14

<210> SEQ ID NO 602
<211> LENGTH: 14
<212> TYPE: DNA
<213> ORGANISM: Artificial Sequence
<220> FEATURE:
<223> OTHER INFORMATION: Synthetic Construct

<400> SEQUENCE: 602
aaactaaact acgc                                                      14

<210> SEQ ID NO 603
<211> LENGTH: 14
<212> TYPE: DNA
<213> ORGANISM: Artificial Sequence
<220> FEATURE:
<223> OTHER INFORMATION: Synthetic Construct

<400> SEQUENCE: 603
ttgaaggttg attt                                                      14

<210> SEQ ID NO 604
<211> LENGTH: 14
<212> TYPE: DNA
<213> ORGANISM: Artificial Sequence
<220> FEATURE:
<223> OTHER INFORMATION: Synthetic Construct

<400> SEQUENCE: 604
aaactaaact acgc                                                      14

<210> SEQ ID NO 605
<211> LENGTH: 14
<212> TYPE: DNA
<213> ORGANISM: Artificial Sequence
<220> FEATURE:
<223> OTHER INFORMATION: Synthetic Construct

<400> SEQUENCE: 605
tgaaggttga tttt                                                      14

<210> SEQ ID NO 606
<211> LENGTH: 14
<212> TYPE: DNA
<213> ORGANISM: Artificial Sequence
<220> FEATURE:
<223> OTHER INFORMATION: Synthetic Construct

<400> SEQUENCE: 606
```
aaactaaact acgc                                                   14

<210> SEQ ID NO 607
<211> LENGTH: 14
<212> TYPE: DNA
<213> ORGANISM: Artificial Sequence
<220> FEATURE:
<223> OTHER INFORMATION: Synthetic Construct

<400> SEQUENCE: 607
gaaggttgat tttt                                                   14

<210> SEQ ID NO 608
<211> LENGTH: 14
<212> TYPE: DNA
<213> ORGANISM: Artificial Sequence
<220> FEATURE:
<223> OTHER INFORMATION: Synthetic Construct

<400> SEQUENCE: 608
aaactaaact acgc                                                   14

<210> SEQ ID NO 609
<211> LENGTH: 14
<212> TYPE: DNA
<213> ORGANISM: Artificial Sequence
<220> FEATURE:
<223> OTHER INFORMATION: Synthetic Construct

<400> SEQUENCE: 609
aaggttgatt tttt                                                   14

<210> SEQ ID NO 610
<211> LENGTH: 14
<212> TYPE: DNA
<213> ORGANISM: Artificial Sequence
<220> FEATURE:
<223> OTHER INFORMATION: Synthetic Construct

<400> SEQUENCE: 610
aaactaaact acgc                                                   14

<210> SEQ ID NO 611
<211> LENGTH: 14
<212> TYPE: DNA
<213> ORGANISM: Artificial Sequence
<220> FEATURE:
<223> OTHER INFORMATION: Synthetic Construct

<400> SEQUENCE: 611
aggttgattt tttt                                                   14

<210> SEQ ID NO 612
<211> LENGTH: 14
<212> TYPE: DNA
<213> ORGANISM: Artificial Sequence
<220> FEATURE:
<223> OTHER INFORMATION: Synthetic Construct

<400> SEQUENCE: 612
aaactaaact acgc                                                   14

<210> SEQ ID NO 613
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 613
ggttgatttt tttt                                                        14

<210> SEQ ID NO 614
<211> LENGTH: 14
<212> TYPE: DNA
<213> ORGANISM: Artificial Sequence
<220> FEATURE:
<223> OTHER INFORMATION: Synthetic Construct

<400> SEQUENCE: 614
aaactaaact acgc                                                        14

<210> SEQ ID NO 615
<211> LENGTH: 14
<212> TYPE: DNA
<213> ORGANISM: Artificial Sequence
<220> FEATURE:
<223> OTHER INFORMATION: Synthetic Construct

<400> SEQUENCE: 615 gttgatttttt ttta                                                       14

<210> SEQ ID NO 616
<211> LENGTH: 14
<212> TYPE: DNA
<213> ORGANISM: Artificial Sequence
<220> FEATURE:
<223> OTHER INFORMATION: Synthetic Construct

<400> SEQUENCE: 616
aaactaaact acgc                                                        14

<210> SEQ ID NO 617
<211> LENGTH: 14
<212> TYPE: DNA
<213> ORGANISM: Artificial Sequence
<220> FEATURE:
<223> OTHER INFORMATION: Synthetic Construct

<400> SEQUENCE: 617 ttgattttttt taa                                                        14

<210> SEQ ID NO 618
<211> LENGTH: 14
<212> TYPE: DNA
<213> ORGANISM: Artificial Sequence
<220> FEATURE:
<223> OTHER INFORMATION: Synthetic Construct

<400> SEQUENCE: 618
aaactaaact acgc                                                        14

<210> SEQ ID NO 619
<211> LENGTH: 14
<212> TYPE: DNA
<213> ORGANISM: Artificial Sequence
<220> FEATURE:
<223> OTHER INFORMATION: Synthetic Construct

<400> SEQUENCE: 619
tgattttttt taaa                                                        14
```

<210> SEQ ID NO 620
<211> LENGTH: 14
<212> TYPE: DNA
<213> ORGANISM: Artificial Sequence
<220> FEATURE:
<223> OTHER INFORMATION: Synthetic Construct

<400> SEQUENCE: 620
aaactaaact acgc                                                         14

<210> SEQ ID NO 621
<211> LENGTH: 14
<212> TYPE: DNA
<213> ORGANISM: Artificial Sequence
<220> FEATURE:
<223> OTHER INFORMATION: Synthetic Construct

<400> SEQUENCE: 621
gatttttttt aaat                                                         14

<210> SEQ ID NO 622
<211> LENGTH: 14
<212> TYPE: DNA
<213> ORGANISM: Artificial Sequence
<220> FEATURE:
<223> OTHER INFORMATION: Synthetic Construct

<400> SEQUENCE: 622
aaactaaact acgc                                                         14

<210> SEQ ID NO 623
<211> LENGTH: 14
<212> TYPE: DNA
<213> ORGANISM: Artificial Sequence
<220> FEATURE:
<223> OTHER INFORMATION: Synthetic Construct

<400> SEQUENCE: 623
atttttttta aatt                                                         14

<210> SEQ ID NO 624
<211> LENGTH: 14
<212> TYPE: DNA
<213> ORGANISM: Artificial Sequence
<220> FEATURE:
<223> OTHER INFORMATION: Synthetic Construct

<400> SEQUENCE: 624
aaactaaact acgc                                                         14

<210> SEQ ID NO 625
<211> LENGTH: 14
<212> TYPE: DNA
<213> ORGANISM: Artificial Sequence
<220> FEATURE:
<223> OTHER INFORMATION: Synthetic Construct

<400> SEQUENCE: 625
ttttttttaa attt                                                         14

<210> SEQ ID NO 626
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 626
aaactaaact acgc                                                        14

<210> SEQ ID NO 627
<211> LENGTH: 14
<212> TYPE: DNA
<213> ORGANISM: Artificial Sequence
<220> FEATURE:
<223> OTHER INFORMATION: Synthetic Construct

<400> SEQUENCE: 627
tttttttaaa tttt                                                        14

<210> SEQ ID NO 628
<211> LENGTH: 14
<212> TYPE: DNA
<213> ORGANISM: Artificial Sequence
<220> FEATURE:
<223> OTHER INFORMATION: Synthetic Construct

<400> SEQUENCE: 628
aaactaaact acgc                                                        14

<210> SEQ ID NO 629
<211> LENGTH: 14
<212> TYPE: DNA
<213> ORGANISM: Artificial Sequence
<220> FEATURE:
<223> OTHER INFORMATION: Synthetic Construct

<400> SEQUENCE: 629 tttttaaat ttta                                                         14

<210> SEQ ID NO 630
<211> LENGTH: 14
<212> TYPE: DNA
<213> ORGANISM: Artificial Sequence
<220> FEATURE:
<223> OTHER INFORMATION: Synthetic Construct

<400> SEQUENCE: 630
aaactaaact acgc                                                        14

<210> SEQ ID NO 631
<211> LENGTH: 14
<212> TYPE: DNA
<213> ORGANISM: Artificial Sequence
<220> FEATURE:
<223> OTHER INFORMATION: Synthetic Construct

<400> SEQUENCE: 631
tttttaaatt ttat                                                        14

<210> SEQ ID NO 632
<211> LENGTH: 14
<212> TYPE: DNA
<213> ORGANISM: Artificial Sequence
<220> FEATURE:
<223> OTHER INFORMATION: Synthetic Construct

<400> SEQUENCE: 632
aaactaaact acgc                                                        14

<210> SEQ ID NO 633
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 633
ttttaaattt tatt                                                      14

<210> SEQ ID NO 634
<211> LENGTH: 14
<212> TYPE: DNA
<213> ORGANISM: Artificial Sequence
<220> FEATURE:
<223> OTHER INFORMATION: Synthetic Construct

<400> SEQUENCE: 634
aaactaaact acgc                                                      14

<210> SEQ ID NO 635
<211> LENGTH: 14
<212> TYPE: DNA
<213> ORGANISM: Artificial Sequence
<220> FEATURE:
<223> OTHER INFORMATION: Synthetic Construct

<400> SEQUENCE: 635
tttaaatttt attt                                                      14

<210> SEQ ID NO 636
<211> LENGTH: 14
<212> TYPE: DNA
<213> ORGANISM: Artificial Sequence
<220> FEATURE:
<223> OTHER INFORMATION: Synthetic Construct

<400> SEQUENCE: 636
aaactaaact acgc                                                      14

<210> SEQ ID NO 637
<211> LENGTH: 14
<212> TYPE: DNA
<213> ORGANISM: Artificial Sequence
<220> FEATURE:
<223> OTHER INFORMATION: Synthetic Construct

<400> SEQUENCE: 637
ttaaatttta tttg                                                      14

<210> SEQ ID NO 638
<211> LENGTH: 14
<212> TYPE: DNA
<213> ORGANISM: Artificial Sequence
<220> FEATURE:
<223> OTHER INFORMATION: Synthetic Construct

<400> SEQUENCE: 638
aaactaaact acgc                                                      14

<210> SEQ ID NO 639
<211> LENGTH: 14
<212> TYPE: DNA
<213> ORGANISM: Artificial Sequence
<220> FEATURE:
<223> OTHER INFORMATION: Synthetic Construct

<400> SEQUENCE: 639
```

```
taaattttat ttgg                                              14

<210> SEQ ID NO 640
<211> LENGTH: 14
<212> TYPE: DNA
<213> ORGANISM: Artificial Sequence
<220> FEATURE:
<223> OTHER INFORMATION: Synthetic Construct

<400> SEQUENCE: 640
aaactaaact acgc                                              14

<210> SEQ ID NO 641
<211> LENGTH: 14
<212> TYPE: DNA
<213> ORGANISM: Artificial Sequence
<220> FEATURE:
<223> OTHER INFORMATION: Synthetic Construct

<400> SEQUENCE: 641
aaattttatt tggg                                              14

<210> SEQ ID NO 642
<211> LENGTH: 14
<212> TYPE: DNA
<213> ORGANISM: Artificial Sequence
<220> FEATURE:
<223> OTHER INFORMATION: Synthetic Construct

<400> SEQUENCE: 642
aaactaaact acgc                                              14

<210> SEQ ID NO 643
<211> LENGTH: 14
<212> TYPE: DNA
<213> ORGANISM: Artificial Sequence
<220> FEATURE:
<223> OTHER INFORMATION: Synthetic Construct

<400> SEQUENCE: 643
aattttattt gggt                                              14

<210> SEQ ID NO 644
<211> LENGTH: 14
<212> TYPE: DNA
<213> ORGANISM: Artificial Sequence
<220> FEATURE:
<223> OTHER INFORMATION: Synthetic Construct

<400> SEQUENCE: 644
aaactaaact acgc                                              14

<210> SEQ ID NO 645
<211> LENGTH: 14
<212> TYPE: DNA
<213> ORGANISM: Artificial Sequence
<220> FEATURE:
<223> OTHER INFORMATION: Synthetic Construct

<400> SEQUENCE: 645
attttatttg ggta                                              14

<210> SEQ ID NO 646
<211> LENGTH: 14
<212> TYPE: DNA
```

```
<213> ORGANISM: Artificial Sequence
<220> FEATURE:
<223> OTHER INFORMATION: Synthetic Construct

<400> SEQUENCE: 646
aaactaaact acgc                                                         14

<210> SEQ ID NO 647
<211> LENGTH: 14
<212> TYPE: DNA
<213> ORGANISM: Artificial Sequence
<220> FEATURE:
<223> OTHER INFORMATION: Synthetic Construct

<400> SEQUENCE: 647
ttttatttgg gtaa                                                         14

<210> SEQ ID NO 648
<211> LENGTH: 14
<212> TYPE: DNA
<213> ORGANISM: Artificial Sequence
<220> FEATURE:
<223> OTHER INFORMATION: Synthetic Construct

<400> SEQUENCE: 648
aaactaaact acgc                                                         14

<210> SEQ ID NO 649
<211> LENGTH: 14
<212> TYPE: DNA
<213> ORGANISM: Artificial Sequence
<220> FEATURE:
<223> OTHER INFORMATION: Synthetic Construct

<400> SEQUENCE: 649
tttatttggg taaa                                                         14

<210> SEQ ID NO 650
<211> LENGTH: 14
<212> TYPE: DNA
<213> ORGANISM: Artificial Sequence
<220> FEATURE:
<223> OTHER INFORMATION: Synthetic Construct

<400> SEQUENCE: 650
aaactaaact acgc                                                         14

<210> SEQ ID NO 651
<211> LENGTH: 14
<212> TYPE: DNA
<213> ORGANISM: Artificial Sequence
<220> FEATURE:
<223> OTHER INFORMATION: Synthetic Construct

<400> SEQUENCE: 651
ttatttgggt aaat                                                         14

<210> SEQ ID NO 652
<211> LENGTH: 14
<212> TYPE: DNA
<213> ORGANISM: Artificial Sequence
<220> FEATURE:
<223> OTHER INFORMATION: Synthetic Construct

<400> SEQUENCE: 652
aaactaaact acgc                                                         14
```

```
<210> SEQ ID NO 653
<211> LENGTH: 14
<212> TYPE: DNA
<213> ORGANISM: Artificial Sequence
<220> FEATURE:
<223> OTHER INFORMATION: Synthetic Construct

<400> SEQUENCE: 653
tatttgggta aata                                                        14

<210> SEQ ID NO 654
<211> LENGTH: 14
<212> TYPE: DNA
<213> ORGANISM: Artificial Sequence
<220> FEATURE:
<223> OTHER INFORMATION: Synthetic Construct

<400> SEQUENCE: 654
aaactaaact acgc                                                        14

<210> SEQ ID NO 655
<211> LENGTH: 14
<212> TYPE: DNA
<213> ORGANISM: Artificial Sequence
<220> FEATURE:
<223> OTHER INFORMATION: Synthetic Construct

<400> SEQUENCE: 655
atttgggtaa atag                                                        14

<210> SEQ ID NO 656
<211> LENGTH: 14
<212> TYPE: DNA
<213> ORGANISM: Artificial Sequence
<220> FEATURE:
<223> OTHER INFORMATION: Synthetic Construct

<400> SEQUENCE: 656
aaactaaact acgc                                                        14

<210> SEQ ID NO 657
<211> LENGTH: 14
<212> TYPE: DNA
<213> ORGANISM: Artificial Sequence
<220> FEATURE:
<223> OTHER INFORMATION: Synthetic Construct

<400> SEQUENCE: 657
tttgggtaaa tagc                                                        14

<210> SEQ ID NO 658
<211> LENGTH: 14
<212> TYPE: DNA
<213> ORGANISM: Artificial Sequence
<220> FEATURE:
<223> OTHER INFORMATION: Synthetic Construct

<400> SEQUENCE: 658
actacctccg ctaa                                                        14

<210> SEQ ID NO 659
<211> LENGTH: 24
<212> TYPE: DNA
<213> ORGANISM: Artificial Sequence
<220> FEATURE:
```

<223> OTHER INFORMATION: Synthetic Construct

<400> SEQUENCE: 659
aggtagggtt cgtttattcg gtgt                                                24

<210> SEQ ID NO 660
<211> LENGTH: 14
<212> TYPE: DNA
<213> ORGANISM: Artificial Sequence
<220> FEATURE:
<223> OTHER INFORMATION: Synthetic Construct

<400> SEQUENCE: 660
ttgggtaaat agcg                                                          14

<210> SEQ ID NO 661
<211> LENGTH: 14
<212> TYPE: DNA
<213> ORGANISM: Artificial Sequence
<220> FEATURE:
<223> OTHER INFORMATION: Synthetic Construct

<400> SEQUENCE: 661
actacctccg ctaa                                                          14

<210> SEQ ID NO 662
<211> LENGTH: 14
<212> TYPE: DNA
<213> ORGANISM: Artificial Sequence
<220> FEATURE:
<223> OTHER INFORMATION: Synthetic Construct

<400> SEQUENCE: 662
tgggtaaata gcgt                                                          14

<210> SEQ ID NO 663
<211> LENGTH: 14
<212> TYPE: DNA
<213> ORGANISM: Artificial Sequence
<220> FEATURE:
<223> OTHER INFORMATION: Synthetic Construct

<400> SEQUENCE: 663
actacctccg ctaa                                                          14

<210> SEQ ID NO 664
<211> LENGTH: 14
<212> TYPE: DNA
<213> ORGANISM: Artificial Sequence
<220> FEATURE:
<223> OTHER INFORMATION: Synthetic Construct

<400> SEQUENCE: 664
gggtaaatag cgtg                                                          14

<210> SEQ ID NO 665
<211> LENGTH: 14
<212> TYPE: DNA
<213> ORGANISM: Artificial Sequence
<220> FEATURE:
<223> OTHER INFORMATION: Synthetic Construct

<400> SEQUENCE: 665
actacctccg ctaa                                                          14

```
<210> SEQ ID NO 666
<211> LENGTH: 14
<212> TYPE: DNA
<213> ORGANISM: Artificial Sequence
<220> FEATURE:
<223> OTHER INFORMATION: Synthetic Construct

<400> SEQUENCE: 666
ggtaaatagc gtga                                                        14

<210> SEQ ID NO 667
<211> LENGTH: 14
<212> TYPE: DNA
<213> ORGANISM: Artificial Sequence
<220> FEATURE:
<223> OTHER INFORMATION: Synthetic Construct

<400> SEQUENCE: 667
actacctccg ctaa                                                        14

<210> SEQ ID NO 668
<211> LENGTH: 14
<212> TYPE: DNA
<213> ORGANISM: Artificial Sequence
<220> FEATURE:
<223> OTHER INFORMATION: Synthetic Construct

<400> SEQUENCE: 668
gtaaatagcg tgat                                                        14

<210> SEQ ID NO 669
<211> LENGTH: 14
<212> TYPE: DNA
<213> ORGANISM: Artificial Sequence
<220> FEATURE:
<223> OTHER INFORMATION: Synthetic Construct

<400> SEQUENCE: 669
actacctccg ctaa                                                        14

<210> SEQ ID NO 670
<211> LENGTH: 14
<212> TYPE: DNA
<213> ORGANISM: Artificial Sequence
<220> FEATURE:
<223> OTHER INFORMATION: Synthetic Construct

<400> SEQUENCE: 670
taaatagcgt gatt                                                        14

<210> SEQ ID NO 671
<211> LENGTH: 14
<212> TYPE: DNA
<213> ORGANISM: Artificial Sequence
<220> FEATURE:
<223> OTHER INFORMATION: Synthetic Construct

<400> SEQUENCE: 671
actacctccg ctaa                                                        14

<210> SEQ ID NO 672
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 672
aaatagcgtg atta                                                     14

<210> SEQ ID NO 673
<211> LENGTH: 14
<212> TYPE: DNA
<213> ORGANISM: Artificial Sequence
<220> FEATURE:
<223> OTHER INFORMATION: Synthetic Construct

<400> SEQUENCE: 673
actacctccg ctaa                                                     14

<210> SEQ ID NO 674
<211> LENGTH: 14
<212> TYPE: DNA
<213> ORGANISM: Artificial Sequence
<220> FEATURE:
<223> OTHER INFORMATION: Synthetic Construct

<400> SEQUENCE: 674
aatagcgtga ttaa                                                     14

<210> SEQ ID NO 675
<211> LENGTH: 14
<212> TYPE: DNA
<213> ORGANISM: Artificial Sequence
<220> FEATURE:
<223> OTHER INFORMATION: Synthetic Construct

<400> SEQUENCE: 675
actacctccg ctaa                                                     14

<210> SEQ ID NO 676
<211> LENGTH: 14
<212> TYPE: DNA
<213> ORGANISM: Artificial Sequence
<220> FEATURE:
<223> OTHER INFORMATION: Synthetic Construct

<400> SEQUENCE: 676
atagcgtgat taaa                                                     14

<210> SEQ ID NO 677
<211> LENGTH: 14
<212> TYPE: DNA
<213> ORGANISM: Artificial Sequence
<220> FEATURE:
<223> OTHER INFORMATION: Synthetic Construct

<400> SEQUENCE: 677
actacctccg ctaa                                                     14

<210> SEQ ID NO 678
<211> LENGTH: 14
<212> TYPE: DNA
<213> ORGANISM: Artificial Sequence
<220> FEATURE:
<223> OTHER INFORMATION: Synthetic Construct

<400> SEQUENCE: 678
tagcgtgatt aaaa                                                     14

<210> SEQ ID NO 679
<211> LENGTH: 14

-continued

<212> TYPE: DNA
<213> ORGANISM: Artificial Sequence
<220> FEATURE:
<223> OTHER INFORMATION: Synthetic Construct

<400> SEQUENCE: 679
actacctccg ctaa                                                    14

<210> SEQ ID NO 680
<211> LENGTH: 14
<212> TYPE: DNA
<213> ORGANISM: Artificial Sequence
<220> FEATURE:
<223> OTHER INFORMATION: Synthetic Construct

<400> SEQUENCE: 680
agcgtgatta aaag                                                    14

<210> SEQ ID NO 681
<211> LENGTH: 14
<212> TYPE: DNA
<213> ORGANISM: Artificial Sequence
<220> FEATURE:
<223> OTHER INFORMATION: Synthetic Construct

<400> SEQUENCE: 681
actacctccg ctaa                                                    14

<210> SEQ ID NO 682
<211> LENGTH: 14
<212> TYPE: DNA
<213> ORGANISM: Artificial Sequence
<220> FEATURE:
<223> OTHER INFORMATION: Synthetic Construct

<400> SEQUENCE: 682
gcgtgattaa aagg                                                    14

<210> SEQ ID NO 683
<211> LENGTH: 14
<212> TYPE: DNA
<213> ORGANISM: Artificial Sequence
<220> FEATURE:
<223> OTHER INFORMATION: Synthetic Construct

<400> SEQUENCE: 683
actacctccg ctaa                                                    14

<210> SEQ ID NO 684
<211> LENGTH: 14
<212> TYPE: DNA
<213> ORGANISM: Artificial Sequence
<220> FEATURE:
<223> OTHER INFORMATION: Synthetic Construct

<400> SEQUENCE: 684
cgtgattaaa aggg                                                    14

<210> SEQ ID NO 685
<211> LENGTH: 14
<212> TYPE: DNA
<213> ORGANISM: Artificial Sequence
<220> FEATURE:
<223> OTHER INFORMATION: Synthetic Construct

<400> SEQUENCE: 685
actacctccg ctaa                                                    14

<210> SEQ ID NO 686
<211> LENGTH: 14
<212> TYPE: DNA
<213> ORGANISM: Artificial Sequence
<220> FEATURE:
<223> OTHER INFORMATION: Synthetic Construct

<400> SEQUENCE: 686
gtgattaaaa gggc                                                    14

<210> SEQ ID NO 687
<211> LENGTH: 14
<212> TYPE: DNA
<213> ORGANISM: Artificial Sequence
<220> FEATURE:
<223> OTHER INFORMATION: Synthetic Construct

<400> SEQUENCE: 687
actacctccg ctaa                                                    14

<210> SEQ ID NO 688
<211> LENGTH: 14
<212> TYPE: DNA
<213> ORGANISM: Artificial Sequence
<220> FEATURE:
<223> OTHER INFORMATION: Synthetic Construct

<400> SEQUENCE: 688
tgattaaaag ggcg                                                    14

<210> SEQ ID NO 689
<211> LENGTH: 14
<212> TYPE: DNA
<213> ORGANISM: Artificial Sequence
<220> FEATURE:
<223> OTHER INFORMATION: Synthetic Construct

<400> SEQUENCE: 689
actacctccg ctaa                                                    14

<210> SEQ ID NO 690
<211> LENGTH: 14
<212> TYPE: DNA
<213> ORGANISM: Artificial Sequence
<220> FEATURE:
<223> OTHER INFORMATION: Synthetic Construct

<400> SEQUENCE: 690
gattaaaagg gcgt                                                    14

<210> SEQ ID NO 691
<211> LENGTH: 14
<212> TYPE: DNA
<213> ORGANISM: Artificial Sequence
<220> FEATURE:
<223> OTHER INFORMATION: Synthetic Construct

<400> SEQUENCE: 691
actacctccg ctaa                                                    14

<210> SEQ ID NO 692
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 692
attaaaaggg cgtt                                                    14

<210> SEQ ID NO 693
<211> LENGTH: 14
<212> TYPE: DNA
<213> ORGANISM: Artificial Sequence
<220> FEATURE:
<223> OTHER INFORMATION: Synthetic Construct

<400> SEQUENCE: 693
actacctccg ctaa                                                    14

<210> SEQ ID NO 694
<211> LENGTH: 14
<212> TYPE: DNA
<213> ORGANISM: Artificial Sequence
<220> FEATURE:
<223> OTHER INFORMATION: Synthetic Construct

<400> SEQUENCE: 694 ttaaagggc gttt                                                     14

<210> SEQ ID NO 695
<211> LENGTH: 14
<212> TYPE: DNA
<213> ORGANISM: Artificial Sequence
<220> FEATURE:
<223> OTHER INFORMATION: Synthetic Construct

<400> SEQUENCE: 695
actacctccg ctaa                                                    14

<210> SEQ ID NO 696
<211> LENGTH: 14
<212> TYPE: DNA
<213> ORGANISM: Artificial Sequence
<220> FEATURE:
<223> OTHER INFORMATION: Synthetic Construct

<400> SEQUENCE: 696 taaagggcg ttta                                                     14

<210> SEQ ID NO 697
<211> LENGTH: 14
<212> TYPE: DNA
<213> ORGANISM: Artificial Sequence
<220> FEATURE:
<223> OTHER INFORMATION: Synthetic Construct

<400> SEQUENCE: 697
actacctccg ctaa                                                    14

<210> SEQ ID NO 698
<211> LENGTH: 14
<212> TYPE: DNA
<213> ORGANISM: Artificial Sequence
<220> FEATURE:
<223> OTHER INFORMATION: Synthetic Construct

<400> SEQUENCE: 698 aaagggcgt ttat                                                     14
```

```
<210> SEQ ID NO 699
<211> LENGTH: 14
<212> TYPE: DNA
<213> ORGANISM: Artificial Sequence
<220> FEATURE:
<223> OTHER INFORMATION: Synthetic Construct

<400> SEQUENCE: 699
actacctccg ctaa                                                        14

<210> SEQ ID NO 700
<211> LENGTH: 14
<212> TYPE: DNA
<213> ORGANISM: Artificial Sequence
<220> FEATURE:
<223> OTHER INFORMATION: Synthetic Construct

<400> SEQUENCE: 700
aaagggcgtt tata                                                        14

<210> SEQ ID NO 701
<211> LENGTH: 14
<212> TYPE: DNA
<213> ORGANISM: Artificial Sequence
<220> FEATURE:
<223> OTHER INFORMATION: Synthetic Construct

<400> SEQUENCE: 701
actacctccg ctaa                                                        14

<210> SEQ ID NO 702
<211> LENGTH: 14
<212> TYPE: DNA
<213> ORGANISM: Artificial Sequence
<220> FEATURE:
<223> OTHER INFORMATION: Synthetic Construct

<400> SEQUENCE: 702
aagggcgttt atat                                                        14

<210> SEQ ID NO 703
<211> LENGTH: 14
<212> TYPE: DNA
<213> ORGANISM: Artificial Sequence
<220> FEATURE:
<223> OTHER INFORMATION: Synthetic Construct

<400> SEQUENCE: 703
actacctccg ctaa                                                        14

<210> SEQ ID NO 704
<211> LENGTH: 14
<212> TYPE: DNA
<213> ORGANISM: Artificial Sequence
<220> FEATURE:
<223> OTHER INFORMATION: Synthetic Construct

<400> SEQUENCE: 704
agggcgttta tatt                                                        14

<210> SEQ ID NO 705
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 705
actacctccg ctaa                                              14

<210> SEQ ID NO 706
<211> LENGTH: 14
<212> TYPE: DNA
<213> ORGANISM: Artificial Sequence
<220> FEATURE:
<223> OTHER INFORMATION: Synthetic Construct

<400> SEQUENCE: 706
gggcgtttat attg                                              14

<210> SEQ ID NO 707
<211> LENGTH: 14
<212> TYPE: DNA
<213> ORGANISM: Artificial Sequence
<220> FEATURE:
<223> OTHER INFORMATION: Synthetic Construct

<400> SEQUENCE: 707
actacctccg ctaa                                              14

<210> SEQ ID NO 708
<211> LENGTH: 14
<212> TYPE: DNA
<213> ORGANISM: Artificial Sequence
<220> FEATURE:
<223> OTHER INFORMATION: Synthetic Construct

<400> SEQUENCE: 708
ggcgtttata ttgg                                              14

<210> SEQ ID NO 709
<211> LENGTH: 14
<212> TYPE: DNA
<213> ORGANISM: Artificial Sequence
<220> FEATURE:
<223> OTHER INFORMATION: Synthetic Construct

<400> SEQUENCE: 709
actacctccg ctaa                                              14

<210> SEQ ID NO 710
<211> LENGTH: 14
<212> TYPE: DNA
<213> ORGANISM: Artificial Sequence
<220> FEATURE:
<223> OTHER INFORMATION: Synthetic Construct

<400> SEQUENCE: 710
gcgtttatat tggt                                              14

<210> SEQ ID NO 711
<211> LENGTH: 14
<212> TYPE: DNA
<213> ORGANISM: Artificial Sequence
<220> FEATURE:
<223> OTHER INFORMATION: Synthetic Construct

<400> SEQUENCE: 711
actacctccg ctaa                                              14

<210> SEQ ID NO 712
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 712
cgtttatatt ggtt                                                        14

<210> SEQ ID NO 713
<211> LENGTH: 14
<212> TYPE: DNA
<213> ORGANISM: Artificial Sequence
<220> FEATURE:
<223> OTHER INFORMATION: Synthetic Construct

<400> SEQUENCE: 713
actacctccg ctaa                                                        14

<210> SEQ ID NO 714
<211> LENGTH: 14
<212> TYPE: DNA
<213> ORGANISM: Artificial Sequence
<220> FEATURE:
<223> OTHER INFORMATION: Synthetic Construct

<400> SEQUENCE: 714
gtttatattg gttc                                                        14

<210> SEQ ID NO 715
<211> LENGTH: 14
<212> TYPE: DNA
<213> ORGANISM: Artificial Sequence
<220> FEATURE:
<223> OTHER INFORMATION: Synthetic Construct

<400> SEQUENCE: 715
actacctccg ctaa                                                        14

<210> SEQ ID NO 716
<211> LENGTH: 14
<212> TYPE: DNA
<213> ORGANISM: Artificial Sequence
<220> FEATURE:
<223> OTHER INFORMATION: Synthetic Construct

<400> SEQUENCE: 716
tttatattgg ttcg                                                        14

<210> SEQ ID NO 717
<211> LENGTH: 14
<212> TYPE: DNA
<213> ORGANISM: Artificial Sequence
<220> FEATURE:
<223> OTHER INFORMATION: Synthetic Construct

<400> SEQUENCE: 717
actacctccg ctaa                                                        14

<210> SEQ ID NO 718
<211> LENGTH: 14
<212> TYPE: DNA
<213> ORGANISM: Artificial Sequence
<220> FEATURE:
<223> OTHER INFORMATION: Synthetic Construct

<400> SEQUENCE: 718
```
ttatattggt tcgg 14

<210> SEQ ID NO 719
<211> LENGTH: 14
<212> TYPE: DNA
<213> ORGANISM: Artificial Sequence
<220> FEATURE:
<223> OTHER INFORMATION: Synthetic Construct

<400> SEQUENCE: 719
actacctccg ctaa 14

<210> SEQ ID NO 720
<211> LENGTH: 14
<212> TYPE: DNA
<213> ORGANISM: Artificial Sequence
<220> FEATURE:
<223> OTHER INFORMATION: Synthetic Construct

<400> SEQUENCE: 720
tatattggtt cggg 14

<210> SEQ ID NO 721
<211> LENGTH: 14
<212> TYPE: DNA
<213> ORGANISM: Artificial Sequence
<220> FEATURE:
<223> OTHER INFORMATION: Synthetic Construct

<400> SEQUENCE: 721
actacctccg ctaa 14

<210> SEQ ID NO 722
<211> LENGTH: 14
<212> TYPE: DNA
<213> ORGANISM: Artificial Sequence
<220> FEATURE:
<223> OTHER INFORMATION: Synthetic Construct

<400> SEQUENCE: 722
atattggttc gggt 14

<210> SEQ ID NO 723
<211> LENGTH: 14
<212> TYPE: DNA
<213> ORGANISM: Artificial Sequence
<220> FEATURE:
<223> OTHER INFORMATION: Synthetic Construct

<400> SEQUENCE: 723
actacctccg ctaa 14

<210> SEQ ID NO 724
<211> LENGTH: 14
<212> TYPE: DNA
<213> ORGANISM: Artificial Sequence
<220> FEATURE:
<223> OTHER INFORMATION: Synthetic Construct

<400> SEQUENCE: 724
tattggttcg ggtt 14

<210> SEQ ID NO 725
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 725
actacctccg ctaa                                                        14

<210> SEQ ID NO 726
<211> LENGTH: 14
<212> TYPE: DNA
<213> ORGANISM: Artificial Sequence
<220> FEATURE:
<223> OTHER INFORMATION: Synthetic Construct

<400> SEQUENCE: 726
attggttcgg gtta                                                        14

<210> SEQ ID NO 727
<211> LENGTH: 14
<212> TYPE: DNA
<213> ORGANISM: Artificial Sequence
<220> FEATURE:
<223> OTHER INFORMATION: Synthetic Construct

<400> SEQUENCE: 727
actacctccg ctaa                                                        14

<210> SEQ ID NO 728
<211> LENGTH: 14
<212> TYPE: DNA
<213> ORGANISM: Artificial Sequence
<220> FEATURE:
<223> OTHER INFORMATION: Synthetic Construct

<400> SEQUENCE: 728
ttggttcggg ttat                                                        14

<210> SEQ ID NO 729
<211> LENGTH: 14
<212> TYPE: DNA
<213> ORGANISM: Artificial Sequence
<220> FEATURE:
<223> OTHER INFORMATION: Synthetic Construct

<400> SEQUENCE: 729
actacctccg ctaa                                                        14

<210> SEQ ID NO 730
<211> LENGTH: 14
<212> TYPE: DNA
<213> ORGANISM: Artificial Sequence
<220> FEATURE:
<223> OTHER INFORMATION: Synthetic Construct

<400> SEQUENCE: 730
tggttcgggt tatt                                                        14

<210> SEQ ID NO 731
<211> LENGTH: 14
<212> TYPE: DNA
<213> ORGANISM: Artificial Sequence
<220> FEATURE:
<223> OTHER INFORMATION: Synthetic Construct

<400> SEQUENCE: 731
actacctccg ctaa                                                        14
```

<210> SEQ ID NO 732
<211> LENGTH: 14
<212> TYPE: DNA
<213> ORGANISM: Artificial Sequence
<220> FEATURE:
<223> OTHER INFORMATION: Synthetic Construct

<400> SEQUENCE: 732
ggttcgggtt attg                                                    14

<210> SEQ ID NO 733
<211> LENGTH: 14
<212> TYPE: DNA
<213> ORGANISM: Artificial Sequence
<220> FEATURE:
<223> OTHER INFORMATION: Synthetic Construct

<400> SEQUENCE: 733
actacctccg ctaa                                                    14

<210> SEQ ID NO 734
<211> LENGTH: 14
<212> TYPE: DNA
<213> ORGANISM: Artificial Sequence
<220> FEATURE:
<223> OTHER INFORMATION: Synthetic Construct

<400> SEQUENCE: 734
gttcgggtta ttgg                                                    14

<210> SEQ ID NO 735
<211> LENGTH: 14
<212> TYPE: DNA
<213> ORGANISM: Artificial Sequence
<220> FEATURE:
<223> OTHER INFORMATION: Synthetic Construct

<400> SEQUENCE: 735
actacctccg ctaa                                                    14

<210> SEQ ID NO 736
<211> LENGTH: 14
<212> TYPE: DNA
<213> ORGANISM: Artificial Sequence
<220> FEATURE:
<223> OTHER INFORMATION: Synthetic Construct

<400> SEQUENCE: 736
ttcgggttat tgga                                                    14

<210> SEQ ID NO 737
<211> LENGTH: 14
<212> TYPE: DNA
<213> ORGANISM: Artificial Sequence
<220> FEATURE:
<223> OTHER INFORMATION: Synthetic Construct

<400> SEQUENCE: 737
actacctccg ctaa                                                    14

<210> SEQ ID NO 738
<211> LENGTH: 14
<212> TYPE: DNA
<213> ORGANISM: Artificial Sequence
<220> FEATURE:

<223> OTHER INFORMATION: Synthetic Construct

<400> SEQUENCE: 738
tcgggttatt ggac                                                        14

<210> SEQ ID NO 739
<211> LENGTH: 14
<212> TYPE: DNA
<213> ORGANISM: Artificial Sequence
<220> FEATURE:
<223> OTHER INFORMATION: Synthetic Construct

<400> SEQUENCE: 739
actacctccg ctaa                                                        14

<210> SEQ ID NO 740
<211> LENGTH: 14
<212> TYPE: DNA
<213> ORGANISM: Artificial Sequence
<220> FEATURE:
<223> OTHER INFORMATION: Synthetic Construct

<400> SEQUENCE: 740
cgggttattg gacg                                                        14

<210> SEQ ID NO 741
<211> LENGTH: 14
<212> TYPE: DNA
<213> ORGANISM: Artificial Sequence
<220> FEATURE:
<223> OTHER INFORMATION: Synthetic Construct

<400> SEQUENCE: 741
actacctccg ctaa                                                        14

<210> SEQ ID NO 742
<211> LENGTH: 14
<212> TYPE: DNA
<213> ORGANISM: Artificial Sequence
<220> FEATURE:
<223> OTHER INFORMATION: Synthetic Construct

<400> SEQUENCE: 742
gggttattgg acgg                                                        14

<210> SEQ ID NO 743
<211> LENGTH: 14
<212> TYPE: DNA
<213> ORGANISM: Artificial Sequence
<220> FEATURE:
<223> OTHER INFORMATION: Synthetic Construct

<400> SEQUENCE: 743
actacctccg ctaa                                                        14

<210> SEQ ID NO 744
<211> LENGTH: 14
<212> TYPE: DNA
<213> ORGANISM: Artificial Sequence
<220> FEATURE:
<223> OTHER INFORMATION: Synthetic Construct

<400> SEQUENCE: 744
ggttattgga cggt                                                        14

```
<210> SEQ ID NO 745
<211> LENGTH: 14
<212> TYPE: DNA
<213> ORGANISM: Artificial Sequence
<220> FEATURE:
<223> OTHER INFORMATION: Synthetic Construct

<400> SEQUENCE: 745
actacctccg ctaa                                                        14

<210> SEQ ID NO 746
<211> LENGTH: 14
<212> TYPE: DNA
<213> ORGANISM: Artificial Sequence
<220> FEATURE:
<223> OTHER INFORMATION: Synthetic Construct

<400> SEQUENCE: 746
gttattggac ggtg                                                        14

<210> SEQ ID NO 747
<211> LENGTH: 14
<212> TYPE: DNA
<213> ORGANISM: Artificial Sequence
<220> FEATURE:
<223> OTHER INFORMATION: Synthetic Construct

<400> SEQUENCE: 747
actacctccg ctaa                                                        14

<210> SEQ ID NO 748
<211> LENGTH: 14
<212> TYPE: DNA
<213> ORGANISM: Artificial Sequence
<220> FEATURE:
<223> OTHER INFORMATION: Synthetic Construct

<400> SEQUENCE: 748
ttattggacg gtgg                                                        14

<210> SEQ ID NO 749
<211> LENGTH: 14
<212> TYPE: DNA
<213> ORGANISM: Artificial Sequence
<220> FEATURE:
<223> OTHER INFORMATION: Synthetic Construct

<400> SEQUENCE: 749
actacctccg ctaa                                                        14

<210> SEQ ID NO 750
<211> LENGTH: 14
<212> TYPE: DNA
<213> ORGANISM: Artificial Sequence
<220> FEATURE:
<223> OTHER INFORMATION: Synthetic Construct

<400> SEQUENCE: 750
tattggacgg tgga                                                        14

<210> SEQ ID NO 751
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 751
actacctccg ctaa                                                    14

<210> SEQ ID NO 752
<211> LENGTH: 14
<212> TYPE: DNA
<213> ORGANISM: Artificial Sequence
<220> FEATURE:
<223> OTHER INFORMATION: Synthetic Construct

<400> SEQUENCE: 752
attggacggt ggag                                                    14

<210> SEQ ID NO 753
<211> LENGTH: 14
<212> TYPE: DNA
<213> ORGANISM: Artificial Sequence
<220> FEATURE:
<223> OTHER INFORMATION: Synthetic Construct

<400> SEQUENCE: 753
actacctccg ctaa                                                    14

<210> SEQ ID NO 754
<211> LENGTH: 14
<212> TYPE: DNA
<213> ORGANISM: Artificial Sequence
<220> FEATURE:
<223> OTHER INFORMATION: Synthetic Construct

<400> SEQUENCE: 754
ttggacggtg gagt                                                    14

<210> SEQ ID NO 755
<211> LENGTH: 14
<212> TYPE: DNA
<213> ORGANISM: Artificial Sequence
<220> FEATURE:
<223> OTHER INFORMATION: Synthetic Construct

<400> SEQUENCE: 755
actacctccg ctaa                                                    14

<210> SEQ ID NO 756
<211> LENGTH: 14
<212> TYPE: DNA
<213> ORGANISM: Artificial Sequence
<220> FEATURE:
<223> OTHER INFORMATION: Synthetic Construct

<400> SEQUENCE: 756
tggacggtgg agtt                                                    14

<210> SEQ ID NO 757
<211> LENGTH: 14
<212> TYPE: DNA
<213> ORGANISM: Artificial Sequence
<220> FEATURE:
<223> OTHER INFORMATION: Synthetic Construct

<400> SEQUENCE: 757
actacctccg ctaa                                                    14

<210> SEQ ID NO 758
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 758
ggacggtgga gttc                                                        14

<210> SEQ ID NO 759
<211> LENGTH: 14
<212> TYPE: DNA
<213> ORGANISM: Artificial Sequence
<220> FEATURE:
<223> OTHER INFORMATION: Synthetic Construct

<400> SEQUENCE: 759
actacctccg ctaa                                                        14

<210> SEQ ID NO 760
<211> LENGTH: 14
<212> TYPE: DNA
<213> ORGANISM: Artificial Sequence
<220> FEATURE:
<223> OTHER INFORMATION: Synthetic Construct

<400> SEQUENCE: 760
gacggtggag ttcg                                                        14

<210> SEQ ID NO 761
<211> LENGTH: 14
<212> TYPE: DNA
<213> ORGANISM: Artificial Sequence
<220> FEATURE:
<223> OTHER INFORMATION: Synthetic Construct

<400> SEQUENCE: 761
cccctccgcc acac                                                        14

<210> SEQ ID NO 762
<211> LENGTH: 25
<212> TYPE: DNA
<213> ORGANISM: Artificial Sequence
<220> FEATURE:
<223> OTHER INFORMATION: Synthetic Construct

<400> SEQUENCE: 762
ggaatagttt taggaatgtg attgc                                            25

<210> SEQ ID NO 763
<211> LENGTH: 14
<212> TYPE: DNA
<213> ORGANISM: Artificial Sequence
<220> FEATURE:
<223> OTHER INFORMATION: Synthetic Construct

<400> SEQUENCE: 763
acggtggagt tcgg                                                        14

<210> SEQ ID NO 764
<211> LENGTH: 14
<212> TYPE: DNA
<213> ORGANISM: Artificial Sequence
<220> FEATURE:
<223> OTHER INFORMATION: Synthetic Construct

<400> SEQUENCE: 764
```
cccctccgcc acac                                                14

<210> SEQ ID NO 765
<211> LENGTH: 14
<212> TYPE: DNA
<213> ORGANISM: Artificial Sequence
<220> FEATURE:
<223> OTHER INFORMATION: Synthetic Construct

<400> SEQUENCE: 765
cggtggagtt cggc                                                14

<210> SEQ ID NO 766
<211> LENGTH: 14
<212> TYPE: DNA
<213> ORGANISM: Artificial Sequence
<220> FEATURE:
<223> OTHER INFORMATION: Synthetic Construct

<400> SEQUENCE: 766
cccctccgcc acac                                                14

<210> SEQ ID NO 767
<211> LENGTH: 14
<212> TYPE: DNA
<213> ORGANISM: Artificial Sequence
<220> FEATURE:
<223> OTHER INFORMATION: Synthetic Construct

<400> SEQUENCE: 767
ggtggagttc ggcg                                                14

<210> SEQ ID NO 768
<211> LENGTH: 14
<212> TYPE: DNA
<213> ORGANISM: Artificial Sequence
<220> FEATURE:
<223> OTHER INFORMATION: Synthetic Construct

<400> SEQUENCE: 768
cccctccgcc acac                                                14

<210> SEQ ID NO 769
<211> LENGTH: 14
<212> TYPE: DNA
<213> ORGANISM: Artificial Sequence
<220> FEATURE:
<223> OTHER INFORMATION: Synthetic Construct

<400> SEQUENCE: 769
gtggagttcg gcgt                                                14

<210> SEQ ID NO 770
<211> LENGTH: 14
<212> TYPE: DNA
<213> ORGANISM: Artificial Sequence
<220> FEATURE:
<223> OTHER INFORMATION: Synthetic Construct

<400> SEQUENCE: 770
cccctccgcc acac                                                14

<210> SEQ ID NO 771
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 771
tggagttcgg cgta                                                        14

<210> SEQ ID NO 772
<211> LENGTH: 14
<212> TYPE: DNA
<213> ORGANISM: Artificial Sequence
<220> FEATURE:
<223> OTHER INFORMATION: Synthetic Construct

<400> SEQUENCE: 772
cccctccgcc acac                                                        14

<210> SEQ ID NO 773
<211> LENGTH: 14
<212> TYPE: DNA
<213> ORGANISM: Artificial Sequence
<220> FEATURE:
<223> OTHER INFORMATION: Synthetic Construct

<400> SEQUENCE: 773
ggagttcggc gtag                                                        14

<210> SEQ ID NO 774
<211> LENGTH: 14
<212> TYPE: DNA
<213> ORGANISM: Artificial Sequence
<220> FEATURE:
<223> OTHER INFORMATION: Synthetic Construct

<400> SEQUENCE: 774
cccctccgcc acac                                                        14

<210> SEQ ID NO 775
<211> LENGTH: 14
<212> TYPE: DNA
<213> ORGANISM: Artificial Sequence
<220> FEATURE:
<223> OTHER INFORMATION: Synthetic Construct

<400> SEQUENCE: 775
gagttcggcg tagt                                                        14

<210> SEQ ID NO 776
<211> LENGTH: 14
<212> TYPE: DNA
<213> ORGANISM: Artificial Sequence
<220> FEATURE:
<223> OTHER INFORMATION: Synthetic Construct

<400> SEQUENCE: 776
cccctccgcc acac                                                        14

<210> SEQ ID NO 777
<211> LENGTH: 14
<212> TYPE: DNA
<213> ORGANISM: Artificial Sequence
<220> FEATURE:
<223> OTHER INFORMATION: Synthetic Construct

<400> SEQUENCE: 777
agttcggcgt agtt                                                        14
```

```
<210> SEQ ID NO 778
<211> LENGTH: 14
<212> TYPE: DNA
<213> ORGANISM: Artificial Sequence
<220> FEATURE:
<223> OTHER INFORMATION: Synthetic Construct

<400> SEQUENCE: 778
cccctccgcc acac                                                        14

<210> SEQ ID NO 779
<211> LENGTH: 14
<212> TYPE: DNA
<213> ORGANISM: Artificial Sequence
<220> FEATURE:
<223> OTHER INFORMATION: Synthetic Construct

<400> SEQUENCE: 779
gttcggcgta gttt                                                        14

<210> SEQ ID NO 780
<211> LENGTH: 14
<212> TYPE: DNA
<213> ORGANISM: Artificial Sequence
<220> FEATURE:
<223> OTHER INFORMATION: Synthetic Construct

<400> SEQUENCE: 780
cccctccgcc acac                                                        14

<210> SEQ ID NO 781
<211> LENGTH: 14
<212> TYPE: DNA
<213> ORGANISM: Artificial Sequence
<220> FEATURE:
<223> OTHER INFORMATION: Synthetic Construct

<400> SEQUENCE: 781
ttcggcgtag ttta                                                        14

<210> SEQ ID NO 782
<211> LENGTH: 14
<212> TYPE: DNA
<213> ORGANISM: Artificial Sequence
<220> FEATURE:
<223> OTHER INFORMATION: Synthetic Construct

<400> SEQUENCE: 782
cccctccgcc acac                                                        14

<210> SEQ ID NO 783
<211> LENGTH: 14
<212> TYPE: DNA
<213> ORGANISM: Artificial Sequence
<220> FEATURE:
<223> OTHER INFORMATION: Synthetic Construct

<400> SEQUENCE: 783
tcggcgtagt ttag                                                        14

<210> SEQ ID NO 784
<211> LENGTH: 14
<212> TYPE: DNA
<213> ORGANISM: Artificial Sequence
<220> FEATURE:
<223> OTHER INFORMATION: Synthetic Construct
```

-continued

```
<400> SEQUENCE: 784
cccctccgcc acac                                                    14

<210> SEQ ID NO 785
<211> LENGTH: 14
<212> TYPE: DNA
<213> ORGANISM: Artificial Sequence
<220> FEATURE:
<223> OTHER INFORMATION: Synthetic Construct

<400> SEQUENCE: 785
cggcgtagtt tagt                                                    14

<210> SEQ ID NO 786
<211> LENGTH: 14
<212> TYPE: DNA
<213> ORGANISM: Artificial Sequence
<220> FEATURE:
<223> OTHER INFORMATION: Synthetic Construct

<400> SEQUENCE: 786
cccctccgcc acac                                                    14

<210> SEQ ID NO 787
<211> LENGTH: 14
<212> TYPE: DNA
<213> ORGANISM: Artificial Sequence
<220> FEATURE:
<223> OTHER INFORMATION: Synthetic Construct

<400> SEQUENCE: 787
ggcgtagttt agtt                                                    14

<210> SEQ ID NO 788
<211> LENGTH: 14
<212> TYPE: DNA
<213> ORGANISM: Artificial Sequence
<220> FEATURE:
<223> OTHER INFORMATION: Synthetic Construct

<400> SEQUENCE: 788
cccctccgcc acac                                                    14

<210> SEQ ID NO 789
<211> LENGTH: 14
<212> TYPE: DNA
<213> ORGANISM: Artificial Sequence
<220> FEATURE:
<223> OTHER INFORMATION: Synthetic Construct

<400> SEQUENCE: 789
gcgtagttta gttt                                                    14

<210> SEQ ID NO 790
<211> LENGTH: 14
<212> TYPE: DNA
<213> ORGANISM: Artificial Sequence
<220> FEATURE:
<223> OTHER INFORMATION: Synthetic Construct

<400> SEQUENCE: 790
cccctccgcc acac                                                    14

<210> SEQ ID NO 791
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 791
cgtagtttag tttc                                                       14

<210> SEQ ID NO 792
<211> LENGTH: 14
<212> TYPE: DNA
<213> ORGANISM: Artificial Sequence
<220> FEATURE:
<223> OTHER INFORMATION: Synthetic Construct

<400> SEQUENCE: 792
cccctccgcc acac                                                       14

<210> SEQ ID NO 793
<211> LENGTH: 14
<212> TYPE: DNA
<213> ORGANISM: Artificial Sequence
<220> FEATURE:
<223> OTHER INFORMATION: Synthetic Construct

<400> SEQUENCE: 793
gtagtttagt ttcg                                                       14

<210> SEQ ID NO 794
<211> LENGTH: 14
<212> TYPE: DNA
<213> ORGANISM: Artificial Sequence
<220> FEATURE:
<223> OTHER INFORMATION: Synthetic Construct

<400> SEQUENCE: 794
cccctccgcc acac                                                       14

<210> SEQ ID NO 795
<211> LENGTH: 14
<212> TYPE: DNA
<213> ORGANISM: Artificial Sequence
<220> FEATURE:
<223> OTHER INFORMATION: Synthetic Construct

<400> SEQUENCE: 795
tagtttagtt tcgt                                                       14

<210> SEQ ID NO 796
<211> LENGTH: 14
<212> TYPE: DNA
<213> ORGANISM: Artificial Sequence
<220> FEATURE:
<223> OTHER INFORMATION: Synthetic Construct

<400> SEQUENCE: 796
cccctccgcc acac                                                       14

<210> SEQ ID NO 797
<211> LENGTH: 14
<212> TYPE: DNA
<213> ORGANISM: Artificial Sequence
<220> FEATURE:
<223> OTHER INFORMATION: Synthetic Construct

<400> SEQUENCE: 797
```
agtttagttt cgtt                                                            14

<210> SEQ ID NO 798
<211> LENGTH: 14
<212> TYPE: DNA
<213> ORGANISM: Artificial Sequence
<220> FEATURE:
<223> OTHER INFORMATION: Synthetic Construct

<400> SEQUENCE: 798
cccctccgcc acac                                                            14

<210> SEQ ID NO 799
<211> LENGTH: 14
<212> TYPE: DNA
<213> ORGANISM: Artificial Sequence
<220> FEATURE:
<223> OTHER INFORMATION: Synthetic Construct

<400> SEQUENCE: 799
gtttagtttc gttt                                                            14

<210> SEQ ID NO 800
<211> LENGTH: 14
<212> TYPE: DNA
<213> ORGANISM: Artificial Sequence
<220> FEATURE:
<223> OTHER INFORMATION: Synthetic Construct

<400> SEQUENCE: 800
cccctccgcc acac                                                            14

<210> SEQ ID NO 801
<211> LENGTH: 14
<212> TYPE: DNA
<213> ORGANISM: Artificial Sequence
<220> FEATURE:
<223> OTHER INFORMATION: Synthetic Construct

<400> SEQUENCE: 801
tttagtttcg ttta                                                            14

<210> SEQ ID NO 802
<211> LENGTH: 14
<212> TYPE: DNA
<213> ORGANISM: Artificial Sequence
<220> FEATURE:
<223> OTHER INFORMATION: Synthetic Construct

<400> SEQUENCE: 802
cccctccgcc acac                                                            14

<210> SEQ ID NO 803
<211> LENGTH: 14
<212> TYPE: DNA
<213> ORGANISM: Artificial Sequence
<220> FEATURE:
<223> OTHER INFORMATION: Synthetic Construct

<400> SEQUENCE: 803
ttagtttcgt ttaa                                                            14

<210> SEQ ID NO 804
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 804
cccctccgcc acac                                                       14

<210> SEQ ID NO 805
<211> LENGTH: 14
<212> TYPE: DNA
<213> ORGANISM: Artificial Sequence
<220> FEATURE:
<223> OTHER INFORMATION: Synthetic Construct

<400> SEQUENCE: 805
tagtttcgtt taag                                                       14

<210> SEQ ID NO 806
<211> LENGTH: 14
<212> TYPE: DNA
<213> ORGANISM: Artificial Sequence
<220> FEATURE:
<223> OTHER INFORMATION: Synthetic Construct

<400> SEQUENCE: 806
cccctccgcc acac                                                       14

<210> SEQ ID NO 807
<211> LENGTH: 14
<212> TYPE: DNA
<213> ORGANISM: Artificial Sequence
<220> FEATURE:
<223> OTHER INFORMATION: Synthetic Construct

<400> SEQUENCE: 807
agtttcgttt aagt                                                       14

<210> SEQ ID NO 808
<211> LENGTH: 14
<212> TYPE: DNA
<213> ORGANISM: Artificial Sequence
<220> FEATURE:
<223> OTHER INFORMATION: Synthetic Construct

<400> SEQUENCE: 808
cccctccgcc acac                                                       14

<210> SEQ ID NO 809
<211> LENGTH: 14
<212> TYPE: DNA
<213> ORGANISM: Artificial Sequence
<220> FEATURE:
<223> OTHER INFORMATION: Synthetic Construct

<400> SEQUENCE: 809
gtttcgttta agtt                                                       14

<210> SEQ ID NO 810
<211> LENGTH: 14
<212> TYPE: DNA
<213> ORGANISM: Artificial Sequence
<220> FEATURE:
<223> OTHER INFORMATION: Synthetic Construct

<400> SEQUENCE: 810
cccctccgcc acac                                                       14
```

<210> SEQ ID NO 811
<211> LENGTH: 14
<212> TYPE: DNA
<213> ORGANISM: Artificial Sequence
<220> FEATURE:
<223> OTHER INFORMATION: Synthetic Construct

<400> SEQUENCE: 811
tttcgtttaa gttt                                                         14

<210> SEQ ID NO 812
<211> LENGTH: 14
<212> TYPE: DNA
<213> ORGANISM: Artificial Sequence
<220> FEATURE:
<223> OTHER INFORMATION: Synthetic Construct

<400> SEQUENCE: 812
cccctccgcc acac                                                         14

<210> SEQ ID NO 813
<211> LENGTH: 14
<212> TYPE: DNA
<213> ORGANISM: Artificial Sequence
<220> FEATURE:
<223> OTHER INFORMATION: Synthetic Construct

<400> SEQUENCE: 813
ttcgtttaag tttt                                                         14

<210> SEQ ID NO 814
<211> LENGTH: 14
<212> TYPE: DNA
<213> ORGANISM: Artificial Sequence
<220> FEATURE:
<223> OTHER INFORMATION: Synthetic Construct

<400> SEQUENCE: 814
cccctccgcc acac                                                         14

<210> SEQ ID NO 815
<211> LENGTH: 14
<212> TYPE: DNA
<213> ORGANISM: Artificial Sequence
<220> FEATURE:
<223> OTHER INFORMATION: Synthetic Construct

<400> SEQUENCE: 815
tcgtttaagt tttt                                                         14

<210> SEQ ID NO 816
<211> LENGTH: 14
<212> TYPE: DNA
<213> ORGANISM: Artificial Sequence
<220> FEATURE:
<223> OTHER INFORMATION: Synthetic Construct

<400> SEQUENCE: 816
cccctccgcc acac                                                         14

<210> SEQ ID NO 817
<211> LENGTH: 14
<212> TYPE: DNA
<213> ORGANISM: Artificial Sequence
<220> FEATURE:

<223> OTHER INFORMATION: Synthetic Construct

<400> SEQUENCE: 817
cgtttaagtt ttta                                                         14

<210> SEQ ID NO 818
<211> LENGTH: 14
<212> TYPE: DNA
<213> ORGANISM: Artificial Sequence
<220> FEATURE:
<223> OTHER INFORMATION: Synthetic Construct

<400> SEQUENCE: 818
cccctccgcc acac                                                         14

<210> SEQ ID NO 819
<211> LENGTH: 14
<212> TYPE: DNA
<213> ORGANISM: Artificial Sequence
<220> FEATURE:
<223> OTHER INFORMATION: Synthetic Construct

<400> SEQUENCE: 819
gtttaagttt ttag                                                         14

<210> SEQ ID NO 820
<211> LENGTH: 14
<212> TYPE: DNA
<213> ORGANISM: Artificial Sequence
<220> FEATURE:
<223> OTHER INFORMATION: Synthetic Construct

<400> SEQUENCE: 820
cccctccgcc acac                                                         14

<210> SEQ ID NO 821
<211> LENGTH: 14
<212> TYPE: DNA
<213> ORGANISM: Artificial Sequence
<220> FEATURE:
<223> OTHER INFORMATION: Synthetic Construct

<400> SEQUENCE: 821
tttaagtttt tagg                                                         14

<210> SEQ ID NO 822
<211> LENGTH: 14
<212> TYPE: DNA
<213> ORGANISM: Artificial Sequence
<220> FEATURE:
<223> OTHER INFORMATION: Synthetic Construct

<400> SEQUENCE: 822
cccctccgcc acac                                                         14

<210> SEQ ID NO 823
<211> LENGTH: 14
<212> TYPE: DNA
<213> ORGANISM: Artificial Sequence
<220> FEATURE:
<223> OTHER INFORMATION: Synthetic Construct

<400> SEQUENCE: 823
ttaagttttt aggt                                                         14

```
<210> SEQ ID NO 824
<211> LENGTH: 14
<212> TYPE: DNA
<213> ORGANISM: Artificial Sequence
<220> FEATURE:
<223> OTHER INFORMATION: Synthetic Construct

<400> SEQUENCE: 824
cccctccgcc acac                                                    14

<210> SEQ ID NO 825
<211> LENGTH: 14
<212> TYPE: DNA
<213> ORGANISM: Artificial Sequence
<220> FEATURE:
<223> OTHER INFORMATION: Synthetic Construct

<400> SEQUENCE: 825
taagttttta ggta                                                    14

<210> SEQ ID NO 826
<211> LENGTH: 14
<212> TYPE: DNA
<213> ORGANISM: Artificial Sequence
<220> FEATURE:
<223> OTHER INFORMATION: Synthetic Construct

<400> SEQUENCE: 826
cccctccgcc acac                                                    14

<210> SEQ ID NO 827
<211> LENGTH: 14
<212> TYPE: DNA
<213> ORGANISM: Artificial Sequence
<220> FEATURE:
<223> OTHER INFORMATION: Synthetic Construct

<400> SEQUENCE: 827 aagttttag gtag                                                     14

<210> SEQ ID NO 828
<211> LENGTH: 14
<212> TYPE: DNA
<213> ORGANISM: Artificial Sequence
<220> FEATURE:
<223> OTHER INFORMATION: Synthetic Construct

<400> SEQUENCE: 828
cccctccgcc acac                                                    14

<210> SEQ ID NO 829
<211> LENGTH: 14
<212> TYPE: DNA
<213> ORGANISM: Artificial Sequence
<220> FEATURE:
<223> OTHER INFORMATION: Synthetic Construct

<400> SEQUENCE: 829 agttttagg tagg                                                     14

<210> SEQ ID NO 830
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 830
cccctccgcc acac                                                      14

<210> SEQ ID NO 831
<211> LENGTH: 14
<212> TYPE: DNA
<213> ORGANISM: Artificial Sequence
<220> FEATURE:
<223> OTHER INFORMATION: Synthetic Construct

<400> SEQUENCE: 831
gtttttaggt aggg                                                      14

<210> SEQ ID NO 832
<211> LENGTH: 14
<212> TYPE: DNA
<213> ORGANISM: Artificial Sequence
<220> FEATURE:
<223> OTHER INFORMATION: Synthetic Construct

<400> SEQUENCE: 832
cccctccgcc acac                                                      14

<210> SEQ ID NO 833
<211> LENGTH: 14
<212> TYPE: DNA
<213> ORGANISM: Artificial Sequence
<220> FEATURE:
<223> OTHER INFORMATION: Synthetic Construct

<400> SEQUENCE: 833
tttttaggta gggt                                                      14

<210> SEQ ID NO 834
<211> LENGTH: 14
<212> TYPE: DNA
<213> ORGANISM: Artificial Sequence
<220> FEATURE:
<223> OTHER INFORMATION: Synthetic Construct

<400> SEQUENCE: 834
cccctccgcc acac                                                      14

<210> SEQ ID NO 835
<211> LENGTH: 14
<212> TYPE: DNA
<213> ORGANISM: Artificial Sequence
<220> FEATURE:
<223> OTHER INFORMATION: Synthetic Construct

<400> SEQUENCE: 835
ttttaggtag ggtt                                                      14

<210> SEQ ID NO 836
<211> LENGTH: 14
<212> TYPE: DNA
<213> ORGANISM: Artificial Sequence
<220> FEATURE:
<223> OTHER INFORMATION: Synthetic Construct

<400> SEQUENCE: 836
cccctccgcc acac                                                      14

<210> SEQ ID NO 837
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 837
tttaggtagg gttc                                                    14

<210> SEQ ID NO 838
<211> LENGTH: 14
<212> TYPE: DNA
<213> ORGANISM: Artificial Sequence
<220> FEATURE:
<223> OTHER INFORMATION: Synthetic Construct

<400> SEQUENCE: 838
cccctccgcc acac                                                    14

<210> SEQ ID NO 839
<211> LENGTH: 14
<212> TYPE: DNA
<213> ORGANISM: Artificial Sequence
<220> FEATURE:
<223> OTHER INFORMATION: Synthetic Construct

<400> SEQUENCE: 839
ttaggtaggg ttcg                                                    14

<210> SEQ ID NO 840
<211> LENGTH: 14
<212> TYPE: DNA
<213> ORGANISM: Artificial Sequence
<220> FEATURE:
<223> OTHER INFORMATION: Synthetic Construct

<400> SEQUENCE: 840
cccctccgcc acac                                                    14

<210> SEQ ID NO 841
<211> LENGTH: 14
<212> TYPE: DNA
<213> ORGANISM: Artificial Sequence
<220> FEATURE:
<223> OTHER INFORMATION: Synthetic Construct

<400> SEQUENCE: 841
taggtagggt tcgt                                                    14

<210> SEQ ID NO 842
<211> LENGTH: 14
<212> TYPE: DNA
<213> ORGANISM: Artificial Sequence
<220> FEATURE:
<223> OTHER INFORMATION: Synthetic Construct

<400> SEQUENCE: 842
cccctccgcc acac                                                    14

<210> SEQ ID NO 843
<211> LENGTH: 14
<212> TYPE: DNA
<213> ORGANISM: Artificial Sequence
<220> FEATURE:
<223> OTHER INFORMATION: Synthetic Construct

<400> SEQUENCE: 843
```
aggtagggtt cgtt          14

<210> SEQ ID NO 844
<211> LENGTH: 14
<212> TYPE: DNA
<213> ORGANISM: Artificial Sequence
<220> FEATURE:
<223> OTHER INFORMATION: Synthetic Construct

<400> SEQUENCE: 844
tcgtaaaacc ctac          14

<210> SEQ ID NO 845
<211> LENGTH: 24
<212> TYPE: DNA
<213> ORGANISM: Artificial Sequence
<220> FEATURE:
<223> OTHER INFORMATION: Synthetic Construct

<400> SEQUENCE: 845
tcgatttata tttagtatta ggac          24

<210> SEQ ID NO 846
<211> LENGTH: 14
<212> TYPE: DNA
<213> ORGANISM: Artificial Sequence
<220> FEATURE:
<223> OTHER INFORMATION: Synthetic Construct

<400> SEQUENCE: 846
ggtagggttc gttt          14

<210> SEQ ID NO 847
<211> LENGTH: 14
<212> TYPE: DNA
<213> ORGANISM: Artificial Sequence
<220> FEATURE:
<223> OTHER INFORMATION: Synthetic Construct

<400> SEQUENCE: 847
tcgtaaaacc ctac          14

<210> SEQ ID NO 848
<211> LENGTH: 14
<212> TYPE: DNA
<213> ORGANISM: Artificial Sequence
<220> FEATURE:
<223> OTHER INFORMATION: Synthetic Construct

<400> SEQUENCE: 848
gtagggttcg ttta          14

<210> SEQ ID NO 849
<211> LENGTH: 14
<212> TYPE: DNA
<213> ORGANISM: Artificial Sequence
<220> FEATURE:
<223> OTHER INFORMATION: Synthetic Construct

<400> SEQUENCE: 849
tcgtaaaacc ctac          14

<210> SEQ ID NO 850
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 850
tagggttcgt ttat                                                         14

<210> SEQ ID NO 851
<211> LENGTH: 14
<212> TYPE: DNA
<213> ORGANISM: Artificial Sequence
<220> FEATURE:
<223> OTHER INFORMATION: Synthetic Construct

<400> SEQUENCE: 851
tcgtaaaacc ctac                                                         14

<210> SEQ ID NO 852
<211> LENGTH: 14
<212> TYPE: DNA
<213> ORGANISM: Artificial Sequence
<220> FEATURE:
<223> OTHER INFORMATION: Synthetic Construct

<400> SEQUENCE: 852
agggttcgtt tatt                                                         14

<210> SEQ ID NO 853
<211> LENGTH: 14
<212> TYPE: DNA
<213> ORGANISM: Artificial Sequence
<220> FEATURE:
<223> OTHER INFORMATION: Synthetic Construct

<400> SEQUENCE: 853
tcgtaaaacc ctac                                                         14

<210> SEQ ID NO 854
<211> LENGTH: 14
<212> TYPE: DNA
<213> ORGANISM: Artificial Sequence
<220> FEATURE:
<223> OTHER INFORMATION: Synthetic Construct

<400> SEQUENCE: 854
gggttcgttt attc                                                         14

<210> SEQ ID NO 855
<211> LENGTH: 14
<212> TYPE: DNA
<213> ORGANISM: Artificial Sequence
<220> FEATURE:
<223> OTHER INFORMATION: Synthetic Construct

<400> SEQUENCE: 855
tcgtaaaacc ctac                                                         14

<210> SEQ ID NO 856
<211> LENGTH: 14
<212> TYPE: DNA
<213> ORGANISM: Artificial Sequence
<220> FEATURE:
<223> OTHER INFORMATION: Synthetic Construct

<400> SEQUENCE: 856
ggttcgttta ttcg                                                         14
```

<210> SEQ ID NO 857
<211> LENGTH: 14
<212> TYPE: DNA
<213> ORGANISM: Artificial Sequence
<220> FEATURE:
<223> OTHER INFORMATION: Synthetic Construct

<400> SEQUENCE: 857
tcgtaaaacc ctac                                                          14

<210> SEQ ID NO 858
<211> LENGTH: 14
<212> TYPE: DNA
<213> ORGANISM: Artificial Sequence
<220> FEATURE:
<223> OTHER INFORMATION: Synthetic Construct

<400> SEQUENCE: 858
gttcgtttat tcgg                                                          14

<210> SEQ ID NO 859
<211> LENGTH: 14
<212> TYPE: DNA
<213> ORGANISM: Artificial Sequence
<220> FEATURE:
<223> OTHER INFORMATION: Synthetic Construct

<400> SEQUENCE: 859
tcgtaaaacc ctac                                                          14

<210> SEQ ID NO 860
<211> LENGTH: 14
<212> TYPE: DNA
<213> ORGANISM: Artificial Sequence
<220> FEATURE:
<223> OTHER INFORMATION: Synthetic Construct

<400> SEQUENCE: 860
ttcgtttatt cggt                                                          14

<210> SEQ ID NO 861
<211> LENGTH: 14
<212> TYPE: DNA
<213> ORGANISM: Artificial Sequence
<220> FEATURE:
<223> OTHER INFORMATION: Synthetic Construct

<400> SEQUENCE: 861
tcgtaaaacc ctac                                                          14

<210> SEQ ID NO 862
<211> LENGTH: 14
<212> TYPE: DNA
<213> ORGANISM: Artificial Sequence
<220> FEATURE:
<223> OTHER INFORMATION: Synthetic Construct

<400> SEQUENCE: 862
tcgtttattc ggtg                                                          14

<210> SEQ ID NO 863
<211> LENGTH: 14
<212> TYPE: DNA
<213> ORGANISM: Artificial Sequence
<220> FEATURE:
<223> OTHER INFORMATION: Synthetic Construct

<400> SEQUENCE: 863
tcgtaaaacc ctac                                                         14

<210> SEQ ID NO 864
<211> LENGTH: 14
<212> TYPE: DNA
<213> ORGANISM: Artificial Sequence
<220> FEATURE:
<223> OTHER INFORMATION: Synthetic Construct

<400> SEQUENCE: 864
cgtttattcg gtgt                                                         14

<210> SEQ ID NO 865
<211> LENGTH: 14
<212> TYPE: DNA
<213> ORGANISM: Artificial Sequence
<220> FEATURE:
<223> OTHER INFORMATION: Synthetic Construct

<400> SEQUENCE: 865
tcgtaaaacc ctac                                                         14

<210> SEQ ID NO 866
<211> LENGTH: 14
<212> TYPE: DNA
<213> ORGANISM: Artificial Sequence
<220> FEATURE:
<223> OTHER INFORMATION: Synthetic Construct

<400> SEQUENCE: 866
gtttattcgg tgtt                                                         14

<210> SEQ ID NO 867
<211> LENGTH: 14
<212> TYPE: DNA
<213> ORGANISM: Artificial Sequence
<220> FEATURE:
<223> OTHER INFORMATION: Synthetic Construct

<400> SEQUENCE: 867
tcgtaaaacc ctac                                                         14

<210> SEQ ID NO 868
<211> LENGTH: 14
<212> TYPE: DNA
<213> ORGANISM: Artificial Sequence
<220> FEATURE:
<223> OTHER INFORMATION: Synthetic Construct

<400> SEQUENCE: 868
tttattcggt gttt                                                         14

<210> SEQ ID NO 869
<211> LENGTH: 14
<212> TYPE: DNA
<213> ORGANISM: Artificial Sequence
<220> FEATURE:
<223> OTHER INFORMATION: Synthetic Construct

<400> SEQUENCE: 869
tcgtaaaacc ctac                                                         14

<210> SEQ ID NO 870

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 870
ttattcggtg ttta                                                       14

<210> SEQ ID NO 871
<211> LENGTH: 14
<212> TYPE: DNA
<213> ORGANISM: Artificial Sequence
<220> FEATURE:
<223> OTHER INFORMATION: Synthetic Construct

<400> SEQUENCE: 871
tcgtaaaacc ctac                                                       14

<210> SEQ ID NO 872
<211> LENGTH: 14
<212> TYPE: DNA
<213> ORGANISM: Artificial Sequence
<220> FEATURE:
<223> OTHER INFORMATION: Synthetic Construct

<400> SEQUENCE: 872
tattcggtgt ttag                                                       14

<210> SEQ ID NO 873
<211> LENGTH: 14
<212> TYPE: DNA
<213> ORGANISM: Artificial Sequence
<220> FEATURE:
<223> OTHER INFORMATION: Synthetic Construct

<400> SEQUENCE: 873
tcgtaaaacc ctac                                                       14

<210> SEQ ID NO 874
<211> LENGTH: 14
<212> TYPE: DNA
<213> ORGANISM: Artificial Sequence
<220> FEATURE:
<223> OTHER INFORMATION: Synthetic Construct

<400> SEQUENCE: 874
attcggtgtt tagc                                                       14

<210> SEQ ID NO 875
<211> LENGTH: 14
<212> TYPE: DNA
<213> ORGANISM: Artificial Sequence
<220> FEATURE:
<223> OTHER INFORMATION: Synthetic Construct

<400> SEQUENCE: 875
tcgtaaaacc ctac                                                       14

<210> SEQ ID NO 876
<211> LENGTH: 14
<212> TYPE: DNA
<213> ORGANISM: Artificial Sequence
<220> FEATURE:
<223> OTHER INFORMATION: Synthetic Construct

<400> SEQUENCE: 876
```
ttcggtgttt agcg 14

<210> SEQ ID NO 877
<211> LENGTH: 14
<212> TYPE: DNA
<213> ORGANISM: Artificial Sequence
<220> FEATURE:
<223> OTHER INFORMATION: Synthetic Construct

<400> SEQUENCE: 877
tcgtaaaacc ctac 14

<210> SEQ ID NO 878
<211> LENGTH: 14
<212> TYPE: DNA
<213> ORGANISM: Artificial Sequence
<220> FEATURE:
<223> OTHER INFORMATION: Synthetic Construct

<400> SEQUENCE: 878
tcggtgttta gcgg 14

<210> SEQ ID NO 879
<211> LENGTH: 14
<212> TYPE: DNA
<213> ORGANISM: Artificial Sequence
<220> FEATURE:
<223> OTHER INFORMATION: Synthetic Construct

<400> SEQUENCE: 879
tcgtaaaacc ctac 14

<210> SEQ ID NO 880
<211> LENGTH: 14
<212> TYPE: DNA
<213> ORGANISM: Artificial Sequence
<220> FEATURE:
<223> OTHER INFORMATION: Synthetic Construct

<400> SEQUENCE: 880
cggtgtttag cgga 14

<210> SEQ ID NO 881
<211> LENGTH: 14
<212> TYPE: DNA
<213> ORGANISM: Artificial Sequence
<220> FEATURE:
<223> OTHER INFORMATION: Synthetic Construct

<400> SEQUENCE: 881
tcgtaaaacc ctac 14

<210> SEQ ID NO 882
<211> LENGTH: 14
<212> TYPE: DNA
<213> ORGANISM: Artificial Sequence
<220> FEATURE:
<223> OTHER INFORMATION: Synthetic Construct

<400> SEQUENCE: 882
ggtgtttagc ggag 14

<210> SEQ ID NO 883
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 883
tcgtaaaacc ctac                                                          14

<210> SEQ ID NO 884
<211> LENGTH: 14
<212> TYPE: DNA
<213> ORGANISM: Artificial Sequence
<220> FEATURE:
<223> OTHER INFORMATION: Synthetic Construct

<400> SEQUENCE: 884
gtgtttagcg gagg                                                          14

<210> SEQ ID NO 885
<211> LENGTH: 14
<212> TYPE: DNA
<213> ORGANISM: Artificial Sequence
<220> FEATURE:
<223> OTHER INFORMATION: Synthetic Construct

<400> SEQUENCE: 885
tcgtaaaacc ctac                                                          14

<210> SEQ ID NO 886
<211> LENGTH: 14
<212> TYPE: DNA
<213> ORGANISM: Artificial Sequence
<220> FEATURE:
<223> OTHER INFORMATION: Synthetic Construct

<400> SEQUENCE: 886
tgtttagcgg aggt                                                          14

<210> SEQ ID NO 887
<211> LENGTH: 14
<212> TYPE: DNA
<213> ORGANISM: Artificial Sequence
<220> FEATURE:
<223> OTHER INFORMATION: Synthetic Construct

<400> SEQUENCE: 887
tcgtaaaacc ctac                                                          14

<210> SEQ ID NO 888
<211> LENGTH: 14
<212> TYPE: DNA
<213> ORGANISM: Artificial Sequence
<220> FEATURE:
<223> OTHER INFORMATION: Synthetic Construct

<400> SEQUENCE: 888
gtttagcgga ggta                                                          14

<210> SEQ ID NO 889
<211> LENGTH: 14
<212> TYPE: DNA
<213> ORGANISM: Artificial Sequence
<220> FEATURE:
<223> OTHER INFORMATION: Synthetic Construct

<400> SEQUENCE: 889
tcgtaaaacc ctac                                                          14
```

<210> SEQ ID NO 890
<211> LENGTH: 14
<212> TYPE: DNA
<213> ORGANISM: Artificial Sequence
<220> FEATURE:
<223> OTHER INFORMATION: Synthetic Construct

<400> SEQUENCE: 890
tttagcggag gtag                                                    14

<210> SEQ ID NO 891
<211> LENGTH: 14
<212> TYPE: DNA
<213> ORGANISM: Artificial Sequence
<220> FEATURE:
<223> OTHER INFORMATION: Synthetic Construct

<400> SEQUENCE: 891
tcgtaaaacc ctac                                                    14

<210> SEQ ID NO 892
<211> LENGTH: 14
<212> TYPE: DNA
<213> ORGANISM: Artificial Sequence
<220> FEATURE:
<223> OTHER INFORMATION: Synthetic Construct

<400> SEQUENCE: 892
ttagcggagg tagt                                                    14

<210> SEQ ID NO 893
<211> LENGTH: 14
<212> TYPE: DNA
<213> ORGANISM: Artificial Sequence
<220> FEATURE:
<223> OTHER INFORMATION: Synthetic Construct

<400> SEQUENCE: 893
tcgtaaaacc ctac                                                    14

<210> SEQ ID NO 894
<211> LENGTH: 14
<212> TYPE: DNA
<213> ORGANISM: Artificial Sequence
<220> FEATURE:
<223> OTHER INFORMATION: Synthetic Construct

<400> SEQUENCE: 894
tagcggaggt agtt                                                    14

<210> SEQ ID NO 895
<211> LENGTH: 14
<212> TYPE: DNA
<213> ORGANISM: Artificial Sequence
<220> FEATURE:
<223> OTHER INFORMATION: Synthetic Construct

<400> SEQUENCE: 895
tcgtaaaacc ctac                                                    14

<210> SEQ ID NO 896
<211> LENGTH: 14
<212> TYPE: DNA
<213> ORGANISM: Artificial Sequence
<220> FEATURE:

<223> OTHER INFORMATION: Synthetic Construct

<400> SEQUENCE: 896
agcggaggta gttt                                                         14

<210> SEQ ID NO 897
<211> LENGTH: 14
<212> TYPE: DNA
<213> ORGANISM: Artificial Sequence
<220> FEATURE:
<223> OTHER INFORMATION: Synthetic Construct

<400> SEQUENCE: 897
tcgtaaaacc ctac                                                         14

<210> SEQ ID NO 898
<211> LENGTH: 14
<212> TYPE: DNA
<213> ORGANISM: Artificial Sequence
<220> FEATURE:
<223> OTHER INFORMATION: Synthetic Construct

<400> SEQUENCE: 898
gcggaggtag tttg                                                         14

<210> SEQ ID NO 899
<211> LENGTH: 14
<212> TYPE: DNA
<213> ORGANISM: Artificial Sequence
<220> FEATURE:
<223> OTHER INFORMATION: Synthetic Construct

<400> SEQUENCE: 899
tcgtaaaacc ctac                                                         14

<210> SEQ ID NO 900
<211> LENGTH: 14
<212> TYPE: DNA
<213> ORGANISM: Artificial Sequence
<220> FEATURE:
<223> OTHER INFORMATION: Synthetic Construct

<400> SEQUENCE: 900
cggaggtagt ttgg                                                         14

<210> SEQ ID NO 901
<211> LENGTH: 14
<212> TYPE: DNA
<213> ORGANISM: Artificial Sequence
<220> FEATURE:
<223> OTHER INFORMATION: Synthetic Construct

<400> SEQUENCE: 901
tcgtaaaacc ctac                                                         14

<210> SEQ ID NO 902
<211> LENGTH: 14
<212> TYPE: DNA
<213> ORGANISM: Artificial Sequence
<220> FEATURE:
<223> OTHER INFORMATION: Synthetic Construct

<400> SEQUENCE: 902
ggaggtagtt tgga                                                         14

```
<210> SEQ ID NO 903
<211> LENGTH: 14
<212> TYPE: DNA
<213> ORGANISM: Artificial Sequence
<220> FEATURE:
<223> OTHER INFORMATION: Synthetic Construct

<400> SEQUENCE: 903
tcgtaaaacc ctac                                                        14

<210> SEQ ID NO 904
<211> LENGTH: 14
<212> TYPE: DNA
<213> ORGANISM: Artificial Sequence
<220> FEATURE:
<223> OTHER INFORMATION: Synthetic Construct

<400> SEQUENCE: 904
gaggtagttt ggaa                                                        14

<210> SEQ ID NO 905
<211> LENGTH: 14
<212> TYPE: DNA
<213> ORGANISM: Artificial Sequence
<220> FEATURE:
<223> OTHER INFORMATION: Synthetic Construct

<400> SEQUENCE: 905
tcgtaaaacc ctac                                                        14

<210> SEQ ID NO 906
<211> LENGTH: 14
<212> TYPE: DNA
<213> ORGANISM: Artificial Sequence
<220> FEATURE:
<223> OTHER INFORMATION: Synthetic Construct

<400> SEQUENCE: 906
aggtagtttg gaat                                                        14

<210> SEQ ID NO 907
<211> LENGTH: 14
<212> TYPE: DNA
<213> ORGANISM: Artificial Sequence
<220> FEATURE:
<223> OTHER INFORMATION: Synthetic Construct

<400> SEQUENCE: 907
tcgtaaaacc ctac                                                        14

<210> SEQ ID NO 908
<211> LENGTH: 14
<212> TYPE: DNA
<213> ORGANISM: Artificial Sequence
<220> FEATURE:
<223> OTHER INFORMATION: Synthetic Construct

<400> SEQUENCE: 908
ggtagtttgg aata                                                        14

<210> SEQ ID NO 909
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 909
tcgtaaaacc ctac                                                       14

<210> SEQ ID NO 910
<211> LENGTH: 14
<212> TYPE: DNA
<213> ORGANISM: Artificial Sequence
<220> FEATURE:
<223> OTHER INFORMATION: Synthetic Construct

<400> SEQUENCE: 910
gtagtttgga atag                                                       14

<210> SEQ ID NO 911
<211> LENGTH: 14
<212> TYPE: DNA
<213> ORGANISM: Artificial Sequence
<220> FEATURE:
<223> OTHER INFORMATION: Synthetic Construct

<400> SEQUENCE: 911
tcgtaaaacc ctac                                                       14

<210> SEQ ID NO 912
<211> LENGTH: 14
<212> TYPE: DNA
<213> ORGANISM: Artificial Sequence
<220> FEATURE:
<223> OTHER INFORMATION: Synthetic Construct

<400> SEQUENCE: 912
tagtttggaa tagt                                                       14

<210> SEQ ID NO 913
<211> LENGTH: 14
<212> TYPE: DNA
<213> ORGANISM: Artificial Sequence
<220> FEATURE:
<223> OTHER INFORMATION: Synthetic Construct

<400> SEQUENCE: 913
tcgtaaaacc ctac                                                       14

<210> SEQ ID NO 914
<211> LENGTH: 14
<212> TYPE: DNA
<213> ORGANISM: Artificial Sequence
<220> FEATURE:
<223> OTHER INFORMATION: Synthetic Construct

<400> SEQUENCE: 914
agtttggaat agtt                                                       14

<210> SEQ ID NO 915
<211> LENGTH: 14
<212> TYPE: DNA
<213> ORGANISM: Artificial Sequence
<220> FEATURE:
<223> OTHER INFORMATION: Synthetic Construct

<400> SEQUENCE: 915
tcgtaaaacc ctac                                                       14

<210> SEQ ID NO 916
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 916
gtttggaata gttt                                                        14

<210> SEQ ID NO 917
<211> LENGTH: 14
<212> TYPE: DNA
<213> ORGANISM: Artificial Sequence
<220> FEATURE:
<223> OTHER INFORMATION: Synthetic Construct

<400> SEQUENCE: 917
tcgtaaaacc ctac                                                        14

<210> SEQ ID NO 918
<211> LENGTH: 14
<212> TYPE: DNA
<213> ORGANISM: Artificial Sequence
<220> FEATURE:
<223> OTHER INFORMATION: Synthetic Construct

<400> SEQUENCE: 918
tttggaatag tttt                                                        14

<210> SEQ ID NO 919
<211> LENGTH: 14
<212> TYPE: DNA
<213> ORGANISM: Artificial Sequence
<220> FEATURE:
<223> OTHER INFORMATION: Synthetic Construct

<400> SEQUENCE: 919
tcgtaaaacc ctac                                                        14

<210> SEQ ID NO 920
<211> LENGTH: 14
<212> TYPE: DNA
<213> ORGANISM: Artificial Sequence
<220> FEATURE:
<223> OTHER INFORMATION: Synthetic Construct

<400> SEQUENCE: 920
ttggaatagt ttta                                                        14

<210> SEQ ID NO 921
<211> LENGTH: 14
<212> TYPE: DNA
<213> ORGANISM: Artificial Sequence
<220> FEATURE:
<223> OTHER INFORMATION: Synthetic Construct

<400> SEQUENCE: 921
tcgtaaaacc ctac                                                        14

<210> SEQ ID NO 922
<211> LENGTH: 14
<212> TYPE: DNA
<213> ORGANISM: Artificial Sequence
<220> FEATURE:
<223> OTHER INFORMATION: Synthetic Construct

<400> SEQUENCE: 922
```

| | |
|---|---|
| tggaatagtt ttag | 14 |

\<210\> SEQ ID NO 923
\<211\> LENGTH: 14
\<212\> TYPE: DNA
\<213\> ORGANISM: Artificial Sequence
\<220\> FEATURE:
\<223\> OTHER INFORMATION: Synthetic Construct

\<400\> SEQUENCE: 923

| | |
|---|---|
| tcgtaaaacc ctac | 14 |

\<210\> SEQ ID NO 924
\<211\> LENGTH: 14
\<212\> TYPE: DNA
\<213\> ORGANISM: Artificial Sequence
\<220\> FEATURE:
\<223\> OTHER INFORMATION: Synthetic Construct

\<400\> SEQUENCE: 924

| | |
|---|---|
| ggaatagttt tagg | 14 |

\<210\> SEQ ID NO 925
\<211\> LENGTH: 14
\<212\> TYPE: DNA
\<213\> ORGANISM: Artificial Sequence
\<220\> FEATURE:
\<223\> OTHER INFORMATION: Synthetic Construct

\<400\> SEQUENCE: 925

| | |
|---|---|
| tcgtaaaacc ctac | 14 |

\<210\> SEQ ID NO 926
\<211\> LENGTH: 14
\<212\> TYPE: DNA
\<213\> ORGANISM: Artificial Sequence
\<220\> FEATURE:
\<223\> OTHER INFORMATION: Synthetic Construct

\<400\> SEQUENCE: 926

| | |
|---|---|
| gaatagtttt agga | 14 |

\<210\> SEQ ID NO 927
\<211\> LENGTH: 14
\<212\> TYPE: DNA
\<213\> ORGANISM: Artificial Sequence
\<220\> FEATURE:
\<223\> OTHER INFORMATION: Synthetic Construct

\<400\> SEQUENCE: 927

| | |
|---|---|
| tcgtaaaacc ctac | 14 |

\<210\> SEQ ID NO 928
\<211\> LENGTH: 14
\<212\> TYPE: DNA
\<213\> ORGANISM: Artificial Sequence
\<220\> FEATURE:
\<223\> OTHER INFORMATION: Synthetic Construct

\<400\> SEQUENCE: 928

| | |
|---|---|
| aatagttta ggaa | 14 |

\<210\> SEQ ID NO 929
\<211\> LENGTH: 14
\<212\> TYPE: DNA
\<213\> ORGANISM: Artificial Sequence

```
<220> FEATURE:
<223> OTHER INFORMATION: Synthetic Construct

<400> SEQUENCE: 929
tcgtaaaacc ctac                                              14

<210> SEQ ID NO 930
<211> LENGTH: 14
<212> TYPE: DNA
<213> ORGANISM: Artificial Sequence
<220> FEATURE:
<223> OTHER INFORMATION: Synthetic Construct

<400> SEQUENCE: 930
atagttttag gaat                                              14

<210> SEQ ID NO 931
<211> LENGTH: 14
<212> TYPE: DNA
<213> ORGANISM: Artificial Sequence
<220> FEATURE:
<223> OTHER INFORMATION: Synthetic Construct

<400> SEQUENCE: 931
tcgtaaaacc ctac                                              14

<210> SEQ ID NO 932
<211> LENGTH: 14
<212> TYPE: DNA
<213> ORGANISM: Artificial Sequence
<220> FEATURE:
<223> OTHER INFORMATION: Synthetic Construct

<400> SEQUENCE: 932
tagttttagg aatg                                              14

<210> SEQ ID NO 933
<211> LENGTH: 14
<212> TYPE: DNA
<213> ORGANISM: Artificial Sequence
<220> FEATURE:
<223> OTHER INFORMATION: Synthetic Construct

<400> SEQUENCE: 933
tcgtaaaacc ctac                                              14

<210> SEQ ID NO 934
<211> LENGTH: 14
<212> TYPE: DNA
<213> ORGANISM: Artificial Sequence
<220> FEATURE:
<223> OTHER INFORMATION: Synthetic Construct

<400> SEQUENCE: 934
agttttagga atgt                                              14

<210> SEQ ID NO 935
<211> LENGTH: 14
<212> TYPE: DNA
<213> ORGANISM: Artificial Sequence
<220> FEATURE:
<223> OTHER INFORMATION: Synthetic Construct

<400> SEQUENCE: 935
tcgtaaaacc ctac                                              14
```

```
<210> SEQ ID NO 936
<211> LENGTH: 14
<212> TYPE: DNA
<213> ORGANISM: Artificial Sequence
<220> FEATURE:
<223> OTHER INFORMATION: Synthetic Construct

<400> SEQUENCE: 936
gttttaggaa tgtg                                                     14

<210> SEQ ID NO 937
<211> LENGTH: 14
<212> TYPE: DNA
<213> ORGANISM: Artificial Sequence
<220> FEATURE:
<223> OTHER INFORMATION: Synthetic Construct

<400> SEQUENCE: 937
tcgtaaaacc ctac                                                     14

<210> SEQ ID NO 938
<211> LENGTH: 14
<212> TYPE: DNA
<213> ORGANISM: Artificial Sequence
<220> FEATURE:
<223> OTHER INFORMATION: Synthetic Construct

<400> SEQUENCE: 938
ttttaggaat gtga                                                     14

<210> SEQ ID NO 939
<211> LENGTH: 14
<212> TYPE: DNA
<213> ORGANISM: Artificial Sequence
<220> FEATURE:
<223> OTHER INFORMATION: Synthetic Construct

<400> SEQUENCE: 939
tcgtaaaacc ctac                                                     14

<210> SEQ ID NO 940
<211> LENGTH: 14
<212> TYPE: DNA
<213> ORGANISM: Artificial Sequence
<220> FEATURE:
<223> OTHER INFORMATION: Synthetic Construct

<400> SEQUENCE: 940
tttaggaatg tgat                                                     14

<210> SEQ ID NO 941
<211> LENGTH: 14
<212> TYPE: DNA
<213> ORGANISM: Artificial Sequence
<220> FEATURE:
<223> OTHER INFORMATION: Synthetic Construct

<400> SEQUENCE: 941
tcgtaaaacc ctac                                                     14

<210> SEQ ID NO 942
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 942
ttaggaatgt gatt                                                         14

<210> SEQ ID NO 943
<211> LENGTH: 14
<212> TYPE: DNA
<213> ORGANISM: Artificial Sequence
<220> FEATURE:
<223> OTHER INFORMATION: Synthetic Construct

<400> SEQUENCE: 943
tcgtaaaacc ctac                                                         14

<210> SEQ ID NO 944
<211> LENGTH: 14
<212> TYPE: DNA
<213> ORGANISM: Artificial Sequence
<220> FEATURE:
<223> OTHER INFORMATION: Synthetic Construct

<400> SEQUENCE: 944
taggaatgtg attg                                                         14

<210> SEQ ID NO 945
<211> LENGTH: 14
<212> TYPE: DNA
<213> ORGANISM: Artificial Sequence
<220> FEATURE:
<223> OTHER INFORMATION: Synthetic Construct

<400> SEQUENCE: 945
tcgtaaaacc ctac                                                         14

<210> SEQ ID NO 946
<211> LENGTH: 14
<212> TYPE: DNA
<213> ORGANISM: Artificial Sequence
<220> FEATURE:
<223> OTHER INFORMATION: Synthetic Construct

<400> SEQUENCE: 946
aggaatgtga ttgc                                                         14

<210> SEQ ID NO 947
<211> LENGTH: 14
<212> TYPE: DNA
<213> ORGANISM: Artificial Sequence
<220> FEATURE:
<223> OTHER INFORMATION: Synthetic Construct

<400> SEQUENCE: 947
tcgtaaaacc ctac                                                         14

<210> SEQ ID NO 948
<211> LENGTH: 14
<212> TYPE: DNA
<213> ORGANISM: Artificial Sequence
<220> FEATURE:
<223> OTHER INFORMATION: Synthetic Construct

<400> SEQUENCE: 948
ggaatgtgat tgcg                                                         14

<210> SEQ ID NO 949
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 949
tcgtaaaacc ctac                                                      14

<210> SEQ ID NO 950
<211> LENGTH: 14
<212> TYPE: DNA
<213> ORGANISM: Artificial Sequence
<220> FEATURE:
<223> OTHER INFORMATION: Synthetic Construct

<400> SEQUENCE: 950
gaatgtgatt gcgt                                                      14

<210> SEQ ID NO 951
<211> LENGTH: 14
<212> TYPE: DNA
<213> ORGANISM: Artificial Sequence
<220> FEATURE:
<223> OTHER INFORMATION: Synthetic Construct

<400> SEQUENCE: 951
tcgtaaaacc ctac                                                      14

<210> SEQ ID NO 952
<211> LENGTH: 14
<212> TYPE: DNA
<213> ORGANISM: Artificial Sequence
<220> FEATURE:
<223> OTHER INFORMATION: Synthetic Construct

<400> SEQUENCE: 952
aatgtgattg cgtg                                                      14

<210> SEQ ID NO 953
<211> LENGTH: 14
<212> TYPE: DNA
<213> ORGANISM: Artificial Sequence
<220> FEATURE:
<223> OTHER INFORMATION: Synthetic Construct

<400> SEQUENCE: 953
tcgtaaaacc ctac                                                      14

<210> SEQ ID NO 954
<211> LENGTH: 14
<212> TYPE: DNA
<213> ORGANISM: Artificial Sequence
<220> FEATURE:
<223> OTHER INFORMATION: Synthetic Construct

<400> SEQUENCE: 954
atgtgattgc gtgt                                                      14

<210> SEQ ID NO 955
<211> LENGTH: 14
<212> TYPE: DNA
<213> ORGANISM: Artificial Sequence
<220> FEATURE:
<223> OTHER INFORMATION: Synthetic Construct

<400> SEQUENCE: 955
```
tcgtaaaacc ctac                                                       14

<210> SEQ ID NO 956
<211> LENGTH: 14
<212> TYPE: DNA
<213> ORGANISM: Artificial Sequence
<220> FEATURE:
<223> OTHER INFORMATION: Synthetic Construct

<400> SEQUENCE: 956
tgtgattgcg tgtg                                                       14

<210> SEQ ID NO 957
<211> LENGTH: 14
<212> TYPE: DNA
<213> ORGANISM: Artificial Sequence
<220> FEATURE:
<223> OTHER INFORMATION: Synthetic Construct

<400> SEQUENCE: 957
tcgtaaaacc ctac                                                       14

<210> SEQ ID NO 958
<211> LENGTH: 14
<212> TYPE: DNA
<213> ORGANISM: Artificial Sequence
<220> FEATURE:
<223> OTHER INFORMATION: Synthetic Construct

<400> SEQUENCE: 958
gtgattgcgt gtgg                                                       14

<210> SEQ ID NO 959
<211> LENGTH: 14
<212> TYPE: DNA
<213> ORGANISM: Artificial Sequence
<220> FEATURE:
<223> OTHER INFORMATION: Synthetic Construct

<400> SEQUENCE: 959
tcgtaaaacc ctac                                                       14

<210> SEQ ID NO 960
<211> LENGTH: 14
<212> TYPE: DNA
<213> ORGANISM: Artificial Sequence
<220> FEATURE:
<223> OTHER INFORMATION: Synthetic Construct

<400> SEQUENCE: 960
tgattgcgtg tggc                                                       14

<210> SEQ ID NO 961
<211> LENGTH: 14
<212> TYPE: DNA
<213> ORGANISM: Artificial Sequence
<220> FEATURE:
<223> OTHER INFORMATION: Synthetic Construct

<400> SEQUENCE: 961
tcgtaaaacc ctac                                                       14

<210> SEQ ID NO 962
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 962
gattgcgtgt ggcg                                                    14

<210> SEQ ID NO 963
<211> LENGTH: 14
<212> TYPE: DNA
<213> ORGANISM: Artificial Sequence
<220> FEATURE:
<223> OTHER INFORMATION: Synthetic Construct

<400> SEQUENCE: 963
tcgtaaaacc ctac                                                    14

<210> SEQ ID NO 964
<211> LENGTH: 14
<212> TYPE: DNA
<213> ORGANISM: Artificial Sequence
<220> FEATURE:
<223> OTHER INFORMATION: Synthetic Construct

<400> SEQUENCE: 964
attgcgtgtg gcgg                                                    14

<210> SEQ ID NO 965
<211> LENGTH: 14
<212> TYPE: DNA
<213> ORGANISM: Artificial Sequence
<220> FEATURE:
<223> OTHER INFORMATION: Synthetic Construct

<400> SEQUENCE: 965
tcgtaaaacc ctac                                                    14

<210> SEQ ID NO 966
<211> LENGTH: 14
<212> TYPE: DNA
<213> ORGANISM: Artificial Sequence
<220> FEATURE:
<223> OTHER INFORMATION: Synthetic Construct

<400> SEQUENCE: 966
ttgcgtgtgg cgga                                                    14

<210> SEQ ID NO 967
<211> LENGTH: 14
<212> TYPE: DNA
<213> ORGANISM: Artificial Sequence
<220> FEATURE:
<223> OTHER INFORMATION: Synthetic Construct

<400> SEQUENCE: 967
aataacgaat actt                                                    14

<210> SEQ ID NO 968
<211> LENGTH: 26
<212> TYPE: DNA
<213> ORGANISM: Artificial Sequence
<220> FEATURE:
<223> OTHER INFORMATION: Synthetic Construct

<400> SEQUENCE: 968
gagcgaggga gaagttgggg aggaga                                       26
```

<210> SEQ ID NO 969
<211> LENGTH: 14
<212> TYPE: DNA
<213> ORGANISM: Artificial Sequence
<220> FEATURE:
<223> OTHER INFORMATION: Synthetic Construct

<400> SEQUENCE: 969
tgcgtgtggc ggag                                                        14

<210> SEQ ID NO 970
<211> LENGTH: 14
<212> TYPE: DNA
<213> ORGANISM: Artificial Sequence
<220> FEATURE:
<223> OTHER INFORMATION: Synthetic Construct

<400> SEQUENCE: 970
aataacgaat actt                                                        14

<210> SEQ ID NO 971
<211> LENGTH: 14
<212> TYPE: DNA
<213> ORGANISM: Artificial Sequence
<220> FEATURE:
<223> OTHER INFORMATION: Synthetic Construct

<400> SEQUENCE: 971
gcgtgtggcg gagg                                                        14

<210> SEQ ID NO 972
<211> LENGTH: 14
<212> TYPE: DNA
<213> ORGANISM: Artificial Sequence
<220> FEATURE:
<223> OTHER INFORMATION: Synthetic Construct

<400> SEQUENCE: 972
aataacgaat actt                                                        14

<210> SEQ ID NO 973
<211> LENGTH: 14
<212> TYPE: DNA
<213> ORGANISM: Artificial Sequence
<220> FEATURE:
<223> OTHER INFORMATION: Synthetic Construct

<400> SEQUENCE: 973
cgtgtggcgg aggg                                                        14

<210> SEQ ID NO 974
<211> LENGTH: 14
<212> TYPE: DNA
<213> ORGANISM: Artificial Sequence
<220> FEATURE:
<223> OTHER INFORMATION: Synthetic Construct

<400> SEQUENCE: 974
aataacgaat actt                                                        14

<210> SEQ ID NO 975
<211> LENGTH: 14
<212> TYPE: DNA
<213> ORGANISM: Artificial Sequence
<220> FEATURE:

<223> OTHER INFORMATION: Synthetic Construct

<400> SEQUENCE: 975
gtgtggcgga gggg                                                14

<210> SEQ ID NO 976
<211> LENGTH: 14
<212> TYPE: DNA
<213> ORGANISM: Artificial Sequence
<220> FEATURE:
<223> OTHER INFORMATION: Synthetic Construct

<400> SEQUENCE: 976
aataacgaat actt                                                14

<210> SEQ ID NO 977
<211> LENGTH: 14
<212> TYPE: DNA
<213> ORGANISM: Artificial Sequence
<220> FEATURE:
<223> OTHER INFORMATION: Synthetic Construct

<400> SEQUENCE: 977
tgtggcggag ggga                                                14

<210> SEQ ID NO 978
<211> LENGTH: 14
<212> TYPE: DNA
<213> ORGANISM: Artificial Sequence
<220> FEATURE:
<223> OTHER INFORMATION: Synthetic Construct

<400> SEQUENCE: 978
aataacgaat actt                                                14

<210> SEQ ID NO 979
<211> LENGTH: 14
<212> TYPE: DNA
<213> ORGANISM: Artificial Sequence
<220> FEATURE:
<223> OTHER INFORMATION: Synthetic Construct

<400> SEQUENCE: 979
gtggcggagg ggag                                                14

<210> SEQ ID NO 980
<211> LENGTH: 14
<212> TYPE: DNA
<213> ORGANISM: Artificial Sequence
<220> FEATURE:
<223> OTHER INFORMATION: Synthetic Construct

<400> SEQUENCE: 980
aataacgaat actt                                                14

<210> SEQ ID NO 981
<211> LENGTH: 14
<212> TYPE: DNA
<213> ORGANISM: Artificial Sequence
<220> FEATURE:
<223> OTHER INFORMATION: Synthetic Construct

<400> SEQUENCE: 981
tggcggaggg gagg                                                14

```
<210> SEQ ID NO 982
<211> LENGTH: 14
<212> TYPE: DNA
<213> ORGANISM: Artificial Sequence
<220> FEATURE:
<223> OTHER INFORMATION: Synthetic Construct

<400> SEQUENCE: 982
aataacgaat actt                                                        14

<210> SEQ ID NO 983
<211> LENGTH: 14
<212> TYPE: DNA
<213> ORGANISM: Artificial Sequence
<220> FEATURE:
<223> OTHER INFORMATION: Synthetic Construct

<400> SEQUENCE: 983
ggcggagggg agga                                                        14

<210> SEQ ID NO 984
<211> LENGTH: 14
<212> TYPE: DNA
<213> ORGANISM: Artificial Sequence
<220> FEATURE:
<223> OTHER INFORMATION: Synthetic Construct

<400> SEQUENCE: 984
aataacgaat actt                                                        14

<210> SEQ ID NO 985
<211> LENGTH: 14
<212> TYPE: DNA
<213> ORGANISM: Artificial Sequence
<220> FEATURE:
<223> OTHER INFORMATION: Synthetic Construct

<400> SEQUENCE: 985
gcggagggga ggaa                                                        14

<210> SEQ ID NO 986
<211> LENGTH: 14
<212> TYPE: DNA
<213> ORGANISM: Artificial Sequence
<220> FEATURE:
<223> OTHER INFORMATION: Synthetic Construct

<400> SEQUENCE: 986
aataacgaat actt                                                        14

<210> SEQ ID NO 987
<211> LENGTH: 14
<212> TYPE: DNA
<213> ORGANISM: Artificial Sequence
<220> FEATURE:
<223> OTHER INFORMATION: Synthetic Construct

<400> SEQUENCE: 987
cggaggggag gaag                                                        14

<210> SEQ ID NO 988
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 988
aataacgaat actt                                                    14

<210> SEQ ID NO 989
<211> LENGTH: 14
<212> TYPE: DNA
<213> ORGANISM: Artificial Sequence
<220> FEATURE:
<223> OTHER INFORMATION: Synthetic Construct

<400> SEQUENCE: 989
ggaggggagg aaga                                                    14

<210> SEQ ID NO 990
<211> LENGTH: 14
<212> TYPE: DNA
<213> ORGANISM: Artificial Sequence
<220> FEATURE:
<223> OTHER INFORMATION: Synthetic Construct

<400> SEQUENCE: 990
aataacgaat actt                                                    14

<210> SEQ ID NO 991
<211> LENGTH: 14
<212> TYPE: DNA
<213> ORGANISM: Artificial Sequence
<220> FEATURE:
<223> OTHER INFORMATION: Synthetic Construct

<400> SEQUENCE: 991
gaggggagga agaa                                                    14

<210> SEQ ID NO 992
<211> LENGTH: 14
<212> TYPE: DNA
<213> ORGANISM: Artificial Sequence
<220> FEATURE:
<223> OTHER INFORMATION: Synthetic Construct

<400> SEQUENCE: 992
aataacgaat actt                                                    14

<210> SEQ ID NO 993
<211> LENGTH: 14
<212> TYPE: DNA
<213> ORGANISM: Artificial Sequence
<220> FEATURE:
<223> OTHER INFORMATION: Synthetic Construct

<400> SEQUENCE: 993
aggggaggaa gaat                                                    14

<210> SEQ ID NO 994
<211> LENGTH: 14
<212> TYPE: DNA
<213> ORGANISM: Artificial Sequence
<220> FEATURE:
<223> OTHER INFORMATION: Synthetic Construct

<400> SEQUENCE: 994
aataacgaat actt                                                    14

<210> SEQ ID NO 995
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 995
ggggaggaag aatt                                                        14

<210> SEQ ID NO 996
<211> LENGTH: 14
<212> TYPE: DNA
<213> ORGANISM: Artificial Sequence
<220> FEATURE:
<223> OTHER INFORMATION: Synthetic Construct

<400> SEQUENCE: 996
aataacgaat actt                                                        14

<210> SEQ ID NO 997
<211> LENGTH: 14
<212> TYPE: DNA
<213> ORGANISM: Artificial Sequence
<220> FEATURE:
<223> OTHER INFORMATION: Synthetic Construct

<400> SEQUENCE: 997
gggaggaaga attg                                                        14

<210> SEQ ID NO 998
<211> LENGTH: 14
<212> TYPE: DNA
<213> ORGANISM: Artificial Sequence
<220> FEATURE:
<223> OTHER INFORMATION: Synthetic Construct

<400> SEQUENCE: 998
aataacgaat actt                                                        14

<210> SEQ ID NO 999
<211> LENGTH: 14
<212> TYPE: DNA
<213> ORGANISM: Artificial Sequence
<220> FEATURE:
<223> OTHER INFORMATION: Synthetic Construct

<400> SEQUENCE: 999
ggaggaagaa ttgg                                                        14

<210> SEQ ID NO 1000
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1000
aataacgaat actt                                                        14

<210> SEQ ID NO 1001
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1001
```
gaggaagaat tggg                                                        14

<210> SEQ ID NO 1002
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1002
aataacgaat actt                                                        14

<210> SEQ ID NO 1003
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1003
aggaagaatt gggt                                                        14

<210> SEQ ID NO 1004
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1004
aataacgaat actt                                                        14

<210> SEQ ID NO 1005
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1005
ggaagaattg ggtg                                                        14

<210> SEQ ID NO 1006
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1006
aataacgaat actt                                                        14

<210> SEQ ID NO 1007
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1007
gaagaattgg gtgt                                                        14

<210> SEQ ID NO 1008
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1008
aataacgaat actt                                                    14

<210> SEQ ID NO 1009
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1009
aagaattggg tgtg                                                    14

<210> SEQ ID NO 1010
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1010
aataacgaat actt                                                    14

<210> SEQ ID NO 1011
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1011
agaattgggt gtga                                                    14

<210> SEQ ID NO 1012
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1012
aataacgaat actt                                                    14

<210> SEQ ID NO 1013
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1013
gaattgggtg tgaa                                                    14

<210> SEQ ID NO 1014
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1014
aataacgaat actt                                                    14
```

<210> SEQ ID NO 1015
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1015
aattgggtgt gaaa                                                    14

<210> SEQ ID NO 1016
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1016
aataacgaat actt                                                    14

<210> SEQ ID NO 1017
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1017
attgggtgtg aaat                                                    14

<210> SEQ ID NO 1018
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1018
aataacgaat actt                                                    14

<210> SEQ ID NO 1019
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1019
ttgggtgtga aata                                                    14

<210> SEQ ID NO 1020
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1020
aataacgaat actt                                                    14

<210> SEQ ID NO 1021
<211> LENGTH: 14
<212> TYPE: DNA
<213> ORGANISM: Artificial Sequence
<220> FEATURE:
<223> OTHER INFORMATION: Synthetic Construct -continued

<400> SEQUENCE: 1021
tgggtgtgaa atag                                                       14

<210> SEQ ID NO 1022
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1022
aataacgaat actt                                                       14

<210> SEQ ID NO 1023
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1023
gggtgtgaaa tagt                                                       14

<210> SEQ ID NO 1024
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1024
aataacgaat actt                                                       14

<210> SEQ ID NO 1025
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1025
ggtgtgaaat agtc                                                       14

<210> SEQ ID NO 1026
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1026
aataacgaat actt                                                       14

<210> SEQ ID NO 1027
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1027
gtgtgaaata gtcg                                                       14

<210> SEQ ID NO 1028

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1028
aataacgaat actt                                                          14

<210> SEQ ID NO 1029
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1029
tgtgaaatag tcga                                                          14

<210> SEQ ID NO 1030
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1030
aataacgaat actt                                                          14

<210> SEQ ID NO 1031
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1031
gtgaaatagt cgat                                                          14

<210> SEQ ID NO 1032
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1032
aataacgaat actt                                                          14

<210> SEQ ID NO 1033
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1033
tgaaatagtc gatt                                                          14

<210> SEQ ID NO 1034
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1034
```
aataacgaat actt                                                        14

<210> SEQ ID NO 1035
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1035
gaaatagtcg attt                                                        14

<210> SEQ ID NO 1036
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1036
aataacgaat actt                                                        14

<210> SEQ ID NO 1037
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1037
aaatagtcga ttta                                                        14

<210> SEQ ID NO 1038
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1038
aataacgaat actt                                                        14

<210> SEQ ID NO 1039
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1039
aatagtcgat ttat                                                        14

<210> SEQ ID NO 1040
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1040
aataacgaat actt                                                        14

<210> SEQ ID NO 1041
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1041
atagtcgatt tata                                                    14

<210> SEQ ID NO 1042
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1042
aataacgaat actt                                                    14

<210> SEQ ID NO 1043
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1043
tagtcgattt atat                                                    14

<210> SEQ ID NO 1044
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1044
aataacgaat actt                                                    14

<210> SEQ ID NO 1045
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1045
agtcgattta tatt                                                    14

<210> SEQ ID NO 1046
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1046
aataacgaat actt                                                    14

<210> SEQ ID NO 1047
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1047
gtcgatttat attt                                                    14
```

<210> SEQ ID NO 1048
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1048
aataacgaat actt                                                    14

<210> SEQ ID NO 1049
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1049
tcgatttata ttta                                                    14

<210> SEQ ID NO 1050
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1050
aataacgaat actt                                                    14

<210> SEQ ID NO 1051
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1051
cgatttatat ttag                                                    14

<210> SEQ ID NO 1052
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1052
aataacgaat actt                                                    14

<210> SEQ ID NO 1053
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1053
gatttatatt tagt                                                    14

<210> SEQ ID NO 1054
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 1054
aataacgaat actt                                                        14

<210> SEQ ID NO 1055
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1055
atttatattt agta                                                        14

<210> SEQ ID NO 1056
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1056
aataacgaat actt                                                        14

<210> SEQ ID NO 1057
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1057
tttatattta gtat                                                        14

<210> SEQ ID NO 1058
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1058
aataacgaat actt                                                        14

<210> SEQ ID NO 1059
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1059
ttatatttag tatt                                                        14

<210> SEQ ID NO 1060
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1060
aataacgaat actt                                                        14
```

```
<210> SEQ ID NO 1061
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1061
tatatttagt atta                                                        14

<210> SEQ ID NO 1062
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1062
aataacgaat actt                                                        14

<210> SEQ ID NO 1063
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1063
atatttagta ttag                                                        14

<210> SEQ ID NO 1064
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1064
aataacgaat actt                                                        14

<210> SEQ ID NO 1065
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1065
tatttagtat tagg                                                        14

<210> SEQ ID NO 1066
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1066
aataacgaat actt                                                        14

<210> SEQ ID NO 1067
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 1067
atttagtatt agga					14

<210> SEQ ID NO 1068
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1068
aataacgaat actt					14

<210> SEQ ID NO 1069
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1069
tttagtatta ggac					14

<210> SEQ ID NO 1070
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1070
cgcaatcgac aacc					14

<210> SEQ ID NO 1071
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1071
gtaggggaga tgttgttttt tcgc					24

<210> SEQ ID NO 1072
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1072
ttagtattag gacg					14

<210> SEQ ID NO 1073
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1073
cgcaatcgac aacc					14

<210> SEQ ID NO 1074
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 1074
tagtattagg acgt                                                         14

<210> SEQ ID NO 1075
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1075
cgcaatcgac aacc                                                         14

<210> SEQ ID NO 1076
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1076
agtattagga cgta                                                         14

<210> SEQ ID NO 1077
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1077
cgcaatcgac aacc                                                         14

<210> SEQ ID NO 1078
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1078
gtattaggac gtag                                                         14

<210> SEQ ID NO 1079
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1079
cgcaatcgac aacc                                                         14

<210> SEQ ID NO 1080
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1080
```
tattaggacg tagg                                                        14

<210> SEQ ID NO 1081
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1081
cgcaatcgac aacc                                                        14

<210> SEQ ID NO 1082
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1082
attaggacgt aggg                                                        14

<210> SEQ ID NO 1083
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1083
cgcaatcgac aacc                                                        14

<210> SEQ ID NO 1084
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1084
ttaggacgta gggt                                                        14

<210> SEQ ID NO 1085
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1085
cgcaatcgac aacc                                                        14

<210> SEQ ID NO 1086
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1086
taggacgtag ggtt                                                        14

<210> SEQ ID NO 1087
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1087
cgcaatcgac aacc                                                    14

<210> SEQ ID NO 1088
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1088
aggacgtagg gttt                                                    14

<210> SEQ ID NO 1089
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1089
cgcaatcgac aacc                                                    14

<210> SEQ ID NO 1090
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1090
ggacgtaggg tttt                                                    14

<210> SEQ ID NO 1091
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1091
cgcaatcgac aacc                                                    14

<210> SEQ ID NO 1092
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1092
gacgtagggt ttta                                                    14

<210> SEQ ID NO 1093
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1093
cgcaatcgac aacc                                                    14
```

```
<210> SEQ ID NO 1094
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1094
acgtagggtt ttac                                                         14

<210> SEQ ID NO 1095
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1095
cgcaatcgac aacc                                                         14

<210> SEQ ID NO 1096
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1096
cgtagggttt tacg                                                         14

<210> SEQ ID NO 1097
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1097
cgcaatcgac aacc                                                         14

<210> SEQ ID NO 1098
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1098
gtagggtttt acga                                                         14

<210> SEQ ID NO 1099
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1099
cgcaatcgac aacc                                                         14

<210> SEQ ID NO 1100
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 1100
tagggtttta cgag                                                         14

<210> SEQ ID NO 1101
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1101
cgcaatcgac aacc                                                         14

<210> SEQ ID NO 1102
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1102
agggttttac gagt                                                         14

<210> SEQ ID NO 1103
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1103
cgcaatcgac aacc                                                         14

<210> SEQ ID NO 1104
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1104
gggttttacg agtt                                                         14

<210> SEQ ID NO 1105
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1105
cgcaatcgac aacc                                                         14

<210> SEQ ID NO 1106
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1106
ggttttacga gtta                                                         14

<210> SEQ ID NO 1107

-continued

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1107
cgcaatcgac aacc                                                       14

<210> SEQ ID NO 1108
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1108
gttttacgag ttat                                                       14

<210> SEQ ID NO 1109
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1109
cgcaatcgac aacc                                                       14

<210> SEQ ID NO 1110
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1110
ttttacgagt tatt                                                       14

<210> SEQ ID NO 1111
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1111
cgcaatcgac aacc                                                       14

<210> SEQ ID NO 1112
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1112
tttacgagtt attt                                                       14

<210> SEQ ID NO 1113
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1113
```
cgcaatcgac aacc                                                    14

<210> SEQ ID NO 1114
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1114
ttacgagtta tttc                                                    14

<210> SEQ ID NO 1115
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1115
cgcaatcgac aacc                                                    14

<210> SEQ ID NO 1116
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1116
tacgagttat ttcg                                                    14

<210> SEQ ID NO 1117
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1117
cgcaatcgac aacc                                                    14

<210> SEQ ID NO 1118
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1118
acgagttatt tcga                                                    14

<210> SEQ ID NO 1119
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1119
cgcaatcgac aacc                                                    14

<210> SEQ ID NO 1120
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1120
cgagttattt cgaa                                                    14

<210> SEQ ID NO 1121
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1121
cgcaatcgac aacc                                                    14

<210> SEQ ID NO 1122
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1122
gagttatttc gaag                                                    14

<210> SEQ ID NO 1123
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1123
cgcaatcgac aacc                                                    14

<210> SEQ ID NO 1124
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1124
agttatttcg aaga                                                    14

<210> SEQ ID NO 1125
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1125
cgcaatcgac aacc                                                    14

<210> SEQ ID NO 1126
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1126
gttatttcga agag                                                    14
```

<210> SEQ ID NO 1127
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1127
cgcaatcgac aacc                                                        14

<210> SEQ ID NO 1128
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1128
ttatttcgaa gagc                                                        14

<210> SEQ ID NO 1129
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1129
cgcaatcgac aacc                                                        14

<210> SEQ ID NO 1130
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1130
tatttcgaag agcg                                                        14

<210> SEQ ID NO 1131
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1131
cgcaatcgac aacc                                                        14

<210> SEQ ID NO 1132
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1132
atttcgaaga gcga                                                        14

<210> SEQ ID NO 1133
<211> LENGTH: 14
<212> TYPE: DNA
<213> ORGANISM: Artificial Sequence
<220> FEATURE:

```
<223> OTHER INFORMATION: Synthetic Construct

<400> SEQUENCE: 1133
cgcaatcgac aacc                                                        14

<210> SEQ ID NO 1134
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1134
tttcgaagag cgag                                                        14

<210> SEQ ID NO 1135
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1135
cgcaatcgac aacc                                                        14

<210> SEQ ID NO 1136
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1136
ttcgaagagc gagg                                                        14

<210> SEQ ID NO 1137
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1137
cgcaatcgac aacc                                                        14

<210> SEQ ID NO 1138
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1138
tcgaagagcg aggg                                                        14

<210> SEQ ID NO 1139
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1139
cgcaatcgac aacc                                                        14
```

```
<210> SEQ ID NO 1140
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1140
cgaagagcga ggga                                                       14

<210> SEQ ID NO 1141
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1141
cgcaatcgac aacc                                                       14

<210> SEQ ID NO 1142
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1142
gaagagcgag ggag                                                       14

<210> SEQ ID NO 1143
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1143
cgcaatcgac aacc                                                       14

<210> SEQ ID NO 1144
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1144
aagagcgagg gaga                                                       14

<210> SEQ ID NO 1145
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1145
cgcaatcgac aacc                                                       14

<210> SEQ ID NO 1146
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1146
agagcgaggg agaa                                                     14

<210> SEQ ID NO 1147
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1147
cgcaatcgac aacc                                                     14

<210> SEQ ID NO 1148
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1148
gagcgaggga gaag                                                     14

<210> SEQ ID NO 1149
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1149
cgcaatcgac aacc                                                     14

<210> SEQ ID NO 1150
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1150
agcgagggag aagt                                                     14

<210> SEQ ID NO 1151
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1151
cgcaatcgac aacc                                                     14

<210> SEQ ID NO 1152
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1152
gcgagggaga agtt                                                     14

<210> SEQ ID NO 1153
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1153
cgcaatcgac aacc                                                         14

<210> SEQ ID NO 1154
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1154
cgagggagaa gttg                                                         14

<210> SEQ ID NO 1155
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1155
cgcaatcgac aacc                                                         14

<210> SEQ ID NO 1156
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1156
gagggagaag ttgg                                                         14

<210> SEQ ID NO 1157
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1157
cgcaatcgac aacc                                                         14

<210> SEQ ID NO 1158
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1158
agggagaagt tggg                                                         14

<210> SEQ ID NO 1159
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1159
```

```
cgcaatcgac aacc                                                      14

<210> SEQ ID NO 1160
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1160
gggagaagtt gggg                                                      14

<210> SEQ ID NO 1161
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1161
cgcaatcgac aacc                                                      14

<210> SEQ ID NO 1162
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1162
ggagaagttg ggga                                                      14

<210> SEQ ID NO 1163
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1163
cgcaatcgac aacc                                                      14

<210> SEQ ID NO 1164
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1164
gagaagttgg ggag                                                      14

<210> SEQ ID NO 1165
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1165
cgcaatcgac aacc                                                      14

<210> SEQ ID NO 1166
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 1166
agaagttggg gagg                                                           14

<210> SEQ ID NO 1167
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1167
cgcaatcgac aacc                                                           14

<210> SEQ ID NO 1168
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1168
gaagttgggg agga                                                           14

<210> SEQ ID NO 1169
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1169
cgcaatcgac aacc                                                           14

<210> SEQ ID NO 1170
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1170
aagttgggga ggag                                                           14

<210> SEQ ID NO 1171
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1171
cgcaatcgac aacc                                                           14

<210> SEQ ID NO 1172
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1172
agttggggag gaga                                                           14
```

```
<210> SEQ ID NO 1173
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1173
cgcaatcgac aacc                                                    14

<210> SEQ ID NO 1174
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1174
gttggggagg agaa                                                    14

<210> SEQ ID NO 1175
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1175
cgcaatcgac aacc                                                    14

<210> SEQ ID NO 1176
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1176
ttggggagga gaaa                                                    14

<210> SEQ ID NO 1177
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1177
cgcaatcgac aacc                                                    14

<210> SEQ ID NO 1178
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1178
tggggaggag aaag                                                    14

<210> SEQ ID NO 1179
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1179
cgcaatcgac aacc                                                        14

<210> SEQ ID NO 1180
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1180
ggggaggaga aagt                                                        14

<210> SEQ ID NO 1181
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1181
cgcaatcgac aacc                                                        14

<210> SEQ ID NO 1182
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1182
gggaggagaa agta                                                        14

<210> SEQ ID NO 1183
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1183
cgcaatcgac aacc                                                        14

<210> SEQ ID NO 1184
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1184
ggaggagaaa gtat                                                        14

<210> SEQ ID NO 1185
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1185
cgcaatcgac aacc                                                        14

<210> SEQ ID NO 1186
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1186
gaggagaaag tatt                                                       14

<210> SEQ ID NO 1187
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1187
cgcaatcgac aacc                                                       14

<210> SEQ ID NO 1188
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1188
aggagaaagt attc                                                       14

<210> SEQ ID NO 1189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1189
cgcaatcgac aacc                                                       14

<210> SEQ ID NO 1190
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1190
ggagaaagta ttcg                                                       14

<210> SEQ ID NO 1191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1191
cgcaatcgac aacc                                                       14

<210> SEQ ID NO 1192
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1192
```
gagaaagtat tcgt    14

<210> SEQ ID NO 1193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1193
acgaactaaa atta    14

<210> SEQ ID NO 1194
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1194
agttcgtagt tcgagttatt tttt    24

<210> SEQ ID NO 1195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1195
agaaagtatt cgtt    14

<210> SEQ ID NO 1196
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1196
acgaactaaa atta    14

<210> SEQ ID NO 1197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1197
gaaagtattc gtta    14

<210> SEQ ID NO 1198
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1198
acgaactaaa atta    14

<210> SEQ ID NO 1199
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1199
aaagtattcg ttat                                                        14

<210> SEQ ID NO 1200
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1200
acgaactaaa atta                                                        14

<210> SEQ ID NO 1201
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1201
aagtattcgt tatt                                                        14

<210> SEQ ID NO 1202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1202
acgaactaaa atta                                                        14

<210> SEQ ID NO 1203
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1203
agtattcgtt attt                                                        14

<210> SEQ ID NO 1204
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1204
acgaactaaa atta                                                        14

<210> SEQ ID NO 1205
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1205
gtattcgtta tttt                                                        14
```

```
<210> SEQ ID NO 1206
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1206
acgaactaaa atta                                                        14

<210> SEQ ID NO 1207
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1207
tattcgttat tttt                                                        14

<210> SEQ ID NO 1208
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1208
acgaactaaa atta                                                        14

<210> SEQ ID NO 1209
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1209
attcgttatt tttg                                                        14

<210> SEQ ID NO 1210
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1210
acgaactaaa atta                                                        14

<210> SEQ ID NO 1211
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1211
ttcgttattt ttgg                                                        14

<210> SEQ ID NO 1212
<211> LENGTH: 14
<212> TYPE: DNA
<213> ORGANISM: Artificial Sequence
<220> FEATURE:
```

<223> OTHER INFORMATION: Synthetic Construct

<400> SEQUENCE: 1212
acgaactaaa atta                                                         14

<210> SEQ ID NO 1213
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1213
tcgttatttt tgga                                                         14

<210> SEQ ID NO 1214
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1214
acgaactaaa atta                                                         14

<210> SEQ ID NO 1215
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1215
cgttattttt ggat                                                         14

<210> SEQ ID NO 1216
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1216
acgaactaaa atta                                                         14

<210> SEQ ID NO 1217
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1217 gttattttg gatt                                                          14

<210> SEQ ID NO 1218
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1218
acgaactaaa atta                                                         14

```
<210> SEQ ID NO 1219
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1219
ttatttttgg attg                                                         14

<210> SEQ ID NO 1220
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1220
acgaactaaa atta                                                         14

<210> SEQ ID NO 1221
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1221 tattttgga ttgg                                                          14

<210> SEQ ID NO 1222
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1222
acgaactaaa atta                                                         14

<210> SEQ ID NO 1223
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1223 attttggat tggc                                                          14

<210> SEQ ID NO 1224
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1224
acgaactaaa atta                                                         14

<210> SEQ ID NO 1225
<211> LENGTH: 14
<212> TYPE: DNA
<213> ORGANISM: Artificial Sequence
<220> FEATURE:
<223> OTHER INFORMATION: Synthetic Construct
```

<400> SEQUENCE: 1225 ttttggatt ggcg                                                    14

<210> SEQ ID NO 1226
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1226
acgaactaaa atta                                                   14

<210> SEQ ID NO 1227
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1227
ttttggattg gcgt                                                   14

<210> SEQ ID NO 1228
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1228
acgaactaaa atta                                                   14

<210> SEQ ID NO 1229
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1229
tttggattgg cgta                                                   14

<210> SEQ ID NO 1230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1230
acgaactaaa atta                                                   14

<210> SEQ ID NO 1231
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1231
ttggattggc gtat                                                   14

<210> SEQ ID NO 1232
<211> LENGTH: 14

```
<212> TYPE: DNA
<213> ORGANISM: Artificial Sequence
<220> FEATURE:
<223> OTHER INFORMATION: Synthetic Construct

<400> SEQUENCE: 1232
acgaactaaa atta                                                        14

<210> SEQ ID NO 1233
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1233
tggattggcg tatt                                                        14

<210> SEQ ID NO 1234
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1234
acgaactaaa atta                                                        14

<210> SEQ ID NO 1235
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1235
ggattggcgt attt                                                        14

<210> SEQ ID NO 1236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1236
acgaactaaa atta                                                        14

<210> SEQ ID NO 1237
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1237
gattggcgta ttta                                                        14

<210> SEQ ID NO 1238
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1238
```
acgaactaaa atta                                          14

<210> SEQ ID NO 1239
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1239
attggcgtat ttat                                          14

<210> SEQ ID NO 1240
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1240
acgaactaaa atta                                          14

<210> SEQ ID NO 1241
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1241
ttggcgtatt tata                                          14

<210> SEQ ID NO 1242
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1242
acgaactaaa atta                                          14

<210> SEQ ID NO 1243
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1243
tggcgtattt atag                                          14

<210> SEQ ID NO 1244
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1244
acgaactaaa atta                                          14

<210> SEQ ID NO 1245
<211> LENGTH: 14
<212> TYPE: DNA
<213> ORGANISM: Artificial Sequence

```
<220> FEATURE:
<223> OTHER INFORMATION: Synthetic Construct

<400> SEQUENCE: 1245
ggcgtattta tagg                                                     14

<210> SEQ ID NO 1246
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1246
acgaactaaa atta                                                     14

<210> SEQ ID NO 1247
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1247
gcgtatttat aggc                                                     14

<210> SEQ ID NO 1248
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1248
acgaactaaa atta                                                     14

<210> SEQ ID NO 1249
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1249
cgtatttata ggcg                                                     14

<210> SEQ ID NO 1250
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1250
acgaactaaa atta                                                     14

<210> SEQ ID NO 1251
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1251
gtatttatag gcgt                                                     14
```

```
<210> SEQ ID NO 1252
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1252
acgaactaaa atta                                                           14

<210> SEQ ID NO 1253
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1253
tatttatagg cgta                                                           14

<210> SEQ ID NO 1254
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1254
acgaactaaa atta                                                           14

<210> SEQ ID NO 1255
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1255
atttataggc gtag                                                           14

<210> SEQ ID NO 1256
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1256
acgaactaaa atta                                                           14

<210> SEQ ID NO 1257
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1257
tttataggcg tagg                                                           14

<210> SEQ ID NO 1258
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1258
acgaactaaa atta                                                    14

<210> SEQ ID NO 1259
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1259
ttataggcgt aggg                                                    14

<210> SEQ ID NO 1260
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1260
acgaactaaa atta                                                    14

<210> SEQ ID NO 1261
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1261
tataggcgta gggg                                                    14

<210> SEQ ID NO 1262
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1262
acgaactaaa atta                                                    14

<210> SEQ ID NO 1263
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1263
ataggcgtag ggga                                                    14

<210> SEQ ID NO 1264
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1264
acgaactaaa atta                                                    14

<210> SEQ ID NO 1265
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1265
taggcgtagg ggag                                                        14

<210> SEQ ID NO 1266
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1266
acgaactaaa atta                                                        14

<210> SEQ ID NO 1267
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1267
aggcgtaggg gaga                                                        14

<210> SEQ ID NO 1268
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1268
acgaactaaa atta                                                        14

<210> SEQ ID NO 1269
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1269
ggcgtagggg agat                                                        14

<210> SEQ ID NO 1270
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1270
acgaactaaa atta                                                        14

<210> SEQ ID NO 1271
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1271
```
gcgtagggga gatg                                                            14

<210> SEQ ID NO 1272
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1272
acgaactaaa atta                                                            14

<210> SEQ ID NO 1273
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1273 cgtagggag atgt                                                             14

<210> SEQ ID NO 1274
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1274
acgaactaaa atta                                                            14

<210> SEQ ID NO 1275
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1275
gtaggggaga tgtt                                                            14

<210> SEQ ID NO 1276
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1276
aaaaaaaaaa aacg                                                            14

<210> SEQ ID NO 1277
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1277
atttttttta gttaagttta ttggg                                                25

<210> SEQ ID NO 1278
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1278 tagggagat gttg                                                          14

<210> SEQ ID NO 1279
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1279
aaaaaaaaaa aacg                                                         14

<210> SEQ ID NO 1280
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1280 agggagatg ttgt                                                          14

<210> SEQ ID NO 1281
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1281
aaaaaaaaaa aacg                                                         14

<210> SEQ ID NO 1282
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1282
ggggagatgt tgtt                                                         14

<210> SEQ ID NO 1283
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1283
aaaaaaaaaa aacg                                                         14

<210> SEQ ID NO 1284
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1284
gggagatgtt gttt                                                         14
```

<210> SEQ ID NO 1285
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1285
aaaaaaaaaa aacg                                                         14

<210> SEQ ID NO 1286
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1286
ggagatgttg tttt                                                         14

<210> SEQ ID NO 1287
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1287
aaaaaaaaaa aacg                                                         14

<210> SEQ ID NO 1288
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1288
gagatgttgt tttt                                                         14

<210> SEQ ID NO 1289
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1289
aaaaaaaaaa aacg                                                         14

<210> SEQ ID NO 1290
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1290
agatgttgtt tttt                                                         14

<210> SEQ ID NO 1291
<211> LENGTH: 14
<212> TYPE: DNA
<213> ORGANISM: Artificial Sequence
<220> FEATURE:

<223> OTHER INFORMATION: Synthetic Construct

<400> SEQUENCE: 1291
aaaaaaaaaa aacg                                                              14

<210> SEQ ID NO 1292
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1292
gatgttgttt tttc                                                              14

<210> SEQ ID NO 1293
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1293
aaaaaaaaaa aacg                                                              14

<210> SEQ ID NO 1294
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1294
atgttgtttt ttcg                                                              14

<210> SEQ ID NO 1295
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1295
aaaaaaaaaa aacg                                                              14

<210> SEQ ID NO 1296
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1296
tgttgttttt tcgc                                                              14

<210> SEQ ID NO 1297
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1297
aaaaaaaaaa aacg                                                              14

```
<210> SEQ ID NO 1298
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1298 gttgttttttt cgcg                                                      14

<210> SEQ ID NO 1299
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1299
aaaaaaaaaa aacg                                                       14

<210> SEQ ID NO 1300
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1300
ttgttttttc gcgg                                                       14

<210> SEQ ID NO 1301
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1301
aaaaaaaaaa aacg                                                       14

<210> SEQ ID NO 1302
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1302 tgtttttcg cggt                                                        14

<210> SEQ ID NO 1303
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1303
aaaaaaaaaa aacg                                                       14

<210> SEQ ID NO 1304
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1304 gtttttcgc ggtt                                                        14

<210> SEQ ID NO 1305
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1305
aaaaaaaaaa aacg                                                       14

<210> SEQ ID NO 1306
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1306 tttttcgcg gttg                                                        14

<210> SEQ ID NO 1307
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1307
aaaaaaaaaa aacg                                                       14

<210> SEQ ID NO 1308
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1308
tttttcgcgg ttgt                                                       14

<210> SEQ ID NO 1309
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1309
aaaaaaaaaa aacg                                                       14

<210> SEQ ID NO 1310
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1310
ttttcgcggt tgtc                                                       14

<210> SEQ ID NO 1311
<211> LENGTH: 14
```

```
<212> TYPE: DNA
<213> ORGANISM: Artificial Sequence
<220> FEATURE:
<223> OTHER INFORMATION: Synthetic Construct

<400> SEQUENCE: 1311
aaaaaaaaaa aacg                                                      14

<210> SEQ ID NO 1312
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1312
tttcgcggtt gtcg                                                      14

<210> SEQ ID NO 1313
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1313
aaaaaaaaaa aacg                                                      14

<210> SEQ ID NO 1314
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1314
ttcgcggttg tcga                                                      14

<210> SEQ ID NO 1315
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1315
aaaaaaaaaa aacg                                                      14

<210> SEQ ID NO 1316
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1316
tcgcggttgt cgat                                                      14

<210> SEQ ID NO 1317
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1317
```

```
aaaaaaaaaa aacg                                                        14

<210> SEQ ID NO 1318
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1318
cgcggttgtc gatt                                                        14

<210> SEQ ID NO 1319
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1319
aaaaaaaaaa aacg                                                        14

<210> SEQ ID NO 1320
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1320
gcggttgtcg attg                                                        14

<210> SEQ ID NO 1321
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1321
aaaaaaaaaa aacg                                                        14

<210> SEQ ID NO 1322
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1322
cggttgtcga ttgc                                                        14

<210> SEQ ID NO 1323
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1323
aaaaaaaaaa aacg                                                        14

<210> SEQ ID NO 1324
<211> LENGTH: 14
<212> TYPE: DNA
<213> ORGANISM: Artificial Sequence
```

```
<220> FEATURE:
<223> OTHER INFORMATION: Synthetic Construct

<400> SEQUENCE: 1324
ggttgtcgat tgcg                                                         14

<210> SEQ ID NO 1325
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1325
aaaaaaaaaa aacg                                                         14

<210> SEQ ID NO 1326
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1326
gttgtcgatt gcgt                                                         14

<210> SEQ ID NO 1327
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1327
aaaaaaaaaa aacg                                                         14

<210> SEQ ID NO 1328
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1328
ttgtcgattg cgtt                                                         14

<210> SEQ ID NO 1329
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1329
aaaaaaaaaa aacg                                                         14

<210> SEQ ID NO 1330
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1330
tgtcgattgc gttt                                                         14
```

<210> SEQ ID NO 1331
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1331
aaaaaaaaaa aacg                                              14

<210> SEQ ID NO 1332
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1332
gtcgattgcg ttta                                              14

<210> SEQ ID NO 1333
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1333
aaaaaaaaaa aacg                                              14

<210> SEQ ID NO 1334
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1334
tcgattgcgt ttag                                              14

<210> SEQ ID NO 1335
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1335
aaaaaaaaaa aacg                                              14

<210> SEQ ID NO 1336
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1336
cgattgcgtt tagt                                              14

<210> SEQ ID NO 1337
<211> LENGTH: 14
<212> TYPE: DNA
<213> ORGANISM: Artificial Sequence
<220> FEATURE:
<223> OTHER INFORMATION: Synthetic Construct

```
<400> SEQUENCE: 1337
aaaaaaaaaa aacg                                                        14

<210> SEQ ID NO 1338
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1338
gattgcgttt agtt                                                        14

<210> SEQ ID NO 1339
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1339
aaaaaaaaaa aacg                                                        14

<210> SEQ ID NO 1340
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1340
attgcgttta gttc                                                        14

<210> SEQ ID NO 1341
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1341
aaaaaaaaaa aacg                                                        14

<210> SEQ ID NO 1342
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1342
ttgcgtttag ttcg                                                        14

<210> SEQ ID NO 1343
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1343
aaaaaaaaaa aacg                                                        14

<210> SEQ ID NO 1344
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1344
tgcgtttagt tcgt                                                     14

<210> SEQ ID NO 1345
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1345
aaaaaaaaaa aacg                                                     14

<210> SEQ ID NO 1346
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1346
gcgtttagtt cgta                                                     14

<210> SEQ ID NO 1347
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1347
aaaaaaaaaa aacg                                                     14

<210> SEQ ID NO 1348
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1348
cgtttagttc gtag                                                     14

<210> SEQ ID NO 1349
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1349
aaaaaaaaaa aacg                                                     14

<210> SEQ ID NO 1350
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1350
```
gtttagttcg tagt 14

<210> SEQ ID NO 1351
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1351
aaaaaaaaaa aacg 14

<210> SEQ ID NO 1352
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1352
tttagttcgt agtt 14

<210> SEQ ID NO 1353
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1353
aaaaaaaaaa aacg 14

<210> SEQ ID NO 1354
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1354
ttagttcgta gttc 14

<210> SEQ ID NO 1355
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1355
aaaaaaaaaa aacg 14

<210> SEQ ID NO 1356
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1356
tagttcgtag ttcg 14

<210> SEQ ID NO 1357
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 1357
aaaaaaaaaa aacg                                                      14

<210> SEQ ID NO 1358
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1358
agttcgtagt tcga                                                      14

<210> SEQ ID NO 1359
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1359
cgaacacgtc aatc                                                      14

<210> SEQ ID NO 1360
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1360
tttaagagta aggaggttt tggg                                            24

<210> SEQ ID NO 1361
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1361
gttcgtagtt cgag                                                      14

<210> SEQ ID NO 1362
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1362
cgaacacgtc aatc                                                      14

<210> SEQ ID NO 1363
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1363
ttcgtagttc gagt                                                      14
```

<210> SEQ ID NO 1364
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1364
cgaacacgtc aatc                                                        14

<210> SEQ ID NO 1365
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1365
tcgtagttcg agtt                                                        14

<210> SEQ ID NO 1366
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1366
cgaacacgtc aatc                                                        14

<210> SEQ ID NO 1367
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1367
cgtagttcga gtta                                                        14

<210> SEQ ID NO 1368
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1368
cgaacacgtc aatc                                                        14

<210> SEQ ID NO 1369
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1369
gtagttcgag ttat                                                        14

<210> SEQ ID NO 1370
<211> LENGTH: 14
<212> TYPE: DNA
<213> ORGANISM: Artificial Sequence
<220> FEATURE:

<223> OTHER INFORMATION: Synthetic Construct

<400> SEQUENCE: 1370
cgaacacgtc aatc                                                                          14

<210> SEQ ID NO 1371
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1371
tagttcgagt tatt                                                                          14

<210> SEQ ID NO 1372
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1372
cgaacacgtc aatc                                                                          14

<210> SEQ ID NO 1373
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1373
agttcgagtt attt                                                                          14

<210> SEQ ID NO 1374
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1374
cgaacacgtc aatc                                                                          14

<210> SEQ ID NO 1375
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1375
gttcgagtta tttt                                                                          14

<210> SEQ ID NO 1376
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1376
cgaacacgtc aatc                                                                          14

```
<210> SEQ ID NO 1377
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1377
ttcgagttat tttt                                                        14

<210> SEQ ID NO 1378
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1378
cgaacacgtc aatc                                                        14

<210> SEQ ID NO 1379
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1379
tcgagttatt tttt                                                        14

<210> SEQ ID NO 1380
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1380
cgaacacgtc aatc                                                        14

<210> SEQ ID NO 1381
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1381
cgagttattt tttt                                                        14

<210> SEQ ID NO 1382
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1382
cgaacacgtc aatc                                                        14

<210> SEQ ID NO 1383
<211> LENGTH: 14
<212> TYPE: DNA
<213> ORGANISM: Artificial Sequence
<220> FEATURE:
<223> OTHER INFORMATION: Synthetic Construct
```

-continued

<400> SEQUENCE: 1383
gagttatttt ttta                                         14

<210> SEQ ID NO 1384
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1384
cgaacacgtc aatc                                         14

<210> SEQ ID NO 1385
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1385
agttattttt ttaa                                         14

<210> SEQ ID NO 1386
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1386
cgaacacgtc aatc                                         14

<210> SEQ ID NO 1387
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1387 gttattttt taat                                          14

<210> SEQ ID NO 1388
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1388
cgaacacgtc aatc                                         14

<210> SEQ ID NO 1389
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1389
ttattttttt aatt                                         14

```
<210> SEQ ID NO 1390
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1390
cgaacacgtc aatc                                                      14

<210> SEQ ID NO 1391
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1391
tattttttta attt                                                      14

<210> SEQ ID NO 1392
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1392
cgaacacgtc aatc                                                      14

<210> SEQ ID NO 1393
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1393 attttttaa tttt                                                       14

<210> SEQ ID NO 1394
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1394
cgaacacgtc aatc                                                      14

<210> SEQ ID NO 1395
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1395
tttttttaat ttta                                                      14

<210> SEQ ID NO 1396
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 1396
cgaacacgtc aatc                                                       14

<210> SEQ ID NO 1397
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1397 tttttaatt ttag                                                        14

<210> SEQ ID NO 1398
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1398
cgaacacgtc aatc                                                       14

<210> SEQ ID NO 1399
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1399
tttttaattt tagt                                                       14

<210> SEQ ID NO 1400
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1400
cgaacacgtc aatc                                                       14

<210> SEQ ID NO 1401
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1401
ttttaatttt agtt                                                       14

<210> SEQ ID NO 1402
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1402
cgaacacgtc aatc                                                       14
```

```
<210> SEQ ID NO 1403
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1403
tttaatttta gttc                                                         14

<210> SEQ ID NO 1404
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1404
cgaacacgtc aatc                                                         14

<210> SEQ ID NO 1405
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1405
ttaattttag ttcg                                                         14

<210> SEQ ID NO 1406
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1406
cgaacacgtc aatc                                                         14

<210> SEQ ID NO 1407
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1407
taattttagt tcgt                                                         14

<210> SEQ ID NO 1408
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1408
cgaacacgtc aatc                                                         14
```

UNITED STATES PATENT AND TRADEMARK OFFICE
CERTIFICATE OF CORRECTION

PATENT NO. : 10,428,390 B2
APPLICATION NO. : 15/710028
DATED : October 1, 2019
INVENTOR(S) : Sung Whan An Page 1 of 1

It is certified that error appears in the above-identified patent and that said Letters Patent is hereby corrected as shown below:

In the Specification

Column 13, Line 53: "NoD" should be -- *Not*I --.

In the Claims

Column 540, Lines 15-16, Claim 5 after SEQ ID NO: 26, the following text should be deleted: ", 107, 190, 393, 536, 659, 762, 815, 968, 1071, 1191, 1277 and 1360".

Signed and Sealed this
Twelfth Day of November, 2019

Andrei Iancu
*Director of the United States Patent and Trademark Office*